US012799175B2

(12) United States Patent
Kadoch et al.

(10) Patent No.: US 12,799,175 B2
(45) Date of Patent: Nov. 17, 2026

(54) COMPOSITIONS COMPRISING MODIFIED SMARCB1 AND USES THEREOF

(71) Applicant: Dana-Farber Cancer Institute, Inc., Boston, MA (US)

(72) Inventors: Cigall Kadoch, Newton, MA (US); Alfredo M. Valencia, Santa Ana, CA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1242 days.

(21) Appl. No.: 17/770,464

(22) PCT Filed: Oct. 21, 2020

(86) PCT No.: PCT/US2020/056574

§ 371 (c)(1),
(2) Date: Apr. 20, 2022

(87) PCT Pub. No.: WO2021/081032

PCT Pub. Date: Apr. 29, 2021

(65) Prior Publication Data

US 2022/0396604 A1 Dec. 15, 2022

Related U.S. Application Data

(60) Provisional application No. 62/926,139, filed on Oct. 25, 2019.

(51) Int. Cl.

| | |
|---|---|
| ***C07K 14/47*** | (2006.01) |
| ***A61K 38/00*** | (2006.01) |
| ***A61K 49/00*** | (2006.01) |
| ***G01N 33/68*** | (2006.01) |

(52) U.S. Cl.

CPC ...... *C07K 14/4702* (2013.01); *A61K 49/0004* (2013.01); *A61K 49/0056* (2013.01); *G01N 33/6875* (2013.01); *A61K 38/00* (2013.01); *G01N 2500/02* (2013.01)

(58) Field of Classification Search

CPC ................ A61K 49/00; A61K 49/0004; A61K 49/0056; A61K 38/00; C07K 14/4702; C07K 2319/20; C07K 2319/60; G01N 33/6875; G01N 2500/02

See application file for complete search history.

(56) References Cited

U.S. PATENT DOCUMENTS

2004/0091487 A1 5/2004 Kalpana

FOREIGN PATENT DOCUMENTS

WO WO-2021/081032 A1 4/2021

OTHER PUBLICATIONS

Diets et al., "A recurrent de novo missense pathogenic variant in SMARCB1 causes severe intellectual disability and choroid plexus hyperplasia with resultant hydrocephalus, " Genet Med, 21(3): 572-579 (2019).
International Search Report and Written Opinion for International Application No. PCT/US20/56574 mailed Feb. 26, 2021.
Sen et al., "Loss of SnfS Induces Formation of an Aberrant SWI/SNF Complex," Cell Rep, 18(9): 2135-2147 (2017).
Yan et al., "Structural Insights into BAF47 and BAF155 Complex Formation," J Mol Bio, 429(11): 1650-1660 (2017).

*Primary Examiner* — D. L. Jones
(74) *Attorney, Agent, or Firm* — Foley Hoag LLP; DeAnn F. Smith

(57) ABSTRACT

The present invention is directed to compositions comprising modified SMARCB1 and uses thereof.

17 Claims, 55 Drawing Sheets

Specification includes a Sequence Listing.

A.

B.

Summary of Coffin-Siris Syndrome Mutations

Total: n=190 sequenced individuals

C.

mSWI/SNF family complexes
(BAF, PBAF, and ncBAF)

D.

E.

F.

G.

H.

I.

L

A.

G.

H.

I.

J.

D. 2D 15N-HSQC (SMARCB1 aa 351-385)

FIG. 4

A.

| Species | Biotin-labeled peptides | Protein Sequence | |
|---|---|---|---|
| *H. sapiens* | Bio-SMARCB1-CC_SCRM | 351-385 | Bio~[illegible] |
| *H. sapiens* | Bio-SMARCB1-CC_WT | 351-385 | Bio~PLLETLTDAEMEKKIRDQDRNTRRMRRLANTAPAW |
| *H. sapiens* | Bio-SMARCB1-CC_K363N | 351-385 | Bio~PLLETLTDAEME[illegible]KIRDQDRNTRRMRRLANTAPAW |
| *H. sapiens* | Bio-SMARCB1-CC_K364del | 351-385 | Bio~PLLETLTDAEMEK-IRDQDRNTRRMRRLANTAPAW |
| *H. sapiens* | Bio-SMARCB1-CC_R366C | 351-385 | Bio~PLLETLTDAEMEKKI[illegible]DQDRNTRRMRRLANTAPAW |
| *H. sapiens* | Bio-SMARCB1-CC_R374Q | 351-385 | Bio~PLLETLTDAEMEKKIRDQDRNTR[illegible]RRLANTAPAW |
| *H. sapiens* | Bio-SMARCB1-CC_R377H | 351-385 | Bio~PLLETLTDAEMEKKIRDQDRNTRRMR[illegible]LANTAPAW |
| *S. cerevisiae* | Bio-S.cerevisae_SNF5CC | 650-684 | Bio~P[illegible] |
| *S.cerevisiae* | Bio-S.cerevisae_SFH1CC | 380-414 | Bio~P[illegible] |
| *C. elegans* | Bio-C.elegans_SNF5CC | 347-381 | Bio~P[illegible]LETLTDAE[illegible]EKK[illegible]RDQDRNTRRMRRL[illegible] |
| *D. melanogaster* | Bio-D.melanogaster_SNR1CC | 336-370 | Bio~P[illegible]LETLTDAEMEKKIRDQDRNTRRMRRLANT[illegible]W |

B.

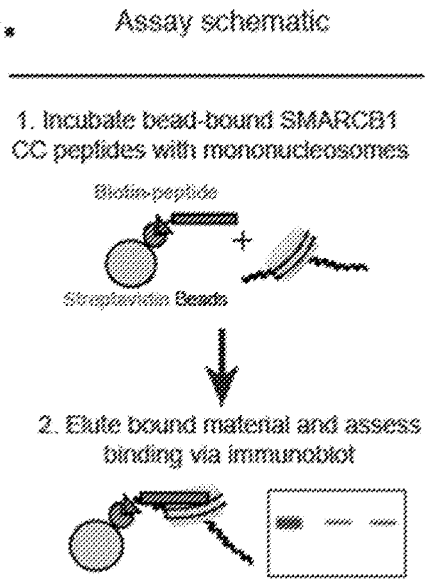

E.

F.

G.

H.

I.

J.

K.

| Minimal SMARCB1-CC (aa 351-385) | Isoelectric point (pI) | net Charge at pH 7 |
|---|---|---|
| WT | [illegible] | 2 |
| K364del | 9.06 | 1 |
| R377H | 8.76 | 1.1 |
| R366C | [illegible] | 0.9 |
| K363N | 9.06 | 1 |
| R374Q | 8.76 | 1 |

L.

M.

N.

D.

F.

G.

H.

G.

H.

I.

J.

J.

A.

D.

E.

M.

N.

O.

SEQUENCE LISTING

<160> NUMBER OF SEQ ID NOS: 54

<210> SEQ ID NO 1
<211> LENGTH: 1749
<212> TYPE: DNA
<213> ORGANISM: Homo sapiens

<400> SEQUENCE: 1
tttgtttgag cggcggcgcg cgcgtcagcg tcaacgccag cgcctgcgca ctgagggcgg 60
cctggtcgtc gtctgcggcg gcggcggcgg ctgaggagcc cggctgaggc gccagtaccc 120
ggcccggtcc gcatttcgcc ttccggcttc ggtttccctc ggcccagcac gccccggccc 180
cgccccagcc ctcctgatcc ctcgcagccc ggctccggcc gcccgcctct gccgccgcaa 240
tgatgatgat ggcgctgagc aagaccttcg ggcagaagcc cgtgaagttc cagctggagg 300
acgacggcga gttctacatg atcggctccg aggtgggaaa ctacctccgt atgttccgag 360
gttctctgta caagagatac ccctcactct ggaggcgact agccactgtg gaagagagga 420
agaaaatagt tgcatcgtca catggtaaaa aaacaaaacc taacactaag gatcacggat 480
acacgactct agccaccagt gtgaccctgt taaaagcctc ggaagtggaa gagattctgg 540
atggcaacga tgagaagtac aaggctgtgt ccatcagcac agagcccccc acctacctca 600
gggaacagaa ggccaagagg aacagccagt gggtacccac cctgcccaac agctcccacc 660
acttagatgc cgtgccatgc tccacaacca tcaacaggaa ccgcatgggc cgagacaaga 720
agagaacctt ccccctttgc tttgatgacc atgacccagc tgtgatccat gagaacgcat 780
ctcagcccga ggtgctggtc cccatccggc tggacatgga gatcgatggg cagaagctgc 840
gagacgcctt cacctggaac atgaatgaga agttgatgac gcctgagatg ttttcagaaa 900
tcctctgtga cgatctggat ttgaacccgc tgacgtttgt gccagccatc gcctctgcca 960
tcagacagca gatcgagtcc taccccacgg acagcatcct ggaggaccag tcagaccagc 1020
gcgtcatcat caagctgaac atccatgtgg gaaacatttc cctggtggac cagtttgagt 1080
gggacatgtc agagaaggag aactcaccag agaagtttgc cctgaagctg tgctcggagc 1140
tggggttggg cggggagttt gtcaccacca tcgcatacag catccgggga cagctgagct 1200
ggcatcagaa gacctacgcc ttcagcgaga accctctgcc cacagtggag attgccatcc 1260
ggaacacggg cgatgcggac cagtggtgcc cactgctgga gactctgaca gacgctgaga 1320
tggagaagaa gatccgcgac caggacagga acacgaggcg gatgaggcgt cttgccaaca 1380
cggccccggc ctggtaacca gcccatcagc acacggctcc cacggagcat ctcagaagat 1440
tgggccgcct ctcctccatc ttctggcaag gacagaggcg aggggacagc ccagcgccat 1500
cctgaggatc gggtgggggt ggagtggggg cttccaggtg gcccttcccg gcacacattc 1560
catttgttga gccccagtcc tgccccccac cccaccctcc ctacccctcc ccagtctctg 1620
gggtcaggaa gaaaccttat tttaggttgt gttttgtttt tgtataggag ccccaggcag 1680
ggctagtaac agtttttaaa taaaaggcaa caggtcatgt tcaatttctt caacaaaaaa 1740
aaaaaaaaa 1749

<210> SEQ ID NO 2
<211> LENGTH: 385
<212> TYPE: PRT
<213> ORGANISM: Homo sapiens

<400> SEQUENCE: 2

Met Met Met Met Ala Leu Ser Lys Thr Phe Gly Gln Lys Pro Val Lys
1 5 10 15

Phe Gln Leu Glu Asp Asp Gly Glu Phe Tyr Met Ile Gly Ser Glu Val
20 25 30

Gly Asn Tyr Leu Arg Met Phe Arg Gly Ser Leu Tyr Lys Arg Tyr Pro
35 40 45

Ser Leu Trp Arg Arg Leu Ala Thr Val Glu Glu Arg Lys Lys Ile Val
50 55 60

Ala Ser Ser His Gly Lys Lys Thr Lys Pro Asn Thr Lys Asp His Gly
65 70 75 80

Tyr Thr Thr Leu Ala Thr Ser Val Thr Leu Leu Lys Ala Ser Glu Val
85 90 95

Glu Glu Ile Leu Asp Gly Asn Asp Glu Lys Tyr Lys Ala Val Ser Ile
100 105 110

Ser Thr Glu Pro Pro Thr Tyr Leu Arg Glu Gln Lys Ala Lys Arg Asn
115 120 125

Ser Gln Trp Val Pro Thr Leu Pro Asn Ser Ser His His Leu Asp Ala
130 135 140

Val Pro Cys Ser Thr Thr Ile Asn Arg Asn Arg Met Gly Arg Asp Lys
145 150 155 160

Lys Arg Thr Phe Pro Leu Cys Phe Asp Asp His Asp Pro Ala Val Ile
165 170 175

His Glu Asn Ala Ser Gln Pro Glu Val Leu Val Pro Ile Arg Leu Asp
180 185 190

Met Glu Ile Asp Gly Gln Lys Leu Arg Asp Ala Phe Thr Trp Asn Met
195 200 205

Asn Glu Lys Leu Met Thr Pro Glu Met Phe Ser Glu Ile Leu Cys Asp
210 215 220

Asp Leu Asp Leu Asn Pro Leu Thr Phe Val Pro Ala Ile Ala Ser Ala
225 230 235 240

Ile Arg Gln Gln Ile Glu Ser Tyr Pro Thr Asp Ser Ile Leu Glu Asp
245 250 255

Gln Ser Asp Gln Arg Val Ile Ile Lys Leu Asn Ile His Val Gly Asn
260 265 270

Ile Ser Leu Val Asp Gln Phe Glu Trp Asp Met Ser Glu Lys Glu Asn
275 280 285

Ser Pro Glu Lys Phe Ala Leu Lys Leu Cys Ser Glu Leu Gly Leu Gly
290 295 300

Gly Glu Phe Val Thr Thr Ile Ala Tyr Ser Ile Arg Gly Gln Leu Ser

```
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
            340                 345                 350

Leu Glu Thr Leu Thr Asp Ala Glu Met Glu Lys Lys Ile Arg Asp Gln
        355                 360                 365

Asp Arg Asn Thr Arg Arg Met Arg Arg Leu Ala Asn Thr Ala Pro Ala
    370                 375                 380

Trp
385


<210> SEQ ID NO 3
<211> LENGTH: 1722
<212> TYPE: DNA
<213> ORGANISM: Homo sapiens

<400> SEQUENCE: 3

tttgtttgag cggcggcgcg cgcgtcagcg tcaacgccag cgcctgcgca ctgagggcgg     60

cctggtcgtc gtctgcggcg gcggcggcgg ctgaggagcc cggctgaggc gccagtaccc    120

ggcccggtcc gcatttcgcc ttccggcttc ggtttccctc ggcccagcac gccccggccc    180

cgccccagcc ctcctgatcc ctcgcagccc ggctccggcc gcccgcctct gccgccgcaa    240

tgatgatgat ggcgctgagc aagaccttcg ggcagaagcc cgtgaagttc cagctggagg    300

acgacggcga gttctacatg atcggctccg aggtgggaaa ctacctccgt atgttccgag    360

gttctctgta caagagatac ccctcactct ggaggcgact agccactgtg gaagagagga    420

agaaaatagt tgcatcgtca catgatcacg gatacacgac tctagccacc agtgtgaccc    480

tgttaaaagc ctcggaagtg gaagagattc tggatggcaa cgatgagaag tacaaggctg    540

tgtccatcag cacagagccc cccacctacc tcagggaaca gaaggccaag aggaacagcc    600

agtgggtacc caccctgccc aacagctccc accacttaga tgccgtgcca tgctccacaa    660

ccatcaacag gaaccgcatg ggccgagaca agaagagaac cttccccctt tgctttgatg    720

accatgaccc agctgtgatc catgagaacg catctcagcc cgaggtgctg gtccccatcc    780

ggctggacat ggagatcgat gggcagaagc tgcgagacgc cttcacctgg aacatgaatg    840

agaagttgat gacgcctgag atgttttcag aaatcctctg tgacgatctg gatttgaacc    900

cgctgacgtt tgtgccagcc atcgcctctg ccatcagaca gcagatcgag tcctacccca    960

cggacagcat cctggaggac cagtcagacc agcgcgtcat catcaagctg aacatccatg   1020

tgggaaacat ttccctggtg gaccagtttg agtgggacat gtcagagaag gagaactcac   1080

cagagaagtt tgccctgaag ctgtgctcgg agctggggtt gggcggggag tttgtcacca   1140

ccatcgcata cagcatccgg ggacagctga gctggcatca gaagacctac gccttcagcg   1200

agaaccctct gcccacagtg gagattgcca tccggaacac gggcgatgcg gaccagtggt   1260

gcccactgct ggagactctg acagacgctg agatggagaa gaagatccgc gaccaggaca   1320

ggaacacgag gcggatgagg cgtcttgcca acacggcccc ggcctggtaa ccagcccatc   1380

agcacacggc tcccacggag catctcagaa gattgggccg cctctcctcc atcttctggc   1440

aaggacagag gcgaggggac agcccagcgc catcctgagg atcgggtggg ggtggagtgg   1500

gggcttccag gtggcccttc ccggcacaca ttccatttgt tgagccccag tcctgccccc   1560

caccccaccc tccctacccc tccccagtct ctggggtcag gaagaaacct tattttaggt   1620
```

```
tgtgttttgt ttttgtatag gagccccagg cagggctagt aacagttttt aaataaaagg   1680

caacaggtca tgttcaattt cttcaacaaa aaaaaaaaaa aa                      1722


<210> SEQ ID NO 4
<211> LENGTH: 376
<212> TYPE: PRT
<213> ORGANISM: Homo sapiens

<400> SEQUENCE: 4

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Asp His Gly Tyr Thr Thr Leu Ala Thr Ser Val Thr
65                  70                  75                  80

Leu Leu Lys Ala Ser Glu Val Glu Glu Ile Leu Asp Gly Asn Asp Glu
                85                  90                  95

Lys Tyr Lys Ala Val Ser Ile Ser Thr Glu Pro Pro Thr Tyr Leu Arg
            100                 105                 110

Glu Gln Lys Ala Lys Arg Asn Ser Gln Trp Val Pro Thr Leu Pro Asn
        115                 120                 125

Ser Ser His His Leu Asp Ala Val Pro Cys Ser Thr Thr Ile Asn Arg
    130                 135                 140

Asn Arg Met Gly Arg Asp Lys Lys Arg Thr Phe Pro Leu Cys Phe Asp
145                 150                 155                 160

Asp His Asp Pro Ala Val Ile His Glu Asn Ala Ser Gln Pro Glu Val
                165                 170                 175

Leu Val Pro Ile Arg Leu Asp Met Glu Ile Asp Gly Gln Lys Leu Arg
            180                 185                 190

Asp Ala Phe Thr Trp Asn Met Asn Glu Lys Leu Met Thr Pro Glu Met
        195                 200                 205

Phe Ser Glu Ile Leu Cys Asp Asp Leu Asp Leu Asn Pro Leu Thr Phe
    210                 215                 220

Val Pro Ala Ile Ala Ser Ala Ile Arg Gln Gln Ile Glu Ser Tyr Pro
225                 230                 235                 240

Thr Asp Ser Ile Leu Glu Asp Gln Ser Asp Gln Arg Val Ile Ile Lys
                245                 250                 255

Leu Asn Ile His Val Gly Asn Ile Ser Leu Val Asp Gln Phe Glu Trp
            260                 265                 270

Asp Met Ser Glu Lys Glu Asn Ser Pro Glu Lys Phe Ala Leu Lys Leu
        275                 280                 285

Cys Ser Glu Leu Gly Leu Gly Gly Glu Phe Val Thr Thr Ile Ala Tyr
    290                 295                 300

Ser Ile Arg Gly Gln Leu Ser Trp His Gln Lys Thr Tyr Ala Phe Ser
305                 310                 315                 320

Glu Asn Pro Leu Pro Thr Val Glu Ile Ala Ile Arg Asn Thr Gly Asp
                325                 330                 335

Ala Asp Gln Trp Cys Pro Leu Leu Glu Thr Leu Thr Asp Ala Glu Met
            340                 345                 350

Glu Lys Lys Ile Arg Asp Gln Asp Arg Asn Thr Arg Arg Met Arg Arg
```

```
        355                 360                 365

Leu Ala Asn Thr Ala Pro Ala Trp
    370                 375


<210> SEQ ID NO 5
<211> LENGTH: 1776
<212> TYPE: DNA
<213> ORGANISM: Homo sapiens

<400> SEQUENCE: 5

tttgtttgag cggcggcgcg cgcgtcagcg tcaacgccag cgcctgcgca ctgagggcgg     60

cctggtcgtc gtctgcggcg gcggcggcgg ctgaggagcc cggctgaggc gccagtaccc    120

ggcccggtcc gcatttcgcc ttccggcttc ggtttccctc ggcccagcac gccccggccc    180

cgccccagcc ctcctgatcc ctcgcagccc ggctccggcc gcccgcctct gccgccgcaa    240

tgatgatgat ggcgctgagc aagaccttcg ggcagaagcc cgtgaagttc cagctggagg    300

acgacggcga gttctacatg atcggctccg aggtgggaaa ctacctccgt atgttccgag    360

gttctctgta caagagatac ccctcactct ggaggcgact agccactgtg gaagagagga    420

agaaaatagt tgcatcgtca catgatcacg gatacacgac tctagccacc agtgtgaccc    480

tgttaaaagc ctcggaagtg gaagagattc tggatggcaa cgatgagaag tacaaggctg    540

tgtccatcag cacagagccc cccacctacc tcagggaaca gaaggccaag aggaacagcc    600

agtgggtacc caccctgccc aacagctccc accacttaga tgccgtgcca tgctccacaa    660

ccatcaacag gaaccgcatg ggccgagaca agaagagaac cttccccctt tggtgtggat    720

gcatcgctgc actcaccctc cgtgctgatt ccgccttagt tctccacttt gatgaccatg    780

acccagctgt gatccatgag aacgcatctc agcccgaggt gctggtcccc atccggctgg    840

acatggagat cgatgggcag aagctgcgag acgccttcac ctggaacatg aatgagaagt    900

tgatgacgcc tgagatgttt tcagaaatcc tctgtgacga tctggatttg aacccgctga    960

cgtttgtgcc agccatcgcc tctgccatca gacagcagat cgagtcctac cccacggaca   1020

gcatcctgga ggaccagtca gaccagcgcg tcatcatcaa gctgaacatc catgtgggaa   1080

acatttccct ggtggaccag tttgagtggg acatgtcaga gaaggagaac tcaccagaga   1140

agtttgccct gaagctgtgc tcggagctgg ggttgggcgg ggagtttgtc accaccatcg   1200

catacagcat ccggggacag ctgagctggc atcagaagac ctacgccttc agcgagaacc   1260

ctctgcccac agtggagatt gccatccgga acacgggcga tgcggaccag tggtgcccac   1320

tgctggagac tctgacagac gctgagatgg agaagaagat ccgcgaccag gacaggaaca   1380

cgaggcggat gaggcgtctt gccaacacgg ccccggcctg gtaaccagcc catcagcaca   1440

cggctcccac ggagcatctc agaagattgg gccgcctctc ctccatcttc tggcaaggac   1500

agaggcgagg ggacagccca gcgccatcct gaggatcggg tgggggtgga gtgggggctt   1560

ccaggtggcc cttcccggca cacattccat ttgttgagcc ccagtcctgc cccccacccc   1620

accctcccta cccctcccca gtctctgggg tcaggaagaa accttatttt aggttgtgtt   1680

ttgtttttgt ataggagccc caggcagggc tagtaacagt ttttaaataa aaggcaacag   1740

gtcatgttca atttcttcaa caaaaaaaaa aaaaaa                              1776


<210> SEQ ID NO 6
<211> LENGTH: 394
<212> TYPE: PRT
<213> ORGANISM: Homo sapiens
```

<400> SEQUENCE: 6

```
Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Asp His Gly Tyr Thr Thr Leu Ala Thr Ser Val Thr
65                  70                  75                  80

Leu Leu Lys Ala Ser Glu Val Glu Glu Ile Leu Asp Gly Asn Asp Glu
                85                  90                  95

Lys Tyr Lys Ala Val Ser Ile Ser Thr Glu Pro Pro Thr Tyr Leu Arg
            100                 105                 110

Glu Gln Lys Ala Lys Arg Asn Ser Gln Trp Val Pro Thr Leu Pro Asn
        115                 120                 125

Ser Ser His His Leu Asp Ala Val Pro Cys Ser Thr Thr Ile Asn Arg
    130                 135                 140

Asn Arg Met Gly Arg Asp Lys Lys Arg Thr Phe Pro Leu Trp Cys Gly
145                 150                 155                 160

Cys Ile Ala Ala Leu Thr Leu Arg Ala Asp Ser Ala Leu Val Leu His
                165                 170                 175

Phe Asp Asp His Asp Pro Ala Val Ile His Glu Asn Ala Ser Gln Pro
            180                 185                 190

Glu Val Leu Val Pro Ile Arg Leu Asp Met Glu Ile Asp Gly Gln Lys
        195                 200                 205

Leu Arg Asp Ala Phe Thr Trp Asn Met Asn Glu Lys Leu Met Thr Pro
    210                 215                 220

Glu Met Phe Ser Glu Ile Leu Cys Asp Asp Leu Asp Leu Asn Pro Leu
225                 230                 235                 240

Thr Phe Val Pro Ala Ile Ala Ser Ala Ile Arg Gln Gln Ile Glu Ser
                245                 250                 255

Tyr Pro Thr Asp Ser Ile Leu Glu Asp Gln Ser Asp Gln Arg Val Ile
            260                 265                 270

Ile Lys Leu Asn Ile His Val Gly Asn Ile Ser Leu Val Asp Gln Phe
        275                 280                 285

Glu Trp Asp Met Ser Glu Lys Glu Asn Ser Pro Glu Lys Phe Ala Leu
    290                 295                 300

Lys Leu Cys Ser Glu Leu Gly Leu Gly Gly Glu Phe Val Thr Thr Ile
305                 310                 315                 320

Ala Tyr Ser Ile Arg Gly Gln Leu Ser Trp His Gln Lys Thr Tyr Ala
                325                 330                 335

Phe Ser Glu Asn Pro Leu Pro Thr Val Glu Ile Ala Ile Arg Asn Thr
            340                 345                 350

Gly Asp Ala Asp Gln Trp Cys Pro Leu Leu Glu Thr Leu Thr Asp Ala
        355                 360                 365

Glu Met Glu Lys Lys Ile Arg Asp Gln Asp Arg Asn Thr Arg Arg Met
    370                 375                 380

Arg Arg Leu Ala Asn Thr Ala Pro Ala Trp
385                 390
```

<210> SEQ ID NO 7

<211> LENGTH: 1803
<212> TYPE: DNA
<213> ORGANISM: Homo sapiens

<400> SEQUENCE: 7

```
tttgtttgag cggcggcgcg cgcgtcagcg tcaacgccag cgcctgcgca ctgagggcgg     60
cctggtcgtc gtctgcggcg gcggcggcgg ctgaggagcc cggctgaggc gccagtaccc    120
ggcccggtcc gcatttcgcc ttccggcttc ggtttccctc ggcccagcac gccccggccc    180
cgccccagcc ctcctgatcc ctcgcagccc ggctccggcc gcccgcctct gccgccgcaa    240
tgatgatgat ggcgctgagc aagaccttcg ggcagaagcc cgtgaagttc cagctggagg    300
acgacggcga gttctacatg atcggctccg aggtgggaaa ctacctccgt atgttccgag    360
gttctctgta caagagatac cctcactct ggaggcgact agccactgtg gaagagagga    420
agaaaatagt tgcatcgtca catggtaaaa aaacaaaacc taacactaag gatcacggat    480
acacgactct agccaccagt gtgaccctgt taaaagcctc ggaagtggaa gagattctgg    540
atggcaacga tgagaagtac aaggctgtgt ccatcagcac agagcccccc acctacctca    600
gggaacagaa ggccaagagg aacagccagt gggtacccac cctgcccaac agctcccacc    660
acttagatgc cgtgccatgc tccacaacca tcaacaggaa ccgcatgggc cgagacaaga    720
agagaacctt ccccctttgg tgtggatgca tcgctgcact caccctccgt gctgattccg    780
ccttagttct ccactttgat gaccatgacc cagctgtgat ccatgagaac gcatctcagc    840
ccgaggtgct ggtccccatc cggctggaca tggagatcga tgggcagaag ctgcgagacg    900
ccttcacctg gaacatgaat gagaagttga tgacgcctga gatgttttca gaaatcctct    960
gtgacgatct ggatttgaac ccgctgacgt ttgtgccagc catcgcctct gccatcagac   1020
agcagatcga gtcctacccc acggacagca tcctggagga ccagtcagac cagcgcgtca   1080
tcatcaagct gaacatccat gtgggaaaca tttccctggt ggaccagttt gagtgggaca   1140
tgtcagagaa ggagaactca ccagagaagt ttgccctgaa gctgtgctcg gagctggggt   1200
tgggcgggga gtttgtcacc accatcgcat acagcatccg ggacagctg agctggcatc    1260
agaagaccta cgccttcagc gagaaccctc tgcccacagt ggagattgcc atccggaaca   1320
cgggcgatgc ggaccagtgg tgcccactgc tggagactct gacagacgct gagatggaga   1380
agaagatccg cgaccaggac aggaacacga ggcggatgag gcgtcttgcc aacacggccc   1440
cggcctggta accagcccat cagcacacgg ctcccacgga gcatctcaga agattgggcc   1500
gcctctcctc catcttctgg caaggacaga ggcgagggga cagcccagcg ccatcctgag   1560
gatcgggtgg gggtggagtg ggggcttcca ggtggccctt cccggcacac attccatttg   1620
ttgagcccca gtcctgcccc ccaccccacc ctccctaccc ctccccagtc tctggggtca   1680
ggaagaaacc ttattttagg ttgtgttttg tttttgtata ggagccccag gcagggctag   1740
taacagtttt taaataaaag gcaacaggtc atgttcaatt tcttcaacaa aaaaaaaaaa   1800
aaa                                                                 1803
```

<210> SEQ ID NO 8
<211> LENGTH: 403
<212> TYPE: PRT
<213> ORGANISM: Homo sapiens

<400> SEQUENCE: 8

```
Met Met Met Met Ala Leu Ser Lys Thr Phe Gly Gln Lys Pro Val Lys
1               5                   10                  15
```

```
Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Pro Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Trp Cys Gly Cys Ile Ala Ala Leu Thr Leu
                165                 170                 175

Arg Ala Asp Ser Ala Leu Val Leu His Phe Asp Asp His Asp Pro Ala
            180                 185                 190

Val Ile His Glu Asn Ala Ser Gln Pro Glu Val Leu Val Pro Ile Arg
        195                 200                 205

Leu Asp Met Glu Ile Asp Gly Gln Lys Leu Arg Asp Ala Phe Thr Trp
    210                 215                 220

Asn Met Asn Glu Lys Leu Met Thr Pro Glu Met Phe Ser Glu Ile Leu
225                 230                 235                 240

Cys Asp Asp Leu Asp Leu Asn Pro Leu Thr Phe Val Pro Ala Ile Ala
                245                 250                 255

Ser Ala Ile Arg Gln Gln Ile Glu Ser Tyr Pro Thr Asp Ser Ile Leu
            260                 265                 270

Glu Asp Gln Ser Asp Gln Arg Val Ile Ile Lys Leu Asn Ile His Val
        275                 280                 285

Gly Asn Ile Ser Leu Val Asp Gln Phe Glu Trp Asp Met Ser Glu Lys
    290                 295                 300

Glu Asn Ser Pro Glu Lys Phe Ala Leu Lys Leu Cys Ser Glu Leu Gly
305                 310                 315                 320

Leu Gly Gly Glu Phe Val Thr Thr Ile Ala Tyr Ser Ile Arg Gly Gln
                325                 330                 335

Leu Ser Trp His Gln Lys Thr Tyr Ala Phe Ser Glu Asn Pro Leu Pro
            340                 345                 350

Thr Val Glu Ile Ala Ile Arg Asn Thr Gly Asp Ala Asp Gln Trp Cys
        355                 360                 365

Pro Leu Leu Glu Thr Leu Thr Asp Ala Glu Met Glu Lys Lys Ile Arg
    370                 375                 380

Asp Gln Asp Arg Asn Thr Arg Arg Met Arg Arg Leu Ala Asn Thr Ala
385                 390                 395                 400

Pro Ala Trp
```

<210> SEQ ID NO 9
<211> LENGTH: 1674
<212> TYPE: DNA
<213> ORGANISM: Mus musculus

<400> SEQUENCE: 9
gtcagcttct ccacgcatgc gcaccgaggg cggcctgctc gttgcagaga cggccaagga 60
gcccagtagt gacacgagcg ctcgcccggt tcgcccggct tgccctgccc gaccttcacc 120
tccaggcctc cgttcctttc ggtccgacgc gcctcggccc cgccctagcc caccggattc 180
tttccagctc gaccccggct gccggtttcc cccgccgcca tgatgatgat ggcgttgagc 240
aagaccttcg ggcagaagcc cgtcaagttt cagctggagg acgacgggga gttctacatg 300
atcggctccg aggtgggaaa ctacctgcgt atgttccgag gttctctgta caagagatac 360
ccctcactct ggcggcgact agccactgtg gaagaaagga agaaaatagt ggcatcgtca 420
catggtaaaa aaacaaaacc taacactaag gatcatggat ataccaccct ggccaccagc 480
gtgacactcc tgaaagcctc agaggtagaa gagatcctgg atggcaatga cgagaagtac 540
aaggctgtgt ccatcagcac agagcccccg acctacctca gggagcagaa ggccaagagg 600
aacagccagt gggtccccac cctgcccaac agctcccacc acctggatgc tgtgccctgt 660
tccaccacca tcaacaggaa ccgcatgggt cgggacaaga agagaacctt cccccttgtgc 720
tttgatgacc acgacccagc tgtgatccat gagaatgcgt cacagcctga ggtgctggtg 780
cccatccggc tcgacatgga gatcgacggg cagaagctgc gagacgcttt tacctggaac 840
atgaatgaga agctaatgac tcctgagatg ttttcagaaa tactttgtga tgacctggat 900
ttgaatccac tgacttttgt gccagctatt gcctctgcca ttcgacagca gattgagtcc 960
taccccacag acagcatcct agaggatcaa tccgaccagc gtgtcatcat caagctgaac 1020
atccacgtgg ggaacatctc cctggtggac cagtttgagt gggacatgtc agagaaagag 1080
aactccccag agaagtttgc cctgaagctg tgctcagagc tgggcttggg cggggagttt 1140
gtcaccacca ttgcatacag catccgagga cagctgagct ggcaccagaa gacctatgcc 1200
ttcagtgaga acccacttcc cacagtggag attgccatcc gaaataccgg agatgctgac 1260
cagtggtgcc ccctgctgga gacactgact gatgccgaga tggagaaaaa gatccgggat 1320
caagatagga acacaaggcg aatgaggcgt cttgccaaca ctgccccagc ctggtgatga 1380
agacatccat gctcgacctc tacggagcat ctcagactgc ctttccttcc tctgtggaaa 1440
gagaaaggca aagggacagc tggtgccatc ctgaggactg gggtaggagc ctcctaggtg 1500
cctcccttca gcacacattc catttgctaa accccaacac tgtcccccag agtctagagt 1560
cggaagcagc ctcattttgg gttgtgtttt gtttttgtat aggagcccag gcagggctgg 1620
taacactttt taaataaaaa gtaccatgtt caatttcaaa aaaaaaaaaa aaaa 1674

<210> SEQ ID NO 10
<211> LENGTH: 385
<212> TYPE: PRT
<213> ORGANISM: Mus musculus

<400> SEQUENCE: 10

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

```
Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Pro Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
                245                 250                 255

Gln Ser Asp Gln Arg Val Ile Ile Lys Leu Asn Ile His Val Gly Asn
            260                 265                 270

Ile Ser Leu Val Asp Gln Phe Glu Trp Asp Met Ser Glu Lys Glu Asn
        275                 280                 285

Ser Pro Glu Lys Phe Ala Leu Lys Leu Cys Ser Glu Leu Gly Leu Gly
    290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
            340                 345                 350

Leu Glu Thr Leu Thr Asp Ala Glu Met Glu Lys Lys Ile Arg Asp Gln
        355                 360                 365

Asp Arg Asn Thr Arg Arg Met Arg Arg Leu Ala Asn Thr Ala Pro Ala
    370                 375                 380

Trp
385
```

<210> SEQ ID NO 11
<211> LENGTH: 1647
<212> TYPE: DNA
<213> ORGANISM: Mus musculus

<400> SEQUENCE: 11

```
gtcagcttct ccacgcatgc gcaccgaggg cggcctgctc gttgcagaga cggccaagga      60

gcccagtagt gacacgagcg ctcgcccggt tcgcccggct tgccctgccc gaccttcacc     120

tccaggcctc cgttcctttc ggtccgacgc gcctcggccc cgccctagcc caccggattc     180

tttccagctc gaccccggct gccggtttcc cccgccgcca tgatgatgat ggcgttgagc     240
```

```
aagaccttcg ggcagaagcc cgtcaagttt cagctggagg acgacgggga gttctacatg    300

atcggctccg aggtgggaaa ctacctgcgt atgttccgag gttctctgta caagagatac    360

ccctcactct ggcggcgact agccactgtg gaagaaagga agaaaatagt ggcatcgtca    420

catgatcatg gatataccac cctggccacc agcgtgacac tcctgaaagc ctcagaggta    480

gaagagatcc tggatggcaa tgacgagaag tacaaggctg tgtccatcag cacagagccc    540

ccgacctacc tcagggagca gaaggccaag aggaacagcc agtgggtccc caccctgccc    600

aacagctccc accacctgga tgctgtgccc tgttccacca ccatcaacag gaaccgcatg    660

ggtcgggaca agaagagaac cttccccttg tgctttgatg accacgaccc agctgtgatc    720

catgagaatg cgtcacagcc tgaggtgctg gtgcccatcc ggctcgacat ggagatcgac    780

gggcagaagc tgcgagacgc ttttacctgg aacatgaatg agaagctaat gactcctgag    840

atgttttcag aaatactttg tgatgacctg gatttgaatc cactgacttt tgtgccagct    900

attgcctctg ccattcgaca gcagattgag tcctacccca cagacagcat cctagaggat    960

caatccgacc agcgtgtcat catcaagctg aacatccacg tggggaacat ctccctggtg   1020

gaccagtttg agtgggacat gtcagagaaa gagaactccc cagagaagtt tgccctgaag   1080

ctgtgctcag agctgggctt gggcggggag tttgtcacca ccattgcata cagcatccga   1140

ggacagctga gctggcacca gaagacctat gccttcagtg agaacccact tcccacagtg   1200

gagattgcca tccgaaatac cggagatgct gaccagtggt gccccctgct ggagacactg   1260

actgatgccg agatggagaa aaagatccgg gatcaagata ggaacacaag gcgaatgagg   1320

cgtcttgcca acactgcccc agcctggtga tgaagacatc catgctcgac ctctacggag   1380

catctcagac tgcctttcct tcctctgtgg aaagagaaag gcaaagggac agctggtgcc   1440

atcctgagga ctggggtagg agcctcctag gtgcctccct tcagcacaca ttccatttgc   1500

taaaccccaa cactgtcccc cagagtctag agtcggaagc agcctcattt tgggttgtgt   1560

tttgtttttg tataggagcc caggcagggc tggtaacact ttttaaataa aaagtaccat   1620

gttcaatttc aaaaaaaaaa aaaaaaa                                        1647
```

```
<210> SEQ ID NO 12
<211> LENGTH: 376
<212> TYPE: PRT
<213> ORGANISM: Mus musculus

<400> SEQUENCE: 12

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Asp His Gly Tyr Thr Thr Leu Ala Thr Ser Val Thr
65                  70                  75                  80

Leu Leu Lys Ala Ser Glu Val Glu Glu Ile Leu Asp Gly Asn Asp Glu
                85                  90                  95

Lys Tyr Lys Ala Val Ser Ile Ser Thr Glu Pro Pro Thr Tyr Leu Arg
            100                 105                 110

Glu Gln Lys Ala Lys Arg Asn Ser Gln Trp Val Pro Thr Leu Pro Asn
        115                 120                 125
```

Ser Ser His His Leu Asp Ala Val Pro Cys Ser Thr Thr Ile Asn Arg
130 135 140

Asn Arg Met Gly Arg Asp Lys Lys Arg Thr Phe Pro Leu Cys Phe Asp
145 150 155 160

Asp His Asp Pro Ala Val Ile His Glu Asn Ala Ser Gln Pro Glu Val
165 170 175

Leu Val Pro Ile Arg Leu Asp Met Glu Ile Asp Gly Gln Lys Leu Arg
180 185 190

Asp Ala Phe Thr Trp Asn Met Asn Glu Lys Leu Met Thr Pro Glu Met
195 200 205

Phe Ser Glu Ile Leu Cys Asp Asp Leu Asp Leu Asn Pro Leu Thr Phe
210 215 220

Val Pro Ala Ile Ala Ser Ala Ile Arg Gln Gln Ile Glu Ser Tyr Pro
225 230 235 240

Thr Asp Ser Ile Leu Glu Asp Gln Ser Asp Gln Arg Val Ile Ile Lys
245 250 255

Leu Asn Ile His Val Gly Asn Ile Ser Leu Val Asp Gln Phe Glu Trp
260 265 270

Asp Met Ser Glu Lys Glu Asn Ser Pro Glu Lys Phe Ala Leu Lys Leu
275 280 285

Cys Ser Glu Leu Gly Leu Gly Gly Glu Phe Val Thr Thr Ile Ala Tyr
290 295 300

Ser Ile Arg Gly Gln Leu Ser Trp His Gln Lys Thr Tyr Ala Phe Ser
305 310 315 320

Glu Asn Pro Leu Pro Thr Val Glu Ile Ala Ile Arg Asn Thr Gly Asp
325 330 335

Ala Asp Gln Trp Cys Pro Leu Leu Glu Thr Leu Thr Asp Ala Glu Met
340 345 350

Glu Lys Lys Ile Arg Asp Gln Asp Arg Asn Thr Arg Arg Met Arg Arg
355 360 365

Leu Ala Asn Thr Ala Pro Ala Trp
370 375

<210> SEQ ID NO 13
<211> LENGTH: 35
<212> TYPE: PRT
<213> ORGANISM: Homo sapiens

<400> SEQUENCE: 13

Pro Leu Leu Glu Thr Leu Thr Asp Ala Glu Met Glu Lys Lys Ile Arg
1 5 10 15

Asp Gln Asp Arg Asn Thr Arg Arg Met Arg Arg Leu Ala Asn Thr Ala
20 25 30

Pro Ala Trp
35

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

Pro Leu Leu Glu Thr Leu Thr Asp Ala Glu Met Glu Lys Ile Arg Asp
1 5 10 15

```
Gln Asp Arg Asn Thr Arg Arg Met Arg Arg Leu Ala Asn Thr Ala Pro
            20                  25                  30

Ala Trp


<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Leu Leu Glu Thr Leu Thr Asp Ala Glu Met Glu Lys Lys Ile Arg
1               5                   10                  15

Asp Gln Asp Arg Asn Thr Arg Arg Met Arg His Leu Ala Asn Thr Ala
            20                  25                  30

Pro Ala Trp
        35


<210> SEQ ID NO 16
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Leu Leu Glu Thr Leu Thr Asp Ala Glu Met Glu Lys Lys Ile Cys
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Pro Leu Leu Glu Thr Leu Thr Asp Ala Glu Met Glu Asn Lys Ile Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Pro Leu Leu Glu Thr Leu Thr Asp Ala Glu Met Glu Lys Lys Ile Arg
1               5                   10                  15
```

```
Asp Gln Asp Arg Asn Thr Arg Gln Met Arg Arg Leu Ala Asn Thr Ala
            20                  25                  30

Pro Ala Trp
        35


<210> SEQ ID NO 19
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Pro Leu Leu Glu Thr Leu Thr Asp Ala Glu Met Glu Lys Ala Ile Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Pro Leu Leu Glu Thr Leu Thr Asp Ala Glu Met Glu Lys Glu Ile Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Pro Leu Leu Glu Thr Leu Thr Asp Ala Glu Met Glu Lys Arg Ile Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Pro Leu Leu Glu Thr Leu Thr Asp Ala Glu Met Glu Lys Pro Ile Arg
```

```
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Pro Leu Leu Glu Thr Leu Thr Asp Ala Glu Met Glu Lys Lys Ala Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Pro Leu Leu Glu Thr Leu Thr Asp Ala Glu Met Glu Ala Ala Ile Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Leu Leu Glu Thr Leu Thr Asp Ala Glu Met Glu Glu Glu Ile Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 26
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26
```

```
Pro Leu Leu Glu Thr Leu Thr Asp Ala Glu Met Glu Ala Lys Ile Arg
1               5                   10                  15

Asp Gln Asp Arg Asn Thr Arg Arg Met Arg Arg Leu Ala Asn Thr Ala
            20                  25                  30

Pro Ala Trp
        35


<210> SEQ ID NO 27
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Pro Leu Leu Glu Thr Leu Thr Asp Ala Glu Met Glu Lys Lys Ile Arg
1               5                   10                  15

Asp Gln Asp Ala Asn Thr Arg Arg Met Arg Arg Leu Ala Asn Thr Ala
            20                  25                  30

Pro Ala Trp
        35


<210> SEQ ID NO 28
<211> LENGTH: 35
<212> TYPE: PRT
<213> ORGANISM: Saccharomyces cerevisiae

<400> SEQUENCE: 28

Pro Asn Leu Leu Gln Ile Ser Ala Ala Glu Leu Glu Arg Leu Asp Lys
1               5                   10                  15

Asp Lys Asp Arg Asp Thr Arg Arg Lys Arg Arg Gln Gly Arg Ser Asn
            20                  25                  30

Arg Arg Gly
        35


<210> SEQ ID NO 29
<211> LENGTH: 35
<212> TYPE: PRT
<213> ORGANISM: Saccharomyces cerevisiae

<400> SEQUENCE: 29

Pro Arg Val Glu Ile Leu Thr Lys Glu Glu Ile Gln Lys Arg Glu Ile
1               5                   10                  15

Glu Lys Glu Arg Asn Leu Arg Arg Leu Lys Arg Glu Thr Asp Arg Leu
            20                  25                  30

Ser Arg Arg
        35


<210> SEQ ID NO 30
<211> LENGTH: 35
<212> TYPE: PRT
<213> ORGANISM: Caenorhabditis elegans

<400> SEQUENCE: 30

Pro Phe Leu Glu Thr Leu Thr Asp Ala Glu Ile Glu Lys Lys Met Arg
1               5                   10                  15

Asp Gln Asp Arg Asn Thr Arg Arg Met Arg Arg Leu Val Gly Gly Gly
            20                  25                  30

Phe Asn Tyr
        35
```

<210> SEQ ID NO 31
<211> LENGTH: 35
<212> TYPE: PRT
<213> ORGANISM: Drosophila melanogaster

<400> SEQUENCE: 31

```
Pro Phe Leu Glu Thr Leu Thr Asp Ala Glu Met Glu Lys Lys Ile Arg
1               5                   10                  15

Asp Gln Asp Arg Asn Thr Arg Arg Met Arg Arg Leu Ala Asn Thr Thr
            20                  25                  30

Thr Gly Trp
        35
```

<210> SEQ ID NO 32
<211> LENGTH: 32
<212> TYPE: PRT
<213> ORGANISM: Homo sapiens

<400> SEQUENCE: 32

```
Pro Leu Leu Glu Thr Leu Thr Asp Ala Glu Met Glu Lys Lys Ile Arg
1               5                   10                  15

Asp Gln Asp Arg Asn Thr Arg Arg Met Arg Arg Leu Ala Asn Thr Ala
            20                  25                  30
```

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Pro Leu Leu Glu Thr Leu Thr Asp Ala Glu Met Glu Lys Ile Arg Asp
1               5                   10                  15

Gln Asp Arg Asn Thr Arg Arg Met Arg Arg Leu Ala Asn Thr Ala
            20                  25                  30
```

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Pro Leu Leu Glu Thr Leu Thr Asp Ala Glu Met Glu Lys Lys Ile Arg
1               5                   10                  15

Asp Gln Asp Arg Asn Thr Arg Arg Met Arg His Leu Ala Asn Thr Ala
            20                  25                  30
```

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Pro Leu Leu Glu Thr Leu Thr Asp Ala Glu Met Glu Lys Lys Ile Cys
1               5                   10                  15
```

```
Asp Gln Asp Arg Asn Thr Arg Arg Met Arg Arg Leu Ala Asn Thr Ala
            20                  25                  30


<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Pro Leu Leu Glu Thr Leu Thr Asp Ala Glu Met Glu Asn Lys Ile Arg
1               5                   10                  15

Asp Gln Asp Arg Asn Thr Arg Arg Met Arg Arg Leu Ala Asn Thr Ala
            20                  25                  30


<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Pro Leu Leu Glu Thr Leu Thr Asp Ala Glu Met Glu Lys Lys Ile Arg
1               5                   10                  15

Asp Gln Asp Arg Asn Thr Arg Gln Met Arg Arg Leu Ala Asn Thr Ala
            20                  25                  30


<210> SEQ ID NO 38
<211> LENGTH: 22
<212> TYPE: PRT
<213> ORGANISM: Homo sapiens

<400> SEQUENCE: 38

Thr Asp Ala Glu Met Glu Lys Lys Ile Arg Asp Gln Asp Arg Asn Thr
1               5                   10                  15

Arg Arg Met Arg Arg Leu
            20


<210> SEQ ID NO 39
<211> LENGTH: 21
<212> TYPE: PRT
<213> ORGANISM: Homo sapiens

<400> SEQUENCE: 39

Thr Asp Ala Glu Met Glu Lys Lys Ile Arg Asp Gln Asp Arg Asn Thr
1               5                   10                  15

Arg Arg Met Arg Arg
            20


<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

ggagaagaag atccgcgacc agg                                          23
```

<210> SEQ ID NO 41
<211> LENGTH: 147
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
ccggaacacg ggcgatgcgg accagtggtg cccactgctg gagactctga cagacgctga 60
gatggaaaaa atacgcgatc aagacaggaa cacgaggtac ccctggccct gtggtcctgg 120
gctctgccca caggcacctg gctttcc 147

<210> SEQ ID NO 42
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Thr Glu Asn Thr Lys Leu Asp Leu Met Arg Ile Pro Glu Asn Lys Leu
1 5 10 15

Ala Arg Ala Thr Arg Trp Arg Gln Thr Asp Leu Glu Ala Arg Pro Met
20 25 30

Asp Ala Arg
35

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Met Ala Pro Pro Gly Met Arg Leu Arg Ser Gly Arg Ser Thr Gly Ala
1 5 10 15

Pro Leu Thr Arg Gly Ser Cys
20

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 44
ggaattgtga gcgctcacaa ttcc 24

<210> SEQ ID NO 45
<211> LENGTH: 41
<212> TYPE: PRT
<213> ORGANISM: Homo sapiens

<400> SEQUENCE: 45

Gly Pro Leu Gly Ser Met Pro Leu Leu Glu Thr Leu Thr Asp Ala Glu
1 5 10 15

Met Glu Lys Lys Ile Arg Asp Gln Asp Arg Asn Thr Arg Arg Met Arg

```
            20                  25                  30

Arg Leu Ala Asn Thr Ala Pro Ala Trp
        35                  40


<210> SEQ ID NO 46
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (71)..(73)
<223> OTHER INFORMATION: "aag" or absent

<400> SEQUENCE: 46

ccggaacacg ggcgatgcgg accagtggtg cccactgctg gagactctga cagacgctga     60

gatggaraar nnnatmcgcg aycargacag gaacacgagg tacccctggc cctgtggtcc    120

tgggctctgc ccacaggcac ctggctttcc                                     150


<210> SEQ ID NO 47
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: K or absent

<400> SEQUENCE: 47

Arg Asn Thr Gly Asp Ala Asp Gln Trp Cys Pro Leu Leu Glu Thr Leu
1               5                   10                  15

Thr Asp Ala Glu Met Glu Lys Xaa Ile Arg Asp Gln Asp Arg Asn Thr
            20                  25                  30

Arg Tyr Pro Trp Pro Cys Gly Pro Gly Leu Cys Pro Gln Ala Pro Gly
        35                  40                  45

Phe


<210> SEQ ID NO 48
<211> LENGTH: 150
<212> TYPE: DNA
<213> ORGANISM: Homo sapiens

<400> SEQUENCE: 48

ccggaacacg ggcgatgcgg accagtggtg cccactgctg gagactctga cagacgctga     60

gatggagaag aagatccgcg accaggacag gaacacgagg tacccctggc cctgtggtcc    120

tgggctctgc ccacaggcac ctggctttcc                                     150


<210> SEQ ID NO 49
<211> LENGTH: 49
<212> TYPE: PRT
<213> ORGANISM: Homo sapiens

<400> SEQUENCE: 49

Arg Asn Thr Gly Asp Ala Asp Gln Trp Cys Pro Leu Leu Glu Thr Leu
1               5                   10                  15

Thr Asp Ala Glu Met Glu Lys Lys Ile Arg Asp Gln Asp Arg Asn Thr
            20                  25                  30
```

```
Arg Tyr Pro Trp Pro Cys Gly Pro Gly Leu Cys Pro Gln Ala Pro Gly
        35                  40                  45

Phe


<210> SEQ ID NO 50
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Arg Asn Thr Gly Asp Ala Asp Gln Trp Cys Pro Leu Leu Glu Thr Leu
1               5                   10                  15

Thr Asp Ala Glu Met Glu Lys Ile Arg Asp Gln Asp Arg Asn Thr Arg
            20                  25                  30

Tyr Pro Trp Pro Cys Gly Pro Gly Leu Cys Pro Gln Ala Pro Gly Phe
        35                  40                  45


<210> SEQ ID NO 51
<211> LENGTH: 174
<212> TYPE: DNA
<213> ORGANISM: Homo sapiens

<400> SEQUENCE: 51

tgcccacagt ggagattgcc atccggaaca cgggcgatgc ggaccagtgg tgcccactgc     60

tggagactct gacagacgct gagatggaga agaagatccg cgaccaggac aggaacacga    120

ggtacccctg gccctgtggt cctgggctct gcccacaggc acctggcttt ccag          174


<210> SEQ ID NO 52
<211> LENGTH: 58
<212> TYPE: PRT
<213> ORGANISM: Homo sapiens

<400> SEQUENCE: 52

Leu Pro Thr Val Glu Ile Ala Ile Arg Asn Thr Gly Asp Ala Asp Gln
1               5                   10                  15

Trp Cys Pro Leu Leu Glu Thr Leu Thr Asp Ala Glu Met Glu Lys Lys
            20                  25                  30

Ile Arg Asp Gln Asp Arg Asn Thr Arg Tyr Pro Trp Pro Cys Gly Pro
        35                  40                  45

Gly Leu Cys Pro Gln Ala Pro Gly Phe Pro
    50                  55


<210> SEQ ID NO 53
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

tgcccacagt ggagattgcc atccggaaca cgggcgatgc ggaccagtgg tgcccactgc     60

tggagactct gacagacgct gagatggaaa aaatacgcga tcaagacagg aacacgaggt    120

acccctggcc ctgtggtcct gggctctgcc cacaggcacc tggctttcca g             171


<210> SEQ ID NO 54
```

```
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

tgcccacagt ggagattgcc ctgtggtcct gggctctgcc cacaggcacc tggctttcca     60

g                                                                     61
```

COMPOSITIONS COMPRISING MODIFIED SMARCB1 AND USES THEREOF

STATEMENT OF RIGHTS

This application is the U.S. national phase of International Patent Application No. PCT/US2020/056574, filed on 21 Oct. 2020, which claims the benefit of priority to U.S. Provisional Application Ser. No. 62/926,139, filed on 25 Oct. 2019; the entire contents of each of said applications are incorporated herein in their entirety by this reference.

SEQUENCE LISTING

The present specification makes reference to a Sequence Listing (submitted electronically as a .txt file named "DFS-27801 Sequence Listing" on Apr. 20, 2022). The .txt file was generated on Dec. 9, 2020 and is 51,828 bytes in size. The entire contents of the Sequence Listing are herein incorporated by reference.

BACKGROUND OF THE INVENTION

Mammalian SWI/SNF (mSWI/SNF) ATP-dependent chromatin remodeling complexes are multi-subunit, combinatorially assembled molecular machines that modulate chromatin architecture to enable DNA accessibility and gene expression (Clapier and Cairns (2009) *Annu. Rev. Biochem.* 78:273-304). mSWI/SNF complexes serve critical roles in cell division, cell and tissue differentiation, and development, and their perturbation is a frequent event in human disease, particularly in over 20% of human cancers (Kadoch and Crabtree (2015) *Sci. Adv.* 1:e1500447-e1500447; Kadoch et al. (2013) *Nat. Genet.* 45:592-601) and in specific neurodevelopmental disorders.

Exome sequencing efforts have recently identified autosomal dominant heterozygous mutations in mSWI/SNF subunit genes in individuals with intellectual disability (ID) syndromes and related cognitive disabilities (Bögershausen and Wollnik (2018) *Front. Mol. Neurosci.* 11:252; Miyake et al. (2014) *Am. J. Med. Genet.* 166C:257-261; Ronan et al. (2013) *Nat. Rev. Genet.* 14:347-359; Santen et al. (2012) *Nat. Genet.* 44:379-380; Santen et al. (2013) *Human Mut.* 34:1519-1528; Santen et al. (2014) *Epigenetics* 7:1219-1224; Sokpor et al. (2017) *Front. Mol. Neurosci.* 10:243; Tsurusaki et al. (2013) *Clin. Genet.* 85:548-554; Tsurusaki et al. (2012) *Nat. Genet.* 44:376-378; Wieczorek et al. (2013) *Hum. Mol. Genet.* 22:5121-5135). However, the mechanisms by which these mutations alter mSWI/SNF complex structure and function on chromatin and subsequently lead to impaired cognitive and physical development remain unknown. Coffin-Siris Syndrome (CSS, OMIM #135900) is a rare intellectual disability disorder in which over 60% of individuals harbor mutations in genes encoding members of the mSWI/SNF chromatin remodeling complex (Kosho et al. (2014) *Am. J. Med. Genet.* 166C:262-275; Miyake et al. (2014) *Am. J. Med. Genet.* 166C:257-261; Tsurusaki et al. (2013) *Clin. Genet.* 85:548-554). Individuals with CSS characteristically exhibit intellectual disability, coupled with a broad range of abnormalities spanning several organ systems, such as hypoplastic fifth digit nails, coarse facial features, generalized muscle hypotonia, immune system deficits, generalized hypertrichosis, sparse scalp hair, genitourinary and gastrointestinal complications, and congenital hear defects in >30% of individuals, at times requiring corrective heart surgery (Kosho et al. (2014) *Am. J. Med. Genet.* 166C:262-275; Kosho et al. (2014) *Am. J. Med. Genet.* 166:241-251; Mannino et al. (2018) *Am. J. Med. Genet.* 176:2250-2258; Santen et al. (2013) *Human Mut.* 34:1519-1528; Nemani et al. (2014) *Ann. Pediatr. Cardiol.* 7:221-226; Dsouza et al. (2019) *CSH Mol. Case Stud.* 5: a003962; Bögershausen and Wollnik (2018) *Front. Mol. Neurosci.* 11:252; Schrier et al. Coffin-Siris Syndrome. 2013 Apr. 4 [Updated 2018 Feb. 8]. In: Adam M P, Ardinger H H, Pagon R A, et al., editors. GeneReviews® [Internet]. Seattle (Wash.): University of Washington, Seattle; 1993-2019). These diverse phenotypes highlight the many cell and tissue types that are affected via CSS-associated mSWI/SNF mutations and indicate that the timing of de novo mutations in these individuals is likely in early stages of development. While homozygous deletions of most mSWI/SNF genes are embryonic lethal in mice and hence would likely not result in live births, heterozygous mutations would be predicted to produce functional effects that are nuanced and/or partial, yet result in significant developmental consequences. Notably, de novo single amino acid residue mutations in the SMARCB1 gene (which encodes the BAF47 or hSNF5 subunit; originally called INI1 (Kalpana et al. (1994) *Science* 266:2002-2006) accumulate within the highly conserved C-terminal putative coiled-coil (CC) domain and are correlated with the most severe intellectual disability cases of CSS. Enrichment of point mutations in the C-terminal domain of SMARCB1 are also found in cancers such as meningioma, adenocarcinoma, schwannoma, among others (cancer.sanger.ac.uk; Tate et al. (2019) *Nucl. Acids Res.* 47:D941-D947; Forbes et al. (2011) *Nucl. Acids Res.* 39:D945-D950; Forbes et al. (2017) *Nucl. Acids Res.* 45:D777-D783; Schmitz et al. (2001) *Br. J. Cancer* 84:199-201). Biallelic inactivation of SMARCB1 is the hallmark feature of malignant rhabdoid tumor and atypical teratoid/rhabdoid tumor, rare and highly aggressive pediatric cancers (Versteege et al. (1998) *Nature* 394:203-206). While SMARCB1 is one of the most evolutionarily conserved SWI/SNF subunits and has been studied in yeast, fly, and mammalian contexts for decades (Cairns et al. (1994) *Proc. Natl. Acad. Sci. USA* 91:1950-1954; Dechassa et al. (2008) *Mol. Cell. Biol.* 28:6010-6021; Dutta et al. (2017) *Cell Reports* 18:2124-2134; Kwon and Wagner (2007) *Trends Genet.* 23:403-412; Peterson et al. (1998) *J. Biol. Chem.* 273:23641-23644; Phelan et al. (1999) *Mol. Cell* 3:247-253; Sen et al. (2017) *Cell Reports* 18:2135-2147; Versteege et al. (1998) *Nature* 394:203-206; Wang et al. (1996) *Genes Dev.* 10:2117-2130; Workman and Kingston (1998) *Annu. Rev. Biochem.* 67:545-579), the specific role for its putative coiled coil or C-terminal domain and hence the impact of such mutations on mSWI/SNF complex function is unknown.

While high-resolution 3D structures of mSWI/SNF complexes have not to date been achieved, owing in large part to heterogenous composition and challenges in recombinant complex or subcomplex reconstitution, several recent studies have provided new insights of relevance to structure-function linkage. One such study is a detailed characterization of the modular organization and order of assembly of mSWI/SNF family complexes (Mashtalir et al. (2018) *Cell* 175:1272-1288), which used physical cross-linking mass spectrometry coupled with genetic deletions to assign subunit-subunit interfaces, the impact of disease-associated mutations on subunit assembly and stability, and the modular architecture of complexes in solution. Further, cryo-EM-determined binding of the yeast SNF2 helicase subunit to the nucleosome (Liu et al. (2017) *Nature* 544:440-445), and characterization of related chromatin remodeler family ATPase subunit interactions with the nucleosome acidic patch (Dann et al. (2017) *Nature* 548:607-611) have begun to define the mechanisms and determinants of remodeling activity, respectively, at least for the ATPase (catalytic) subunits. However, it remains to be determined if and where other subunits of mSWI/SNF complexes interact directly with nucleosomes and how these interactions impact overall complex function.

Accordingly, there remains a great need in the art to elucidate the architecture mSWI/SNF-nucleosome complexes in order to better understand their structure, function and the consequences of disease-associated mutations.

SUMMARY OF THE INVENTION

The present invention is based, at least in part, on the elucidation of the architecture and function of the interaction between the mSWI/SNF complex SMARCB1 subunit c-terminal domain and the nucleosome acidic patch that enables mSWI/SNF complex-mediated nucleosome remodeling activity in vitro and genome-wide chromatin accessibility in cells. Extensive biochemical, structural, genomic, and cell differentiation approaches were used to demonstrate the SMARCB1 C-terminal domain, such as a CC domain that contains a dense region of basic, positively-charged amino acids in an alpha helix, which directly bind the acidic patch region of the nucleosome and that single amino acid mutations within this region, which cause the intellectual disability syndrome, CSS, or mutations in the nucleosome acidic patch, hinder SMARCB1:nucleosome binding and mSWI/SNF complex remodeling to modulate a variety of gene expression and phenotypic effects. These findings decouple the genome-wide binding (localization on chromatin) of mutant mSWI/SNF complexes from their nucleosome remodeling activity and reveal the underlying mechanism by which mutations in the SMARCB1 C-terminal domain exert a dominant negative effect on mSWI/SNF activities in both CSS and cancer.

In one aspect, an isolated modified protein complex selected from the group consisting of protein complexes listed in Table 3, wherein an isolated modified protein complex comprises a SMARCB1 subunit that is modified, is provided.

Numerous embodiments are further provided that can be applied to any aspect of the present invention and/or combined with any other embodiment described herein. For example, in one embodiment, a modified SMARCB1 subunit is a modification in a SMARCB1 SMARCB1 coiled coil (CC) C-terminal domain (e.g., amino acid residues 335-385 of human SMARCB1), optionally wherein the modification is in an alpha helix of the CC domain. In another embodiment, an isolated modified protein complex comprising the modified SMARCB1 subunit has at least one of the following as compared to a protein complex comprising the wild-type SMARCB1 subunit rather than a modified SMARCB1 subunit: a. reduced nucleosome binding activity; b. reduced nucleosome remodeling activity; c. reduced nucleosome ATPase activity; d. reduced chromatin accessibility activity; or e. reduced gene expression at mSWI/SNF target genes. In still another embodiment, a modified SMARCB1 subunit has one or more of the following modifications as compared to a wild-type SMARCB1 subunit: a. replacement of at least one basic amino acid for a neutral or an acidic amino acid, optionally wherein the basic amino acid is an outward-facing residue of the alpha helix; b. deletion of at least one basic amino acid, optionally wherein the basic amino acid is an outward-facing residue of the alpha helix; c. reduced isoelectric point, reduced charge potential, and/or reduced net positive charge; d. reduced or eliminated interaction with a canonical nucleosome acidic patch and/or related residues, optionally wherein an interaction is with histone residues H2AE56, H2AE61, H2AE64, H2AD90, H2AE91, H2AE92, H2BE105, H2BE113, and/or H4E52; e. partial competitive binding with LANA peptide; e. a deletion or missense mutation at residue K363, K364, R366, R370, R373, R374, R376, R377 and/or deletion of any residue within SMARCB1 residues 357-378 that disrupts the positive charge cluster face of human SMARCB1, or a corresponding residue in an ortholog thereof, and/or f. comprises a sequence selected from the group of sequences shown in Table 1 or Table 2, or a sequence that is at least 30% identical to the sequence and has a positively charged face capable of binding nucleosomes. In yet another embodiment, the at least one subunit comprises a heterologous amino acid sequence, optionally wherein at least one subunit is SMARCB1, such as an affinity tag or a label (e.g., Glutathione-S-Transferase (GST), calmodulin binding protein (CBP), protein C tag, Myc tag, HaloTag, HA tag, Flag tag, His tag, biotin tag, V5 tag, and/or a fluorescent protein).

In another aspect, a pharmaceutical composition comprising an isolated modified protein complex described herein and a carrier is provided.

In still another aspect, a process for preparing an isolated modified protein complex described herein comprising: a) expressing a modified SMARCB1 subunit of a modified protein complex, optionally further expressing a subunit comprising a heterologous amino acid sequence, in a host cell or organism; and b) isolating a modified protein complex comprising a modified subunit, is provided. In one embodiment, an isolating step comprises density sedimentation analysis.

In yet another aspect, a method for screening for an agent that modulates formation or stability of an interaction between a modified protein complex described herein and a nucleosome, comprising a) contacting a modified protein complex, or a host cell or organism expressing a modified protein complex, with a test agent, and b) determining an amount of the modified protein complex bound to a nucleosome in the presence of a test agent, wherein a difference in the amount of the modified protein complex bound to a nucleosome as determined in step (b) relative to the amount of the modified protein complex bound to a nucleosome determined in the absence of the test agent indicates that the test agent modulates the formation or stability of the interaction between the modified protein complex and the nucleosome. It is contemplated that the nucleosome may be present in any form, such as chromatin, isolated nucleosomes, modified nucleosomes, arrays of nucleosomes, tetramers of nucleosomes, and the like. Screening methods are useful for a variety purposes, such as finding agents like inhibitors that are specific for a complex family (mSWI/SNF) and, even more so, specific to cBAF or PBAF subcomplexes within this family. This provides an ability to allosterically inhibit activity of the complexes.

As described above, numerous embodiments are further provided that can be applied to any aspect of the present invention and/or combined with any other embodiment described herein. For example, in one embodiment, a method further comprises incubating subunits of an isolated modified protein complex under conditions conducive to form an interaction between an isolated modified protein complex and a nucleosome prior to step (a). In another embodiment, a method further comprises determining a presence and/or amount of one or more individual subunits in an isolated modified protein complex. In still another embodiment, a step of contacting occurs in vivo, ex vivo, or in vitro. In yet another embodiment, a SMARCB1 subunit of an isolated modified protein complex is a mutant form that is identified in a human disease. In another embodiment, an agent increases formation or stability of an interaction between an isolated modified protein complex and a nucleosome.

In another aspect, an isolated SMARCB1 fragment comprising the SMARCB1 CC domain is provided.

As described above, numerous embodiments are further provided that can be applied to any aspect of the present invention and/or combined with any other embodiment described herein. For example, in one embodiment, a SMARCB1 fragment comprises a modification in a SMARCB1 CC domain. In another embodiment, a SMARCB1 fragment has reduced nucleosome binding activity as compared to the wild-type SMARCB1 fragment. In still another embodiment, a SMARCB1 fragment has one or more of the following compared to the wild-type SMARCB1 fragment: a. replacement of at least one basic amino acid for a neutral or an acidic amino acid, optionally wherein the basic amino acid is an outward-facing residue of the alpha helix; b. deletion of at least one basic amino acid, optionally wherein the basic amino acid is an outward-facing residue of the alpha helix; c. reduced isoelectric point, reduced charge potential, and/or reduced net positive charge; d. reduced or eliminated interaction with a canonical nucleosome acidic patch and/or related residues, optionally wherein the interaction is with histone residues H2AE56, H2AE61, H2AE64, H2AD90, H2AE91, H2AE92, H2BE105, H2BE113, and/or H4E52; e. partial competitive binding with LANA peptide; and/or f. a deletion or missense mutation at residue K363, K364, R366, R370, R373, R374, R376, R377 and/or deletion of any residue within SMARCB1 residues 357-378 that disrupts the positive charge cluster face of human SMARCB1, or a corresponding residue in an ortholog thereof. In yet another embodiment, a SMARCB1 fragment further comprises a heterologous amino acid sequence, such as an affinity tag or a label (e.g., Glutathione-S-Transferase (GST), calmodulin binding protein (CBP), protein C tag, Myc tag, HaloTag, HA tag, Flag tag, His tag, biotin tag, V5 tag, and/or a fluorescent protein). In another embodiment, a SMARCB1 fragment comprises a SMARCB1 fragment listed in Table 2, or a sequence that is at least 30% identical to the sequence and has a positively charged face capable of binding nucleosomes.

In still another aspect, a pharmaceutical composition comprising an isolated SMARCB1 fragment described herein and a pharmaceutically acceptable carrier, is provided.

In yet another aspect, an isolated nucleic acid that encodes an isolated SMARCB1 fragment described herein, is provided.

In another aspect, a vector comprising an isolated nucleic acid described herein, optionally wherein the vector is an expression vector, is provided.

In still another aspect, a host cell which comprises an isolated nucleic acid described herein, that expresses an isolated SMARCB1 fragment described herein, and/or comprises a vector described herein, is provided.

In yet another aspect, a method of producing an isolated SMARCB1 fragment described herein, comprising the steps of (i) culturing a host cell described herein under conditions suitable to allow expression of an isolated SMARCB1 fragment, is provided.

In another aspect, a method for screening for an agent that modulates formation or stability of an interaction between a SMARCB1 fragment described herein and a nucleosome, comprising a) contacting a SMARCB1 fragment, or a host cell or organism expressing an SMARCB1 fragment, with a test agent, and b) determining an amount of the SMARCB1 fragment bound to a nucleosome in the presence of the test agent, wherein a difference in the amount of the SMARCB1 fragment bound to a nucleosome as determined in step (b) relative to the amount of the SMARCB1 fragment bound to a nucleosome determined in the absence of the test agent indicates that the test agent modulates formation or stability of the interaction between the SMARCB1 fragment and the nucleosome. It is contemplated that the nucleosome may be present in any form, such as chromatin, isolated nucleosomes, modified nucleosomes, arrays of nucleosomes, tetramers of nucleosomes, and the like. As described above, screening methods are useful for a variety purposes, such as finding agents like inhibitors that are specific for a complex family (mSWI/SNF) and, even more so, specific to cBAF or PBAF subcomplexes within this family. This provides an ability to allosterically inhibit activity of the complexes.

As described above, numerous embodiments are further provided that can be applied to any aspect of the present invention and/or combined with any other embodiment described herein. For example, in one embodiment, a method further comprises incubating a SMARCB1 fragment under conditions conducive to form an interaction between a SMARCB1 fragment and a nucleosome prior to step (a). In another embodiment, a method further comprises determining a presence and/or amount of contacts between residues of a SMARCB1 fragment and residues of a nucleosome. In still another embodiment, a step of contacting occurs in vivo, ex vivo, in vitro, or in silico. In yet another embodiment, an agent increases formation or stability of an interaction between a SMARCB1 fragment and a nucleosome.

In still another aspect, a method for screening for an agent that modulates formation or stability of an interaction between a modified SMARCB1 protein described herein and a nucleosome, comprising a) contacting a modified SMARCB1 protein, or a host cell or organism expressing a modified SMARCB1 protein, with a test agent, and b) determining an amount of the modified SMARCB1 protein bound to a nucleosome in the presence of the test agent, wherein a difference in the amount of the modified SMARCB1 protein bound to a nucleosome as determined in step (b) relative to the amount of the modified SMARCB1 protein bound to a nucleosome determined in the absence of the test agent indicates that the test agent modulates the formation or stability of the interaction between the modified SMARCB1 protein and the nucleosome.

As described above, numerous embodiments are further provided that can be applied to any aspect of the present invention and/or combined with any other embodiment described herein. For example, in one embodiment, a method further comprises incubating a modified SMARCB1 protein under conditions conducive to form an interaction between a modified SMARCB1 protein and a nucleosome prior to step (a). In another embodiment, a method further comprises determining a presence and/or amount of contacts between residues of a modified SMARCB1 protein and residues of a nucleosome. In still another embodiment, a step of contacting occurs in vivo, ex vivo, in vitro, or in silico. In yet another embodiment, an agent increases formation or stability of an interaction between a modified SMARCB1 protein and a nucleosome. In another embodiment, a modified SMARCB1 protein is a mutant form that is identified in a human disease.

BRIEF DESCRIPTION OF THE DRAWINGS

FIG. 1A shows a summary of SMARCB1-associated mutations in intellectual disability (ID) syndromes and cancer (COSMIC). Legends are indicated. FIG. 1B shows a summary of n=190 total reported mutations in individuals with CSS. The pie chart represents the breakdown between mSWI/SNF complex subunits, transcription factors, and unknown origins. "*" represents individuals with ARID2 mutations characterized as having overlapping features between CSS and Nicolaides-Baraitser Syndrome. FIG. 1C shows that mSWI/SNF complexes exist in three distinct, final-form subcomplexes: BAF, PBAF, and ncBAF. Complex-specific subunits are marked in color, SMARCB1, present only in canonical BAF and PBAF complexes, is emphasized in red. FIG. 1D shows a schematic for SMARCB1 reintroduction experiments in HEK-293T SMARCB1 knockout (KO) cell lines and malignant rhabdoid tumor (MRT; SMARCB1-deficient) cell lines. FIG. 1E shows the SMARCB1 WT and mutant variants used. FIG. 1F-FIG. 1G show immunoblots (FIG. 1F) and immunoprecipitations (FIG. 1G) resulting from experiments performed on nuclear extracts isolated from SMARCB1 KO HEK-293T cells containing SMARCB1 WT or mutant variant rescue. FIG. 1H shows that RPT1 and RPT2 domains of SMARCB1 are required for BAF complex binding. Western blot of input and BRG1-IP nuclear extract material from G401 malignant rhabdoid tumor cell line infected with SMARCB1 variants. FIG. 1I shows a time course for nucleosome remodeling of WT and mutant SMARCB1-containing complexes and the data correspond with those shown in FIG. 2G. DNA was visualized using an Agilent D1000 HS TapeStation. FIG. 1J shows the results of REAA nucleosome remodeling assays wherein DNA is visualized on a TBE gel and quantitated from Agilent TapeStation data (FIG. 1F) (30° C., 90 min) and this is the same DNA run on TapeStation, as well as quantification of data shown, in FIG. 2F. FIG. 1K and FIG. 1L show the results of ATPase assays performed on mSWI/SNF complexes purified via ARID1A IP (for canonical BAF complexes) (i.e., enriched via ARID1A-IP and washed to remove non-ARID1A0boudng protein material) in solution with NCP DNA Widom or on recombinant mononucleosomes (30° C., 90 min). The luminescence signal is plotted (mean±S.D., n=2; AdjP-values determined by Dunnett's multiple comparison test). Western blots confirm equal complex capture across conditions. The data presented in FIG. 1J and FIG. 2F (see below) correspond to one another and resulted from experiments using purified complexes shown in FIG. 2D. Data shown in FIG. 2G also resulted from experiments using purified complexes. The data in FIG. 1K, FIG. 2I, and FIG. 2J correspond to each other in that they were performed using the ARID1A-immunoprecipitation (IP) material shown in FIG. 1L and FIG. 2H.

FIG. 2A shows a summary of missense and indel mutations in SMARCB1-associated intellectual disability (ID) syndromes (Coffin-Siris syndrome, Nicolaides-Baraitser syndrome, Kleefstra syndrome, and non-syndromatic severe ID), and cancer (COSMIC). Legends are indicated. FIG. 2B shows an immunoblot performed on total nuclear protein and anti-HA immunoprecipitations in SMARCB1-deficient HEK-293T cells. FIG. 2C shows proteomic mass spectrometry results of HA-purified 293T-SMARCB1 knockout 293Ts expressing WT or mutant HA-tagged SMARCB1 constructs. FIG. 2D shows the results of HA-epitope purification of HA-tagged SMARCB1 WT- and mutant variant-bound complexes from SMARCB1-deficient HEK-293T cells. Silver staining confirmed capture of expected mSWI/SNF subunits and their stoichiometry. FIG. 2E shows a schematic for restriction enzyme accessibility assay (REAA) with ST601-GATC1 nucleosome core particle (NCP) harboring a DpnII restriction cut site used to assess nucleosome remodeling of purified mSWI/SNF complexes. FIG. 2F shows nucleosome remodeling (REAA) comparing SMARCB1 WT and mutant variant complexes (200 ng purified complexes, 30° C., 90 min) as visualized by TapeStation D1000 and which data is shown in a different way that in FIG. 1J above. FIG. 2G shows a summary of nucleosome remodeling assay data from REAA comparing all SMARCB1 WT and mutant variants over time course (200 ng purified complexes, 30° C., 0-60 minutes, mean±S.D., n=2; AdjP-values determined by Dunnett's multiple comparison test compared to WT at each time point) and represent quantification of TapeStation results shown above in FIG. 1I. FIG. 2H demonstrates endogenous ARID1A IP of SMARCB1 WT- and mutant variant-bound complexes. FIG. 2I shows the results of ATPase assays performed on mSWI/SNF complexes via ARID1A IP (for canonical BAF complexes from FIG. 2H) in solution with 601 widom DNA, on recombinant tetra polynucleosomes, or on HeLa polynucleosomes (30° C., 90 min). The luminescence signal is plotted (mean±S.D., n=2; AdjP-values determined by Dunnett's multiple comparison test to WT for each substrate). FIG. 2J shows the results of a REAA remodeling assay performed in parallel to FIG. 2I with recombinant mononucleosomes.

FIG. 3A (top panel) shows the conservation of SNF5 homology putative coiled-coil (homologoy region 3) domains across species showing ConSurf conservation score, mean pI, sequence logo, and similarity. CSS-associated mutated residues are highlighted in gray. FIG. 3A (bottom panel) shows N-terminally biotinylated SMARCB1-CC peptide (aa 351-385) variants generated. FIG. 3B shows *H. sapiens* SMARCB1 CC WT and mutant intellectual disability-associated biotin-tagged peptide pull downs of mammalian mononucleosomes. Immunoblots for histone H3 and histone H2B are shown. FIG. 3C shows an immunoblot of peptide pull-down of mammalian mononucleosomes across SMARCB1 C-terminal homologues (*H. sapiens* SMARCB1 scramble and wild-type, *D. melanogaster* SNR1, *C. elegans* CeSNF5, or *S. cerevisiae* SNF5 and SFH1). FIG. 3D shows a backbone assignment based on 2D 15N-HSQC spectrum of 0.5 mM 15N-BAF47-CC in PBS, pH 6.5 acquired at 15° C. The backbone NH peaks from SMARCB1-CC residues are assigned in red, and residues from N-terminal cloning tag are assigned in blue. FIG. 3E shows the superposition of backbone traces of the 10 lowest-energy structures of the SMARCB1 C-terminal domain (aa 351-385). FIG. 3F shows a barrel view diagram of a representative structure from the SMARCB1 C-terminal alpha helix highlighting CSS mutated residues in dark blue and additional positive (Arg/Lys) residues in light blue (aa 357-378). FIG. 3G shows an electrostatic surface potential of the SMARCB1-C terminus, calculated using ABPS (Dolinsky et al. (2004) *Nucl. Acids Res.* 32:W665-W667), from −5.0 kTEˆ−1 (red) to +5.0 kTEˆ−1 (blue). 180 degree rotations are shown.

FIG. 4A shows the sequences of SMARCB1 (human) CC domain peptides generated and SNF5-like CC domain homologues. Residue changes from wild-type SMARCB1 emphasized in red. FIG. 4N shows an electrostatic surface potential of the alpha helix within the SMARCB1-CC domain in WT and mutant variant forms calculated using ABPS (Dolinsky et al. (2004) *Nucl. Acids Res.* 32:W665-W667), from −5.0 kTEˆ−1 (red) to +5.0 kTEˆ−1 (blue). N- and C-termini are indicated on the WT structure.

FIG. 5A shows an assay schematic for photocrosslinking-based assessment of SMARCB1 C-terminal domain binding sites with photocrosslinkable histone residues. FIG. 5B-FIG. 5C show SDS-PAGE immunoblots for biotin resolving Histones H2A/B and H4, as well as non-crosslinked peptide, across acidic patch residues for WT and mutant SMARCB1 C-terminal peptides. FIG. 5D shows a summary of crosslinking results within the nucleosome acidic patch (PDB ID: 1ZLA). FIG. 5E shows the results of WT SMARCB1 C-terminal peptide pull-down of WT and acidic patch mutant recombinant mononucleosomes. FIG. 5F (left panel) shows the electrostatic potential of nucleosome (PDB ID: 1KX5) highlighting acidic patch, with 180 degree rotations. FIG. 5F (right panel) shows the ZDOCK predicted docking region of SMARCB1-CC (aa 357-377) on nucleosome overlayed in light blue (averaged across binding constraints) (Pierce et al. (2014) *Bioinform.* 30:1771-1773). LANA peptide binding region is highlighted in green overlayed with SMARCB1-C-terminal alpha helix docking. H2A is highlighted in green, H2B is highlighted in cyan, H3 is highlighted in maroon, and H4 is highlighted in yellow.

FIG. 6A shows the results of LANA peptide competition experiments indicating minimal changes in SMARCB1 C-terminal domain peptide-nucleosome binding across a 1-20 uM concentration gradient. Visualization of H3 is shown. FIG. 6B-FIG. 6C show the results of competitive crosslinking experiments with Biotin-SMARCB1 CC and either HA-LANA (aa 2-22) (FIG. 6B) or Biotin labeled minimal LANA (aa 2-15) (FIG. 6C) at a variety of Histone H2A, H2B, and H4 photocrosslinkable residues. FIG. 6D-FIG. 6G show visualization of ZDOCK-predicted SMARCB1-C-terminal alpha helix (aa 358-377): nucleosome acidic patch interactions. FIG. 6D shows the top 10 predictions for 0-3 histone face constraints shown (i.e., experimentally observed direct contacts by based on photo-crosslinking and mutant nucleosome pull-down studies). SMARCB1-C-terminal alpha helix (aa 358-377) depicted in a variety of colors. FIG. 6E shows the top 10 predictions for 0 or 1 histone face constraints overlayed on nucleosome. Histones are indicated by color. FIG. 6F shows a side view of the top 10 ZDOCK predictions with H2AE91 binding constraint. FIG. 6G shows representative examples of predicted binding of SMARCB1-CC (358-377) to the nucleosome acidic patch near the H2A-H2B interface (nucleosome PDB ID: 1kx5). Positively charged residues are colored blue. FIG. 6H shows the overlay of LANA peptide: nucleosome binding and ZDOCK predicted docking of the SMARCB1-C terminal alpha helix on the nucleosome.

FIG. 7A shows the results of introduction of C-terminal V5-tagged SMARCB1 WT and mutant variants in TTC1240 SMARCB1-deficient MRT cells. An immunoblot for BRG1, SMARCB1, and TBP is shown. FIG. 7B shows a heatmap showing chromatin occupancy of mSWI/SNF complexes (marked by SMARCB1, SMARCC1, and SMARCA4) and H3K27Ac occupancy mapped over overlapped merged SMARCB1/SMARCC1 peaks. FIG. 7C shows a heatmap of ATAC-seq genomic accessibility reads over residual and SMARCB1-driven gained sites. FIG. 7D shows summary plots reflecting accessibility at residual (top panel) and gained sites (bottom panel) for empty vector, SMARCB1 WT, and SMARCB1 C-terminal mutant conditions. FIG. 7E shows a metaplot of MNase-seq over all SMARCA4 WT summits (top panel) and SMARCB1-driven gained sites. FIG. 7F shows representative exemplary ChIP-seq and ATAC-seq tracks over the RIFN1 (top panel) and CAPZB (bottom panel) loci. FIG. 7G shows the results of PCA analyses performed on ATAC-seq peaks overlapping SMARCB1 ChIP-seq sites and experimental replicates for empty vector, SMARCB1 WT, and SMARCB1 C-terminal mutant conditions. FIG. 7H shows the results of PCA performed on RNA-seq experimental replicates for empty vector, SMARCB1 WT, and SMARCB1 C-terminal mutant conditions (top 10% most variable genes).

FIG. 8A shows a schematic for SMARCB1 reintroduction experiments in to the SMARCB1-deficient MRT cell lines, TTC1240 and G401. FIG. 8P shows a schematic for WT, delN-term, and delC-term variants used, the heatmap of ATAC-seq peaks at residual and de novo sites for comparing empty vector control and WT SMARCB1 to delNterm and delCterm variants of SMARCB1.

FIG. 9A shows that CRISPR-Cas9 mediated genome editing was used to obtain heterozygous SMARCB1 K364del and indel mutant iPSCs which underwent NGN2-mediated neuronal differentiation with RNA-seq collected along an 8 day timecourse for WT and K364del mutant cells. ChIP-seq and ATAC-seq were collected at Day 0 and Day 0, 4, respectively. FIG. 9B shows a heatmap of ChIP-seq for mSWI/SNF subunits (SMARCB1, SMARCC1, SMARCA4) and H3K27ac, as well as ATAC-seq of SMARCB1+/+ and K364del/+ iPSCs. FIG. 9C shows a box plot of normalized difference between WT and K364del/+ mutant SMARCB1, SMARCC1, SMARCA4, H3K27ac ChIP-seq and ATAC-seq results. FIG. 9D shows results of HOMER motif analysis of sites with reduced ATAC-seq accessibility in the K364del mutant versus WT iPSCs. FIG. 9E shows a heatmap of a gene cluster downregulated in K364del versus WT cells at Day 8 of NGN2-induced differentiation (Cluster 6). Select differentially regulated genes are highlighted. FIG. 9F show a Venn diagram depicting overlap of Cluster 6 genes with intellectual disability- and NGN2-induced differentiation-associated genes. FIG. 9G shows bar graphs of intellectual-disability associated genes downregulated in the mutant versus wild-type cells along the differentiation time course.

FIG. 10A shows an overlay of SMARCB1 exon 8 target site and single stranded oligodeoxynucleotide (ssODN) donor strand used for homology directed repair with CRISPR-Cas9 gene editing. K364del residue is highlighted. The asterisk (*) denotes a silent ssODN mutation.

FIG. 10O shows imaging of DAPI (DNA), TUJ1, and NGN2 in SAH iPSCs at Day 6 and Day 8 of differentiation.

FIG. 11A shows a model of SMARCB1 C-terminal alpha helix bound to nucleosomes in complex with SNF2h bound (left) at the SHL2 position (PDB ID: 5X0Y) and (right) at the SHL6 nucleosomal position (PDB ID: 5X0X) generated using ZDOCK with H2AE91 binding restraint. FIG. 11B shows a model of mammalian SWI/SNF complex based on mSW/SNF crosslinking (Mashtalir et al. (2018) *Cell* 175:1272-1288) with WT or C-terminal mutant SMARCB1 subunit as part of core module. FIG. 11C shows a model of genome-wide BAF complex occupancy (ChIP-seq), chromatin accessibility (ATAC-seq), nucleosome occupancy (MNase-seq) and gene expression between SMARCB1-null, WT, and C-terminal mutant conditions at SMARCB1-driven BAF complex sites.

Figure 1:
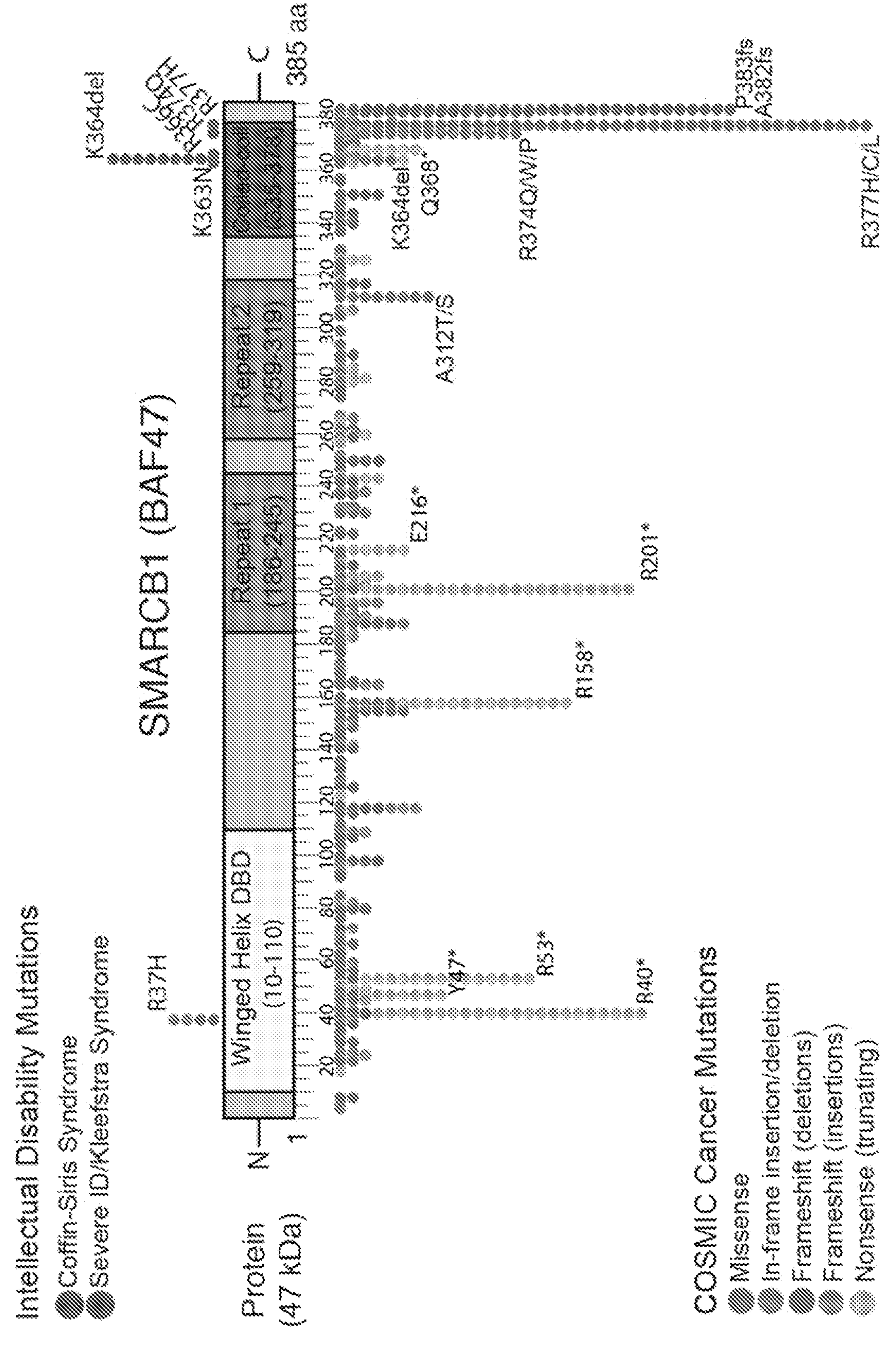
FIG. 1A-FIG. 1L further characterize CSS-associated mutations in the mSWI/SNF core functional module subunit, SMARCB1.
Figure 1:
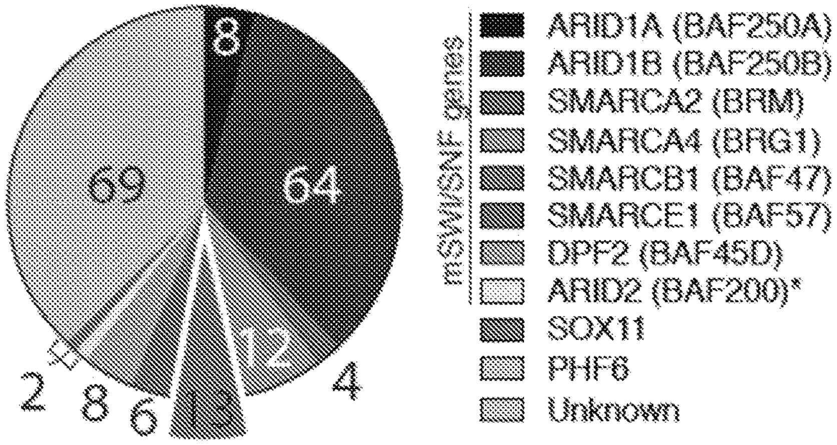
Figure 1:
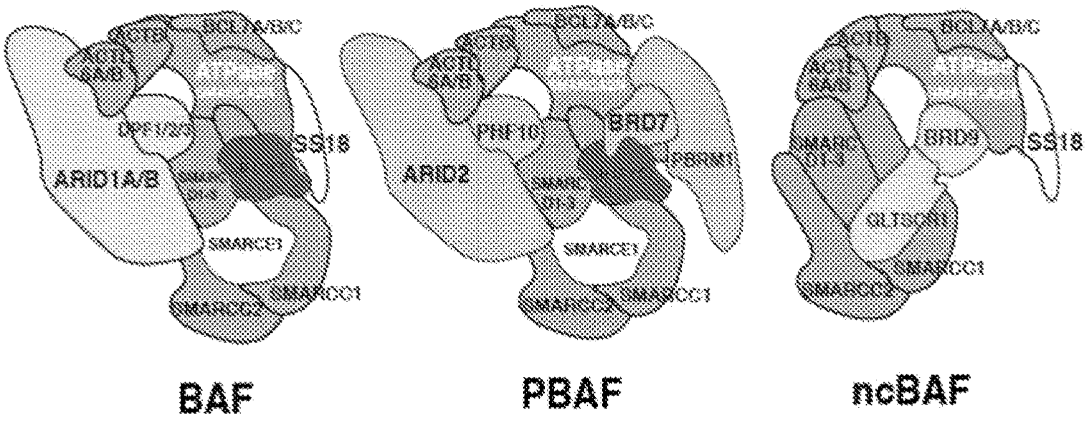
Figure 1:
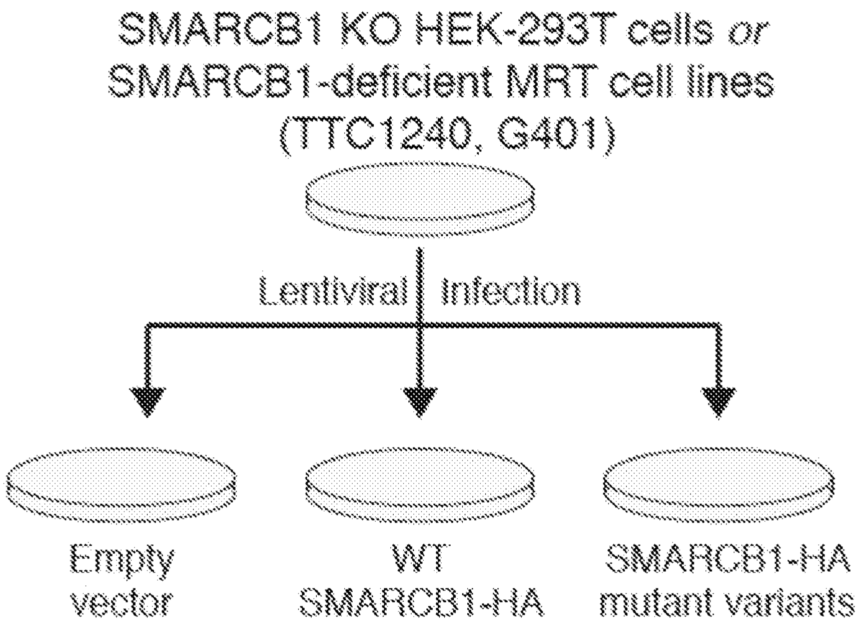
Figure 1:
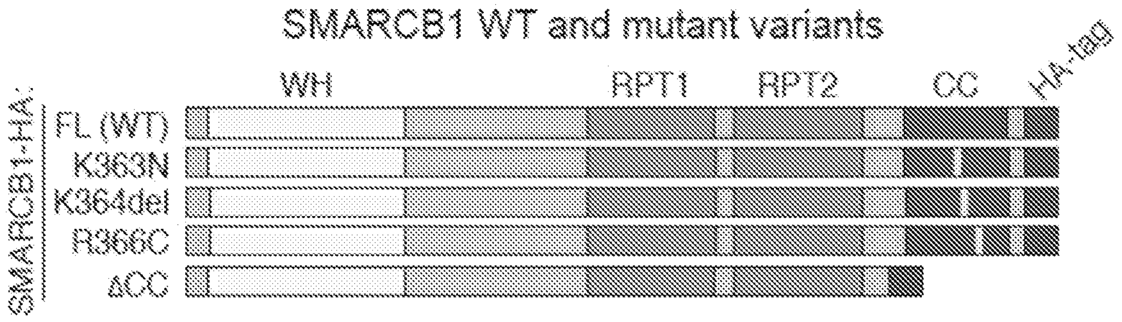
Figure 1:
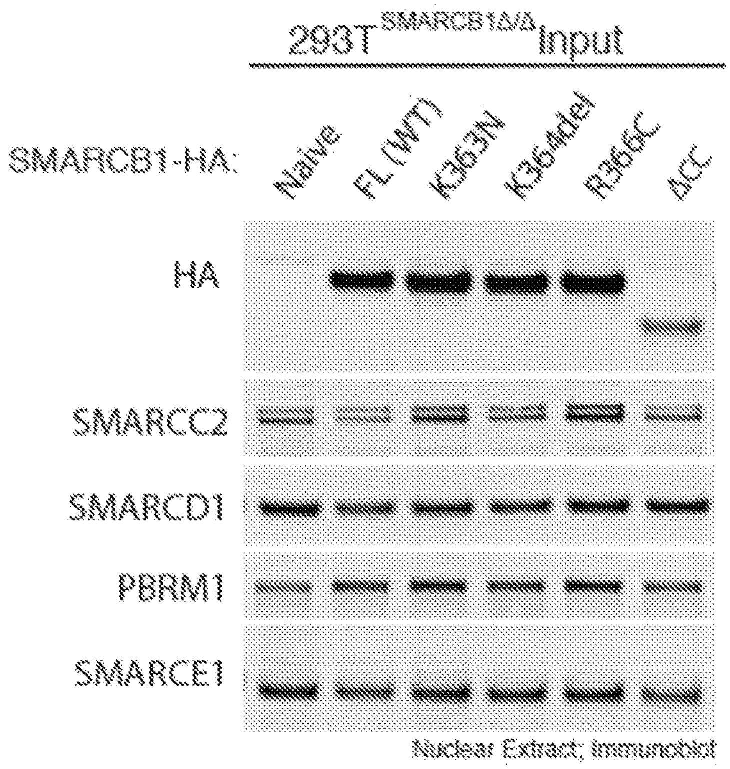
Figure 1:
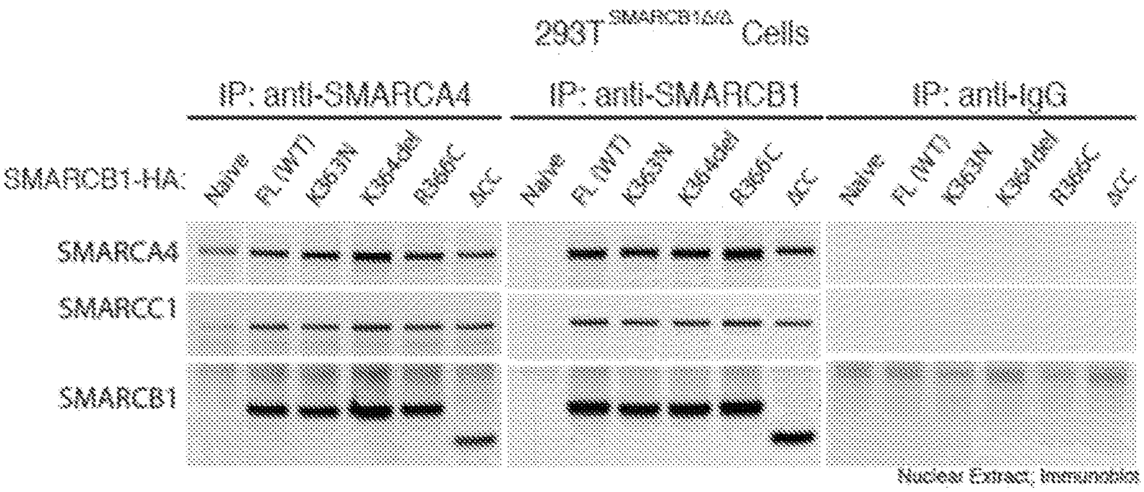
Figure 1:
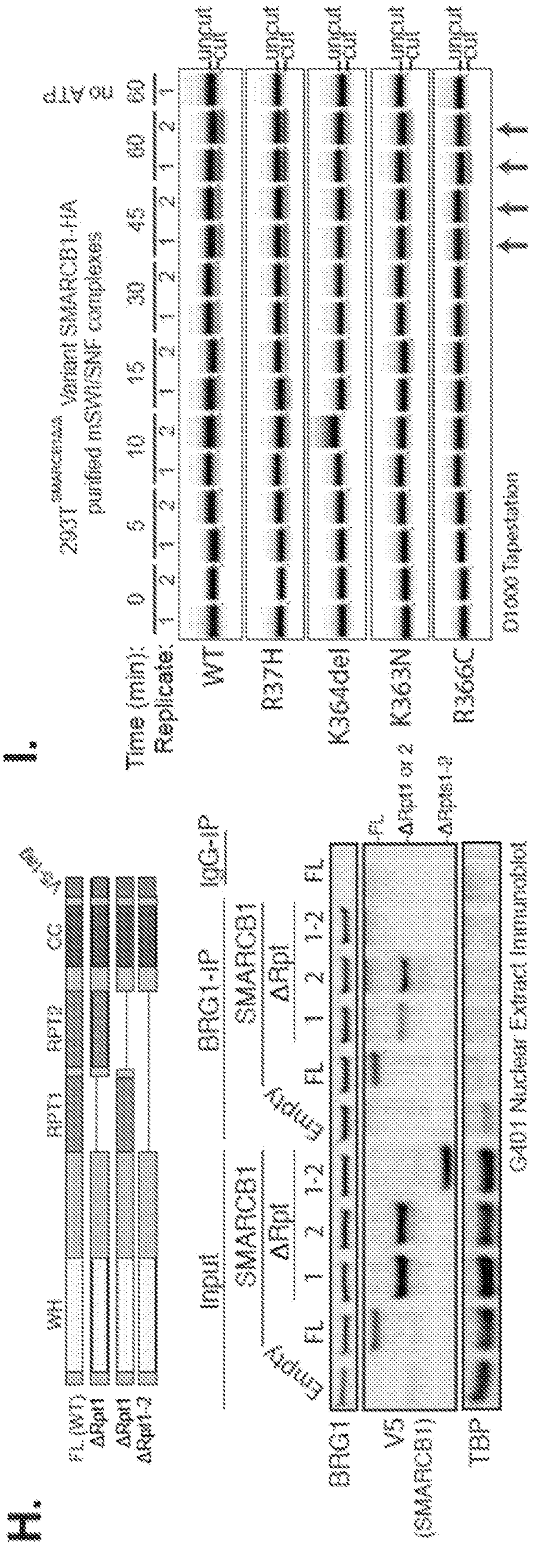
Figure 1:
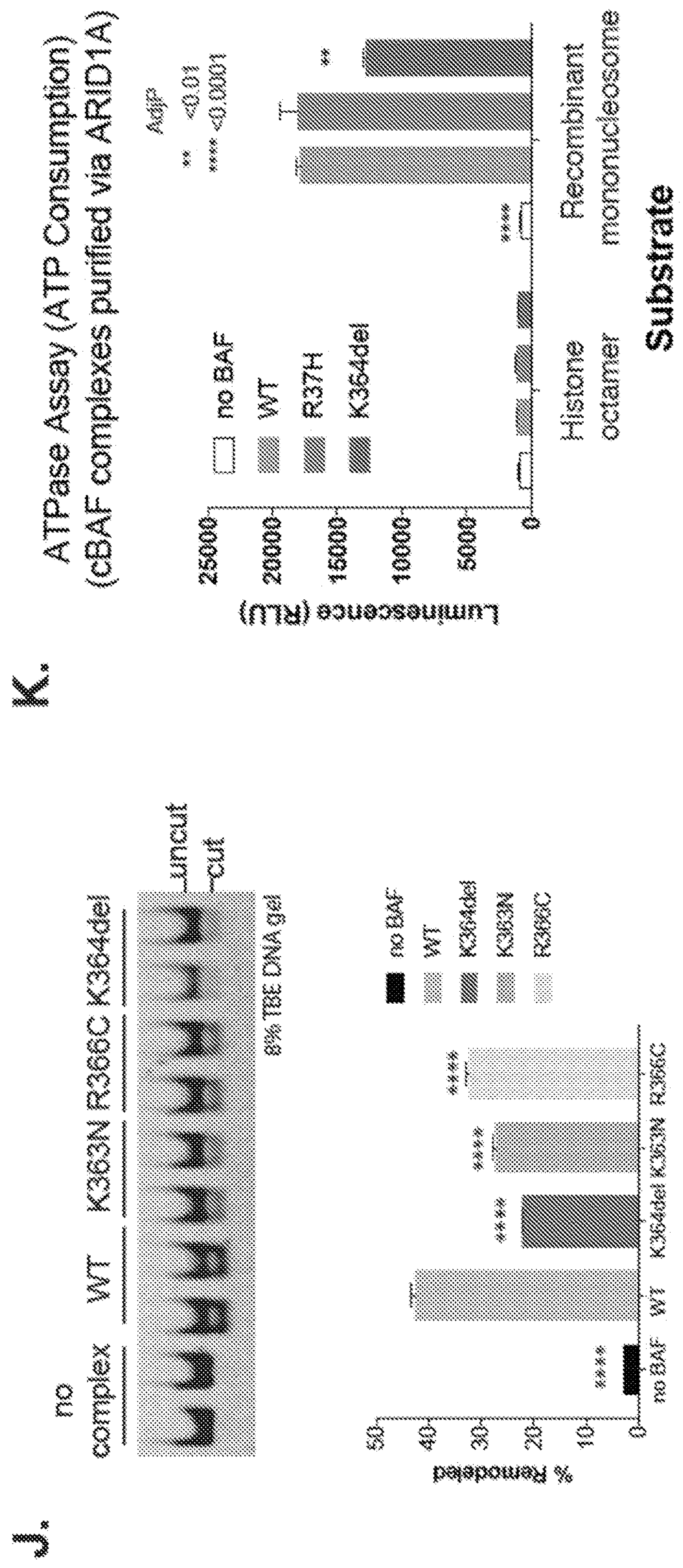
Figure 1:
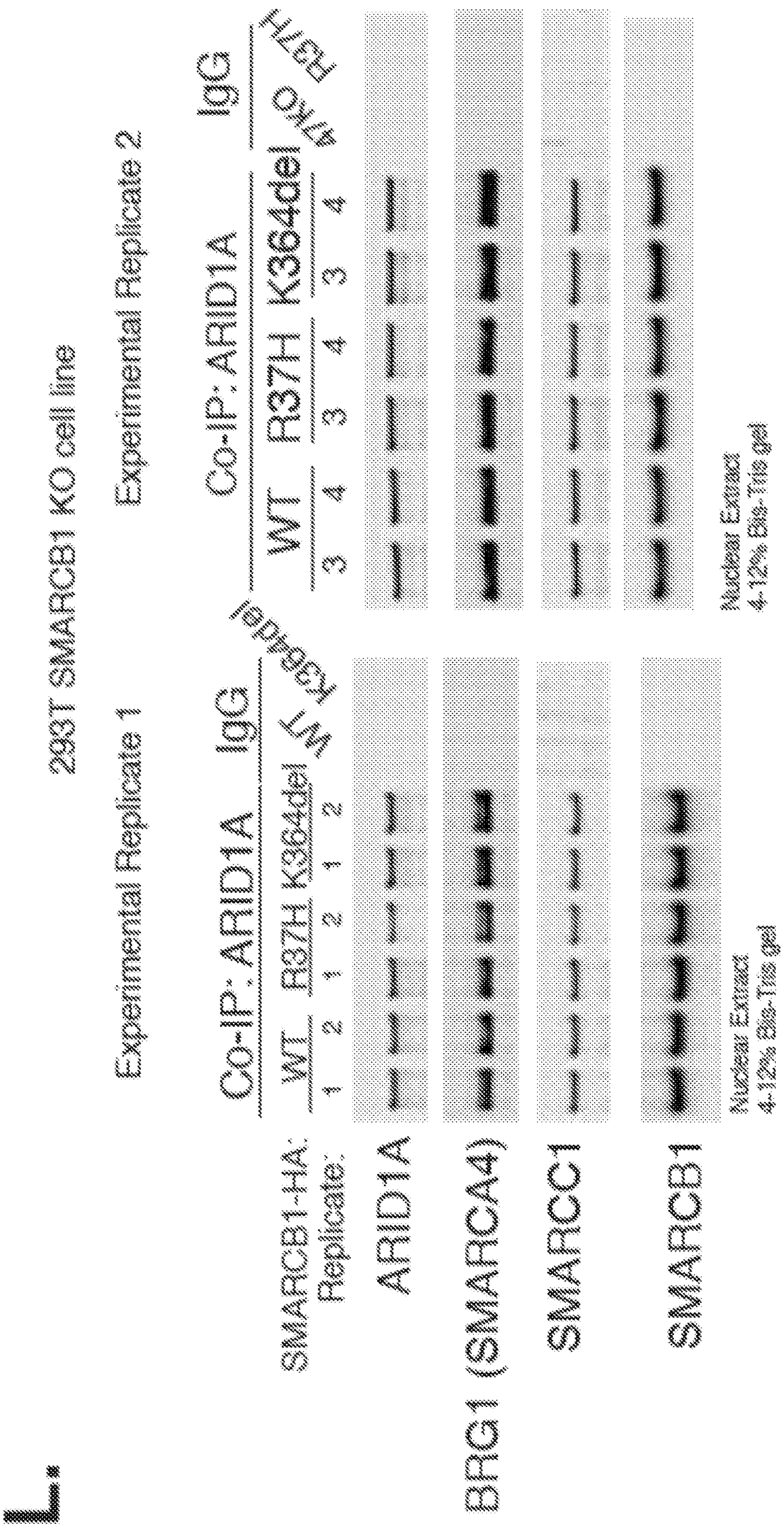

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

The present invention is based, at least in part, on the elucidation of the architecture and mechanism underlying particular subunit- and domain-specific interactions between the SMARCB1 component of mammalian SWI/SNF (BAF) complexes and nucleosomes. The molecular, structural, and genome-wide regulatory consequences of recurrent, single-residue mutations in the putative coiled-coil (CC) C-terminal domain (CTD) of the SMARCB1 (BAF47) subunit, which cause the intellectual disability disorder, Coffin-Siris syndrome (CSS) and are found in cancer, were analyzed. It was found that the SMARCB1 CTD contains a basic alpha-helix that binds directly to the nucleosome acidic patch. All CSS-associated mutations were determined to disrupt this binding. In addition, it is was determined that these mutations significantly abrogate mSWI/SNF nucleosome remodeling activity in vitro and enhancer DNA accessibility in cells, without changes in genome-wide complex localization. It was also determined that heterozygous CSS-associated SMARCB1 mutations result in dominant gene regulatory and morphologic changes during iPSC-neuronal differentiation and impede proper Ngn2-mediated neuronal differentiation. These results unmask an evolutionarily conserved structural role of the SMARCB1 CTD that is perturbed in human disease (e.g., intellectual disability and cancer). Accordingly, compositions based on the identified modified SMARCB1 polypeptides and SWI/SNF complexes comprising same are provided, as well as methods of screening for modulators of formation and/or stability of such polypeptides and complexes with each other and with substrates, such as nucleosomes, are also provided.

I. Definitions

The articles "a" and "an" are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

Unless otherwise specified here within, the terms "antibody" and "antibodies" broadly encompass naturally-occurring forms of antibodies (e.g. IgG, IgA, IgM, IgE) and recombinant antibodies, such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a protein complex encompassed by the present invention, or a subunit thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, protein subunit peptide and a C-terminal polyhistidine tag to make bivalent and biotinylated scFv polypeptides (Kipriyanov et al. (19b94) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies encompassed by the present invention bind specifically or substantially specifically to a protein complex. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies encompassed by the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, have been grafted onto human framework sequences.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

As used herein, the term "isotype" refers to the antibody class (e.g., IgM, IgG1, IgG2C, and the like) that is encoded by heavy chain constant region genes.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "inhibiting" and grammatical equivalents thereof refer decrease, limiting, and/or blocking a particular action, function, or interaction. A reduced level of a given output or parameter need not, although it may, mean an absolute absence of the output or parameter. The invention does not require, and is not limited to, methods that wholly eliminate the output or parameter. The given output or parameter can be determined using methods well-known in the art, including, without limitation, immunohistochemical, molecular biological, cell biological, clinical, and biochemical assays, as discussed herein and in the examples. The opposite terms "promoting," "increasing," and grammatical equivalents thereof refer to the increase in the level of a given output or parameter that is the reverse of that described for inhibition or decrease.

As used herein, the term "interacting" or "interaction" means that two protein domains, fragments or complete proteins exhibit sufficient physical affinity to each other so as to bring the two "interacting protein domains, fragments or proteins physically close to each other. An extreme case of interaction is the formation of a chemical bond that results in continual and stable proximity of the two entities. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, Van der Waals force, ionic force, covalent linkages, and combinations thereof. The state of proximity between the interaction domains, fragments, proteins or entities may be transient or permanent, reversible or irreversible. In any event, it is in contrast to and distinguishable from contact caused by natural random movement of two entities. Typically, although not necessarily, an "interaction" is exhibited by the binding between the interaction domains, fragments, proteins, or entities. Examples of interactions include specific interactions between antigen and antibody, ligand and receptor, enzyme and substrate, and the like.

Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

An "interaction" between two protein domains, fragments or complete proteins can be determined by a number of methods. For example, an interaction can be determined by functional assays. Such as the two-hybrid Systems. Protein-protein interactions can also be determined by various biophysical and biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, (1995) *Microbiol. Rev.,* 59:94-123.

As used herein, a "kit" is any manufacture (e.g. a package or container) comprising at least one reagent, e.g. a probe, for specifically detecting or modulating the expression of a marker encompassed by the present invention. The kit may be promoted, distributed, or sold as a unit for performing the methods encompassed by the present invention.

As used herein, the term "modulate" includes up-regulation and down-regulation, e.g., enhancing or inhibiting the formation and/or stability of an protein complex encompassed by the present invention.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the protein subunit of a protein complex encompassed by the present invention, or fusion protein or fragment thereof, is derived, or substantially free from chemical precursors or other chemicals when chemically synthesized. The language "substantially free of cellular material" includes preparations of a protein subunit of a protein complex encompassed by the present invention, in which the protein is separated from cellular components of the cells from which it is isolated or recombinantly produced. In one embodiment, the language "substantially free of cellular material" includes preparations of a protein subunit, having less than about 30% (by dry weight) of non-subunit protein (also referred to herein as a "contaminating protein"), more preferably less than about 20% of non-subunit protein, still more preferably less than about 10% of non-subunit protein, and most preferably less than about 5% non-subunit protein. When protein subunit of a protein complex encompassed by the present invention, or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" is intended to refer to a nucleic acid molecule in which the nucleotide sequences are free of other nucleotide sequences, which other sequences may naturally flank the nucleic acid in human genomic DNA.

The term "nucleosome" refers to the fundamental unit of chromatin. The term "chromatin" refer to the larger-scale nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a "nucleosome" core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

The term "histone" refers to highly alkaline proteins found in eukaryotic cell nuclei that package and order DNA into structural units called nucleosomes. They are the chief protein components of chromatin, acting as spools around which DNA winds, and play a role in gene regulation. In certain embodiments, the histone is histone H1 (e.g., histone H1F, histone H1H1). In certain embodiments, the histone is histone H2A (e.g., histone H2AF, histone H2A1, or histone H2A2). In certain embodiments, the histone is histone H2B (e.g., histone H2BF, histone H2B1, or histone H2B2). In certain embodiments, the histone is histone H3 (e.g., histone H3A1, histone H3A2, or histone H3A3). In certain embodiments, the histone is histone H4 (e.g., histone H41, or histone H44).

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases The accessibility of chromatin is mediated in part by interactions with SWI/SNF (BAF) complexes via interactions with the nucleosome "acidic patch." This canonical structural region of nucleosomes is well-known in the art (see, for example, Dann et al. (2017) *Nature* 548:607-611 and Luger et al. (1997) *J. Mol. Biol.* 272:301-311) and is described further herein. In certain assays useful according to the present invention, nucleosomal interactions with DNA and/or proteins (e.g., SMARCB1 and/or SMARCB1-containing protein complexes), can be analyzed. Certain such assays measure changes to DNA lengths. The preferential protection against degradation may be due to the DNA being wrapped around one or more histone proteins, preferably an octomer of histone proteins. The threshold size may be the size of a complete turn of the DNA about a histone core+/−22 bases. The threshold size may be between 100 and 160 bases, preferably between 110 and 140 bases, more preferably between 120 and 130 bases and ideally 125 bases+/−1 base. The threshold size may be a size equal to or greater than 100 bases, more preferably equal to or greater than 110 bases still more preferably equal to or greater than 120 bases and ideally 125 bases or more.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences encompassed by the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules encompassed by the present invention. BLAST protein searches can be performed with the XBLAST program, score=50, wordlength=3 to obtain amino acid sequences homologous to the protein molecules encompassed by the present invention. To obtain gapped alignments for comparison purposes, Gapped BLAST can be utilized as described in Altschul et al., (1997) *Nucleic Acids Res.* 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well-known in the art (see, F. Ausubel, et al., ed. Current Protocols in Molecular Biology, Greene Publishing and Wiley Interscience, New York (1987)).

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a subunit nucleic acid and normal post-transcriptional processing (e.g. splicing), if any, of the RNA transcript, and reverse transcription of the RNA transcript.

An "RNA interfering agent" as used herein, is defined as any agent which interferes with or inhibits expression of a target protein subunit gene by RNA interference (RNAi). Such RNA interfering agents include, but are not limited to, nucleic acid molecules including RNA molecules which are homologous to a protein subunit gene encompassed by the present invention, or a fragment thereof, short interfering RNA (siRNA), and small molecules which interfere with or inhibit expression of a target protein subunit nucleic acid by RNA interference (RNAi).

"RNA interference (RNAi)" is an evolutionally conserved process whereby the expression or introduction of RNA of a sequence that is identical or highly similar to a target protein subunit nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target protein subunit nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target protein subunit nucleic acids. As used herein, "inhibition of a protein subunit nucleic acid expression" or "inhibition of protein subunit gene expression" includes any decrease in expression or protein activity or level of the protein subunit nucleic acid or protein encoded by the protein subunit nucleic acid. The decrease may be of at least 30%, 40%, 50%, 60%, 70%, 80%, 90%, 95% or 99% or more as compared to the expression of a protein subunit nucleic acid or the activity or level of the protein encoded by a protein subunit nucleic acid which has not been targeted by an RNA interfering agent.

In addition to RNAi, genome editing can be used to modulate the copy number or genetic sequence of a protein subunit of interest, such as constitutive or induced knockout or mutation of a protein subunit of interest, such as a protein subunit of an isolated modified protein complexes encompassed by the present invention. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326: 1509-1512; Moscou and Bogdanove (2009) *Science* 326: 1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

"Piwi-interacting RNA (piRNA)" is the largest class of small non-coding RNA molecules. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity. However, like other small RNAs, piRNAs are thought to be involved in gene silencing, specifically the silencing of transposons. The majority of piRNAs are antisense to transposon sequences, suggesting that transposons are the piRNA target. In mammals it appears that the activity of piRNAs in transposon silencing is most important during the development of the embryo, and in both *C. elegans* and humans, piRNAs are necessary for spermatogenesis. piRNA has a role in RNA silencing via the formation of an RNA-induced silencing complex (RISC).

"Aptamers" are oligonucleotide or peptide molecules that bind to a specific target molecule. "Nucleic acid aptamers" are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. "Peptide aptamers" are artificial proteins selected or engineered to bind specific target molecules. These proteins consist of one or more peptide loops of variable sequence displayed by a protein scaffold. They are typically isolated from combinatorial libraries and often subsequently improved by directed mutation or rounds of variable region mutagenesis and selection. The "Affimer protein", an evolution of peptide aptamers, is a small, highly stable protein engineered to display peptide loops which provides a high affinity binding surface for a specific target protein. It is a protein of low molecular weight, 12-14 kDa, derived from the cysteine protease inhibitor family of cystatins. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

"Short interfering RNA" (siRNA), also referred to herein as "small interfering RNA" is defined as an agent which functions to inhibit expression of a protein subunit nucleic acid, e.g., by RNAi. A siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, a siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a host cell or organism, to inhibit expression of a protein subunit gene of a protein complex encompassed by the present invention and thereby inhibit the formation of the protein complex.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

As used herein, the term "protein complex" means a composite unit that is a combination of two or more proteins formed by interaction between the proteins. Typically, but not necessarily, a "protein complex" is formed by the binding of two or more proteins together through specific non-covalent binding interactions. However, covalent bonds may also be present between the interacting partners. For instance, the two interacting partners can be covalently crosslinked so that the protein complex becomes more stable. The protein complex may or may not include and/or be associated with other molecules such as nucleic acid, such as RNA or DNA, or lipids or further cofactors or moieties selected from a metal ions, hormones, second messengers, phosphate, sugars. A "protein complex" encompassed by the present invention may also be part of or a unit of a larger physiological protein assembly.

The term "isolated protein complex" means a protein complex present in a composition or environment that is different from that found in nature, in its native or original cellular or body environment. Preferably, an "isolated protein complex" is separated from at least 50%, more preferably at least 75%, most preferably at least 90% of other naturally co-existing cellular or tissue components. Thus, an "isolated protein complex" may also be a naturally existing protein complex in an artificial preparation or a non-native host cell. An "isolated protein complex" may also be a "purified protein complex", that is, a substantially purified form in a substantially homogenous preparation substantially free of other cellular components, other polypeptides, viral materials, or culture medium, or, when the protein components in the protein complex are chemically synthesized, free of chemical precursors or by-products associated with the chemical synthesis. A "purified protein complex" typically means a preparation containing preferably at least 75%, more preferably at least 85%, and most preferably at least 95% of a particular protein complex. A "purified protein complex" may be obtained from natural or recombinant host cells or other body samples by standard purification techniques, or by chemical synthesis.

The term "modified polypeptide" or "modified protein complex" refers to a polypeptide or a protein complex present in a composition that is different from that found in nature in its native or original cellular or body environment. The term "modification" as used herein refers to all modifications of a protein or protein complex encompassed by the present invention including cleavage and addition or removal of a group. In some embodiments, the "modified polypeptide" or "modified protein complex" comprises at least one modification (e.g., fragment, mutation, and the like) or subunit that is modified, i.e., different from that found in nature, in its native or original cellular or body environment. The "modified subunit" may be, e.g., a derivative or fragment of the native subunit from which it derives.

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

If not stated otherwise, the term "compound" as used herein are include but are not limited to peptides, nucleic acids, carbohydrates, natural product extract libraries, organic molecules, preferentially small organic molecules, inorganic molecules, including but not limited to chemicals, metals and organometallic molecules.

The terms "derivatives" or "analogs of subunit proteins" or "variants" as used herein include, but are not limited, to molecules comprising regions that are substantially homologous to the subunit proteins, in various embodiments, by at least 30%, 40%, 50%, 60%, 70%, 80%, 90%, 95% or 99% identity over an amino acid sequence of identical size or when compared to an aligned sequence in which the alignment is done by a computer homology program known in the art, or whose encoding nucleic acid is capable of hybridizing to a sequence encoding the component protein under stringent, moderately stringent, or nonstringent conditions. It means a protein which is the outcome of a modification of the naturally occurring protein, by amino acid substitutions, deletions and additions, respectively, which derivatives still exhibit the biological function of the naturally occurring protein although not necessarily to the same degree. The biological function of such proteins can e.g. be examined by suitable available in vitro assays as provided in the invention.

The term "functionally active" as used herein refers to a polypeptide, namely a fragment or derivative, having structural, regulatory, or biochemical functions of the protein according to the embodiment of which this polypeptide, namely fragment or derivative is related to.

"Function-conservative variants" are those in which a given amino acid residue in a protein or enzyme has been changed without altering the overall conformation and function of the polypeptide, including, but not limited to, replacement of an amino acid with one having similar properties (e.g., polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxyl-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "host cell" is intended to refer to a cell into which a nucleic acid encompassed by the present invention, such as a recombinant expression vector encompassed by the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

The term "activity" when used in connection with proteins or protein complexes means any physiological or biochemical activities displayed by or associated with a particular protein or protein complex including but not limited to activities exhibited in biological processes and cellular functions, ability to interact with or bind another molecule or a moiety thereof, binding affinity or specificity to certain molecules, in vitro or in vivo stability (e.g., protein degradation rate, or in the case of protein complexes ability to maintain the form of protein complex), antigenicity and immunogenicity, enzymatic activities, etc. Such activities may be detected or assayed by any of a variety of suitable methods as will be apparent to skilled artisans.

As used herein, the term "interaction antagonist" means a compound that interferes with, blocks, disrupts or destabilizes a protein-protein interaction; blocks or interferes with the formation of a protein complex, or destabilizes, disrupts or dissociates an existing protein complex.

The term "interaction agonist" as used herein means a compound that triggers, initiates, propagates, nucleates, or otherwise enhances the formation of a protein protein interaction; triggers, initiates, propagates, nucleates, or otherwise enhances the formation of a protein complex; or stabilizes an existing protein complex.

The terms "polypeptides" and "proteins" are, where applicable, used interchangeably herein. They may be chemically modified, e.g. post-translationally modified. For example, they may be glycosylated or comprise modified amino acid residues. They may also be modified by the addition of a signal sequence to promote their secretion from a cell where the polypeptide does not naturally contain such a sequence. They may be tagged with a tag. They may be tagged with different labels which may assists in identification of the proteins in a protein complex. Polypeptides/proteins for use in the invention may be in a substantially isolated form. It will be understood that the polypeptide/protein may be mixed with carriers or diluents which will not interfere with the intended purpose of the polypeptide and still be regarded as substantially isolated. A polypeptide/protein for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide encompassed by the present invention.

The terms “hybrid protein”, “hybrid polypeptide,” “hybrid peptide”, “fusion protein”, “fusion polypeptide”, and “fusion peptide” are used herein interchangeably to mean a non-naturally occurring protein having a specified polypeptide molecule covalently linked to one or more polypeptide molecules that do not naturally link to the specified polypeptide. Thus, a “hybrid protein” may be two naturally occurring proteins or fragments thereof linked together by a covalent linkage. A “hybrid protein” may also be a protein formed by covalently linking two artificial polypeptides together. Typically but not necessarily, the two or more polypeptide molecules are linked or fused together by a peptide bond forming a single non-branched polypeptide chain.

The term “tag” as used herein is meant to be understood in its broadest sense and to include, but is not limited to any suitable enzymatic, fluorescent, or radioactive labels and suitable epitopes, including but not limited to HA-tag, Myc-tag, T7, His-tag, FLAG-tag, Calmodulin binding proteins, glutathione-S-transferase, strep-tag, KT3-epitope, EEF-epitopes, green-fluorescent protein and variants thereof.

Figure 3:
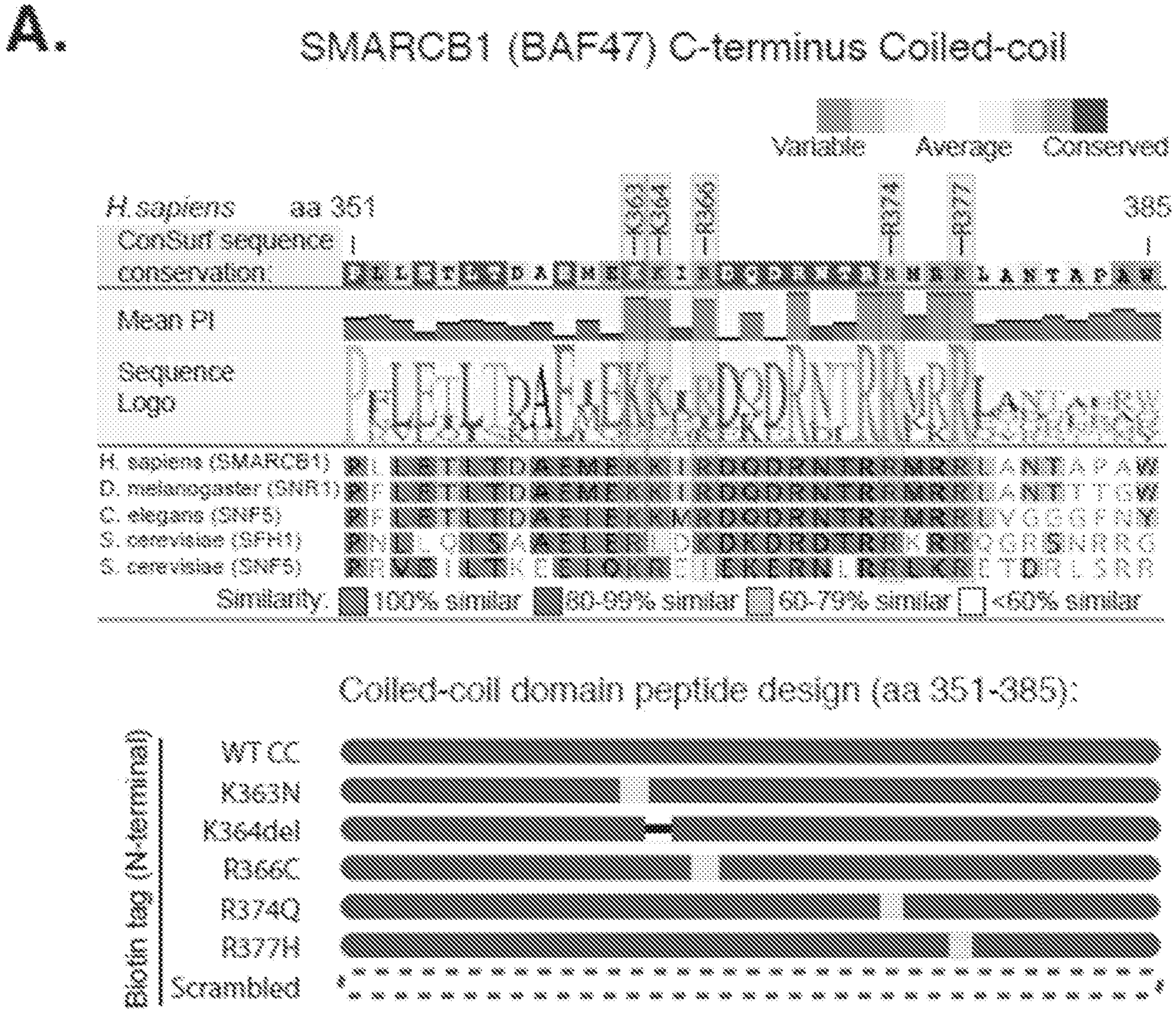
FIG. 3A-FIG. 3G show that the SMARCB1 C-terminal alpha helical domain binds directly to nucleosomes, mediated by a basic amino acid cluster.
Figure 3:
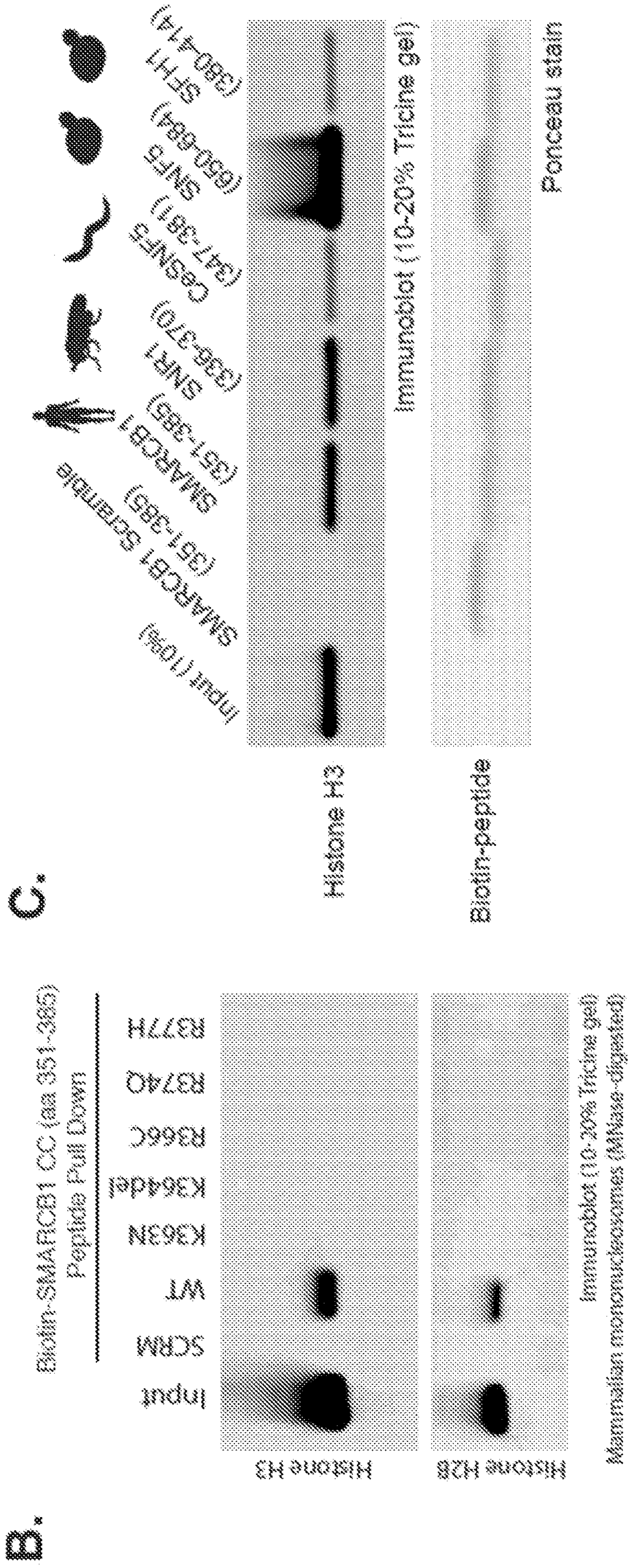
Figure 3:
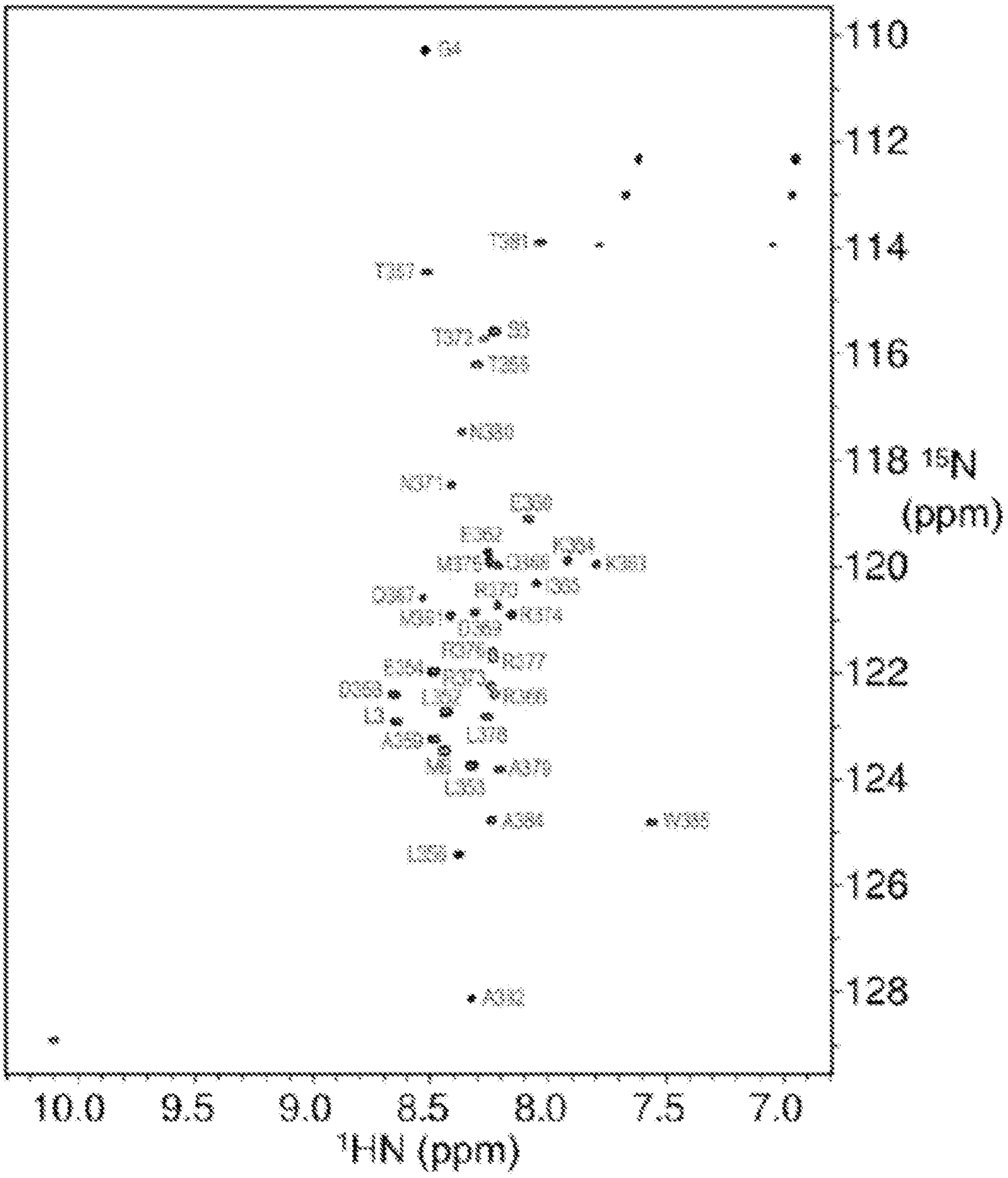
Figure 3:
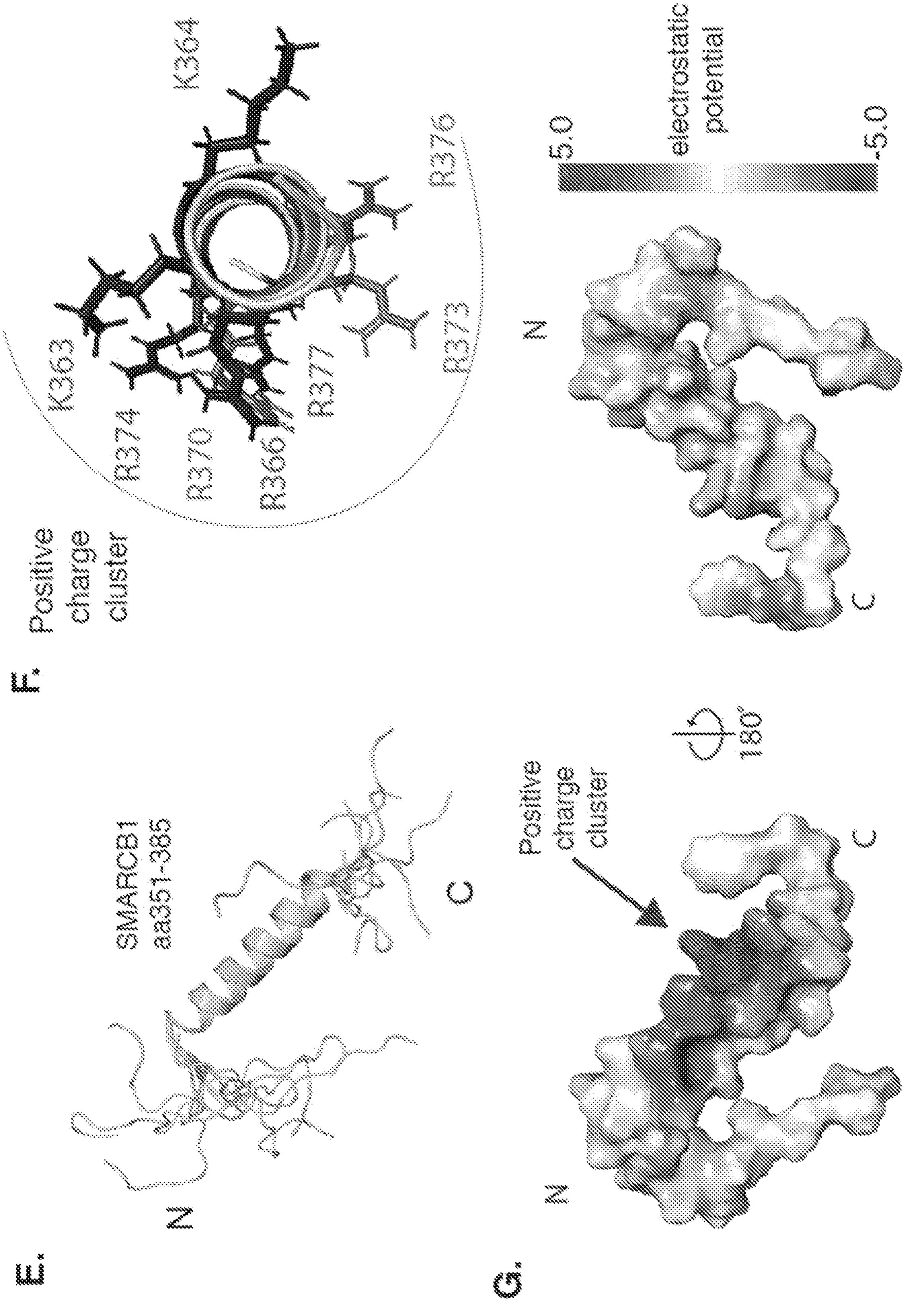
Figure 9:
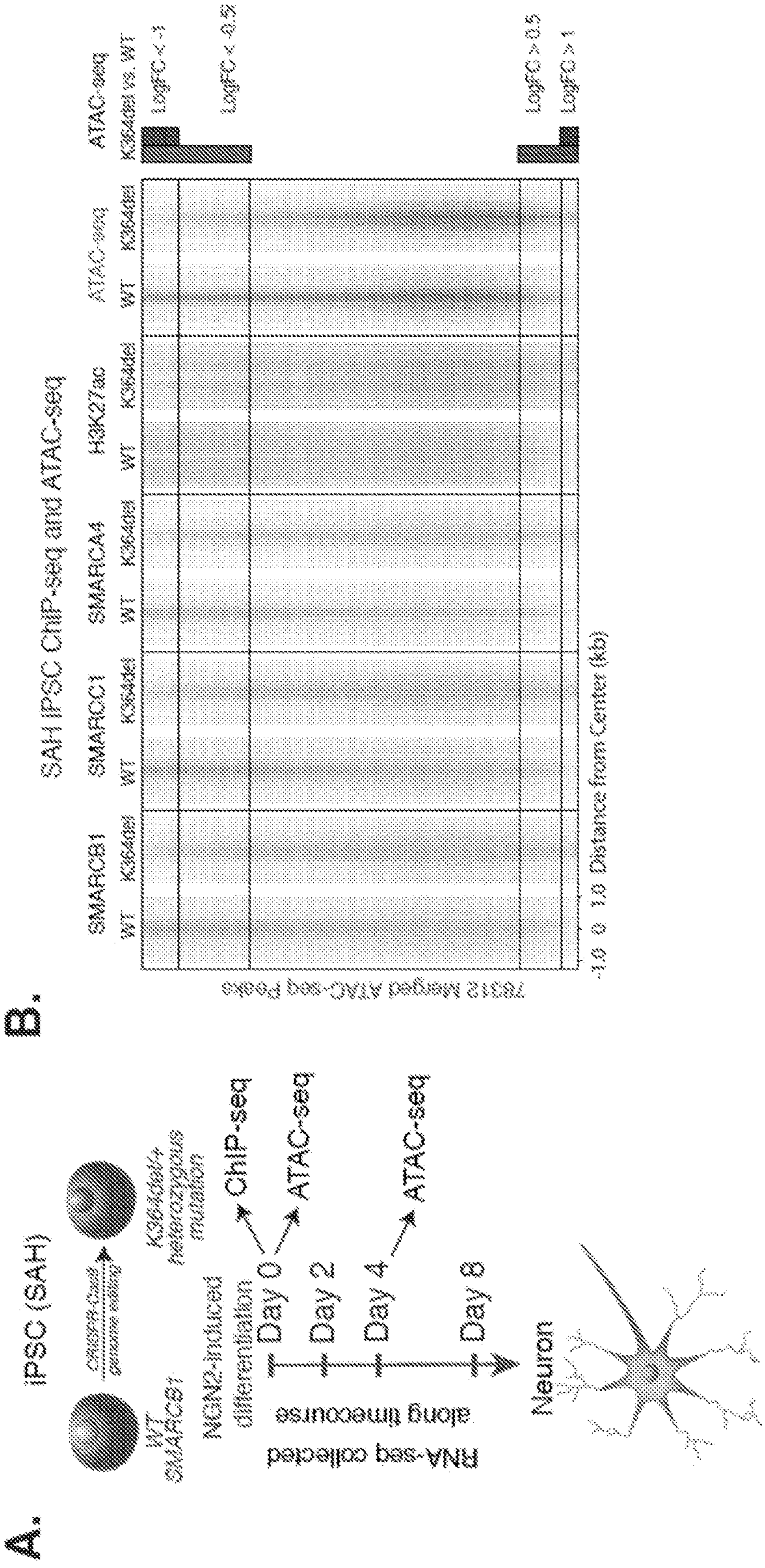
FIG. 9A-FIG. 9J show that CSS-associated heterozygous SMARCB1 mutations in iPSCs impede neuronal differentiation.
Figure 9:
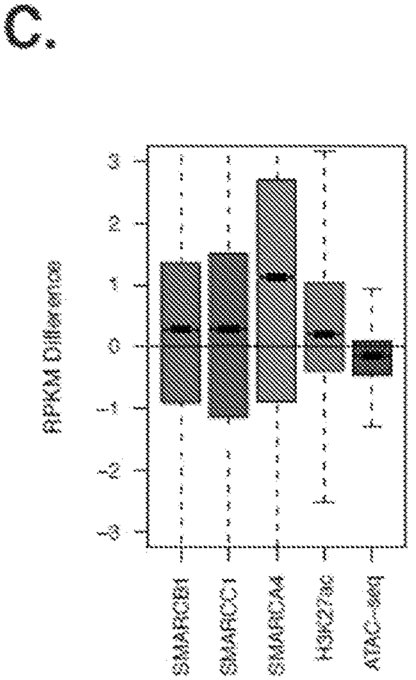
Figure 9:
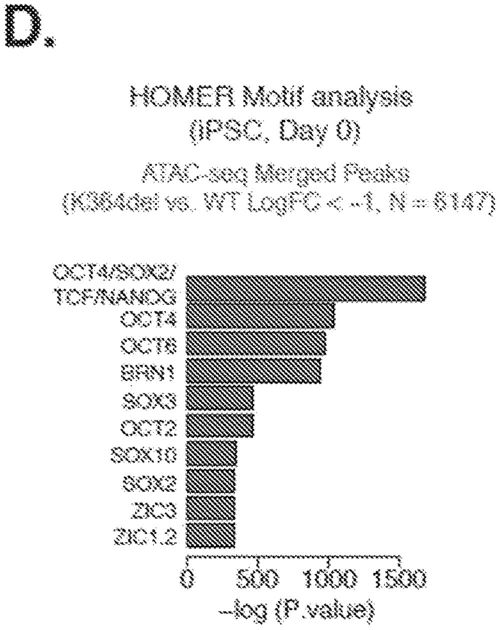
Figure 9:
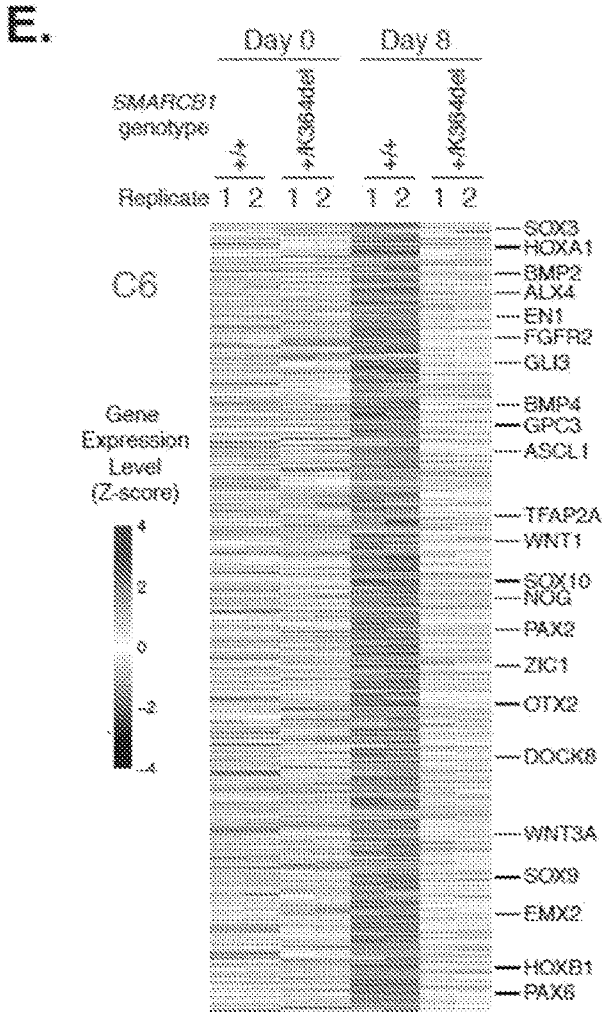
Figure 9:
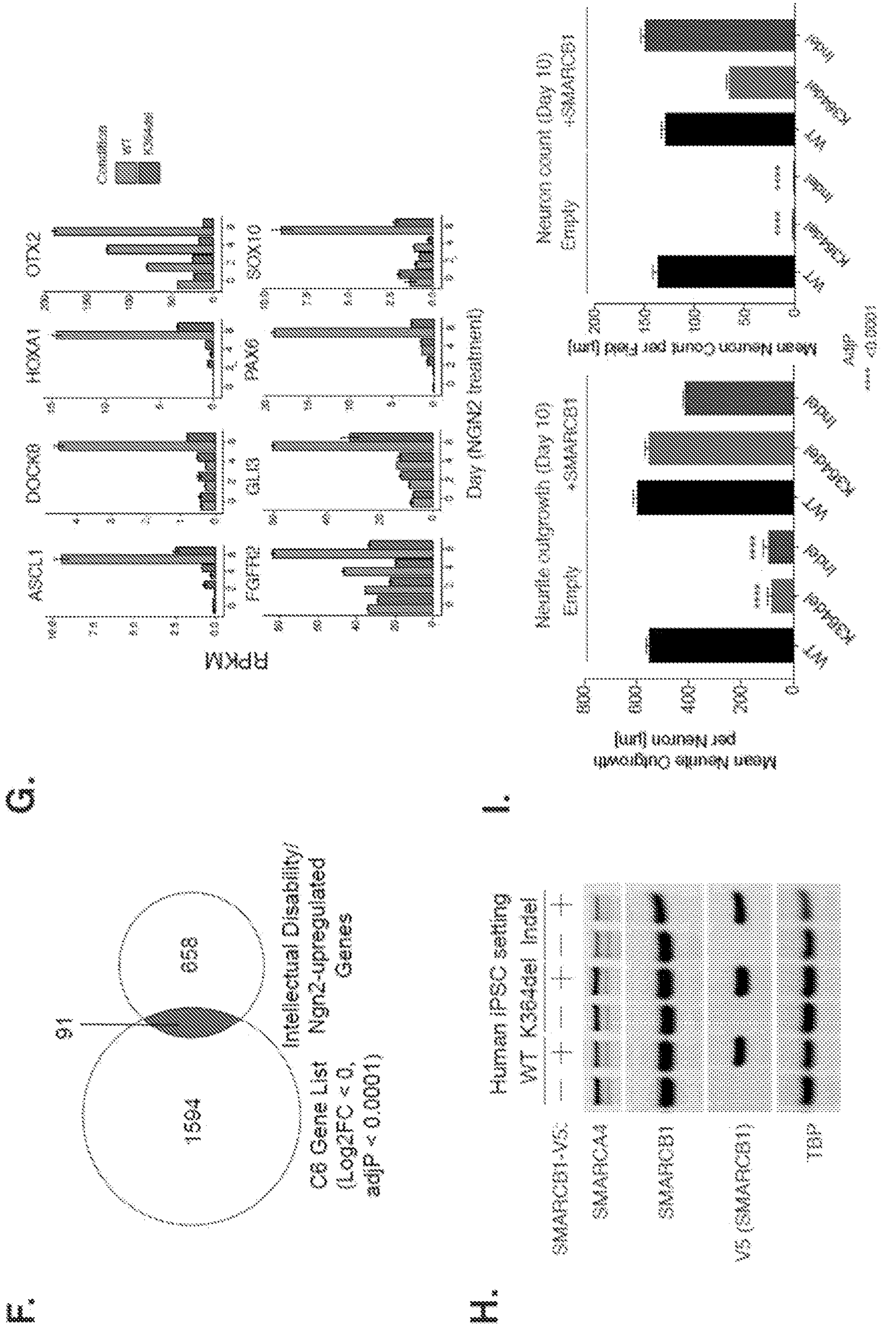
Figure 9:
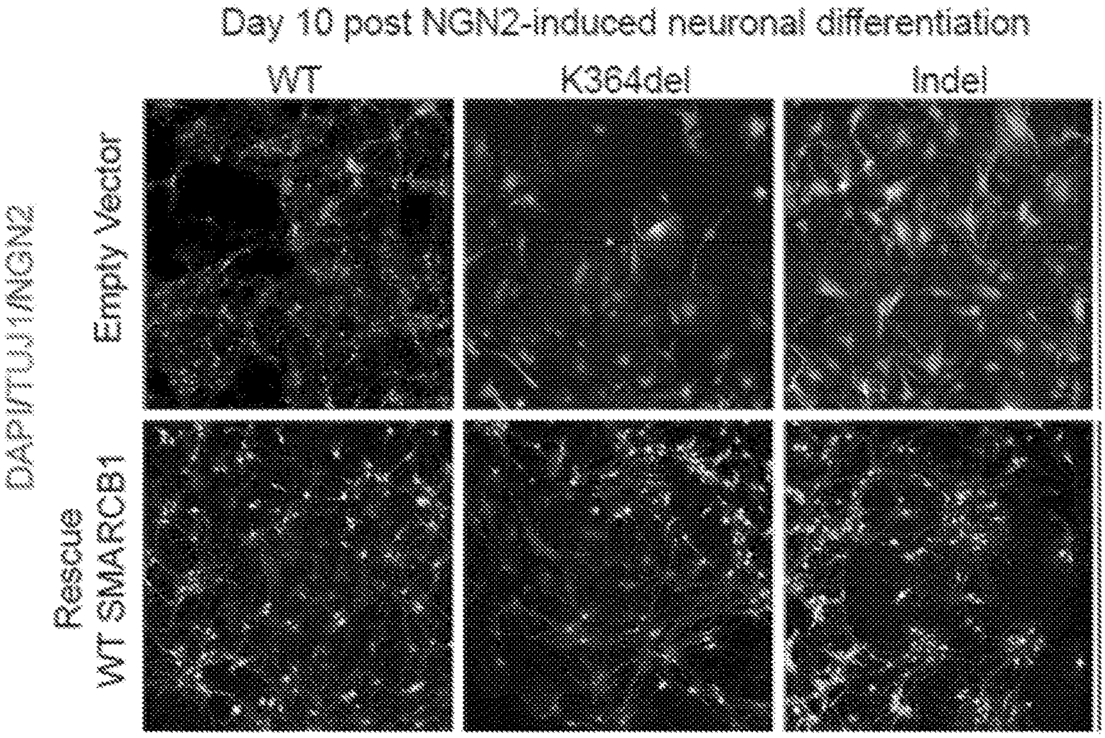

The term “SWI/SNF complex” refers to SWItch/Sucrose Non-Fermentable, a nucleosome remodeling complex found in both eukaryotes and prokaryotes (Neigeborn Carlson (1984) *Genetics* 108:845-858; Stern et al. (1984) *J. Mol. Biol.* 178:853-868). The SWI/SNF complex was first discovered in the yeast, *Saccharomyces cerevisiae*, named after yeast mating types switching (SWI) and sucrose nonfermenting (SNF) pathways (Workman and Kingston (1998) *Annu Rev Biochem.* 67:545-579; Sudarsanam and Winston (2000) *Trends Genet.* 16:345-351). It is a group of proteins comprising, at least, SWI1, SWI2/SNF2, SWI3, SWI5, and SWI6, as well as other polypeptides (Pazin and Kadonaga (1997) *Cell* 88:737-740). A genetic screening for suppressive mutations of the SWI/SNF phenotypes identified different histones and chromatin components, suggesting that these proteins were possibly involved in histone binding and chromatin organization (Winston and Carlson (1992) *Trends Genet.* 8:387-391). Biochemical purification of the SWI/SNF2p in *S. cerevisiae* demonstrated that this protein was part of a complex containing an additional 11 polypeptides, with a combined molecular weight over 1.5 MDa. The SWI/SNF complex contains the ATPase Swi2/Snf2p, two actin-related proteins (Arp7p and Arp9) and other subunits involved in DNA and protein-protein interactions. The purified SWI/SNF complex was able to alter the nucleosome structure in an ATP-dependent manner (Workman and Kingston (1998), supra; Vignali et al. (2000) *Mol Cell Biol.* 20:1899-1910). The structures of the SWI/SNF and RSC complexes are highly conserved but not identical, reflecting an increasing complexity of chromatin (e.g., an increased genome size, the presence of DNA methylation, and more complex genetic organization) through evolution. For this reason, the SWI/SNF complex in higher eukaryotes maintains core components, but also substitute or add on other components with more specialized or tissue-specific domains. Yeast contains two distinct and similar remodeling complexes, SWI/SNF and RSC (Remodeling the Structure of Chromatin). In *Drosophila*, the two complexes are called BAP (Brahma Associated Protein) and PBAP (Polybromo-associated BAP) complexes. The human analogs are BAF (Brg1 Associated Factors, or SWI/SNF-A) and PBAF (Polybromo-associated BAF, or SWI/SNF-B). As shown in FIG. 9, the BAF complex comprises, at least, BAF250A (ARID1A), BAF250B (ARID1B), BAF57 (SMARCE1), BAF190/BRM (SMARCA2), BAF47 (SMARCB1), BAF53A (ACTL6A), BRG1/BAF190 (SMARCA4), BAF155 (SMARCC1), and BAF170 (SMARCC2). The PBAF complex comprises, at last, BAF200 (ARID2), BAF180 (PBRM1), BRD7, BAF45A (PHF10), BRG1/BAF190 (SMARCA4), BAF155 (SMARCC1), and BAF170 (SMARCC2). As in *Drosophila*, human BAF and PBAF share the different core components BAF47, BAF57, BAF60, BAF155, BAF170, BAF45 and the two actins b-Actin and BAF53 (Mohrmann and Verrijzer (2005) *Biochim Biophys Acta.* 1681:59-73). The central core of the BAF and PBAF is the ATPase catalytic subunit BRG1/hBRM, which contains multiple domains to bind to other protein subunits and acetylated histones. For a summary of different complex subunits and their domain structure, see Tang et al. (2010) *Prog Biophys Mol Biol.* 102:122-128 (e.g., FIG. 3), Hohmann and Vakoc (2014) *Trends Genet.* 30:356-363 (e.g., FIG. 1), and Kadoch and Crabtree (2015) *Sci. Adv.* 1:e1500447. For chromatin remodeling, the SWI/SNF complex use the energy of ATP hydrolysis to slide the DNA around the nucleosome. The first step consists in the binding between the remodeler and the nucleosome. This binding occurs with nanomolar affinity and reduces the digestion of nucleosomal DNA by nucleases. The 3-D structure of the yeast RSC complex was first solved and imaged using negative stain electron microscopy (Asturias et al. (2002) *Proc Natl Acad Sci USA* 99:13477-13480). The first Cryo-EM structure of the yeast SWI/SNF complex was published in 2008 (Dechassa et al. 2008). DNA footprinting data showed that the SWI/SNF complex makes close contacts with only one gyre of nucleosomal DNA. Protein crosslinking showed that the ATPase SWI2/SNF2p and Swi5p (the homologue of Ini1p in human), Snf6, Swi29, Snf11 and Sw82p (not conserved in human) make close contact with the histones. Several individual SWI/SNF subunits are encoded by gene families, whose protein products are mutually exclusive in the complex (Wu et al. (2009) *Cell* 136: 200-206). Thus, only one paralog is incorporated in a given SWI/SNF assembly. The only exceptions are BAF155 and BAF170, which are always present in the complex as homo- or hetero-dimers.

Combinatorial association of SWI/SNF subunits could in principle give rise to hundreds of distinct complexes, although the exact number has yet to be determined (Wu et al. (2009), supra). Genetic evidence suggests that distinct subunit configurations of SWI/SNF are equipped to perform specialized functions. As an example, SWI/SNF contains one of two ATPase subunits, BRG1 or BRM/SMARCA2, which share 75% amino acid sequence identity (Khavari et al. (1993) *Nature* 366:170-174). While in certain cell types BRG1 and BRM can compensate for loss of the other subunit, in other contexts these two ATPases perform divergent functions (Strobeck et al. (2002) *J Biol Chem.* 277: 4782-4789; Hoffman et al. (2014) *Proc Natl Acad Sci USA.* 111:3128-3133). In some cell types, BRG1 and BRM can even functionally oppose one another to regulate differentiation (Flowers et al. (2009) *J Biol Chem.* 284:10067-10075). The functional specificity of BRG1 and BRM has been linked to sequence variations near their N-terminus, which have different interaction specificities for transcription factors (Kadam and Emerson (2003) *Mol Cell.* 11:377-389). Another example of paralogous subunits that form mutually exclusive SWI/SNF complexes are ARID1A/BAF250A, ARID1B/BAF250B, and ARID2/BAF200. ARID1A and ARID1B share 60% sequence identity, but yet can perform opposing functions in regulating the cell cycle, with MYC being an important downstream target of each paralog (Nagl et al. (2007) *EMBO J.* 26:752-763). ARID2 has diverged considerably from ARID1A/ARID1B and exists in a unique SWI/SNF assembly known as PBAF (or SWI/SNF-B), which contains several unique subunits not found in ARID1A/B-containing complexes. The composition of SWI/SNF can also be dynamically reconfigured during cell fate transitions through cell type-specific expression patterns of certain subunits. For example, BAF53A/ACTL6A is repressed and replaced by BAF53B/ACTL6B during neuronal differentiation, a switch that is essential for proper neuronal functions in vivo (Lessard et al. (2007) *Neuron* 55:201-215). These studies stress that SWI/SNF in fact represents a collection of multi-subunit complexes whose integrated functions control diverse cellular processes, which is also incorporated in the scope of definitions of the instant disclosure. Two recently published meta-analyses of cancer genome sequencing data estimate that nearly 20% of human cancers harbor mutations in one (or more) of the genes encoding SWI/SNF (Kadoch et al. (2013) *Nat Genet.* 45:592-601; Shain and Pollack (2013) *PLoS One.* 8:e55119). Such mutations are generally loss-of-function, implicating SWI/SNF as a major tumor suppressor in diverse cancers. Specific SWI/SNF gene mutations are generally linked to a specific subset of cancer lineages: SNF5 is mutated in malignant rhabdoid tumors (MRT), PBRM1/BAF180 is frequently inactivated in renal carcinoma, and BRG1 is mutated in non-small cell lung cancer (NSCLC) and several other cancers. In the instant disclosure, the scope of "SWI/SNF complex" may cover at least one fraction or the whole complex (e.g., some or all subunit proteins/other components), either in the human BAF/PBAF forms or their homologs/orthologs in other species (e.g., the yeast and *Drosophila* forms described herein). Preferably, a "SWI/SNF complex" described herein contains at least part of the full complex bio-functionality, such as binding to other subunits/components, binding to DNA/histone, catalyzing ATP, promoting chromatin remodeling, etc.

The term "BAF complex" refers to at least one type of mammalian SWI/SNF complexes. Its nucleosome remodeling activity can be reconstituted with a set of four core subunits (BRG1/SMARCA4, SNF5/SMARCB1, BAF155/SMARCC1, and BAF170/SMARCC2), which have orthologs in the yeast complex (Phelan et al. (1999) *Mol Cell.* 3:247-253). However, mammalian SWI/SNF contains several subunits not found in the yeast counterpart, which can provide interaction surfaces for chromatin (e.g. acetyl-lysine recognition by bromodomains) or transcription factors and thus contribute to the genomic targeting of the complex (Wang et al. (1996) *EMBO J.* 15:5370-5382; Wang et al. (1996) *Genes Dev.* 10:2117-2130; Nie et al. (2000)). A key attribute of mammalian SWI/SNF is the heterogeneity of subunit configurations that can exist in different tissues and even in a single cell type (e.g., as BAF, PBAF, neural progenitor BAF (npBAF), neuron BAF (nBAF), embryonic stem cell BAF (esBAF), etc.). In some embodiments, the BAF complex described herein refers to one type of mammalian SWI/SNF complexes, which is different from PBAF complexes.

The term "PBAF complex" refers to one type of mammalian SWI/SNF complexes originally known as SWI/SNF-B. It is highly related to the BAF complex and can be separated with conventional chromatographic approaches. For example, human BAF and PBAF complexes share multiple identical subunits (such as BRG, BAF170, BAF155, BAF60, BAF57, BAF53, BAF45, actin, SS18, and hSNF5/INI1). However, while BAF contains BAF250 subunit, PBAF contains BAF180 and BAF200, instead (Lemon et al. (2001) *Nature* 414:924-998; Yan et al. (2005) *Genes Dev.* 19:1662-1667). Moreover, they do have selectivity in regulating interferon-responsive genes (Yan et al. (2005), supra, showing that BAF200, but not BAF180, is required for PBAF to mediate expression of IFITM1 gene induced by IFN-α, while the IFITM3 gene expression is dependent on BAF but not PBAF). Due to these differences, PBAF, but not BAF, was able to activate vitamin D receptor-dependent transcription on a chromatinzed template in vitro (Lemon et al. (2001), supra). The 3-D structure of human PBAF complex preserved in negative stain was found to be similar to yeast RSC but dramatically different from yeast SWI/SNF (Leschziner et al. (2005) *Structure* 13:267-275).

The term "BRG" or "BRG1/BAF190 (SMARCA4)" refers to a subunit of the SWI/SNF complex, which can be find in either BAF or PBAF complex. It is an ATP-dependent helicase and a transcription activator, encoded by the SMARCA4 gene.

BRG1 can also bind BRCA1, as well as regulate the expression of the tumorigenic protein CD44. BRG1 is important for development past the pre-implantation stage. Without having a functional BRG1, exhibited with knockout research, the embryo will not hatch out of the zona pellucida, which will inhibit implantation from occurring on the endometrium (uterine wall). BRG1 is also crucial to the development of sperm. During the first stages of meiosis in spermatogenesis there are high levels of BRG1. When BRG1 is genetically damaged, meiosis is stopped in prophase 1, hindering the development of sperm and would result in infertility. More knockout research has concluded BRG1's aid in the development of smooth muscle. In a BRG1 knockout, smooth muscle in the gastrointestinal tract lacks contractility, and intestines are incomplete in some cases. Another defect occurring in knocking out BRG1 in smooth muscle development is heart complications such as an open ductus arteriosus after birth (Kim et al. (2012) *Development* 139:1133-1140; Zhang et al. (2011) *Mol. Cell. Biol.* 31:2618-2631). Mutations in SMARCA4 were first recognized in human lung cancer cell lines (Medina et al. (2008) *Hum. Mut.* 29:617-622). Later it was recognized that mutations exist in a significant frequency of medulloblastoma and pancreatic cancers among other tumor subtypes (Jones et al. (2012) *Nature* 488:100-105; Shain et al. (2012) *Proc Natl Acad Sci USA* 109:E252-E259; Shain and Pollack (2013), supra). Mutations in BRG1 (or SMARCA4) appear to be mutually exclusive with the presence of activation at any of the MYC-genes, which indicates that the BRG1 and MYC proteins are functionally related. Another recent study demonstrated a causal role of BRG1 in the control of retinoic acid and glucocorticoid-induced cell differentiation in lung cancer and in other tumor types.

This enables the cancer cell to sustain undifferentiated gene expression programs that affect the control of key cellular processes. Furthermore, it explains why lung cancer and other solid tumors are completely refractory to treatments based on these compounds that are effective therapies for some types of leukemia (Romero et al. (2012) *EMBO Mol. Med.* 4:603-616). The role of BRG1 in sensitivity or resistance to anti-cancer drugs had been recently highlighted by the elucidation of the mechanisms of action of darinaparsin, an arsenic-based anti-cancer drugs. Darinaparsin has been shown to induce phosphorylation of BRG1, which leads to its exclusion from the chromatin. When excluded from the chromatin, BRG1 can no longer act as a transcriptional co-regulator. This leads to the inability of cells to express HO-1, a cytoprotective enzyme. BRG1 has been shown to interact with proteins such as ACTL6A, ARID1A, ARID1B, BRCA1, CTNNB1, CBX5, CREBBP, CCNE1, ESR1, FANCA, HSP90B1, ING1, Myc, NR3C1, P53, POLR2A, PHB, SIN3A, SMARCB1, SMARCC1, SMARCC2, SMARCE1, STAT2, STK11, etc.

The term "BRG" or "BRG1/BAF190 (SMARCA4)" is intended to include fragments, variants (e.g., allelic variants), and derivatives thereof. Representative human BRG1 (SMARCA4) cDNA and human BRG1 protein sequences are well-known in the art and are publicly available from the National Center for Biotechnology Information (NCBI). For example, seven different human BRG1 isoforms are known. Human BRG1 isoform A (NP_001122321.1) is encodable by the transcript variant 1 (NM_001128849.1), which is the longest transcript. Human BRG1 isoform B (NP_001122316.1 or NP_003063.2) is encodable by the transcript variant 2 (NM_001128844.1), which differs in the 5' UTR and lacks an alternate exon in the 3' coding region, compared to the variant 1, and also by the transcript variant 3 (NM_003072.3), which lacks an alternate exon in the 3' coding region compared to variant 1. Human BRG1 isoform C (NP_001122317.1) is encodable by the transcript variant 4 (NM_001128845.1), which lacks two alternate in-frame exons and uses an alternate splice site in the 3' coding region, compared to variant 1. Human BRG1 isoform D (NP_001122318.1) is encodable by the transcript variant 5 (NM_001128846.1), which lacks two alternate in-frame exons and uses two alternate splice sites in the 3' coding region, compared to variant 1. Human BRG1 isoform E (NP_001122319.1) is encodable by the transcript variant 6 (NM_001128847.1), which lacks two alternate in-frame exons in the 3' coding region, compared to variant 1. Human BRG1 isoform F (NP_001122320.1) is encodable by the transcript variant 7 (NM_001128848.1), which lacks two alternate in-frame exons and uses an alternate splice site in the 3' coding region, compared to variant 1. Nucleic acid and polypeptide sequences of BRG1 orthologs in organisms other than humans are well-known and include, for example, chimpanzee BRG1 (XM_016935029.1 and XP_016790518.1, XM_016935038.1 and XP_016790527.1, XM_016935039.1 and XP_016790528.1, XM_016935036.1 and XP_016790525.1, XM_016935037.1 and XP_016790526.1, XM_016935041.1 and XP_016790530.1, XM_016935040.1 and XP_016790529.1, XM_016935042.1 and XP_016790531.1, XM_016935043.1 and XP_016790532.1, XM_016935035.1 and XP_016790524.1, XM_016935032.1 and XP_016790521.1, XM_016935033.1 and XP_016790522.1, XM_016935030.1 and XP_016790519.1, XM_016935031.1 and XP_016790520.1, and XM_016935034.1 and XP_016790523.1), Rhesus monkey BRG1 (XM_015122901.1 and XP_014978387.1, XM_015122902.1 and XP_014978388.1, XM_015122903.1 and XP_014978389.1, XM_015122906.1 and XP_014978392.1, XM_015122905.1 and XP_014978391.1, XM_015122904.1 and XP_014978390.1, XM_015122907.1 and XP_014978393.1, XM_015122909.1 and XP_014978395.1, and XM_015122910.1 and XP_014978396.1), dog BRG1 (XM_014122046.1 and XP_013977521.1, XM_014122043.1 and XP_013977518.1, XM_014122042.1 and XP_013977517.1, XM_014122041.1 and XP_013977516.1, XM_014122045.1 and XP_013977520.1, and XM_014122044.1 and XP_013977519.1), cattle BRG1 (NM_001105614.1 and NP_001099084.1), rat BRG1 (NM_134368.1 and NP_599195.1).

Anti-BRG1 antibodies suitable for detecting BRG1 protein are well-known in the art and include, for example, MABE1118, MABE121, MABE60, and 07-478 (poly- and mono-clonal antibodies from EMD Millipore, Billerica, MA), AM26021PU-N, AP23972PU-N, TA322909, TA322910, TA327280, TA347049, TA347050, TA347851, and TA349038 (antibodies from OriGene Technologies, Rockville, MD), NB100-2594, AF5738, NBP2-22234, NBP2-41270, NBP1-51230, and NBP1-40379 (antibodes from Novus Biologicals, Littleton, CO), ab110641, ab4081, ab215998, ab108318, ab70558, ab118558, ab133257, ab92496, ab196535, and ab196315 (antibodies from AbCam, Cambridge, MA), Cat #: 720129, 730011, 730051, MA1-10062, PA5-17003, and PA5-17008 (antibodies from ThermoFisher Scientific, Waltham, MA), GTX633391, GTX32478, GTX31917, GTX16472, and GTX50842 (antibodies from GeneTex, Irvine, CA), antibody 7749 (ProSci, Poway, CA), Brg-1 (N-15), Brg-1 (N-15) X, Brg-1 (H-88), Brg-1 (H-88) X, Brg-1 (P-18), Brg-1 (P-18) X, Brg-1 (G-7), Brg-1 (G-7) X, Brg-1 (H-10), and Brg-1 (H-10) X (antibodies from Santa Cruz Biotechnology, Dallas, TX), antibody of Cat. AF5738 (R&D Systems, Minneapolis, MN), etc. In addition, reagents are well-known for detecting BRG1 expression. Moreover, multiple siRNA, shRNA, CRISPR constructs for reducing BRG1 Expression can be found in the commercial product lists of the above-referenced companies. PFI 3 is a known small molecule inhibitor of polybromo 1 and BRG1 (e.g., Cat. B7744 from APExBIO, Houston, TX). It is to be noted that the term can further be used to refer to any combination of features described herein regarding BRG1 molecules. For example, any combination of sequence composition, percentage identify, sequence length, domain structure, functional activity, etc. can be used to describe an BRG1 molecule encompassed by the present invention.

The term "BRM" or "BRM/BAF190 (SMARCA2)" refers to a subunit of the SWI/SNF complex, which can be found in either BAF or PBAF complexes. It is an ATP-dependent helicase and a transcription activator, encoded by the SMARCA2 gene. The catalytic core of the SWI/SNF complex can be either of two closely related ATPases, BRM or BRG1, with the potential that the choice of alternative subunits is a key determinant of specificity. Instead of impeding differentiation as was seen with BRG1 depletion, depletion of BRM caused accelerated progression to the differentiation phenotype. BRM was found to regulate genes different from those as BRG1 targets and be capable of overriding BRG1-dependent activation of the osteocalcin promoter, due to its interaction with different ARID family members (Flowers et al. (2009), supra). The known binding partners for BRM include, for example, ACTL6A, ARID1B, CEBPB, POLR2A, Prohibitin, SIN3A, SMARCB1, and SMARCC1.

The term "BRM" or "BRM/BAF190 (SMARCA2)" is intended to include fragments, variants (e.g., allelic variants), and derivatives thereof. Representative human BRM (SMARCA2) cDNA and human BRM protein sequences are well-known in the art and are publicly available from the National Center for Biotechnology Information (NCBI). For example, seven different human BRM isoforms are known. Human BRM (SMARCA2) isoform A (NP_003061.3 or NP_001276325.1) is encodable by the transcript variant 1 (NM_003070.4), which is the longest transcript, or the transcript variant 3 (NM_001289396.1), which differs in the 5' UTR, compared to variant 1. Human BRM (SMARCA2) isoform B (NP_620614.2) is encodable by the transcript variant 2 (NM_139045.3), which lacks an alternate in-frame exon in the coding region, compared to variant 1. Human BRM (SMARCA2) isoform C (NP_001276326.1) is encodable by the transcript variant 4 (NM_001289397.1), which uses an alternate in-frame splice site and lacks an alternate in-frame exon in the 3' coding region, compared to variant 1. Human BRM (SMARCA2) isoform D (NP_001276327.1) is encodable by the transcript variant 5 (NM_001289398.1), which differs in the 5' UTR, lacks a portion of the 5' coding region, and initiates translation at an alternate downstream start codon, compared to variant 1. Human BRM (SMARCA2) isoform E (NP_001276328.1) is encodable by the transcript variant 6 (NM_001289399.1), which differs in the 5' UTR, lacks a portion of the 5' coding region, and initiates translation at an alternate downstream start codon, compared to variant 1. Human BRM (SMARCA2) isoform F (NP_001276329.1) is encodable by the transcript variant 7 (NM_001289400.1), which differs in the 5' UTR, lacks a portion of the 5' coding region, and initiates translation at an alternate downstream start codon, compared to variant 1. Nucleic acid and polypeptide sequences of BRM orthologs in organisms other than humans are well-known and include, for example, chimpanzee BRM (XM_016960529.2 and XP_016816018.2), dog BRM (XM_005615906.3 and XP_005615963.1, XM_845066.5 and XP_850159.1, XM_005615905.3 and XP_005615962.1, XM_022421616.1 and XP_022277324.1, XM_005615903.3 and XP_005615960.1, and XM_005615902.3 and XP_005615959.1), cattle BRM (NM_001099115.2 and NP_001092585.1), mouse BRM (NM_011416.2 and NP_035546.2, NM_026003.2 and NP_080279.1, and NM_001347439.1 and NP_001334368.1), rat BRM (NM_001004446.1 and NP_001004446.1), chicken BRM (NM_205139.1 and NP_990470.1), and zebrafish BRM (NM_001044775.2 and NP_001038240.1).

Anti-BRM antibodies suitable for detecting BRM protein are well-known in the art and include, for example, antibody MABE89 (EMD Millipore, Billerica, MA), antibody TA351725 (OriGene Technologies, Rockville, MD), NBP1-90015, NBP1-80042, NB100-55308, NB100-55309, NB100-55307, and H00006595-M06 (antibodes from Novus Biologicals, Littleton, CO), ab15597, ab12165, ab58188, and ab200480 (antibodies from AbCam, Cambridge, MA), Cat #: 11966 and 6889 (antibodies from Cell Signaling, Danvers, MA), etc. In addition, reagents are well-known for detecting BRM expression. Multiple clinical tests of SMARCA2 are available in NIH Genetic Testing Registry (GTR®) (e.g., GTR Test ID: GTR000517266.2, offered by Fulgent Clinical Diagnostics Lab (Temple City, CA)). Moreover, multiple siRNA, shRNA, CRISPR constructs for reducing BRM Expression can be found in the commercial product lists of the above-referenced companies. For example, BRM RNAi product H00006595-R02 (Novus Biologicals), siRNA products #sc-29831 and sc-29834 and CRISPR product #sc-401049-KO-2 from Santa Cruz Biotechnology, RNAi products SR304470 and TL301508V, and CRISPR product KN215950 (Origene), and multiple CRISPR products from GenScript (Piscataway, N.J.). It is to be noted that the term can further be used to refer to any combination of features described herein regarding BRM molecules. For example, any combination of sequence composition, percentage identify, sequence length, domain structure, functional activity, etc. can be used to describe an BRM molecule encompassed by the present invention.

The term "BAF250A" or "ARID1A" refers to AT-rich interactive domain-containing protein 1A, a subunit of the SWI/SNF complex, which can be find in BAF but not PBAF complex. In humans there are two BAF250 isoforms, BAF250A/ARID1A and BAF250B/ARID1B. They are thought to be E3 ubiquitin ligases that target histone H2B (Li et al. (2010) *Mol. Cell. Biol.* 30:1673-1688). ARID1A is highly expressed in the spleen, thymus, prostate, testes, ovaries, small intestine, colon and peripheral leukocytes. ARID1A is involved in transcriptional activation and repression of select genes by chromatin remodeling. It is also involved in vitamin D-coupled transcription regulation by associating with the WINAC complex, a chromatin-remodeling complex recruited by vitamin D receptor. ARID1A belongs to the neural progenitors-specific chromatin remodeling (npBAF) and the neuron-specific chromatin remodeling (nBAF) complexes, which are involved in switching developing neurons from stem/progenitors to post-mitotic chromatin remodeling as they exit the cell cycle and become committed to their adult state. ARID1A also plays key roles in maintaining embryonic stem cell pluripotency and in cardiac development and function (Lei et al. (2012) *J. Biol. Chem.* 287:24255-24262; Gao et al. (2008) *Proc. Natl. Acad. Sci. U.S.A.* 105:6656-6661). Loss of BAF250a expression was seen in 42% of the ovarian clear cell carcinoma samples and 21% of the endometrioid carcinoma samples, compared with just 1% of the high-grade serous carcinoma samples. ARID1A deficiency also impairs the DNA damage checkpoint and sensitizes cells to PARP inhibitors (Shen et al. (2015) *Cancer Discov.* 5:752-767). Human ARID1A protein has 2285 amino acids and a molecular mass of 242045 Da, with at least a DNA-binding domain that can specifically bind an AT-rich DNA sequence, recognized by a SWI/SNF complex at the beta-globin locus, and a C-terminus domain for glucocorticoid receptor-dependent transcriptional activation. ARID1A has been shown to interact with proteins such as SMARCB1/BAF47 (Kato et al. (2002) *J. Biol. Chem.* 277:5498-505; Wang et al. (1996) *EMBO J.* 15:5370-5382) and SMARCA4/BRG1 (Wang et al. (1996), supra; Zhao et al. (1998) *Cell* 95:625-636), etc.

The term "BAF250A" or "ARID1A" is intended to include fragments, variants (e.g., allelic variants), and derivatives thereof. Representative human BAF250A (ARID1A) cDNA and human BAF250A (ARID1A) protein sequences are well-known in the art and are publicly available from the National Center for Biotechnology Information (NCBI). For example, two different human ARID1A isoforms are known. Human ARID1A isoform A (NP_006006.3) is encodable by the transcript variant 1 (NM_006015.4), which is the longer transcript. Human ARID1A isoform B (NP_624361.1) is encodable by the transcript variant 2 (NM_139135.2), which lacks a segment in the coding region compared to variant 1. Isoform B thus lacks an internal segment, compared to isoform A. Nucleic acid and polypeptide sequences of ARID1A orthologs in organisms other than humans are well-known and include, for example, chimpanzee ARID1A (XM_016956953.1 and XP_016812442.1, XM_016956958.1 and XP_016812447.1, and XM_009451423.2 and XP_009449698.2), Rhesus monkey ARID1A (XM_015132119.1 and XP_014987605.1, and XM_015132127.1 and XP_014987613.1), dog ARID1A (XM_847453.5 and XP_852546.3, XM_005617743.2 and XP_005617800.1, XM_005617742.2 and XP_005617799.1, XM_005617744.2 and XP_005617801.1, XM_005617746.2 and XP_005617803.1, and XM_005617745.2 and XP_005617802.1), cattle ARID1A (NM_001205785.1 and NP_001192714.1), rat ARID1A (NM_001106635.1 and NP_001100105.1).

Anti-ARID1A antibodies suitable for detecting ARID1A protein are well-known in the art and include, for example, antibody Cat #04-080 (EMD Millipore, Billerica, MA), antibodies TA349170, TA350870, and TA350871 (OriGene Technologies, Rockville, MD), antibodies NBP1-88932, NB100-55334, NBP2-43566, NB100-55333, and H00008289-Q01 (Novus Biologicals, Littleton, CO), antibodies ab182560, ab182561, ab176395, and ab97995 (AbCam, Cambridge, MA), antibodies Cat #: 12354 and 12854 (Cell Signaling Technology, Danvers, MA), antibodies GTX129433, GTX129432, GTX632013, GTX12388, and GTX31619 (GeneTex, Irvine, CA), etc. In addition, reagents are well-known for detecting ARID1A expression. For example, multiple clinical tests for ARID1A are available at NIH Genetic Testing Registry (GTR©) (e.g., GTR Test ID: GTR000520952.1 for mental retardation, offered by Centogene AG, Germany). Moreover, multiple siRNA, shRNA, CRISPR constructs for reducing ARID1A Expression can be found in the commercial product lists of the above-referenced companies, such as RNAi products H00008289-R01, H00008289-R02, and H00008289-R03 (Novus Biologicals) and CRISPR products KN301547G1 and KN301547G2 (Origene). Other CRISPR products include sc-400469 (Santa Cruz Biotechnology) and those from GenScript (Piscataway, N.J.). It is to be noted that the term can further be used to refer to any combination of features described herein regarding ARID1A molecules. For example, any combination of sequence composition, percentage identify, sequence length, domain structure, functional activity, etc. can be used to describe an ARID1A molecule encompassed by the present invention.

The term "BAF250B" or "ARID1B" refers to AT-rich interactive domain-containing protein 1B, a subunit of the SWI/SNF complex, which can be find in BAF but not PBAF complex. ARID1B and ARID1A are alternative and mutually exclusive ARID-subunits of the SWI/SNF complex. Germline mutations in ARID1B are associated with Coffin-Siris syndrome (Tsurusaki et al. (2012) *Nat. Genet.* 44:376-378; Santen et al. (2012) *Nat. Genet.* 44:379-380). Somatic mutations in ARID1B are associated with several cancer subtypes, suggesting that it is a tumor suppressor gene (Shai and Pollack (2013) *PLoS ONE* 8:e55119; Sausen et al. (2013) *Nat. Genet.* 45:12-17; Shain et al. (2012) *Proc. Natl. Acad. Sci. U.S.A.* 109:E252-E259; Fujimoto et al. (2012) *Nat. Genet.* 44:760-764). Human ARID1A protein has 2236 amino acids and a molecular mass of 236123 Da, with at least a DNA-binding domain that can specifically bind an AT-rich DNA sequence, recognized by a SWI/SNF complex at the beta-globin locus, and a C-terminus domain for glucocorticoid receptor-dependent transcriptional activation. ARID1B has been shown to interact with SMARCA4/BRG1 (Hurlstone et al. (2002) *Biochem. J.* 364:255-264; Inoue et al. (2002) *J. Biol. Chem.* 277:41674-41685 and SMARCA2/BRM (Inoue et al. (2002), supra).

The term "BAF250B" or "ARID1B" is intended to include fragments, variants (e.g., allelic variants), and derivatives thereof. Representative human BAF250B (ARID1B) cDNA and human BAF250B (ARID1B) protein sequences are well-known in the art and are publicly available from the National Center for Biotechnology Information (NCBI). For example, three different human ARID1B isoforms are known. Human ARID1B isoform A (NP_059989.2) is encodable by the transcript variant 1 (NM_017519.2). Human ARID1B isoform B (NP_065783.3) is encodable by the transcript variant 2 (NM_020732.3). Human ARID1B isoform C (NP_001333742.1) is encodable by the transcript variant 3 (NM_001346813.1). Nucleic acid and polypeptide sequences of ARID1B orthologs in organisms other than humans are well-known and include, for example, Rhesus monkey ARID1B (XM_015137088.1 and XP_014992574.1), dog ARID1B (XM_014112912.1 and XP_013968387.1), cattle ARID1B (XM_010808714.2 and XP_010807016.1, and XM_015464874.1 and XP_015320360.1), rat ARID1B (XM_017604567.1 and XP_017460056.1).

Anti-ARID1B antibodies suitable for detecting ARID1B protein are well-known in the art and include, for example, antibody Cat #ABE316 (EMD Millipore, Billerica, MA), antibody TA315663 (OriGene Technologies, Rockville, MD), antibodies H00057492-M02, H00057492-M01, NB100-57485, NBP1-89358, and NB100-57484 (Novus Biologicals, Littleton, CO), antibodies ab57461, ab69571, ab84461, and ab163568 (AbCam, Cambridge, MA), antibodies Cat #: PA5-38739, PA5-49852, and PA5-50918 (ThermoFisher Scientific, Danvers, MA), antibodies GTX130708, GTX60275, and GTX56037 (GeneTex, Irvine, CA), ARID1B (KMN1) Antibody and other antibodies (Santa Cruz Biotechnology), etc. In addition, reagents are well-known for detecting ARID1B expression. For example, multiple clinical tests for ARID1B are available at NIH Genetic Testing Registry (GTR©) (e.g., GTR Test ID: GTR000520953.1 for mental retardation, offered by Centogene AG, Germany). Moreover, multiple siRNA, shRNA, CRISPR constructs for reducing ARID1B Expression can be found in the commercial product lists of the above-referenced companies, such as RNAi products H00057492-R03, H00057492-R01, and H00057492-R02 (Novus Biologicals) and CRISPR products KN301548 and KN214830 (Origene). Other CRISPR products include sc-402365 (Santa Cruz Biotechnology) and those from GenScript (Piscataway, N.J.). It is to be noted that the term can further be used to refer to any combination of features described herein regarding ARID1B molecules. For example, any combination of sequence composition, percentage identify, sequence length, domain structure, functional activity, etc. can be used to describe an ARID1B molecule encompassed by the present invention.

The term "PBRM1" or "BAF180" refers to protein Polybromo-1, which is a subunit of ATP-dependent chromatin-remodeling complexes. PBRM1 functions in the regulation of gene expression as a constituent of the evolutionary-conserved SWI/SNF chromatin remodelling complexes (Euskirchen et al. (2012) *J. Biol. Chem.* 287:30897-30905). Beside BRD7 and BAF200, PBRM1 is one of the unique components of the SWI/SNF-B complex, also known as polybromo/BRG1-associated factors (or PBAF), absent in the SWI/SNF-A (BAF) complex (Xue et al. (2000) *Proc Natl Acad Sci USA.* 97:13015-13020; Brownlee et al. (2012) *Biochem Soc Trans.* 40:364-369). On that account, and because it contains bromodomains known to mediate binding to acetylated histones, PBRM1 has been postulated to target PBAF complex to specific chromatin sites, therefore providing the functional selectivity for the complex (Xue et al. (2000), supra; Lemon et al. (2001) *Nature* 414:924-928; Brownlee et al. (2012), supra). Although direct evidence for PBRM1 involvement is lacking, SWI/SNF complexes have also been shown to play a role in DNA damage response (Park et al. (2006) *EMBO J.* 25:3986-3997). In vivo studies have shown that PBRM1 deletion leads to embryonic lethality in mice, where PBRM1 is required for mammalian cardiac chamber maturation and coronary vessel formation (Wang et al. (2004) *Genes Dev.* 18:3106-3116; Huang et al. (2008) *Dev Biol.* 319:258-266). PBRM1 mutations are most predominant in renal cell carcinomas (RCCs) and have been detected in over 40% of cases, placing PBRM1 second (after VHL) on the list of most frequently mutated genes in this cancer (Varela et al. (2011) *Nature* 469:539-542; Hakimi et al. (2013) *Eur Urol.* 63:848-854; Pena-Llopis et al. (2012) *Nat Genet.* 44:751-759; Pawlowski et al. (2013) *Int J Cancer.* 132:E11-E17). PBRM1 mutations have also been found in a smaller group of breast and pancreatic cancers (Xia et al. (2008) *Cancer Res.* 68:1667-1674; Shain et al. (2012) *Proc Natl Acad Sci USA.* 109:E252-E259; Numata et al. (2013) *Int J Oncol.* 42:403-410). PBRM1 mutations are more common in patients with advance stages (Hakimi et al. (2013), supra) and loss of PBRM1 protein expression has been associated with advanced tumour stage, low differentiation grade and worse patient outcome (Pawlowski et al. (2013), supra). In another study, no correlation between PBRM1 status and tumour grade was found (Pena-Llopis et al. (2012), supra). Although PBRM1-mutant tumours are associated with better prognosis than BAP1-mutant tumours, tumours mutated for both PBRM1 and BAP1 exhibit the greatest aggressiveness (Kapur et al. (2013) *Lancet Oncol.* 14:159-167). PBRM1 is ubiquitously expressed during mouse embryonic development (Wang et al. (2004), supra) and has been detected in various human tissues including pancreas, kidney, skeletal muscle, liver, lung, placenta, brain, heart, intestine, ovaries, testis, prostate, thymus and spleen (Xue et al. (2000), supra; Horikawa and Barrett (2002) *DNA Seq.* 13:211-215).

PBRM1 protein localises to the nucleus of cells (Nicolas and Goodwin (1996) *Gene* 175:233-240). As a component of the PBAF chromatin-remodelling complex, it associates with chromatin (Thompson (2009) *Biochimie.* 91:309-319), and has been reported to confer the localisation of PBAF complex to the kinetochores of mitotic chromosomes (Xue et al. (2000), supra). Human PBRM1 gene encodes a 1582 amino acid protein, also referred to as BAF180. Six bromodomains (BD1-6), known to recognize acetylated lysine residues and frequently found in chromatin-associated proteins, constitute the N-terminal half of PBRM1 (e.g., six BD domains at amino acid residue no. 44-156, 182-284, 383-484, 519-622, 658-762, and 775-882 of SEQ ID NO:2). The C-terminal half of PBRM1 contains two bromo-adjacent homology (BAH) domains (BAH1 and BAH2, e.g., at amino acid residue no. 957-1049 and 1130-1248 of SE ID NO:2), present in some proteins involved in transcription regulation. High mobility group (HMG) domain is located close to the C-terminus of PBRM1 (e.g., amino acid residue no. 1328-1377 of SEQ ID NO:2). HMG domains are found in a number of factors regulating DNA-dependent processes where HMG domains often mediate interactions with DNA.

The term "PBRM1" is intended to include fragments, variants (e.g., allelic variants), and derivatives thereof. Representative human PBRM1 cDNA and human PBRM1 protein sequences are well-known in the art and are publicly available from the National Center for Biotechnology Information (NCBI). For example, two different human PBRM1 isoforms are known. Human PBRM1 transcript variant 2 (NM_181042.4) represents the longest transcript. Human PBRM1 transcript variant 1 (NM_018313.4, having a CDS from the 115-4863 nucleotide residue of SEQ ID NO:1) differs in the 5' UTR and uses an alternate exon and splice site in the 3' coding region, thus encoding a distinct protein sequence (NP_060783.3, as SEQ ID NO:2) of the same length as the isoform (NP_851385.1) encoded by variant 2. Nucleic acid and polypeptide sequences of PBRM1 orthologs in organisms other than humans are well-known and include, for example, chimpanzee PBRM1 (XM_009445611.2 and XP_009443886.1, XM_009445608.2 and XP_009443883.1, XM_009445602.2 and XP_009443877.1, XM_016941258.1 and XP_016796747.1, XM_016941256.1 and XP_016796745.1, XM_016941249.1 and XP_016796738.1, XM_016941260.1 and XP_016796749.1, XM_016941253.1 and XP_016796742.1, XM_016941250.1 and XP_016796739.1, XM_016941261.1 and XP_016796750.1, XM_009445605.2 and XP_009443880.1, XM_016941252.1 and XP_016796741.1, XM_009445603.2 and XP_009443878.1, XM_016941263.1 and XP_016796752.1, XM_016941262.1 and XP_016796751.1, XM_009445604.2 and XP_009443879.1, XM_016941251.1 and XP_016796740.1, XM_016941257.1 and XP_016796746.1, XM_016941255.1 and XP_016796744.1, XM_016941254.1 and XP_016796743.1, XM_016941265.1 and XP_016796754.1, XM_016941264.1 and XP_016796753.1, XM_016941248.1 and XP_016796737.1, XM_009445617.2 and XP_009443892.1, XM_009445616.2 and XP_009443891.1, XM_009445619.2 and XP_009443894.1 XM_009445615.2 and XP_009443890.1, XM_009445618.2 and XP_009443893.1, and XM_016941266.1 and XP_016796755.1), rhesus monkey PBRM1 (XM_015130736.1 and XP_014986222.1, XM_015130739.1 and XP_014986225.1, XM_015130737.1 and XP_014986223.1, XM_015130740.1 and XP_014986226.1, XM_015130727.1 and XP_014986213.1, XM_015130726.1 and XP_014986212.1, XM_015130728.1 and XP_014986214.1, XM_015130743.1 and XP_014986229.1, XM_015130731.1 and XP_014986217.1, XM_015130745.1 and XP_014986231.1, XM_015130741.1 and XP_014986227.1, XM_015130734.1 and XP_014986220.1, XM_015130744.1 and XP_014986230.1, XM_015130748.1 and XP_014986234.1, XM_015130746.1 and XP_014986232.1, XM_015130742.1 and XP_014986228.1, XM_015130747.1 and XP_014986233.1, XM_015130730.1 and XP_014986216.1, XM_015130732.1 and XP_014986218.1, XM_015130733.1 and XP_014986219.1, XM_015130735.1 and XP_014986221.1, XM_015130738.1 and XP_014986224.1, and XM_015130725.1 and XP_014986211.1), dog PBRM1 (XM_005632441.2 and XP_005632498.1, XM_014121868.1 and XP_013977343.1, XM_005632451.2 and XP_005632508.1, XM_014121867.1 and XP_013977342.1, XM_005632440.2 and XP_005632497.1, XM_005632446.2 and XP_005632503.1, XM_533797.5 and XP_533797.4, XM_005632442.2 and XP_005632499.1, XM_005632439.2 and XP_005632496.1, XM_014121869.1 and XP_013977344.1, XM_005632448.1 and XP_005632505.1, XM_005632449.1 and XP_005632506.1, XM_005632452.1 and XP_005632509.1, XM_005632445.1 and XP_005632502.1, XM_005632450.1 and XP_005632507.1, XM_005632453.1 and XP_005632510.1, XM_014121870.1 and XP_013977345.1, XM_005632443.1 and XP_005632500.1, XM_005632444.1 and XP_005632501.1, and XM_005632447.2 and XP_005632504.1), cow PBRM1 (XM_005222983.3 and XP_005223040.1, XM_005222979.3 and XP_005223036.1, XM_015459550.1 and XP_015315036.1, XM_015459551.1 and XP_015315037.1, XM_015459548.1 and XP_015315034.1, XM_010817826.1 and XP_010816128.1, XM_010817829.1 and XP_010816131.1, XM_010817830.1 and XP_010816132.1, XM_010817823.1 and XP_010816125.1, XM_010817824.2 and XP_010816126.1, XM_010817819.2 and XP_010816121.1, XM_010817827.2 and XP_010816129.1, XM_010817828.2 and XP_010816130.1, XM_010817817.2 and XP_010816119.1, and XM_010817818.2 and XP_010816120.1), mouse PBRM1 (NM_001081251.1 and NP_001074720.1), chicken PBRM1 (NM_205165.1 and NP_990496.1), tropical clawed frog PBRM1 (XM_018090224.1 and XP_017945713.1), zebrafish PBRM1 (XM_009305786.2 and XP_009304061.1, XM_009305785.2 and XP_009304060.1, and XM_009305787.2 and XP_009304062.1), fruit fly PBRM1 (NM_143031.2 and NP_651288.1), and worm PBRM1 (NM_001025837.3 and NP_001021008.1 and. NM_001025838.2 and NP_001021009.1).

Anti-PBRM1 antibodies suitable for detecting PBRM1 protein are well-known in the art and include, for example, ABE70 (rabbit polyclonal antibody, EMD Millipore, Billerica, MA), TA345237 and TA345238 (rabbit polyclonal antibodies, OriGene Technologies, Rockville, MD), NBP2-30673 (mouse monoclonal) and other polyclonal antibodes (Novus Biologicals, Littleton, CO), ab196022 (rabiit mAb, AbCam, Cambridge, MA), PAH437Hu01 and PAH437Hu02 (rabbit polyclonal antibodies, Cloud-Clone Corp., Houston, TX), GTX100781 (GeneTex, Irvine, CA), 25-498 (ProSci, Poway, CA), sc-367222 (Santa Cruz Biotechnology, Dallas, TX), etc. In addition, reagents are well-known for detecting PBRM1 expression (see, for example, PBRM1 Hu-Cy3 or Hu-Cy5 SmartFlare™ RNA Detection Probe (EMD Millipore). Moreover, multiple siRNA, shRNA, CRISPR constructs for reducing PBRM1 expression can be found in the commercial product lists of the above-referenced companies. Ribavirin and PFI 3 are known PBRM1 inhibitors. It is to be noted that the term can further be used to refer to any combination of features described herein regarding PBRM1 molecules. For example, any combination of sequence composition, percentage identify, sequence length, domain structure, functional activity, etc. can be used to describe an PBRM1 molecule encompassed by the present invention.

The term "BAF200" or "ARID2" refers to AT-rich interactive domain-containing protein 2, a subunit of the SWI/SNF complex, which can be found in PBAF but not BAF complexes. It facilitates ligand-dependent transcriptional activation by nuclear receptors. The ARID2 gene, located on chromosome 12q in humans, consists of 21 exons; orthologs are known from mouse, rat, cattle, chicken, and mosquito (Zhao et al. (2011) *Oncotarget* 2:886-891). A conditional knockout mouse line, called Arid2$^{tm1a(EUCOMM)Wtsi}$ was generated as part of the International Knockout Mouse Consortium program, a high-throughput mutagenesis project to generate and distribute animal models of disease (Skarnes et al. (2011) *Nature* 474:337-342). Human ARID2 protein has 1835 amino acids and a molecular mass of 197391 Da. The ARID2 protein contains two conserved C-terminal C2H2 zinc fingers motifs, a region rich in the amino acid residues proline and glutamine, a RFX (regulatory factor X)-type winged-helix DNA-binding domain (e.g., amino acids 521-601 of SEQ ID NO:8), and a conserved N-terminal AT-rich DNA interaction domain (e.g., amino acids 19-101 of SEQ ID NO:8; Zhao et al. (2011), supra). Mutation studies have revealed ARID2 to be a significant tumor suppressor in many cancer subtypes. ARID2 mutations are prevalent in hepatocellular carcinoma (Li et al. (2011) *Nature Genetics.* 43:828-829) and melanoma (Hodis et al. (2012) *Cell* 150:251-263; Krauthammer et al. (2012) *Nature Genetics.* 44:1006-1014). Mutations are present in a smaller but significant fraction in a wide range of other tumors (Shain and Pollack (2013), supra). ARID2 mutations are enriched in hepatitis C virus-associated hepatocellular carcinoma in the U.S. and European patient populations compared with the overall mutation frequency (Zhao et al. (2011), supra). The known binding partners for ARID2 include, e.g., Serum Response Factor (SRF) and SRF cofactors MYOCD, NKX2-5 and SRFBP1.

The term "BAF200" or "ARID2" is intended to include fragments, variants (e.g., allelic variants), and derivatives thereof. Representative human ARID2 cDNA and human ARID2 protein sequences are well-known in the art and are publicly available from the National Center for Biotechnology Information (NCBI). For example, two different human ARID2 isoforms are known. Human ARID2 isoform A (NP_689854.2) is encodable by the transcript variant 1 (NM_152641.3), which is the longer transcript. Human ARID2 isoform B (NP_001334768.1) is encodable by the transcript variant 2 (NM_001347839.1), which differs in the 3' UTR and 3' coding region compared to isoform A. The encoded isoform B has a shorter C-terminus compared to isoform A. Nucleic acid and polypeptide sequences of ARID2 orthologs in organisms other than humans are well-known and include, for example, chimpanzee ARID2 (XM_016923581.1 and XP_016779070.1, and XM_016923580.1 and XP_016779069.1), Rhesus monkey ARID2 (XM_015151522.1 and XP_015007008.1), dog ARID2 (XM_003433553.2 and XP_003433601.2; and XM_014108583.1 and XP_013964058.1), cattle ARID2 (XM_002687323.5 and XP_002687369.1; and XM_015463314.1 and XP_015318800.1), mouse ARID2 (NM_175251.4 and NP_780460.3), rat ARID2 (XM_345867.8 and XP_345868.4; and XM_008776620.1 and XP_008774842.1), chicken ARID2 (XM_004937552.2 and XP_004937609.1, XM_004937551.2 and XP_004937608.1, XM_004937554.2 and XP_004937611.1, and XM_416046.5 and XP_416046.2), tropical clawed frog ARID2 (XM_002932805.4 and XP_002932851.1, XM_018092278.1 and XP_017947767.1, and XM_018092279.1 and XP_017947768.1), and zebrafish ARID2 (NM_001077763.1 and NP_001071231.1, and XM_005164457.3 and XP_005164514.1).

Anti-ARID2 antibodies suitable for detecting ARID2 protein are well-known in the art and include, for example, antibodies ABE316 and 04-080 (EMD Millipore, Billerica, MA), antibodies NBP1-26615, NBP2-43567, and NBP1-26614 (Novus Biologicals, Littleton, CO), antibodies ab51019, ab166850, ab113283, and ab56082 (AbCam, Cambridge, MA), antibodies Cat #: PA5-35857 and PA5-51258 (ThermoFisher Scientific, Waltham, MA), antibodies GTX129444, GTX129443, and GTX632011 (GeneTex, Irvine, CA), ARID2 (H-182) Antibody, ARID2 (H-182) X Antibody, ARID2 (S-13) Antibody, ARID2 (S-13) X Antibody, ARID2 (E-3) Antibody, and ARID2 (E-3) X Antibody (Santa Cruz Biotechnology), etc. In addition, reagents are well-known for detecting ARID2 expression. Multiple clinical tests of PBRM1 are available in NIH Genetic Testing Registry (GTR®) (e.g., GTR Test ID: GTR000541481.2, offered by Fulgent Clinical Diagnostics Lab (Temple City, CA)). Moreover, multiple siRNA, shRNA, CRISPR constructs for reducing ARID2 expression can be found in the commercial product lists of the above-referenced companies, such as siRNA product #SR316272, shRNA products #TR306601, TR505226, TG306601, SR420583, and CRISPER products #KN212320 and KN30154 from Origene Technologies (Rockville, MD), RNAi product H00196528-R01 (Novus Biologicals), CRISPER gRNA products from GenScript (Cat. #KN301549 and KN212320, Piscataway, N.J.) and from Santa Cruz (sc-401863), and RNAi products from Santa Cruz (Cat #sc-96225 and sc-77400). It is to be noted that the term can further be used to refer to any combination of features described herein regarding ARID2 molecules.

For example, any combination of sequence composition, percentage identify, sequence length, domain structure, functional activity, etc. can be used to describe an ARID2 molecule encompassed by the present invention.

The term "BRD7" refers to Bromodomain-containing protein 7, a subunit of the SWI/SNF complex, which can be found in PBAF but not BAF complexes. BRD7 is a transcriptional corepressor that binds to target promoters (e.g., the ESR1 promoter) and down-regulates the expression of target genes, leading to increased histone H3 acetylation at Lys-9 (H3K9ac). BRD7 can recruit other proteins such as BRCA1 and POU2F1 to, e.g., the ESR1 promoter for its function. BRD7 activates the Wnt signaling pathway in a DVL1-dependent manner by negatively regulating the GSK3B phosphotransferase activity, while BRD7 induces dephosphorylation of GSK3B at Tyr-216. BRD7 is also a coactivator for TP53-mediated activation of gene transcription and is required for TP53-mediated cell-cycle arrest in response to oncogene activation. BRD7 promotes acetylation of TP53 at Lys-382, and thereby promotes efficient recruitment of TP53 to target promoters. BRD7 also inhibits cell cycle progression from G1 to S phase. For studies on BRD7 functions, see Zhou et al. (2006) *J. Cell. Biochem.* 98:920-930; Harte et al. (2010) *Cancer Res.* 70:2538-2547; Drost et al. (2010) *Nat. Cell Biol.* 12:380-389. The known binding partners for BRD7 also include, e.g., Tripartite Motif Containing 24 (TRIM24), Protein Tyrosine Phosphatase, Non-Receptor Type 13 (PTPN13), Dishevelled Segment Polarity Protein 1 (DVL1), interferon regulatory factor 2 (IRF2) (Staal et al. (2000) *J. Cell. Physiol.* US 185:269-279) and heterogeneous nuclear ribonucleoprotein U-like protein 1 (HNRPUL1) (Kzhyshkowska et al. (2003) *Biochem. J. England.* 371:385-393). Human BRD7 protein has 651 amino acids and a molecular mass of 74139 Da, with a N-terminal nuclear localization signal (e.g., amino acids 65-96 of SEQ ID NO:14), a Bromo-BRD7-like domain (e.g., amino acids 135-232 of SEQ ID NO:14), and a DUF3512 domain (e.g., amino acids 287-533 of SEQ ID NO:14).

The term "BRD7" is intended to include fragments, variants (e.g., allelic variants), and derivatives thereof. Representative human BRD7 cDNA and human BRD7 protein sequences are well-known in the art and are publicly available from the National Center for Biotechnology Information (NCBI). For example, two different human BRD7 isoforms are known. Human BRD7 isoform A (NP_001167455.1) is encodable by the transcript variant 1 (NM_001173984.2), which is the longer transcript. Human BRD7 isoform B (NP_037395.2) is encodable by the transcript variant 2 (NM_013263.4), which uses an alternate in-frame splice site in the 3' coding region, compared to variant 1. The resulting isoform B lacks one internal residue, compared to isoform A. Nucleic acid and polypeptide sequences of BRD7 orthologs in organisms other than humans are well-known and include, for example, chimpanzee BRD7 (XM_009430766.2 and XP_009429041.1, XM_016929816.1 and XP_016785305.1, XM_016929815.1 and XP_016785304.1, and XM_003315094.4 and XP_003315142.1), Rhesus monkey BRD7 (XM_015126104.1 and XP_014981590.1, XM_015126103.1 and XP_014981589.1, XM_001083389.3 and XP_001083389.2, and XM_015126105.1 and XP_014981591.1), dog BRD7 (XM_014106954.1 and XP_013962429.1), cattle BRD7 (NM_001103260.2 and NP_001096730.1), mouse BRD7 (NM_012047.2 and NP_036177.1), chicken BRD7 (NM_001005839.1 and NP_001005839.1), tropical clawed frog BRD7 (NM_001008007.1 and NP_001008008.1), and zebrafish BRD7 (NM_213366.2 and NP_998531.2).

Anti-BRD7 antibodies suitable for detecting BRD7 protein are well-known in the art and include, for example, antibody TA343710 (Origene), antibody NBP1-28727 (Novus Biologicals, Littleton, CO), antibodies ab56036, ab46553, ab202324, and ab114061 (AbCam, Cambridge, MA), antibodies Cat #: 15125 and 14910 (Cell Signaling), antibody GTX118755 (GeneTex, Irvine, CA), BRD7 (P-13) Antibody, BRD7 (T-12) Antibody, BRD7 (H-77) Antibody, BRD7 (H-2) Antibody, and BRD7 (B-8) Antibody (Santa Cruz Biotechnology), etc. In addition, reagents are well-known for detecting BRD7 expression. A clinical test of BRD7 is available in NIH Genetic Testing Registry (GTR®) with GTR Test ID: GTR000540400.2, offered by Fulgent Clinical Diagnostics Lab (Temple City, CA)). Moreover, multiple siRNA, shRNA, CRISPR constructs for reducing BRD7 expression can be found in the commercial product lists of the above-referenced companies, such as shRNA product #TR100001 and CRISPER products #KN302255 and KN208734 from Origene Technologies (Rockville, MD), RNAi product H00029117-R01 (Novus Biologicals), and small molecule inhibitors BI 9564 and TP472 (Tocris Bioscience, UK). It is to be noted that the term can further be used to refer to any combination of features described herein regarding BRD7 molecules. For example, any combination of sequence composition, percentage identify, sequence length, domain structure, functional activity, etc. can be used to describe an BRD7 molecule encompassed by the present invention.

The term "BAF45A" or "PHF10" refers to PHD finger protein 10, a subunit of the PBAF complex having two zinc finger domains at its C-terminus. PHF10 belongs to the neural progenitors-specific chromatin remodeling complex (npBAF complex) and is required for the proliferation of neural progenitors. During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. PHF10 gene encodes at least two types of evolutionarily conserved, ubiquitously expressed isoforms that are incorporated into the PBAF complex in a mutually exclusive manner. One isoform contains C-terminal tandem PHD fingers, which in the other isoform are replaced by the consensus sequence for phosphorylation-dependent SUMO 1 conjugation (PDSM) (Brechalov et al. (2014) *Cell Cycle* 13:1970-1979). PBAF complexes containing different PHF10 isoforms can bind to the promoters of the same genes but produce different effects on the recruitment of Pol II to the promoter and on the level of gene transcription. PHF10 is a transcriptional repressor of caspase 3 and impairs the programmed cell death pathway in human gastric cancer at the transcriptional level (Wei et al. (2010) *Mol Cancer Ther.* 9:1764-1774). Knockdown of PHF10 expression in gastric cancer cells led to significant induction of caspase-3 expression at both the RNA and protein levels and thus induced alteration of caspase-3 substrates in a time-dependent manner (Wei et al. (2010), supra). Results from luciferase assays by the same group indicated that PHF10 acted as a transcriptional repressor when the two PHD domains contained in PHF10 were intact. Human PHF1 protein has 498 amino acids and a molecular mass of 56051 Da, with two domains essential to induce neural progenitor proliferation (e.g., amino acids 89-185 and 292-334 of SEQ ID NO:20) and two PHD finger domains (e.g., amino acids 379-433 and 435-478 of SEQ ID NO:20). By similarity, PHF 10 binds to ACTL6A/BAF53A, SMARCA2/BRM/BAF190B, SMARCA4/BRG1/BAF190A and PBRM1/BAF180.

The term “BAF45A” or “PHF10” is intended to include fragments, variants (e.g., allelic variants), and derivatives thereof. Representative human PHF10 cDNA and human PHF10 protein sequences are well-known in the art and are publicly available from the National Center for Biotechnology Information (NCBI). For example, two different human PHF10 isoforms are known. Human PHF10 isoform A (NP_060758.2) is encodable by the transcript variant 1 (NM_018288.3), which is the longer transcript. Human PHF10 isoform B (NP_579866.2) is encodable by the transcript variant 2 (NM_133325.2), which uses an alternate splice junction which results in six fewer nt when compared to variant 1. The isoform B lacks 2 internal amino acids compared to isoform A. Nucleic acid and polypeptide sequences of PHF10 orthologs in organisms other than humans are well-known and include, for example, chimpanzee PHF10 (XM_016956680.1 and XP_016812169.1, XM_016956679.1 and XP_016812168.1, and XM_016956681.1 and XP_016812170.1), Rhesus monkey PHF10 (XM_015137735.1 and XP_014993221.1, and XM_015137734.1 and XP_014993220.1), dog PHF10 (XM_005627727.2 and XP_005627784.1, XM_005627726.2 and XP_005627783.1, XM_532272.5 and XP_532272.4, XM_014118230.1 and XP_013973705.1, and XM_014118231.1 and XP_013973706.1), cattle PHF10 (NM_001038052.1 and NP_001033141.1), mouse PHF10 (NM_024250.4 and NP_077212.3), rat PHF10 (NM_001024747.2 and NP_001019918.2), chicken PHF10 (XM_015284374.1 and XP_015139860.1), tropical clawed frog PHF10 (NM_001030472.1 and NP_001025643.1), zebrafish PHF10 (NM_200655.3 and NP_956949.3), and *C. elegans* PHF10 (NM_001047648.2 and NP_001041113.1, NM_001047647.2 and NP_001041112.1, and NM_001313168.1 and NP_001300097.1).

Anti-PHF10 antibodies suitable for detecting PHF10 protein are well-known in the art and include, for example, antibody TA346797 (Origene), antibodies NBP1-52879, NBP2-19795, NBP2-33759, and H00055274-B01P (Novus Biologicals, Littleton, CO), antibodies ab154637, ab80939, and ab68114 (AbCam, Cambridge, MA), antibody Cat #PA5-30678 (ThermoFisher Scientific), antibody Cat #26-352 (ProSci, Poway, CA), etc. In addition, reagents are well-known for detecting PHF10 expression. A clinical test of PHF10 for hereditary disease is available with the test ID no. GTR000536577 in NIH Genetic Testing Registry (GTR©), offered by Fulgent Clinical Diagnostics Lab (Temple City, CA). Moreover, multiple siRNA, shRNA, CRISPR constructs for reducing PHF10 expression can be found in the commercial product lists of the above-referenced companies, such as siRNA product #sc-95343 and sc-152206 and CRISPER products #sc-410593 from Santa Cruz Biotechnology, RNAi products H00055274-R01 and H00055274-R02 (Novus Biologicals), and multiple CRISPER products from GenScript (Piscataway, N.J.). Human PHF10 knockout cell (from HAP1 cell line) is also available from Horizon Discovery (Cat #HZGHC002778c011, UK). It is to be noted that the term can further be used to refer to any combination of features described herein regarding PHF10 molecules. For example, any combination of sequence composition, percentage identify, sequence length, domain structure, functional activity, etc. can be used to describe an PHF10 molecule encompassed by the present invention.

The term “SMARCC1” refers to SWI/SNF related, matrix associated, actin dependent regulator of chromatin subfamily c member 1. SMARCC1 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and contains a predicted leucine zipper motif typical of many transcription factors. SMARCC1 is a component of SWI/SNF chromatin remodeling complexes that carry out key enzymatic activities, changing chromatin structure by altering DNA-histone contacts within a nucleosome in an ATP-dependent manner. SMARCC1 stimulates the ATPase activity of the catalytic subunit of the complex (Phelan et al. (1999) *Mol Cell* 3:247-253). SMARCC1 belongs to the neural progenitors-specific chromatin remodeling complex (npBAF complex) and the neuron-specific chromatin remodeling complex (nBAF complex). During neural development a switch from a stem/progenitor to a postmitotic chromatin remodeling mechanism occurs as neurons exit the cell cycle and become committed to their adult state. The transition from proliferating neural stem/progenitor cells to postmitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. Human SMARCC1 protein has 1105 amino acids and a molecular mass of 122867 Da. Binding partners of SMARCC1 include, e.g., NR33C1, SMARD1, TRIP12, CEBPB, KDM6B, and MKKS.

The term "SMARCC1" is intended to include fragments, variants (e.g., allelic variants), and derivatives thereof. Representative human SMARCC1 cDNA and human SMARCC1 protein sequences are well-known in the art and are publicly available from the National Center for Biotechnology Information (NCBI). For example, human SMARCC1 protein (NP_003065.3) is encodable by the transcript (NM_003074.3). Nucleic acid and polypeptide sequences of SMARCC1 orthologs in organisms other than humans are well-known and include, for example, chimpanzee SMARCC1 (XM_016940956.2 and XP_016796445.1, XM_001154676.6 and XP_001154676.1, XM_016940957.1 and XP_016796446.1, and XM_009445383.3 and XP_009443658.1), Rhesus monkey SMARCC1 (XM_015126104.1 and XP_014981590.1, XM_015126103.1 and XP_014981589.1, XM_001083389.3 and XP_001083389.2, and XM_015126105.1 and XP_014981591.1), dog SMARCC1 (XM_533845.6 and XP_533845.2, XM_014122183.2 and XP_013977658.1, and XM_014122184.2 and XP_013977659.1), cattle SMARCC1 (XM_024983285.1 and XP_024839053.1), mouse SMARCC1 (NM_009211.2 and NP_033237.2), rat SMARCC1 (NM_001106861.1 and NP_001100331.1), chicken SMARCC1 (XM_025147375.1 and XP_025003143.1, and XM_015281170.2 and XP_015136656.2), tropical clawed frog SMARCC1 (XM_002942718.4 and XP_002942764.2), and zebrafish SMARCC1 (XM_003200246.5 and XP_003200294.1, and XM_005158282.4 and XP_005158339.1).

Anti-SMARCC1 antibodies suitable for detecting SMARCC1 protein are well-known in the art and include, for example, antibody TA334040 (Origene), antibodies NBP1-88720, NBP2-20415, NBP1-88721, and NB100-55312 (Novus Biologicals, Littleton, CO), antibodies ab172638, ab126180, and ab22355 (AbCam, Cambridge, MA), antibody Cat #PA5-30174 (ThermoFisher Scientific), antibody Cat #27-825 (ProSci, Poway, CA), etc. In addition, reagents are well-known for detecting SMARCC1. A clinical test of SMARCC1 for hereditary disease is available with the test ID no. GTR000558444.1 in NIH Genetic Testing Registry (GTR®), offered by Tempus Labs, Inc., (Chicago, Ill.). Moreover, multiple siRNA, shRNA, CRISPR constructs for reducing SMARCC1 expression can be found in the commercial product lists of the above-referenced companies, such as siRNA products #sc-29780 and sc-29781 and CRISPR product #sc-400838 from Santa Cruz Biotechnology, RNAi products SR304474 and TL309245V, and CRISPR product KN208534 (Origene), and multiple CRISPR products from GenScript (Piscataway, N.J.). It is to be noted that the term can further be used to refer to any combination of features described herein regarding SMARCC1 molecules. For example, any combination of sequence composition, percentage identify, sequence length, domain structure, functional activity, etc. can be used to describe a SMARCC1 molecule encompassed by the present invention.

The term "SMARCC2" refers to SWI/SNF related, matrix associated, actin dependent regulator of chromatin subfamily c member 2. SMARCC2 is an important paralog of gene SMARCC1. SMARCC2 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and contains a predicted leucine zipper motif typical of many transcription factors. SMARCC2 is a component of SWI/SNF chromatin remodeling complexes that carry out key enzymatic activities, changing chromatin structure by altering DNA-histone contacts within a nucleosome in an ATP-dependent manner (Kadam et al. (2000) *Genes Dev* 14:2441-2451). SMARCC2 can stimulate the ATPase activity of the catalytic subunit of the complex (Phelan et al. (1999) *Mol Cell* 3:247-253). SMARCC2 is required for CoREST dependent repression of neuronal specific gene promoters in non-neuronal cells (Battaglioli et al. (2002) *J Biol Chem* 277:41038-41045). SMARCC2 belongs to the neural progenitors-specific chromatin remodeling complex (npBAF complex) and the neuron-specific chromatin remodeling complex (nBAF complex). SMARCC2 is a critical regulator of myeloid differentiation, controlling granulocytopoiesis and the expression of genes involved in neutrophil granule formation. Human SMARCC2 protein has 1214 amino acids and a molecular mass of 132879 Da. Binding partners of SMARCC2 include, e.g., SIN3A, SMARD1, KDM6B, and RCOR1.

The term "SMARCC2" is intended to include fragments, variants (e.g., allelic variants), and derivatives thereof. Representative human SMARCC2 cDNA (NM_003074.3) and human SMARCC2 protein sequences (NP_003065.3) are well-known in the art and are publicly available from the National Center for Biotechnology Information (NCBI). For example, four different human SMARCC2 isoforms are known. Human SMARCC2 isoform a (NP_003066.2) is encodable by the transcript variant 1 (NM_003075.4). Human SMARCC2 isoform b (NP_620706.1) is encodable by the transcript variant 2 (NM_139067.3), which contains an alternate in-frame exon in the central coding region and uses an alternate in-frame splice site in the 3' coding region, compared to variant 1. The encoded isoform (b), contains a novel internal segment, lacks a segment near the C-terminus, and is shorter than isoform a. Human SMARCC2 isoform c (NP_001123892.1) is encodable by the transcript variant 3 (NM_001130420.2), which contains an alternate in-frame exon in the central coding region and contains alternate in-frame segment in the 3' coding region, compared to variant 1. The encoded isoform (c), contains a novel internal segment, lacks a segment near the C-terminus, and is shorter than isoform a. Human SMARCC2 isoform d (NP_001317217.1) is encodable by the transcript variant 4 (NM_001330288.1), which contains an alternate in-frame exon in the central coding region compared to variant 1. The encoded isoform (d), contains the same N- and C-termini, but is longer than isoform a. Nucleic acid and polypeptide sequences of SMARCC2 orthologs in organisms other than humans are well-known and include, for example, chimpanzee SMARCC2 (XM_016923208.2 and XP_016778697.1, XM_016923212.2 and XP_016778701.1, XM_016923214.2 and XP_016778703.1, XM_016923210.2 and XP_016778699.1, XM_016923209.2 and XP_016778698.1, XM_016923213.2 and XP_016778702.1, XM_016923211.2 and XP_016778700.1, and XM_016923216.2 and XP_016778705.1), Rhesus monkey SMARCC2 (XM_015151975.1 and XP_015007461.1, XM_015151976.1 and XP_015007462.1, XM_015151974.1 and XP_015007460.1, XM_015151969.1 and XP_015007455.1, XM_015151972.1 and XP_015007458.1, XM_015151973.1 and XP_015007459.1, and XM_015151970.1 and XP_015007456.1), dog SMARCC2 (XM_022424046.1 and XP_022279754.1, XM_014117150.2 and XP_013972625.1, XM_014117149.2 and XP_013972624.1, XM_005625493.3 and XP_005625550.1, XM_014117151.2 and XP_013972626.1, XM_005625492.3 and XP_005625549.1, XM_005625495.3 and XP_005625552.1, XM_005625494.3 and XP_005625551.1, and XM_022424047.1 and XP_022279755.1), cattle SMARCC2 (NM_001172224.1 and NP_001165695.1), mouse SMARCC1 (NM_001114097.1 and NP_001107569.1, NM_001114096.1 and NP_001107568.1, and NM_198160.2 and NP_937803.1), rat SMARCC2 (XM_002729767.5 and XP_002729813.2, XM_006240805.3 and XP_006240867.1, XM_006240806.3 and XP_006240868.1, XM_001055795.6 and XP_001055795.1, XM_006240807.3 and XP_006240869.1, XM_008765050.2 and XP_008763272.1, XM_017595139.1 and XP_017450628.1, XM_001055673.6 and XP_001055673.1, and XM_001055738.6 and XP_001055738.1), and zebrafish SMARCC2 (XM_021474611.1 and XP_021330286.1).

Anti-SMARCC2 antibodies suitable for detecting SMARCC2 protein are well-known in the art and include, for example, antibody TA314552 (Origene), antibodies NBP1-90017 and NBP2-57277 (Novus Biologicals, Littleton, CO), antibodies ab71907, ab84453, and ab64853 (AbCam, Cambridge, MA), antibody Cat #PA5-54351 (ThermoFisher Scientific), etc. In addition, reagents are well-known for detecting SMARCC2. A clinical test of SMARCC2 for hereditary disease is available with the test ID no. GTR000546600.2 in NIH Genetic Testing Registry (GTR®), offered by Fulgent Clinical Diagnostics Lab (Temple City, CA). Moreover, multiple siRNA, shRNA, CRISPR constructs for reducing SMARCC2 expression can be found in the commercial product lists of the above-referenced companies, such as siRNA products #sc-29782 and sc-29783 and CRISPR product #sc-402023 from Santa Cruz Biotechnology, RNAi products SR304475 and TL301505V, and CRISPR product KN203744 (Origene), and multiple CRISPR products from GenScript (Piscataway, N.J.). It is to be noted that the term can further be used to refer to any combination of features described herein regarding SMARCC2 molecules. For example, any combination of sequence composition, percentage identify, sequence length, domain structure, functional activity, etc. can be used to describe a SMARCC2 molecule encompassed by the present invention.

The term "SMARCD1" refers to SWI/SNF related, matrix associated, actin dependent regulator of chromatin subfamily D member 1. SMARCD1 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and has sequence similarity to the yeast Swp73 protein. SMARCD1 is a component of SWI/SNF chromatin remodeling complexes that carry out key enzymatic activities, changing chromatin structure by altering DNA-histone contacts within a nucleosome in an ATP-dependent manner (Wang et al. (1996) Genes Dev 10:2117-2130). SMARCD1 belongs to the neural progenitors-specific chromatin remodeling complex (npBAF complex) and the neuron-specific chromatin remodeling complex (nBAF complex). SMARCD1 has a strong influence on vitamin D-mediated transcriptional activity from an enhancer vitamin D receptor element (VDRE). SMARCD1 a link between mammalian SWI-SNF-like chromatin remodeling complexes and the vitamin D receptor (VDR) heterodimer (Koszewski et al. (2003) *J Steroid Biochem Mol Biol* 87:223-231). SMARCD1 mediates critical interactions between nuclear receptors and the BRG1/SMARCA4 chromatin-remodeling complex for transactivation (Hsiao et al. (2003) *Mol Cell Biol* 23:6210-6220). Human SMARCD1 protein has 515 amino acids and a molecular mass of 58233 Da. Binding partners of SMARCD1 include, e.g., ESR1, NR3C1, NR1H4, PGR, SMARCA4, SMARCC1 and SMARCC2.

The term "SMARCD1" is intended to include fragments, variants (e.g., allelic variants), and derivatives thereof. Representative human SMARCD1 cDNA and human SMARCD1 protein sequences are well-known in the art and are publicly available from the National Center for Biotechnology Information (NCBI). For example, two different human SMARCD1 isoforms are known. Human SMARCD1 isoform a (NP_003067.3) is encodable by the transcript variant 1 (NM_003076.4), which is the longer transcript. Human SMARCD1 isoform b (NP_620710.2) is encodable by the transcript variant 2 (NM_139071.2), which lacks an alternate in-frame exon, compared to variant 1, resulting in a shorter protein (isoform b), compared to isoform a. Nucleic acid and polypeptide sequences of SMARCD1 orthologs in organisms other than humans are well-known and include, for example, chimpanzee SMARCD1 (XM_016923432.2 and XP_016778921.1, XM_016923431.2 and XP_016778920.1, and XM_016923433.2 and XP_016778922.1), Rhesus monkey SMARCD1 (XM_001111275.3 and XP_001111275.3, XM_001111166.3 and XP_001111166.3, and XM_001111207.3 and XP_001111207.3), dog SMARCD1 (XM_543674.6 and XP_543674.4), cattle SMARCD1 (NM_001038559.2 and NP_001033648.1), mouse SMARCD1 (NM_031842.2 and NP_114030.2), rat SMARCD1 (NM_001108752.1 and NP_001102222.1), chicken SMARCD1 (XM_424488.6 and XP_424488.3), tropical clawed frog SMARCD1 (NM_001004862.1 and NP_001004862.1), and zebrafish SMARCD1 (NM_198358.1 and NP_938172.1).

Anti-SMARCD1 antibodies suitable for detecting SMARCD1 protein are well-known in the art and include, for example, antibody TA344378 (Origene), antibodies NBP1-88719 and NBP2-20417 (Novus Biologicals, Littleton, CO), antibodies ab224229, ab83208, and ab86029 (AbCam, Cambridge, MA), antibody Cat #PA5-52049 (ThermoFisher Scientific), etc. In addition, reagents are well-known for detecting SMARCD1. A clinical test of SMARCD1 for hereditary disease is available with the test ID no. GTR000558444.1 in NIH Genetic Testing Registry (GTR®), offered by Tempus Labs, Inc., (Chicago, Ill.). Moreover, multiple siRNA, shRNA, CRISPR constructs for reducing SMARCD1 expression can be found in the commercial product lists of the above-referenced companies, such as siRNA products #sc-72597 and sc-725983 and CRISPR product #sc-402641 from Santa Cruz Biotechnology, RNAi products SR304476 and TL301504V, and CRISPR product KN203474 (Origene), and multiple CRISPR products from GenScript (Piscataway, N.J.). It is to be noted that the term can further be used to refer to any combination of features described herein regarding SMARCD1 molecules. For example, any combination of sequence composition, percentage identify, sequence length, domain structure, functional activity, etc. can be used to describe a SMARCD1 molecule encompassed by the present invention.

The term "SMARCD2" refers to SWI/SNF related, matrix associated, actin dependent regulator of chromatin subfamily D member 2. SMARCD2 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and has sequence similarity to the yeast Swp73 protein. SMARCD2 is a component of SWI/SNF chromatin remodeling complexes that carry out key enzymatic activities, changing chromatin structure by altering DNA-histone contacts within a nucleosome in an ATP-dependent manner (Euskirchen et al. (2012) *J Biol Chem* 287:30897-30905; Kadoch et al. (2015) *Sci Adv* 1(5):e1500447). SMARCD2 is a critical regulator of myeloid differentiation, controlling granulocytopoiesis and the expression of genes involved in neutrophil granule formation (Witzel et al. (2017) *Nat Genet* 49:742-752). Human SMARCD2 protein has 531 amino acids and a molecular mass of 589213 Da. Binding partners of SMARCD2 include, e.g., UNKL and CEBPE.

The term "SMARCD2" is intended to include fragments, variants (e.g., allelic variants), and derivatives thereof. Representative human SMARCD2 cDNA and human SMARCD2 protein sequences are well-known in the art and are publicly available from the National Center for Biotechnology Information (NCBI). For example, three different human SMARCD2 isoforms are known. Human SMARCD2 isoform 1 (NP_001091896.1) is encodable by the transcript variant 1 (NM_001098426.1). Human SMARCD2 isoform 2 (NP_001317368.1) is encodable by the transcript variant 2 (NM_001330439.1). Human SMARCD2 isoform 3 (NP_001317369.1) is encodable by the transcript variant 3 (NM_001330440.1). Nucleic acid and polypeptide sequences of SMARCD2 orthologs in organisms other than humans are well-known and include, for example, chimpanzee SMARCD2 (XM_009433047.3 and XP_009431322.1, XM_001148723.6 and XP_001148723.1, XM_009433048.3 and XP_009431323.1, XM_009433049.3 and XP_009431324.1, XM_024350546.1 and XP_024206314.1, and XM_024350547.1 and XP_024206315.1), Rhesus monkey SMARCD2 (XM_015120093.1 and XP_014975579.1), dog SMARCD2 (XM_022422831.1 and XP_022278539.1, XM_005624251.3 and XP_005624308.1, XM_845276.5 and XP_850369.1, and XM_005624252.3 and XP_005624309.1), cattle SMARCD2 (NM_001205462.3 and NP_001192391.1), mouse SMARCC1 (NM_001130187.1 and NP_001123659.1, and NM_031878.2 and NP_114084.2), rat SMARCD2 (NM_031983.2 and NP_114189.1), chicken SMARCD2 (XM_015299406.2 and XP_015154892.1), tropical clawed frog SMARCD2 (NM_001045802.1 and NP_001039267.1), and zebrafish SMARCD2 (XM_687657.6 and XP_692749.2, and XM_021480266.1 and XP_021335941.1).

Anti-SMARCD2 antibodies suitable for detecting SMARCD2 protein are well-known in the art and include, for example, antibody TA335791 (Origene), antibodies H00006603-M02 and H00006603-M01 (Novus Biologicals, Littleton, CO), antibodies ab81622, ab56241, and ab221084 (AbCam, Cambridge, MA), antibody Cat #51-805 (ProSci, Poway, CA), etc. In addition, reagents are well-known for detecting SMARCD2. A clinical test of SMARCD2 for hereditary disease is available with the test ID no. GTR000558444.1 in NIH Genetic Testing Registry (GTR®), offered by Tempus Labs, Inc., (Chicago, Ill.). Moreover, multiple siRNA, shRNA, CRISPR constructs for reducing SMARCD2 expression can be found in the commercial product lists of the above-referenced companies, such as siRNA products #sc-93762 and sc-153618 and CRISPR product #sc-403091 from Santa Cruz Biotechnology, RNAi products SR304477 and TL309244V, and CRISPR product KN214286 (Origene), and multiple CRISPR products from GenScript (Piscataway, N.J.). It is to be noted that the term can further be used to refer to any combination of features described herein regarding SMARCD2 molecules. For example, any combination of sequence composition, percentage identify, sequence length, domain structure, functional activity, etc. can be used to describe a SMARCD2 molecule encompassed by the present invention.

The term "SMARCD3" refers to SWI/SNF related, matrix associated, actin dependent regulator of chromatin subfamily D member 3. SMARCD3 is a member of the SWI/SNF family of proteins, whose members display helicase and ATPase activities and which are thought to regulate transcription of certain genes by altering the chromatin structure around those genes. The encoded protein is part of the large ATP-dependent chromatin remodeling complex SNF/SWI and has sequence similarity to the yeast Swp73 protein. SMARCD3 is a component of SWI/SNF chromatin remodeling complexes that carry out key enzymatic activities, changing chromatin structure by altering DNA-histone contacts within a nucleosome in an ATP-dependent manner. SMARCD3 stimulates nuclear receptor mediated transcription. SMARCD3 belongs to the neural progenitors-specific chromatin remodeling complex (npBAF complex) and the neuron-specific chromatin remodeling complex (nBAF complex). Human SMARCD3 protein has 483 amino acids and a molecular mass of 55016 Da. Binding partners of SMARCD3 include, e.g., PPARG/NR1C3, RXRA/NR1F1, ESR1, NR5A1, NR5A2/LRH1 and other transcriptional activators including the HLH protein SREBF1/SREBP1 and the homeobox protein PBX1.

The term "SMARCD3" is intended to include fragments, variants (e.g., allelic variants), and derivatives thereof. Representative human SMARCD3 cDNA and human SMARCD3 protein sequences are well-known in the art and are publicly available from the National Center for Biotechnology Information (NCBI). For example, two different human SMARCD3 isoforms are known. Human SMARCD3 isoform 1 (NP_001003802.1 and NP_003069.2) is encodable by the transcript variant 1 (NM_001003802.1) and the transcript variant 2 (NM_003078.3). Human SMARCD2 isoform 2 (NP_001003801.1) is encodable by the transcript variant 3 (NM_001003801.1). Nucleic acid and polypeptide sequences of SMARCD3 orthologs in organisms other than humans are well-known and include, for example, chimpanzee SMARCD3 (XM_016945944.2 and XP_016801433.1, XM_016945946.2 and XP_016801435.1, XM_016945945.2 and XP_016801434.1, and XM_016945943.2 and XP_016801432.1), Rhesus monkey SMARCD3 (NM_001260684.1 and NP_001247613.1), cattle SMARCD3 (NM_001078154.1 and NP_001071622.1), mouse SMARCC3 (NM_025891.3 and NP_080167.3), rat SMARCD3 (NM_001011966.1 and NP_001011966.1).

Anti-SMARCD3 antibodies suitable for detecting SMARCD3 protein are well-known in the art and include, for example, antibody TA811107 (Origene), antibodies H00006604-M01 and NBP2-39013 (Novus Biologicals, Littleton, CO), antibodies ab171075, ab131326, and ab50556 (AbCam, Cambridge, MA), antibody Cat #720131 (ThermoFisher Scientific), antibody Cat #28-327 (ProSci, Poway, CA), etc. In addition, reagents are well-known for detecting SMARCD3. A clinical test of SMARCD3 for hereditary disease is available with the test ID no. GTR000558444.1 in NIH Genetic Testing Registry (GTR®), offered by Tempus Labs, Inc., (Chicago, Ill.). Moreover, multiple siRNA, shRNA, CRISPR constructs for reducing SMARCD3 expression can be found in the commercial product lists of the above-referenced companies, such as siRNA products #sc-89355 and sc-108054 and CRISPR product #sc-402705 from Santa Cruz Biotechnology, RNAi products SR304478 and TL309243V, and CRISPR product KN201135 (Origene), and multiple CRISPR products from GenScript (Piscataway, N.J.). It is to be noted that the term can further be used to refer to any combination of features described herein regarding SMARCD3 molecules. For example, any combination of sequence composition, percentage identify, sequence length, domain structure, functional activity, etc. can be used to describe a SMARCD3 molecule encompassed by the present invention.

The term "SMARCB1" refers to SWI/SNF related, matrix associated, actin dependent regulator of chromatin subfamily B member 1. The protein encoded by this gene is part of a complex that relieves repressive chromatin structures, allowing the transcriptional machinery to access its targets more effectively. The encoded nuclear protein may also bind to and enhance the DNA joining activity of HIV-1 integrase. This gene has been found to be a tumor suppressor, and mutations in it have been associated with malignant rhabdoid tumors. SMARCB1 is a core component of the BAF (SWI/SNF) complex. This ATP-dependent chromatin-remodeling complex plays important roles in cell proliferation and differentiation, in cellular antiviral activities and inhibition of tumor formation. The BAF complex is able to create a stable, altered form of chromatin that constrains fewer negative supercoils than normal. This change in supercoiling would be due to the conversion of up to one-half of the nucleosomes on polynucleosomal arrays into asymmetric structures, termed altosomes, each composed of 2 histones octamers. SMARCB1 stimulates in vitro the remodeling activity of SMARCA4/BRG1/BAF190A. SMARCB1 is involved in activation of CSF1 promoter. SMARCB1 belongs to the neural progenitors-specific chromatin remodeling complex (npBAF complex) and the neuron-specific chromatin remodeling complex (nBAF complex). SMARCB1 plays a key role in cell-cycle control and causes cell cycle arrest in G0/G1. Human SMARCB1 protein has 385 amino acids and a molecular mass of 44141 Da. Binding partners of SMARCB1 include, e.g., CEBPB, PIH1D1, MYK, PPP1R15A, and MAEL. SMARCB1 binds tightly to the human immunodeficiency virus-type 1 (HIV-1) integrase in vitro and stimulates its DNA-joining activity. SMARCB1 interacts with human papillomavirus 18 E1 protein to stimulate its viral replication (Lee et al. (1999) *Nature* 399:487-491). SMARCB1 interacts with Epstein-Barr virus protein EBNA-2 (Wu et al. (1996) *J Virol* 70:6020-6028). SMARCB1 binds to double-stranded DNA.

The term "SMARCB1" is intended to include fragments, variants (e.g., allelic variants), and derivatives thereof. Representative human SMARCB1 cDNA and human SMARCB1 protein sequences are well-known in the art and are publicly available from the National Center for Biotechnology Information (NCBI). For example, four different human SMARCB1 isoforms are known. Human SMARCB1 isoform a (NP_003064.2) is encodable by the transcript variant 1 (NM_003073.4). Human SMARCB1 isoform b (NP_001007469.1) is encodable by the transcript variant 2 (NM_001007468.2). Human SMARCB1 isoform c (NP_001304875.1) is encodable by the transcript variant 3 (NM_001317946.1). Human SMARCB1 isoform d (NP_001349806.1) is encodable by the transcript variant 4 (NM_001362877.1). Nucleic acid and polypeptide sequences of SMARCB1 orthologs in organisms other than humans are well-known and include, for example, chimpanzee SMARCC1 (XM_001169712.6 and XP_001169712.1, XM_016939577.2 and XP_016795066.1, XM_515023.6 and XP_515023.2, and XM_016939576.2 and XP_016795065.1), Rhesus monkey SMARCB1 (NM_001257888.2 and NP_001244817.1), dog SMARCB1 (XM_543533.6 and XP_543533.2, and XM_852177.5 and XP_857270.2), cattle SMARCB1 (NM_001040557.2 and NP_001035647.1), mouse SMARCB1 (NM_011418.2 and NP_035548.1, and NM_001161853.1 and NP_001155325.1), rat SMARCB1 (NM_001025728.1 and NP_001020899.1), chicken SMARCB1 (NM_001039255.1 and NP_001034344.1), tropical clawed frog SMARCB1 (NM_001006818.1 and NP_001006819.1), and zebrafish SMARCB1 (NM_001007296.1 and NP_001007297.1). Representative sequences of SMARCB1 orthologs are presented below in Table 1.

Anti-SMARCB1 antibodies suitable for detecting SMARCB1 protein are well-known in the art and include, for example, antibody TA350434 (Origene), antibodies H00006598-M01 and NBP1-90014 (Novus Biologicals, Littleton, CO), antibodies ab222519, ab12167, and ab192864 (AbCam, Cambridge, MA), antibody Cat #PA5-53932 (ThermoFisher Scientific), antibody Cat #51-916 (ProSci, Poway, CA), etc. In addition, reagents are well-known for detecting SMARCB1. A clinical test of SMARCB1 for hereditary disease is available with the test ID no. GTR000517131.2 in NIH Genetic Testing Registry (GTR®), offered by Fulgent Genetics Clinical Diagnostics Lab (Temple City, CA). Moreover, multiple siRNA, shRNA, CRISPR constructs for reducing SMARCB1 expression can be found in the commercial product lists of the above-referenced companies, such as siRNA products #sc-304473 and sc-35670 and CRISPR product #sc-401485 from Santa Cruz Biotechnology, RNAi products SR304478 and TL309246V, and CRISPR product KN217885 (Origene), and multiple CRISPR products from GenScript (Piscataway, N.J.). It is to be noted that the term can further be used to refer to any combination of features described herein regarding SMARCB1 molecules. For example, any combination of sequence composition, percentage identify, sequence length, domain structure, functional activity, etc. can be used to describe a SMARCB1 molecule encompassed by the present invention.

In some embodiments, the term "modified SMARCB1" refers to any mutation in a SMARCB1-related nucleic acid or protein that results in modification of a desired (e.g., reduced or eliminated) SMARCB1 amount and/or function. For example, nucleic acid mutations include single-base substitutions, multi-base substitutions, insertion mutations, deletion mutations, frameshift mutations, missense mutations, nonsense mutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of SMARCB1. Such mutations modulate SMARCB1 protein amounts and/or function by modifying coding sequences required for SMARCB1 protein translation and/or coding for SMARCB1 proteins that are non-functional or have modified function (e.g., change in charge of structural domains, modulation of protein stability, alteration of sub-cellular localization, and the like). Such mutations are well-known in the art. In addition, a representative list describing a wide variety of structural mutations correlated with the functional result of modifying SMARCB1 protein amounts and/or function is described in the Tables and the Examples.

The term "SMARCE1" refers to SWI/SNF related, matrix associated, actin dependent regulator of chromatin subfamily E member 1. The protein encoded by this gene is part of the large ATP-dependent chromatin remodeling complex SWI/SNF, which is required for transcriptional activation of genes normally repressed by chromatin. The encoded protein, either alone or when in the SWI/SNF complex, can bind to 4-way junction DNA, which is thought to mimic the topology of DNA as it enters or exits the nucleosome. The protein contains a DNA-binding HMG domain, but disruption of this domain does not abolish the DNA-binding or nucleosome-displacement activities of the SWI/SNF complex. Unlike most of the SWI/SNF complex proteins, this protein has no yeast counterpart. SMARCE1 is a component of SWI/SNF chromatin remodeling complexes that carry out key enzymatic activities, changing chromatin structure by altering DNA-histone contacts within a nucleosome in an ATP-dependent manner. SMARCE1 belongs to the neural progenitors-specific chromatin remodeling complex (npBAF complex) and the neuron-specific chromatin remodeling complex (nBAF complex). SMARCE1 is required for the coactivation of estrogen responsive promoters by SWI/SNF complexes and the SRC/p160 family of histone acetyltransferases (HATs). SMARCE1 also specifically interacts with the CoREST corepressor resulting in repression of neuronal specific gene promoters in non-neuronal cells. Human SMARCE1 protein has 411 amino acids and a molecular mass of 46649 Da. SMARCE1 interacts with BRDT, and also binds to the SRC/p160 family of histone acetyltransferases (HATs) composed of NCOA1, NCOA2, and NCOA3. SMARCE1 interacts with RCOR1/CoREST, NR3C1 and ZMIM2/ZIMP7.

The term "SMARCE1" is intended to include fragments, variants (e.g., allelic variants), and derivatives thereof. Representative human SMARCE1 cDNA and human SMARCE1 protein sequences are well-known in the art and are publicly available from the National Center for Biotechnology Information (NCBI). For example, human SMARCE1 protein (NP_003070.3) is encodable by transcript (NM_003079.4). Nucleic acid and polypeptide sequences of SMARCE1 orthologs in organisms other than humans are well-known and include, for example, chimpanzee SMARCE1 (XM_009432223.3 and XP_009430498.1, XM_511478.7 and XP_511478.2, XM_009432222.3 and XP_009430497.1, and XM_001169953.6 and XP_001169953.1), Rhesus monkey SMARCE1 (NM_001261306.1 and NP_001248235.1), cattle SMARCE1 (NM_001099116.2 and NP_001092586.1), mouse SMARCE1 (NM_020618.4 and NP_065643.1), rat SMARCE1 (NM_001024993.1 and NP_001020164.1), chicken SMARCE1 (NM_001006335.2 and NP_001006335.2), tropical clawed frog SMARCE1 (NM_001005436.1 and NP_001005436.1), and zebrafish SMARCE1 (NM_201298.1 and NP_958455.2).

Anti-SMARCE1 antibodies suitable for detecting SMARCE1 protein are well-known in the art and include, for example, antibody TA335790 (Origene), antibodies NBP1-90012 and NB100-2591 (Novus Biologicals, Littleton, CO), antibodies ab131328, ab228750, and ab137081 (AbCam, Cambridge, MA), antibody Cat #PA5-18185 (ThermoFisher Scientific), antibody Cat #57-670 (ProSci, Poway, CA), etc. In addition, reagents are well-known for detecting SMARCE1. A clinical test of SMARCE1 for hereditary disease is available with the test ID no. GTR000558444.1 in NIH Genetic Testing Registry (GTR®), offered by Tempus Labs, Inc., (Chicago, Ill.). Moreover, multiple siRNA, shRNA, CRISPR constructs for reducing SMARCE1 expression can be found in the commercial product lists of the above-referenced companies, such as siRNA products #sc-45940 and sc-45941 and CRISPR product #sc-404713 from Santa Cruz Biotechnology, RNAi products SR304479 and TL309242, and CRISPR product KN217885 (Origene), and multiple CRISPR products from GenScript (Piscataway, N.J.). It is to be noted that the term can further be used to refer to any combination of features described herein regarding SMARCE1 molecules. For example, any combination of sequence composition, percentage identify, sequence length, domain structure, functional activity, etc. can be used to describe a SMARCE1 molecule encompassed by the present invention.

The term "DPF1" refers to Double PHD Fingers 1. DPF1 has an important role in developing neurons by participating in regulation of cell survival, possibly as a neurospecific transcription factor. DPF1 belongs to the neuron-specific chromatin remodeling complex (nBAF complex). During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. Human DPF1 protein has 380 amino acids and a molecular mass of 425029 Da. DPF1 is a component of neuron-specific chromatin remodeling complex (nBAF complex) composed of at least, ARID1A/BAF250A or ARID1B/BAF250B, SMARCD1/BAF60A, SMARCD3/BAF60C, SMARCA2/BRM/BAF190B, SMARCA4/BRG1/BAF190A, SMARCB1/BAF47, SMARCC1/BAF155, SMARCE1/BAF57, SMARCC2/BAF170, DPF1/BAF45B, DPF3/BAF45C, ACTL6B/BAF53B and actin.

The term "DPF1" is intended to include fragments, variants (e.g., allelic variants), and derivatives thereof. Representative human DPF1 cDNA and human DPF1 protein sequences are well-known in the art and are publicly available from the National Center for Biotechnology Information (NCBI). For example, five different human DPF1 isoforms are known. Human DPF1 isoform a (NP_001128627.1) is encodable by the transcript variant 1 (NM_001135155.2). Human DPF1 isoform b (NP_004638.2) is encodable by the transcript variant 2 (NM_004647.3). Human DPF1 isoform c (NP_001128628.1) is encodable by the transcript variant 3 (NM_001135156.2). Human DPF1 isoform d (NP_001276907.1) is encodable by the transcript variant 4

(NM_001289978.1). Human DPF1 isoform e (NP_001350508.1) is encodable by the transcript variant 5 (NM_001363579.1). Nucleic acid and polypeptide sequences of DPF1 orthologs in organisms other than humans are well-known and include, for example, Rhesus monkey DPF1 (XM_015123830.1 and XP_014979316.1, XM_015123829.1 and XP_014979315.1, XM_015123835.1 and XP_014979321.1, XM_015123831.1 and XP_014979317.1, XM_015123833.1 and XP_014979319.1, and XM_015123832.1 and XP_014979318.1), cattle DPF1 (NM_001076855.1 and NP_001070323.1), mouse DPF1 (NM_013874.2 and NP_038902.1), rat DPF1 (NM_001105729.3 and NP_001099199.2), and tropical clawed frog DPF1 (NM_001097276.1 and NP_001090745.1).

Anti-DPF1 antibodies suitable for detecting DPF1 protein are well-known in the art and include, for example, antibody TA311193 (Origene), antibodies NBP2-13932 and NBP2-19518 (Novus Biologicals, Littleton, CO), antibodies ab199299, ab173160, and ab3940 (AbCam, Cambridge, MA), antibody Cat #PA5-61895 (ThermoFisher Scientific), antibody Cat #28-079 (ProSci, Poway, CA), etc. In addition, reagents are well-known for detecting DPF1. Moreover, multiple siRNA, shRNA, CRISPR constructs for reducing DPF1 expression can be found in the commercial product lists of the above-referenced companies, such as siRNA products #sc-97084 and sc-143155 and CRISPR product #sc-409539 from Santa Cruz Biotechnology, RNAi products SR305389 and TL313388V, and CRISPR product KN213721 (Origene), and multiple CRISPR products from GenScript (Piscataway, N.J.). It is to be noted that the term can further be used to refer to any combination of features described herein regarding DPF1 molecules. For example, any combination of sequence composition, percentage identify, sequence length, domain structure, functional activity, etc. can be used to describe a DPF1 molecule encompassed by the present invention.

The term "DPF2" refers to Double PHD Fingers 2. DPF2 protein is a member of the d4 domain family, characterized by a zinc finger-like structural motif. It functions as a transcription factor which is necessary for the apoptotic response following deprivation of survival factors. It likely serves a regulatory role in rapid hematopoietic cell growth and turnover. This gene is considered a candidate gene for multiple endocrine neoplasia type I, an inherited cancer syndrome involving multiple parathyroid, enteropancreatic, and pituitary tumors. DPF2 is a transcription factor required for the apoptosis response following survival factor withdrawal from myeloid cells. DPF2 also has a role in the development and maturation of lymphoid cells. Human DPF2 protein has 391 amino acids and a molecular mass of 44155 Da.

The term "DPF2" is intended to include fragments, variants (e.g., allelic variants), and derivatives thereof. Representative human DPF2 cDNA and human DPF2 protein sequences are well-known in the art and are publicly available from the National Center for Biotechnology Information (NCBI). For example, two different human DPF2 isoforms are known. Human DPF2 isoform 1 (NP_006259.1) is encodable by the transcript variant 1 (NM_006268.4). Human DPF2 isoform 2 (NP_001317237.1) is encodable by the transcript variant 2 (NM_001330308.1). Nucleic acid and polypeptide sequences of DPF2 orthologs in organisms other than humans are well-known and include, for example, chimpanzee DPF2 (NM_001246651.1 and NP_001233580.1), Rhesus monkey DPF2 (XM_002808062.2 and XP_002808108.2, and XM_015113800.1 and XP_014969286.1), dog DPF2 (XM_861495.5 and XP_866588.1, and XM_005631484.3 and XP_005631541.1), cattle DPF2 (NM_001100356.1 and NP_001093826.1), mouse DPF2 (NM_001291078.1 and NP_001278007.1, and NM_011262.5 and NP_035392.1), rat DPF2 (NM_001108516.1 and NP_001101986.1), chicken DPF2 (NM_204331.1 and NP_989662.1), tropical clawed frog DPF2 (NM_001197172.2 and NP_001184101.1), and zebrafish DPF2 (NM_001007152.1 and NP_001007153.1).

Anti-DPF2 antibodies suitable for detecting DPF2 protein are well-known in the art and include, for example, antibody TA312307 (Origene), antibodies NBP1-76512 and NBP1-87138 (Novus Biologicals, Littleton, CO), antibodies ab134942, ab232327, and ab227095 (AbCam, Cambridge, MA), etc. In addition, reagents are well-known for detecting DPF2. A clinical test of DPF2 for hereditary disease is available with the test ID no. GTR000536833.2 in NIH Genetic Testing Registry (GTR®), offered by Fulgent Genetics Clinical Diagnostics Lab (Temple City, CA). Moreover, multiple siRNA, shRNA, CRISPR constructs for reducing DPF2 expression can be found in the commercial product lists of the above-referenced companies, such as siRNA products #sc-97031 and sc-143156 and CRISPR product #sc-404801-KO-2 from Santa Cruz Biotechnology, RNAi products SR304035 and TL313387V, and CRISPR product KN202364 (Origene), and multiple CRISPR products from GenScript (Piscataway, N.J.). It is to be noted that the term can further be used to refer to any combination of features described herein regarding DPF2 molecules. For example, any combination of sequence composition, percentage identify, sequence length, domain structure, functional activity, etc. can be used to describe a DPF2 molecule encompassed by the present invention.

The term "DPF3" refers to Double PHD Fingers 3, a member of the D4 protein family. The encoded protein is a transcription regulator that binds acetylated histones and is a component of the BAF chromatin remodeling complex. DPF3 belongs to the neuron-specific chromatin remodeling complex (nBAF complex). During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth (By similarity). DPF3 is a muscle-specific component of the BAF complex, a multiprotein complex involved in transcriptional activation and repression of select genes by chromatin remodeling (alteration of DNA-nucleosome topology). DPF3 specifically binds acetylated lysines on histone 3 and 4 (H3K14ac, H3K9ac, H4K5ac, H4K8ac, H4K12ac, H4K16ac). In the complex, DPF3 acts as a tissue-specific anchor between histone acetylations and methylations and chromatin remodeling. DPF3 plays an essential role in heart and skeletal muscle development. Human DPF3 protein has 378 amino acids and a molecular mass of 43084 Da. The PHD-type zinc fingers of DPF3 mediate its binding to acetylated histones. DPF3 belongs to the requiem/DPF family.

The term "DPF3" is intended to include fragments, variants (e.g., allelic variants), and derivatives thereof. Representative human DPF3 cDNA and human DPF3 protein sequences are well-known in the art and are publicly available from the National Center for Biotechnology Information (NCBI). For example, four different human DPF3 isoforms are known. Human DPF3 isoform 1 (NP_036206.3) is encodable by the transcript variant 1 (NM_012074.4). Human DPF3 isoform 2 (NP_001267471.1) is encodable by the transcript variant 2 (NM_001280542.1). Human DPF3 isoform 3 (NP_001267472.1) is encodable by the transcript variant 3 (NM_001280543.1). Human DPF3 isoform 4 (NP_001267473.1) is encodable by the transcript variant 4 (NM_001280544.1). Nucleic acid and polypeptide sequences of DPF3 orthologs in organisms other than humans are well-known and include, for example, chimpanzee DPF3 (XM_016926314.2 and XP_016781803.1, XM_016926316.2 and XP_016781805.1, and XM_016926315.2 and XP_016781804.1), dog DPF3 (XM_014116039.1 and XP_013971514.1), mouse DPF3 (NM_001267625.1 and NP_001254554.1, NM_001267626.1 and NP_001254555.1, and NM_058212.2 and NP_478119.1), chicken DPF3 (NM_204639.2 and NP_989970.1), tropical clawed frog DPF3 (NM_001278413.1 and NP_001265342.1), and zebrafish DPF3 (NM_001111169.1 and NP_001104639.1).

Anti-DPF3 antibodies suitable for detecting DPF3 protein are well-known in the art and include, for example, antibody TA335655 (Origene), antibodies NBP2-49494 and NBP2-14910 (Novus Biologicals, Littleton, CO), antibodies ab180914, ab127703, and ab85360 (AbCam, Cambridge, MA), antibody PA5-38011 (ThermoFisher Scientific), antibody Cat #7559 (ProSci, Poway, CA), etc. In addition, reagents are well-known for detecting DPF3. Moreover, multiple siRNA, shRNA, CRISPR constructs for reducing DPF3 expression can be found in the commercial product lists of the above-referenced companies, such as siRNA products #sc-97031 and sc-92150 and CRISPR product #sc-143157 from Santa Cruz Biotechnology, RNAi products SR305368 and TL313386V, and CRISPR product KN218937 (Origene), and multiple CRISPR products from GenScript (Piscataway, N.J.). It is to be noted that the term can further be used to refer to any combination of features described herein regarding DPF3 molecules. For example, any combination of sequence composition, percentage identify, sequence length, domain structure, functional activity, etc. can be used to describe a DPF3 molecule encompassed by the present invention.

The term "ACTL6A" refers to Actin Like 6A, a family member of actin-related proteins (ARPs), which share significant amino acid sequence identity to conventional actins. Both actins and ARPs have an actin fold, which is an ATP-binding cleft, as a common feature. The ARPs are involved in diverse cellular processes, including vesicular transport, spindle orientation, nuclear migration and chromatin remodeling. This gene encodes a 53 kDa subunit protein of the BAF (BRG1/brm-associated factor) complex in mammals, which is functionally related to SWI/SNF complex in *S. cerevisiae* and *Drosophila*; the latter is thought to facilitate transcriptional activation of specific genes by antagonizing chromatin-mediated transcriptional repression. Together with beta-actin, it is required for maximal ATPase activity of BRG1, and for the association of the BAF complex with chromatin/matrix. ACTL6A is a component of SWI/SNF chromatin remodeling complexes that carry out key enzymatic activities, changing chromatin structure by altering DNA-histone contacts within a nucleosome in an ATP-dependent manner. ACTL6A is required for maximal ATPase activity of SMARCA4/BRG1/BAF190A and for association of the SMARCA4/BRG1/BAF190A containing remodeling complex BAF with chromatin/nuclear matrix. ACTL6A belongs to the neural progenitors-specific chromatin remodeling complex (npBAF complex) and is required for the proliferation of neural progenitors. During neural development a switch from a stem/progenitor to a post-mitotic chromatin remodeling mechanism occurs as neurons exit the cell cycle and become committed to their adult state. The transition from proliferating neural stem/progenitor cells to post-mitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. ACTL6A is a component of the NuA4 histone acetyltransferase (HAT) complex which is involved in transcriptional activation of select genes principally by acetylation of nucleosomal histones H4 and H2A. This modification may both alter nucleosome—DNA interactions and promote interaction of the modified histones with other proteins which positively regulate transcription. This complex may be required for the activation of transcriptional programs associated with oncogene and proto-oncogene mediated growth induction, tumor suppressor mediated growth arrest and replicative senescence, apoptosis, and DNA repair. NuA4 may also play a direct role in DNA repair when recruited to sites of DNA damage. Putative core component of the chromatin remodeling INO80 complex which is involved in transcriptional regulation, DNA replication and probably DNA repair. Human ACTL6A protein has 429 amino acids and a molecular mass of 47461 Da.

The term "ACTL6A" is intended to include fragments, variants (e.g., allelic variants), and derivatives thereof. Representative human ACTL6A cDNA and human ACTL6A protein sequences are well-known in the art and are publicly available from the National Center for Biotechnology Information (NCBI). For example, two different human ACTL6A isoforms are known. Human ACTL6A isoform 1 (NP_004292.1) is encodable by the transcript variant 1 (NM_004301.4). Human ACTL6A isoform 2 (NP_817126.1 and NP_829888.1) is encodable by the transcript variant 2 (NM_177989.3) and transcript variant 3 (NM_178042.3). Nucleic acid and polypeptide sequences of ACTL6A orthologs in organisms other than humans are well-known and include, for example, chimpanzee ACTL6A (NM_001271671.1 and NP_001258600.1), Rhesus monkey ACTL6A (NM_001104559.1 and NP_001098029.1), cattle ACTL6A (NM_001105035.1 and NP_001098505.1), mouse ACTL6A (NM_019673.2 and NP_062647.2), rat ACTL6A (NM_001039033.1 and NP_001034122.1), chicken ACTL6A (XM_422784.6 and XP_422784.3), tropical clawed frog ACTL6A (NM_204006.1 and NP_989337.1), and zebrafish ACTL6A (NM_173240.1 and NP_775347.1).

Anti-ACTL6A antibodies suitable for detecting ACTL6A protein are well-known in the art and include, for example, antibody TA345058 (Origene), antibodies NB100-61628 and NBP2-55376 (Novus Biologicals, Littleton, CO), antibodies ab131272 and ab189315 (AbCam, Cambridge, MA), antibody 702414 (ThermoFisher Scientific), antibody Cat #45-314 (ProSci, Poway, CA), etc. In addition, reagents are well-known for detecting ACTL6A. Moreover, multiple siRNA, shRNA, CRISPR constructs for reducing ACTL6A expression can be found in the commercial product lists of the above-referenced companies, such as siRNA products #sc-60239 and sc-60240 and CRISPR product #sc-403200-KO-2 from Santa Cruz Biotechnology, RNAi products SR300052 and TL306860V, and CRISPR product KN201689 (Origene), and multiple CRISPR products from GenScript (Piscataway, N.J.). It is to be noted that the term can further be used to refer to any combination of features described herein regarding ACTL6A molecules. For example, any combination of sequence composition, percentage identify, sequence length, domain structure, functional activity, etc. can be used to describe an ACTL6A molecule encompassed by the present invention.

The term "β-Actin" refers to Actin Beta. This gene encodes one of six different actin proteins. Actins are highly conserved proteins that are involved in cell motility, structure, integrity, and intercellular signaling. The encoded protein is a major constituent of the contractile apparatus and one of the two nonmuscle cytoskeletal actins that are ubiquitously expressed. Mutations in this gene cause Baraitser-Winter syndrome 1, which is characterized by intellectual disability with a distinctive facial appearance in human patients. Numerous pseudogenes of this gene have been identified throughout the human genome. Actins are highly conserved proteins that are involved in various types of cell motility and are ubiquitously expressed in all eukaryotic cells. Actin is found in two main states: G-actin is the globular monomeric form, whereas F-actin forms helical polymers. Both G- and F-actin are intrinsically flexible structures. Human f-Actin protein has 375 amino acids and a molecular mass of 41737 Da. The binding partners of β-Actin include, e.g., CPNE1, CPNE4, DHX9, GCSAM, ERBB2, XPO6, and EMD.

The term "β-Actin" is intended to include fragments, variants (e.g., allelic variants), and derivatives thereof. Representative human β-Actin cDNA and human 3-Actin protein sequences are well-known in the art and are publicly available from the National Center for Biotechnology Information (NCBI). For example, human β-Actin (NP_001092.1) is encodable by the transcript (NM_001101.4). Nucleic acid and polypeptide sequences of 3-Actin orthologs in organisms other than humans are well-known and include, for example, chimpanzee β-Actin (NM_001009945.1 and NP_001009945.1), Rhesus monkey β-Actin (NM_001033084.1 and NP_001028256.1), dog f-Actin (NM_001195845.2 and NP_001182774.2), cattle f-Actin (NM_173979.3 and NP_776404.2), mouse 3-Actin (NM_007393.5 and NP_031419.1), rat 3-Actin (NM_031144.3 and NP_112406.1), chicken β-Actin (NM_205518.1 and NP_990849.1), and tropical clawed frog f-Actin (NM_213719.1 and NP_998884.1).

Anti-β-Actin antibodies suitable for detecting f-Actin protein are well-known in the art and include, for example, antibody TA353557 (Origene), antibodies NB600-501 and NB600-503 (Novus Biologicals, Littleton, CO), antibodies ab8226 and ab8227 (AbCam, Cambridge, MA), antibody AM4302 (ThermoFisher Scientific), antibody Cat #PM-7669-biotin (ProSci, Poway, CA), etc. In addition, reagents are well-known for detecting β-Actin. Moreover, multiple siRNA, shRNA, CRISPR constructs for reducing β-Actin expression can be found in the commercial product lists of the above-referenced companies, such as siRNA products #sc-108069 and sc-108070 and CRISPR product #sc-400000-KO-2 from Santa Cruz Biotechnology, RNAi products SR300047 and TL314976V, and CRISPR product KN203643 (Origene), and multiple CRISPR products from GenScript (Piscataway, N.J.). It is to be noted that the term can further be used to refer to any combination of features described herein regarding β-Actin molecules. For example, any combination of sequence composition, percentage identify, sequence length, domain structure, functional activity, etc. can be used to describe a β-Actin molecule encompassed by the present invention.

The term "BCL7A" refers to BCL Tumor Suppressor 7A. This gene is directly involved, with Myc and IgH, in a three-way gene translocation in a Burkitt lymphoma cell line. As a result of the gene translocation, the N-terminal region of the gene product is disrupted, which is thought to be related to the pathogenesis of a subset of high-grade B cell non-Hodgkin lymphoma. The N-terminal segment involved in the translocation includes the region that shares a strong sequence similarity with those of BCL7B and BCL7C. Diseases associated with BCL7A include Lymphoma and Burkitt Lymphoma. An important paralog of this gene is BCL7C. Human BCL7A protein has 210 amino acids and a molecular mass of 22810 Da.

The term "BCL7A" is intended to include fragments, variants (e.g., allelic variants), and derivatives thereof. Representative human BCL7A cDNA and human BCL7A protein sequences are well-known in the art and are publicly available from the National Center for Biotechnology Information (NCBI). For example, two different human BCL7A isoforms are known. Human BCL7A isoform a (NP_066273.1) is encodable by the transcript variant 1 (NM_020993.4). Human BCL7A isoform b (NP_001019979.1) is encodable by the transcript variant 2 (NM_001024808.2). Nucleic acid and polypeptide sequences of BCL7A orthologs in organisms other than humans are well-known and include, for example, chimpanzee BCL7A (XM_009426452.3 and XP_009424727.2, and XM_016924434.2 and XP_016779923.1), Rhesus monkey BCL7A (XM_015153012.1 and XP_015008498.1, and XM_015153013.1 and XP_015008499.1), dog BCL7A (XM_543381.6 and XP_543381.2, and XM_854760.5 and XP_859853.1), cattle BCL7A (XM_024977701.1 and XP_024833469.1, and XM_024977700.1 and XP_024833468.1), mouse BCL7A (NM_029850.3 and NP_084126.1), rat BCL7A (XM_017598515.1 and XP_017454004.1), chicken BCL7A (XM_004945565.3 and XP_004945622.1, and XM_415148.6 and XP_415148.2), tropical clawed frog BCL7A (NM_001006871.1 and NP_001006872.1), and zebrafish BCL7A (NM_212560.1 and NP_997725.1).

Anti-BCL7A antibodies suitable for detecting BCL7A protein are well-known in the art and include, for example, antibody TA344744 (Origene), antibodies NBP1-30941 and NBP1-91696 (Novus Biologicals, Littleton, CO), antibodies ab137362 and ab1075 (AbCam, Cambridge, MA), antibody PA5-27123 (ThermoFisher Scientific), antibody Cat #45-325 (ProSci, Poway, CA), etc. In addition, reagents are well-known for detecting BCL7A. Multiple clinical tests of BCL7A are available in NIH Genetic Testing Registry (GTR®) (e.g., GTR Test ID: GTR000541481.2, offered by Fulgent Clinical Diagnostics Lab (Temple City, CA)). Moreover, multiple siRNA, shRNA, CRISPR constructs for reducing BCL7A expression can be found in the commercial product lists of the above-referenced companies, such as siRNA products #sc-96136 and sc-141671 and CRISPR product #sc-410702 from Santa Cruz Biotechnology, RNAi products SR300417 and TL314490V, and CRISPR product KN210489 (Origene), and multiple CRISPR products from GenScript (Piscataway, N.J.). It is to be noted that the term can further be used to refer to any combination of features described herein regarding BCL7A molecules. For example, any combination of sequence composition, percentage identify, sequence length, domain structure, functional activity, etc. can be used to describe a BCL7A molecule encompassed by the present invention.

The term "BCL7B" refers to BCL Tumor Suppressor 7B, a member of the BCL7 family including BCL7A, BCL7B and BCL7C proteins. This member is BCL7B, which contains a region that is highly similar to the N-terminal segment of BCL7A or BCL7C proteins. The BCL7A protein is encoded by the gene known to be directly involved in a three-way gene translocation in a Burkitt lymphoma cell line. This gene is located at a chromosomal region commonly deleted in Williams syndrome. This gene is highly conserved from *C. elegans* to human. BCL7B is a positive regulator of apoptosis. BCL7B plays a role in the Wnt signaling pathway, negatively regulating the expression of Wnt signaling components CTNNB1 and HMGA1 (Uehara et al. (2015) *PLoS Genet* 11(1):e1004921). BCL7B is involved in cell cycle progression, maintenance of the nuclear structure and stem cell differentiation (Uehara et al. (2015) *PLoS Genet* 11(1):e1004921). It plays a role in lung tumor development or progression. Human BCL7B protein has 202 amino acids and a molecular mass of 22195 Da.

The term "BCL7B" is intended to include fragments, variants (e.g., allelic variants), and derivatives thereof. Representative human BCL7B cDNA and human BCL7B protein sequences are well-known in the art and are publicly available from the National Center for Biotechnology Information (NCBI). For example, three different human BCL7B isoforms are known. Human BCL7B isoform 1 (NP_001698.2) is encodable by the transcript variant 1 (NM_001707.3). Human BCL7B isoform 2 (NP_001184173.1) is encodable by the transcript variant 2 (NM_001197244.1). Human BCL7B isoform 3 (NP_001287990.1) is encodable by the transcript variant 3 (NM_001301061.1). Nucleic acid and polypeptide sequences of BCL7B orthologs in organisms other than humans are well-known and include, for example, chimpanzee BCL7B (XM_003318671.3 and XP_003318719.1, and XM_003318672.3 and XP_003318720.1), Rhesus monkey BCL7B (NM_001194509.1 and NP_001181438.1), dog BCL7B (XM_546926.6 and XP_546926.1, and XM_005620975.2 and XP_005621032.1), cattle BCL7B (NM_001034775.2 and NP_001029947.1), mouse BCL7B (NM_009745.2 and NP_033875.2), chicken BCL7B (XM_003643231.4 and XP_003643279.1, XM_004949975.3 and XP_004950032.1, and XM_025142155.1 and XP_024997923.1), tropical clawed frog BCL7B (NM_001103072.1 and NP_001096542.1), and zebrafish BCL7B (NM_001006018.1 and NP_001006018.1, and NM_213165.1 and NP_998330.1).

Anti-BCL7B antibodies suitable for detecting BCL7B protein are well-known in the art and include, for example, antibody TA809485 (Origene), antibodies H00009275-M01 and NBP2-34097 (Novus Biologicals, Littleton, CO), antibodies ab130538 and ab172358 (AbCam, Cambridge, MA), antibody MA527163 (ThermoFisher Scientific), antibody Cat #58-996 (ProSci, Poway, CA), etc. In addition, reagents are well-known for detecting BCL7B. Moreover, multiple siRNA, shRNA, CRISPR constructs for reducing BCL7B expression can be found in the commercial product lists of the above-referenced companies, such as siRNA products #sc-89728 and sc-141672 and CRISPR product #sc-411262 from Santa Cruz Biotechnology, RNAi products SR306141 and TL306418V, and CRISPR product KN201696 (Origene), and multiple CRISPR products from GenScript (Piscataway, N.J.). It is to be noted that the term can further be used to refer to any combination of features described herein regarding BCL7B molecules. For example, any combination of sequence composition, percentage identify, sequence length, domain structure, functional activity, etc. can be used to describe a BCL7B molecule encompassed by the present invention.

The term "BCL7C" refers to BCL Tumor Suppressor 7C, a member of the BCL7 family including BCL7A, BCL7B and BCL7C proteins. This gene is identified by the similarity of its product to the N-terminal region of BCL7A protein. BCL7C may play an anti-apoptotic role. Diseases associated with BCL7C include Lymphoma. Human BCL7C protein has 217 amino acids and a molecular mass of 23468 Da.

The term "BCL7C" is intended to include fragments, variants (e.g., allelic variants), and derivatives thereof. Representative human BCL7C cDNA and human BCL7C protein sequences are well-known in the art and are publicly available from the National Center for Biotechnology Information (NCBI). For example, two different human BCL7C isoforms are known. Human BCL7C isoform 1 (NP_001273455.1) is encodable by the transcript variant 1 (NM_001286526.1). Human BCL7C isoform 2 (NP_004756.2) is encodable by the transcript variant 2 (NM_004765.3). Nucleic acid and polypeptide sequences of BCL7C orthologs in organisms other than humans are well-known and include, for example, chimpanzee BCL7C (XM_016929717.2 and XP_016785206.1, XM_016929716.2 and XP_016785205.1, and XM_016929718.2 and XP_016785207.1), Rhesus monkey BCL7C (NM_001265776.2 and NP_001252705.1), cattle BCL7C (NM_001099722.1 and NP_001093192.1), mouse BCL7C (NM_001347652.1 and NP_001334581.1, and NM_009746.2 and NP_033876.1), and rat BCL7C (NM_001106298.1 and NP_001099768.1).

Anti-BCL7C antibodies suitable for detecting BCL7C protein are well-known in the art and include, for example, antibody TA347083 (Origene), antibodies NBP2-15559 and NBP1-86441 (Novus Biologicals, Littleton, CO), antibodies ab126944 and ab231278 (AbCam, Cambridge, MA), antibody PA5-30308 (ThermoFisher Scientific), etc. In addition, reagents are well-known for detecting BCL7C. Multiple clinical tests of BCL7C are available in NIH Genetic Testing Registry (GTR®) (e.g., GTR Test ID: GTR000540637.2, offered by Fulgent Clinical Diagnostics Lab (Temple City, CA)). Moreover, multiple siRNA, shRNA, CRISPR constructs for reducing BCL7C expression can be found in the commercial product lists of the above-referenced companies, such as siRNA products #sc-93022 and sc-141673 and CRISPR product #sc-411261 from Santa Cruz Biotechnology, RNAi products SR306140 and TL315552V, and CRISPR product KN205720 (Origene), and multiple CRISPR products from GenScript (Piscataway, N.J.). It is to be noted that the term can further be used to refer to any combination of features described herein regarding BCL7C molecules. For example, any combination of sequence composition, percentage identify, sequence length, domain structure, functional activity, etc. can be used to describe a BCL7C molecule encompassed by the present invention.

The term "SMARCA4" refers to SWI/SNF related, matrix associated, actin dependent regulator of chromatin, subfamily a, member 4, a member of the SWI/SNF family of proteins and is highly similar to the brahma protein of *Drosophila*. Members of this family have helicase and ATPase activities and are thought to regulate transcription of certain genes by altering the chromatin structure around those genes. The encoded protein is part of the large ATP-dependent chromatin remodeling complex SNF/SWI, which is required for transcriptional activation of genes normally repressed by chromatin. In addition, this protein can bind BRCA1, as well as regulate the expression of the tumorigenic protein CD44. Mutations in this gene cause rhabdoid tumor predisposition syndrome type 2. SMARCA4 is a component of SWI/SNF chromatin remodeling complexes that carry out key enzymatic activities, changing chromatin structure by altering DNA-histone contacts within a nucleosome in an ATP-dependent manner. SMARCA4 is a component of the CREST-BRG1 complex, a multiprotein complex that regulates promoter activation by orchestrating a calcium-dependent release of a repressor complex and a recruitment of an activator complex. In resting neurons, transcription of the c-FOS promoter is inhibited by BRG1-dependent recruitment of a phospho-RB1-HDAC repressor complex. Upon calcium influx, RB1 is dephosphorylated by calcineurin, which leads to release of the repressor complex. At the same time, there is increased recruitment of CREBBP to the promoter by a CREST-dependent mechanism, which leads to transcriptional activation. The CREST-BRG1 complex also binds to the NR2B promoter, and activity-dependent induction of NR2B expression involves a release of HDAC1 and recruitment of CREBBP. SMARCA4 belongs to the neural progenitors-specific chromatin remodeling complex (npBAF complex) and the neuron-specific chromatin remodeling complex (nBAF complex). During neural development a switch from a stem/progenitor to a postmitotic chromatin remodeling mechanism occurs as neurons exit the cell cycle and become committed to their adult state. The transition from proliferating neural stem/progenitor cells to postmitotic neurons requires a switch in subunit composition of the npBAF and nBAF complexes. As neural progenitors exit mitosis and differentiate into neurons, npBAF complexes which contain ACTL6A/BAF53A and PHF10/BAF45A, are exchanged for homologous alternative ACTL6B/BAF53B and DPF1/BAF45B or DPF3/BAF45C subunits in neuron-specific complexes (nBAF). The npBAF complex is essential for the self-renewal/proliferative capacity of the multipotent neural stem cells. The nBAF complex along with CREST plays a role regulating the activity of genes essential for dendrite growth. SMARCA4/BAF190A promote neural stem cell self-renewal/proliferation by enhancing Notch-dependent proliferative signals, while concurrently making the neural stem cell insensitive to SHH-dependent differentiating cues. SMARCA4 acts as a corepressor of ZEB1 to regulate E-cadherin transcription and is required for induction of epithelial-mesenchymal transition (EMT) by ZEB1. Human SMARCA4 protein has 1647 amino acids and a molecular mass of 184646 Da. The known binding partners of SMARCA4 include, e.g., PHF10/BAF45A, MYOG, IKFZ1, ZEB1, NR3C1, PGR, SMARD1, TOPBP1 and ZMIM2/ZIMP7.

The term “SMARCA4” is intended to include fragments, variants (e.g., allelic variants), and derivatives thereof. Representative human SMARCA4 cDNA and human SMARCA4 protein sequences are well-known in the art and are publicly available from the National Center for Biotechnology Information (NCBI). For example, six different human SMARCA4 isoforms are known. Human SMARCA4 isoform A (NP_001122321.1) is encodable by the transcript variant 1 (NM_001128849.1). Human SMARCA4 isoform B (NP_001122316.1 and NP_003063.2) is encodable by the transcript variant 2 (NM_001128844.1) and the transcript variant 3 (NM_003072.3). Human SMARCA4 isoform C (NP_001122317.1) is encodable by the transcript variant 4 (NM_001128845.1). Human SMARCA4 isoform D (NP_001122318.1) is encodable by the transcript variant 5 (NM_001128846.1). Human SMARCA4 isoform E (NP_001122319.1) is encodable by the transcript variant 6 (NM_001128847.1). Human SMARCA4 isoform F (NP_001122320.1) is encodable by the transcript variant 7 (NM_001128848.1). Nucleic acid and polypeptide sequences of SMARCA4 orthologs in organisms other than humans are well-known and include, for example, Rhesus monkey SMARCA4 (XM_015122901.1 and XP_014978387.1, XM_015122902.1 and XP_014978388.1, XM_015122903.1 and XP_014978389.1, XM_015122906.1 and XP_014978392.1, XM_015122905.1 and XP_014978391.1, XM_015122904.1 and XP_014978390.1, XM_015122907.1 and XP_014978393.1, XM_015122909.1 and XP_014978395.1, and XM_015122910.1 and XP_014978396.1), cattle SMARCA4 (NM_001105614.1 and NP_001099084.1), mouse SMARCA4 (NM_001174078.1 and NP_001167549.1, NM_011417.3 and NP_035547.2, NM_001174079.1 and NP_001167550.1, NM_001357764.1 and NP_001344693.1), rat SMARCA4 (NM_134368.1 and NP_599195.1), chicken SMARCA4 (NM_205059.1 and NP_990390.1), and zebrafish SMARCA4 (NM_181603.1 and NP_853634.1).

Anti-SMARCA4 antibodies suitable for detecting SMARCA4 protein are well-known in the art and include, for example, antibody AM26021PU-N(Origene), antibodies NB100-2594 and AF5738 (Novus Biologicals, Littleton, CO), antibodies ab110641 and ab4081 (AbCam, Cambridge, MA), antibody 720129 (ThermoFisher Scientific), antibody 7749 (ProSci), etc. In addition, reagents are well-known for detecting SMARCA4. Multiple clinical tests of SMARCA4 are available in NIH Genetic Testing Registry (GTR®) (e.g., GTR Test ID: GTR000517106.2, offered by Fulgent Clinical Diagnostics Lab (Temple City, CA)). Moreover, multiple siRNA, shRNA, CRISPR constructs for reducing SMARCA4 expression can be found in the commercial product lists of the above-referenced companies, such as siRNA products #sc-29827 and sc-44287 and CRISPR product #sc-400168 from Santa Cruz Biotechnology, RNAi products SR321835 and TL309249V, and CRISPR product KN219258 (Origene), and multiple CRISPR products from GenScript (Piscataway, N.J.). It is to be noted that the term can further be used to refer to any combination of features described herein regarding SMARCA4 molecules. For example, any combination of sequence composition, percentage identify, sequence length, domain structure, functional activity, etc. can be used to describe a SMARCA4 molecule encompassed by the present invention.

The term “SS18” refers to SS18, NBAF Chromatin Remodeling Complex Subunit. SS18 functions synergistically with RBM14 as a transcriptional coactivator. Isoform 1 and isoform 2 of SS18 function in nuclear receptor coactivation. Isoform 1 and isoform 2 of SS18 function in general transcriptional coactivation. Diseases associated with SS18 include Sarcoma, Synovial Cell Sarcoma. Among its related pathways are transcriptional misregulation in cancer and chromatin regulation/acetylation. Human SS18 protein has 418 amino acids and a molecular mass of 45929

Da. The known binding partners of SS18 include, e.g., MLLT10 and RBM14 isoform 1.

The term "SS18" is intended to include fragments, variants (e.g., allelic variants), and derivatives thereof. Representative human SS18 cDNA and human SS18 protein sequences are well-known in the art and are publicly available from the National Center for Biotechnology Information (NCBI). For example, three different human SS18 isoforms are known. Human SS18 isoform 1 (NP_001007560.1) is encodable by the transcript variant 1 (NM_001007559.2). Human SS18 isoform 2 (NP_005628.2) is encodable by the transcript variant 2 (NM_005637.3). Human SS18 isoform 3 (NP_001295130.1) is encodable by the transcript variant 3 (NM_001308201.1). Nucleic acid and polypeptide sequences of SS18 orthologs in organisms other than humans are well-known and include, for example, dog SS18 (XM_005622940.3 and XP_005622997.1, XM_537295.6 and XP_537295.3, XM_003434925.4 and XP_003434973.1, and XM_005622941.3 and XP_005622998.1), mouse SS18 (NM_009280.2 and NP_033306.2, NM_001161369.1 and NP_001154841.1, NM_001161370.1 and NP_001154842.1, and NM_001161371.1 and NP_001154843.1), rat SS18 (NM_001100900.1 and NP_001094370.1), chicken SS18 (XM_015277943.2 and XP_015133429.1, and XM_015277944.2 and XP_015133430.1), tropical clawed frog SS18 (XM_012964966.1 and XP_012820420.1, XM_018094711.1 and XP_017950200.1, XM_012964964.2 and XP_012820418.1, and XM_012964965.2 and XP_012820419.1), and zebrafish SS18 (NM_001291325.1 and NP_001278254.1, and NM_199744.2 and NP_956038.1).

Anti-SS18 antibodies suitable for detecting SS18 protein are well-known in the art and include, for example, antibody TA314572 (Origene), antibodies NBP2-31777 and NBP2-31612 (Novus Biologicals, Littleton, CO), antibodies ab179927 and ab89086 (AbCam, Cambridge, MA), antibody PA5-63745 (ThermoFisher Scientific), etc. In addition, reagents are well-known for detecting SS18. Multiple clinical tests of SS18 are available in NIH Genetic Testing Registry (GTR®) (e.g., GTR Test ID: GTR000546059.2, offered by Fulgent Clinical Diagnostics Lab (Temple City, CA)). Moreover, multiple siRNA, shRNA, CRISPR constructs for reducing SS18 expression can be found in the commercial product lists of the above-referenced companies, such as siRNA products #sc-38449 and sc-38450 and CRISPR product #sc-401575 from Santa Cruz Biotechnology, RNAi products SR304614 and TL309102V, and CRISPR product KN215192 (Origene), and multiple CRISPR products from GenScript (Piscataway, N.J.). It is to be noted that the term can further be used to refer to any combination of features described herein regarding SS18 molecules. For example, any combination of sequence composition, percentage identify, sequence length, domain structure, functional activity, etc. can be used to describe a SS18 molecule encompassed by the present invention.

The term "SS18L1" refers to SS18L1, NBAF Chromatin Remodeling Complex Subunit.
This gene encodes a calcium-responsive transactivator which is an essential subunit of a neuron-specific chromatin-remodeling complex. The structure of this gene is similar to that of the SS18 gene. Mutations in this gene are involved in amyotrophic lateral sclerosis (ALS). SS18L1 is a transcriptional activator which is required for calcium-dependent dendritic growth and branching in cortical neurons. SS18L1 recruits CREB-binding protein (CREBBP) to nuclear bodies. SS18L1 is a component of the CREST-BRG1 complex, a multiprotein complex that regulates promoter activation by orchestrating a calcium-dependent release of a repressor complex and a recruitment of an activator complex. In resting neurons, transcription of the c-FOS promoter is inhibited by BRG1-dependent recruitment of a phospho-RB1-HDAC1 repressor complex. Upon calcium influx, RB1 is dephosphorylated by calcineurin, which leads to release of the repressor complex. At the same time, there is increased recruitment of CREBBP to the promoter by a CREST-dependent mechanism, which leads to transcriptional activation. The CREST-BRG1 complex also binds to the NR2B promoter, and activity-dependent induction of NR2B expression involves a release of HDAC1 and recruitment of CREBBP. Human SS18L1 protein has 396 amino acids and a molecular mass of 42990 Da. The known binding partners of SS18L1 include, e.g., CREBBP (via N-terminus), EP300 and SMARCA4/BRG1.

The term "SS18L1" is intended to include fragments, variants (e.g., allelic variants), and derivatives thereof. Representative human SS18L1 cDNA and human SS18L1 protein sequences are well-known in the art and are publicly available from the National Center for Biotechnology Information (NCBI). For example, two different human SS18L1 isoforms are known. Human SS18L1 isoform 1 (NP_945173.1) is encodable by the transcript variant 1 (NM_198935.2), which encodes the longer isoform. Human SS18L1 isoform 2 (NP_001288707.1) is encodable by the transcript variant 2 (NM_001301778.1), which has an additional exon in the 5' region and an alternate splice acceptor site, which results in translation initiation at a downstream AUG start codon, compared to variant 1. The resulting isoform (2) has a shorter N-terminus, compared to isoform 1. Nucleic acid and polypeptide sequences of SS18L1 orthologs in organisms other than humans are well-known and include, for example, Rhesus monkey SS18 (XM_015148655.1 and XP_015004141.1, XM_015148658.1 and XP_015004144.1, XM_015148656.1 and XP_015004142.1, XM_015148657.1 and XP_015004143.1, and XM_015148654.1 and XP_015004140.1), dog SS18L1 (XM_005635257.3 and XP_005635314.2), cattle SS18 (NM_001078095.1 and NP_001071563.1), mouse SS18L1 (NM_178750.5 and NP_848865.4), rat SS18L1 (NM_138918.1 and NP_620273.1), chicken SS18L1 (XM_417402.6 and XP_417402.4), and tropical clawed frog SS18L1 (NM_001195706.2 and NP_001182635.1).

Anti-SS18L1 antibodies suitable for detecting SS18L1 protein are well-known in the art and include, for example, antibody TA333342 (Origene), antibodies NBP2-20486 and NBP2-20485 (Novus Biologicals, Littleton, CO), antibody PA5-30571 (ThermoFisher Scientific), antibody 59-703 (ProSci), etc. In addition, reagents are well-known for detecting SS18L1. Multiple clinical tests of SS18L1 are available in NIH Genetic Testing Registry (GTR®) (e.g., GTR Test ID: GTR000546798.2, offered by Fulgent Clinical Diagnostics Lab (Temple City, CA)). Moreover, multiple siRNA, shRNA, CRISPR constructs for reducing SS18L1 expression can be found in the commercial product lists of the above-referenced companies, such as siRNA products #sc-60442 and sc-60441 and CRISPR product #sc-403134 from Santa Cruz Biotechnology, RNAi products SR308680 and TF301381, and CRISPR product KN212373 (Origene), and multiple CRISPR products from GenScript (Piscataway, N.J.). It is to be noted that the term can further be used to refer to any combination of features described herein regarding SS18L1 molecules. For example, any combination of sequence composition, percentage identify, sequence length, domain structure, functional activity, etc. can be used to describe a SS18L1 molecule encompassed by the present invention.

The term "GLTSCR1" or "BICRA" refers to BRD4 Interacting Chromatin Remodeling Complex Associated Protein. GLTSCR1 plays a role in BRD4-mediated gene transcription. Diseases associated with BICRA include Acoustic Neuroma and Neuroma. An important paralog of this gene is BICRAL. Human GLTSCR1 protein has 1560 amino acids and a molecular mass of 158490 Da. The known binding partners of GLTSCR1 include, e.g., BRD4.

The term "GLTSCR1" is intended to include fragments, variants (e.g., allelic variants), and derivatives thereof. Representative human GLTSCR1 cDNA and human GLTSCR1 protein sequences are well-known in the art and are publicly available from the National Center for Biotechnology Information (NCBI). For example, human GLTSCR1 (NP_056526.3) is encodable by the transcript variant 1 (NM_015711.3). Nucleic acid and polypeptide sequences of GLTSCR1 orthologs in organisms other than humans are well-known and include, for example, chimpanzee GLTSCR1 (XM_003316479.3 and XP_003316527.1, XM_009435940.2 and XP_009434215.1, XM_009435938.3 and XP_009434213.1, and XM_009435941.2 and XP_009434216.1), Rhesus monkey GLTSCR1 (XM_015124361.1 and XP_014979847.1, and XM_015124362.1 and XP_014979848.1), dog GLTSCR1 (XM_014116569.2 and XP_013972044.1), mouse GLTSCR1 (NM_001081418.1 and NP_001074887.1), rat GLTSCR1 (NM_001106226.2 and NP_001099696.2), chicken GLTSCR1 (XM_025144460.1 and XP_025000228.1), and tropical clawed frog GLTSCR1 (NM_001113827.1 and NP_001107299.1).

Anti-GLTSCR1 antibodies suitable for detecting GLTSCR1 protein are well-known in the art and include, for example, antibody AP51862PU-N(Origene), antibody NBP2-30603 (Novus Biologicals, Littleton, CO), etc. In addition, reagents are well-known for detecting GLTSCR1. Multiple clinical tests of GLTSCR1 are available in NIH Genetic Testing Registry (GTR®) (e.g., GTR Test ID: GTR000534926.2, offered by Fulgent Clinical Diagnostics Lab (Temple City, CA)). Moreover, multiple siRNA, shRNA, CRISPR constructs for reducing GLTSCR1 expression can be found in the commercial product lists of the above-referenced companies, such as RNAi products SR309337 and TL304311V, and CRISPR product KN214080 (Origene), and multiple CRISPR products from GenScript (Piscataway, N.J.). It is to be noted that the term can further be used to refer to any combination of features described herein regarding GLTSCR1 molecules. For example, any combination of sequence composition, percentage identify, sequence length, domain structure, functional activity, etc. can be used to describe a GLTSCR1 molecule encompassed by the present invention.

The term "GLTSCR1L" or "BICRAL" refers to BRD4 Interacting Chromatin Remodeling Complex Associated Protein Like. An important paralog of this gene is BICRA. Human GLTSCR1L protein has 1079 amino acids and a molecular mass of 115084 Da.

The term "GLTSCR1L" is intended to include fragments, variants (e.g., allelic variants), and derivatives thereof. Representative human GLTSCR1L cDNA and human GLTSCR1L protein sequences are well-known in the art and are publicly available from the National Center for Biotechnology Information (NCBI). For example, human GLTSCR1L protein (NP_001305748.1 and NP_056164.1) is encodable by the transcript variant 1 (NM_001318819.1) and the transcript variant 2 (NM_015349.2). Nucleic acid and polypeptide sequences of GLTSCR1 orthologs in organisms other than humans are well-known and include, for example, chimpanzee GLTSCR1L (XM_016955520.2 and XP_016811009.1, XM_024357216.1 and XP_024212984.1, XM_016955522.2 and XP_016811011.1, XM_009451272.3 and XP_009449547.1, and XM_001135166.6 and XP_001135166.1), Rhesus monkey GLTSCR1L (XM_015136397.1 and XP_014991883.1), dog GLTSCR1L (XM_005627362.3 and XP_005627419.1, XM_014118453.2 and XP_013973928.1, and XM_005627363.3 and XP_005627420.1), cattle GLTSCR1L (NM_001205780.1 and NP_001192709.1), mouse GLTSCR1L (NM_001100452.1 and NP_001093922.1), tropical clawed frog GLTSCR1L (XM_002934681.4 and XP_002934727.2, and XM_018094119.1 and XP_017949608.1), and zebrafish GLTSCR1L (XM_005156379.4 and XP_005156436.1, and XM_682390.9 and XP_687482.4).

Anti-GLTSCR1L antibodies suitable for detecting GLTSCR1L protein are well-known in the art and include, for example, antibodies NBP1-86359 and NBP1-86360 (Novus Biologicals, Littleton, CO), etc. In addition, reagents are well-known for detecting GLTSCR1L. Multiple clinical tests of GLTSCR1L are available in NIH Genetic Testing Registry (GTR®) (e.g., GTR Test ID: GTR000534926.2, offered by Fulgent Clinical Diagnostics Lab (Temple City, CA)). Moreover, multiple siRNA, shRNA, CRISPR constructs for reducing GLTSCR1L expression can be found in the commercial product lists of the above-referenced companies, such as RNAi products SR308318 and TL303775V, and CRISPR product KN211609 (Origene), and multiple CRISPR products from GenScript (Piscataway, N.J.). It is to be noted that the term can further be used to refer to any combination of features described herein regarding GLTSCR1L molecules. For example, any combination of sequence composition, percentage identify, sequence length, domain structure, functional activity, etc. can be used to describe a GLTSCR1L molecule encompassed by the present invention.

The term "BRD9" refers to Bromodomain Containing 9. An important paralog of this gene is BRD7. BRD9 plays a role in chromatin remodeling and regulation of transcription (Filippakopouplos et al. (2012) *Cell* 149:214-231; Flynn et al. (2015) *Structure* 23:1801-1814). BRD9 acts as a chromatin reader that recognizes and binds acylated histones. BRD9 binds histones that are acetylated and/or butyrylated (Flynn et al. (2015) *Structure* 23:1801-1814). Human BRD9 protein has 597 amino acids and a molecular mass of 67000 Da. BRD9 binds acetylated histones H3 and H4, as well as butyrylated histone H4.

The term "BRD9" is intended to include fragments, variants (e.g., allelic variants), and derivatives thereof. Representative human BRD9 cDNA and human BRD9 protein sequences are well-known in the art and are publicly available from the National Center for Biotechnology Information (NCBI). For example, three different human BRD9 isoforms are known. Human BRD9 isoform 1 (NP_076413.3) is encodable by the transcript variant 1 (NM_023924.4). Human BRD9 isoform 2 (NP_001009877.2) is encodable by the transcript variant 2 (NM_001009877.2). Human BRD9 isoform 3 (NP_001304880.1) is encodable by the transcript variant 3 (NM_001317951.1). Nucleic acid and polypeptide sequences of BRD9 orthologs in organisms other than humans are well-known and include, for example, chimpanzee BRD9 (XM_016952886.2 and XP_016808375.1, XM_016952888.2 and XP_016808377.1, XM_016952889.1 and XP_016808378.1, and XM_024356518.1 and XP_024212286.1), Rhesus monkey BRD9 (NM_001261189.1 and NP_001248118.1), dog BRD9 (XM_014110323.2 and XP_013965798.2), cattle BRD9 (NM_001193092.2 and NP_001180021.1), mouse BRD9 (NM_001024508.3 and NP_001019679.2, and NM_001308041.1 and NP_001294970.1), rat BRD9 (NM_001107453.1 and NP_001100923.1), chicken BRD9 (XM_015275919.2 and XP_015131405.1, XM_015275920.2 and XP_015131406.1, and XM_015275921.2 and XP_015131407.1), tropical clawed frog BRD9 (NM_213697.2 and NP_998862.1), and zebrafish BRD9 (NM_200275.1 and NP_956569.1).

Anti-BRD9 antibodies suitable for detecting BRD9 protein are well-known in the art and include, for example, antibody TA337992 (Origene), antibodies NBP2-15614 and NBP2-58517 (Novus Biologicals, Littleton, CO), antibodies ab155039 and ab137245 (AbCam, Cambridge, MA), antibody PA5-31847 (ThermoFisher Scientific), antibody 28-196 (ProSci), etc. In addition, reagents are well-known for detecting BRD9. Multiple clinical tests of BRD9 are available in NIH Genetic Testing Registry (GTR®) (e.g., GTR Test ID: GTR000540343.2, offered by Fulgent Clinical Diagnostics Lab (Temple City, CA)). Moreover, multiple siRNA, shRNA, CRISPR constructs for reducing BRD9 expression can be found in the commercial product lists of the above-referenced companies, such as siRNA products #sc-91975 and sc-141743 and CRISPR product #sc-404933 from Santa Cruz Biotechnology, RNAi products SR312243 and TL314434, and CRISPR product KN208315 (Origene), and multiple CRISPR products from GenScript (Piscataway, N.J.). It is to be noted that the term can further be used to refer to any combination of features described herein regarding BRD9 molecules. For example, any combination of sequence composition, percentage identify, sequence length, domain structure, functional activity, etc. can be used to describe a BRD9 molecule encompassed by the present invention.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |

-continued

| GENETIC CODE | |
|---|---|
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a protein subunit nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for subunits of the SWI/SNF protein complexes encompassed by the present invention are well-known in the art and readily available on publicly available databases, such as the National Center for Biotechnology Information (NCBI). For example, exemplary nucleic acid and amino acid sequences derived from publicly available sequence databases are provided in Table 1 below.

TABLE 1

| Representative SMARCB1 |
|---|
| Primate SMARCB1 |
| Rodent SMARCB1 |
| Mammalian SMARCB1 |
| Human SMARCB1 |

SEQ ID NO: 1 Human SMARCB1 cDNA Sequence Variant 1 (NM_00373.4, CDS: 240-1397)

```
   1  tttgtttgag cggcggcgcg cgcgtcagcg tcaacgccag cgcctgcgca ctgagggcgg
  61  cctggtcgtc gtctgcggcg gcggcggcgg ctgaggagcc cggctgaggc gccagtaccc
 121  ggcccggtcc gcatttcgcc ttccggcttc ggtttccctc ggcccagcac gccccggccc
 181  cgccccagcc ctcctgatcc ctcgcagccc ggctccggcc gcccgcctct gccgccgcaa
 241  tgatgatgat ggcgctgagc aagaccttcg ggcagaagcc cgtgaagttc cagctggagg
 301  acgacggcga gttctacatg atcggctccg aggtgggaaa ctacctccgt atgttccgag
 361  gttctctgta caagagatac ccctcactct ggaggcgact agccactgtg gaagagagga
 421  agaaaatagt tgcatcgtca catggtaaaa aaacaaaacc taacactaag gatcacggat
 481  acacgactct agccaccagt gtgaccctgt taaaagcctc ggaagtggaa gagattctgg
 541  atggcaacga tgagaagtac aaggctgtgt ccatcagcac agagcccccc acctacctca
 601  gggaacagaa ggccaagagg aacagccagt gggtacccac cctgcccaac agctcccacc
 661  acttagatgc cgtgccatgc tccacaacca tcaacaggaa ccgcatgggc cgagacaaga
 721  agagaacctt cccccttgc tttgatgacc atgacccagc tgtgatccat gagaacgcat
 781  ctcagcccga ggtgctggtc cccatccggc tggacatgga gatcgatggg cagaagctgc
 841  gagacgcctt cacctggaac atgaatgaga agttgatgac gcctgagatg ttttcagaaa
 901  tcctctgtga cgatctggat ttgaaccccgc tgacgtttgt gccagccatc gcctctgcca
 961  tcagacagca gatcgagtcc taccccacgg acagcatcct ggaggaccag tcagaccagc
1021  gcgtcatcat caagctgaac atccatgtgg gaaacatttc cctggtggac cagtttgagt
1081  gggacatgtc agagaaggag aactcaccag agaagtttgc cctgaagctg tgctcggagc
1141  tggggttggg cggggagttt gtcaccacca tcgcatacag catccgggga cagctgagct
1201  ggcatcagaa gacctacgcc ttcagcgaga accctctgcc cacagtggag attgccatcc
1261  ggaacacggg cgatgcggac cagtggtgcc cactgctgga gactctgaca gacgctgaga
1321  tggagaagaa gatccgcgac caggacagga acacgaggcg gatgaggcgt cttgccaaca
1381  cggccccggc ctggtaacca gcccatcagc acacggctcc cacggagcat ctcagaagat
1441  tgggccgcct ctcctccatc ttctggcaag gacagaggcg aggggacagc ccagcgccat
1501  cctgaggatc gggtgggggt ggagtggggg cttccaggtg gcccttcccg gcacacattc
1561  catttgttga gccccagtcc tgcccccac cccaccctcc ctacccctcc ccagtctctg
1621  gggtcaggaa gaaaccttat tttaggttgt gttttgtttt tgtataggag ccccaggcag
1681  ggctagtaac agtttttaaa taaaaggcaa caggtcatgt tcaatttctt caacaaaaaa
1741  aaaaaaaaa
```

SEQ ID NO: 2 Human SMARCB1 Amino Acid Sequence Isoform A (NP_003064.2)

```
   1  mmmmalsktf gqkpvkfqle ddgefymigs evgnylrmfr gslykrypsl wrrlatveer
  61  kkivasshgk ktkpntkdhg yttlatsvtl lkaseveeil dgndekykav sistepptyl
 121  reqkakrnsq wvptlpnssh hldavpcstt inrnrmgrdk krtfplcfdd hdpavihena
 181  sqpevlvpir ldmeidgqkl rdaftwnmne klmtpemfse ilcddldlnp ltfvpaiasa
```

TABLE 1-continued

Representative SMARCB1

241 irqqiesypt dsiledqsdq rviiklnihv gnislvdqfe wdmsekensp ekfalklcse 301 lglggefvtt iaysirgqls whqktyafse nplptveiai rntgdadqwc plletltdae 361 mekkirdqdr ntrrmrrlan tapaw SEQ ID NO: 3 Human SMARCB1 cDNA Sequence Variant 2 (NM_001007468.2, CDS: 240-1370)

1 tttgtttgag cggcggcgcg cgcgtcagcg tcaacgccag cgcctgcgca ctgagggcgg 61 cctggtcgtc gtctgcggcg gcggcggcgg ctgaggagcc cggctgaggc gccagtaccc 121 ggcccggtcc gcatttcgcc ttccggcttc ggtttccctc ggcccagcac gccccggccc 181 cgccccagcc ctcctgatcc ctcgcagccc ggctccggcc gcccgcctct gccgccgcaa 241 tgatgatgat ggcgctgagc aagaccttcg ggcagaagcc cgtgaagttc cagctggagg 301 acgacggcga gttctacatg atcggctccg aggtgggaaa ctacctccgt atgttccgag 361 gttctctgta caagagatac ccctcactct ggaggcgact agccactgtg gaagagagga 421 agaaaatagt tgcatcgtca catgatcacg gatacacgac tctagccacc agtgtgaccc 481 tgttaaaagc ctcggaagtg gaagagattc tggatggcaa cgatgagaag tacaaggctg 541 tgtccatcag cacagagccc cccacctacc tcagggaaca gaaggccaag aggaacagcc 601 agtgggtacc caccctgccc aacagctccc accacttaga tgccgtgcca tgctccacaa 661 ccatcaacag gaaccgcatg ggccgagaca agaagagaac cttcccccctt tgctttgatg 721 accatgaccc agctgtgatc catgagaacg catctcagcc cgaggtgctg gtccccatcc 781 ggctggacat ggagatcgat gggcagaagc tgcgagacgc cttcacctgg aacatgaatg 841 agaagttgat gacgcctgag atgttttcag aaatcctctg tgacgatctg gatttgaacc 901 cgctgacgtt tgtgccagcc atcgcctctg ccatcagaca gcagatcgag tcctacccca 961 cggacagcat cctggaggac cagtcagacc agcgcgtcat catcaagctg aacatccatg 1021 tgggaaacat ttccctggtg gaccagtttg agtgggacat gtcagagaag gagaactcac 1081 cagagaagtt tgccctgaag ctgtgctcgg agctggggtt gggcggggag tttgtcacca 1141 ccatcgcata cagcatccgg ggacagctga gctggcatca gaagacctac gccttcagcg 1201 agaaccctct gcccacagtg gagattgcca tccggaacac gggcgatgcg gaccagtggt 1261 gcccactgct ggagactctg acagacgctg agatggagaa gaagatccgc gaccaggaca 1321 ggaacacgag gcggatgagg cgtcttgcca acacggcccc ggcctggtaa ccagcccatc 1381 agcacacggc tcccacggag catctcagaa gattgggccg cctctcctcc atcttctggc 1441 aaggacagag gcgaggggac agcccagcgc catcctgagg atcgggtggg ggtggagtgg 1501 gggcttccag gtggcccttc ccggcacaca ttccatttgt tgagccccag tcctgccccc 1561 caccccaccc tccctacccc tccccagtct ctggggtcag gaagaaacct tattttaggt 1621 tgtgttttgt ttttgtatag gagccccagg cagggctagt aacagttttt aaataaaagg 1681 caacaggtca tgttcaattt cttcaacaaa aaaaaaaaaa aa SEQ ID NO: 4 Human SMARCB1 Amino Acid Sequence Isoform B (NP_001007469.1)

1 mmmmalsktf gqkpvkfqle ddgefymigs evgnylrmfr gslykrypsl wrrlatveer 61 kkivasshdh gyttaltsvt llkaseveei ldgndekyka vsisteppty lreqkakrns 121 qwvptlpnss hhldavpcst tinrnrmgrd kkrtfplcfd dhdpavihen asqpevlvpi 181 rldmeidgqk lrdaftwnmn eklmtpemfs eilcddldln pltfvpaias airqqiesyp 241 tdsiledqsd qrviiklnih vgnislvdqf ewdmsekens pekfalklcs elglggefvt TABLE 1-continued

| Representative SMARCB1 |
|---|

301 tiaysirgql swhqktyafs enplptveia irntgdadqw cplletltda emekkirdqd 361 rntrrmrrla ntapaw SEQ ID NO: 5 Human SMARCB1 cDNA Sequence Variant 3 (NM_001317946.1, CDS: 240-1424)

1 tttgtttgag cggcggcgcg cgcgtcagcg tcaacgccag cgcctgcgca ctgagggcgg 61 cctggtcgtc gtctgcggcg gcggcggcgg ctgaggagcc cggctgaggc gccagtaccc 121 ggcccggtcc gcatttcgcc ttccggcttc ggtttccctc ggcccagcac gccccggccc 181 cgccccagcc ctcctgatcc ctcgcagccc ggctccggcc gcccgcctct gccgccgcaa 241 tgatgatgat ggcgctgagc aagaccttcg ggcagaagcc cgtgaagttc cagctggagg 301 acgacggcga gttctacatg atcggctccg aggtgggaaa ctacctccgt atgttccgag 361 gttctctgta caagagatac ccctcactct ggaggcgact agccactgtg gaagagagga 421 agaaaatagt tgcatcgtca catgatcacg gatacacgac tctagccacc agtgtgaccc 481 tgttaaaagc ctcggaagtg gaagagattc tggatggcaa cgatgagaag tacaaggctg 541 tgtccatcag cacagagccc cccacctacc tcagggaaca gaaggccaag aggaacagcc 601 agtgggtacc caccctgccc aacagctccc accacttaga tgccgtgcca tgctccacaa 661 ccatcaacag gaaccgcatg ggccgagaca agaagagaac cttccccctt tggtgtggat 721 gcatcgctgc actcaccctc cgtgctgatt ccgccttagt tctccacttt gatgaccatg 781 acccagctgt gatccatgag aacgcatctc agcccgaggt gctggtcccc atccggctgg 841 acatggagat cgatgggcag aagctgcgag acgccttcac ctggaacatg aatgagaagt 901 tgatgacgcc tgagatgttt tcagaaatcc tctgtgacga tctggatttg aacccgctga 961 cgtttgtgcc agccatcgcc tctgccatca gacagcagat cgagtcctac cccacggaca 1021 gcatcctgga ggaccagtca gaccagcgcg tcatcatcaa gctgaacatc catgtgggaa 1081 acatttccct ggtggaccag tttgagtggg acatgtcaga gaaggagaac tcaccagaga 1141 agtttgccct gaagctgtgc tcggagctgg ggttgggcgg ggagtttgtc accaccatcg 1201 catacagcat ccggggacag ctgagctggc atcagaagac ctacgccttc agcgagaacc 1261 ctctgcccac agtggagatt gccatccgga acacgggcga tgcggaccag tggtgcccac 1321 tgctggagac tctgacagac gctgagatgg agaagaagat ccgcgaccag gacaggaaca 1381 cgaggcggat gaggcgtctt gccaacacgg ccccggcctg gtaaccagcc catcagcaca 1441 cggctcccac ggagcatctc agaagattgg gccgcctctc ctccatcttc tggcaaggac 1501 agaggcgagg ggacagccca gcgccatcct gaggatcggg tgggggtgga gtgggggctt 1561 ccaggtggcc cttcccggca cacattccat ttgttgagcc ccagtcctgc cccccacccc 1621 accctcccta cccctcccca gtctctgggg tcaggaagaa accttatttt aggttgtgtt 1681 ttgtttttgt ataggagccc caggcagggc tagtaacagt ttttaaataa aaggcaacag 1741 gtcatgttca atttcttcaa caaaaaaaaa aaaaaa SEQ ID NO: 6 Human SMARCB1 Amino Acid Sequence Isoform C (NP_001304875.1)

1 mmmmalsktf gqkpvkfqle ddgefymigs evgnylrmfr gslykrypsl wrrlatveer 61 kkivasshdh gyttlatsvt llkaseveei ldgndekyka vsisteppty lreqkakrns 121 qwvptlpnss hhldavpcst tinrnrmgrd kkrtfplwcg ciaaltlrad salvlhfddh 181 dpavihenas qpevlvpirl dmeidgqklr daftwnmnek lmtpemfsei lcddldlnpl 241 tfvpaiasai rqqiesyptd siledqsdqr viiklnihvg nislvdqfew dmsekenspe TABLE 1-continued

| Representative SMARCB1 |
|---|
| 301 kfalklcsel glggefvtti aysirgqlsw hqktyafsen plptveiair ntgdadqwcp |
| 361 lletltdaem ekkirdqdrn trrmrrlant apaw |
| SEQ ID NO: 7 Human SMARCB1 cDNA Sequence Variant 4 (NM_001362877.1, CDS: 240-1451) |
| 1 tttgtttgag cggcggcgcg cgcgtcagcg tcaacgccag cgcctgcgca ctgagggcgg |
| 61 cctggtcgtc gtctgcggcg gcggcggcgg ctgaggagcc cggctgaggc gccagtaccc |
| 121 ggcccggtcc gcatttcgcc ttccggcttc ggtttccctc ggcccagcac gccccggccc |
| 181 cgccccagcc ctcctgatcc ctcgcagccc ggctccggcc gcccgcctct gccgccgcaa |
| 241 tgatgatgat ggcgctgagc aagaccttcg ggcagaagcc cgtgaagttc cagctggagg |
| 301 acgacggcga gttctacatg atcggctccg aggtgggaaa ctacctccgt atgttccgag |
| 361 gttctctgta caagagatac ccctcactct ggaggcgact agccactgtg gaagagagga |
| 421 agaaaatagt tgcatcgtca catggtaaaa aaacaaaacc taacactaag gatcacggat |
| 481 acacgactct agccaccagt gtgaccctgt taaaagcctc ggaagtggaa gagattctgg |
| 541 atggcaacga tgagaagtac aaggctgtgt ccatcagcac agagcccccc acctacctca |
| 601 gggaacagaa ggccaagagg aacagccagt gggtacccac cctgcccaac agctcccacc |
| 661 acttagatgc cgtgccatgc tccacaacca tcaacaggaa ccgcatgggc cgagacaaga |
| 721 agagaacctt ccccctttgg tgtggatgca tcgctgcact caccctccgt gctgattccg |
| 781 ccttagttct ccactttgat gaccatgacc cagctgtgat ccatgagaac gcatctcagc |
| 841 ccgaggtgct ggtccccatc cggctggaca tggagatcga tgggcagaag ctgcgagacg |
| 901 ccttcacctg gaacatgaat gagaagttga tgacgcctga gatgttttca gaaatcctct |
| 961 gtgacgatct ggatttgaac ccgctgacgt ttgtgccagc catcgcctct gccatcagac |
| 1021 agcagatcga gtcctacccc acggacagca tcctggagga ccagtcagac cagcgcgtca |
| 1081 tcatcaagct gaacatccat gtgggaaaca tttccctggt ggaccagttt gagtgggaca |
| 1141 tgtcagagaa ggagaactca ccagagaagt ttgccctgaa gctgtgctcg gagctggggt |
| 1201 tgggcgggga gtttgtcacc accatcgcat acagcatccg gggacagctg agctggcatc |
| 1261 agaagaccta cgccttcagc gagaaccctc tgcccacagt ggagattgcc atccggaaca |
| 1321 cgggcgatgc ggaccagtgg tgcccactgc tggagactct gacagacgct gagatggaga |
| 1381 agaagatccg cgaccaggac aggaacacga ggcggatgag gcgtcttgcc aacacggccc |
| 1441 cggcctggta accagcccat cagcacacgg ctcccacgga gcatctcaga agattgggcc |
| 1501 gcctctcctc catcttctgg caaggacaga ggcgagggga cagcccagcg ccatcctgag |
| 1561 gatcgggtgg gggtggagtg ggggcttcca ggtggccctt cccggcacac attccatttg |
| 1621 ttgagcccca gtcctgcccc ccaccccacc ctccctaccc ctccccagtc tctggggtca |
| 1681 ggaagaaacc ttattttagg ttgtgttttg tttttgtata ggagccccag gcagggctag |
| 1741 taacagtttt taaataaaag gcaacaggtc atgttcaatt tcttcaacaa aaaaaaaaaa |
| 1801 aaa |
| SEQ ID NO: 8 Human SMARCB1 Amino Acid Sequence Isoform D (NP_001349806.1) |
| 1 mmmmalsktf gqkpvkfqle ddgefymigs evgnylrmfr gslykrypsl wrrlatveer |
| 61 kkivasshgk ktkpntkdhg yttlatsvtl lkaseveeil dgndekykav sistepptyl |
| 121 reqkakrnsq wvptlpnssh hldavpcstt inrnrmgrdk krtfplwcgc iaaltlrads |
| 181 alvlhfddhd pavihenasq pevlvpirld meidgqklrd aftwnmnekl mtpemfseil |

TABLE 1-continued

| Representative SMARCB1 |
|---|
| 241 cddldlnplt fvpaiasair qqiesyptds iledqsdqrv iiklnihvgn islvdqfewd |
| 301 msekenspek falklcselg lggefvttia ysirgqlswh qktyafsenp lptveiairn |
| 361 tgdadqwcpl letltdaeme kkirdqdrnt rrmrrlanta paw |
| SEQ ID NO: 9 Mouse SMARCB1 cDNA Sequence Variant 1 (NM_011418.2, CDS: 220-1377) |
| 1 gtcagcttct ccacgcatgc gcaccgaggg cggcctgctc gttgcagaga cggccaagga |
| 61 gcccagtagt gacacgagcg ctcgcccggt tcgcccggct tgccctgccc gaccttcacc |
| 121 tccaggcctc cgttcctttc ggtccgacgc gcctcggccc cgccctagcc caccggattc |
| 181 tttccagctc gaccccggct gccggtttcc cccgccgcca tgatgatgat ggcgttgagc |
| 241 aagaccttcg ggcagaagcc cgtcaagttt cagctggagg acgacgggga gttctacatg |
| 301 atcggctccg aggtgggaaa ctacctgcgt atgttccgag gttctctgta caagagatac |
| 361 ccctcactct ggcggcgact agccactgtg gaagaaagga agaaaaatagt ggcatcgtca |
| 421 catggtaaaa aaacaaaacc taacactaag gatcatggat ataccaccct ggccaccagc |
| 481 gtgacactcc tgaaagcctc agaggtagaa gagatcctgg atggcaatga cgagaagtac |
| 541 aaggctgtgt ccatcagcac agagcccccg acctacctca gggagcagaa ggccaagagg |
| 601 aacagccagt gggtccccac cctgcccaac agctcccacc acctggatgc tgtgccctgt |
| 661 tccaccacca tcaacaggaa ccgcatgggt cgggacaaga agagaacctt ccccttgtgc |
| 721 tttgatgacc acgacccagc tgtgatccat gagaatgcgt cacagcctga ggtgctggtg |
| 781 cccatccggc tcgacatgga gatcgacggg cagaagctgc gagacgcttt tacctggaac |
| 841 atgaatgaga agctaatgac tcctgagatg ttttcagaaa tactttgtga tgacctggat |
| 901 ttgaatccac tgacttttgt gccagctatt gcctctgcca ttcgacagca gattgagtcc |
| 961 taccccacag acagcatcct agaggatcaa tccgaccagc gtgtcatcat caagctgaac |
| 1021 atccacgtgg ggaacatctc cctggtggac cagtttgagt gggacatgtc agagaaagag |
| 1081 aactccccag agaagtttgc cctgaagctg tgctcagagc tgggcttggg cggggagttt |
| 1141 gtcaccacca ttgcatacag catccgagga cagctgagct ggcaccagaa gacctatgcc |
| 1201 ttcagtgaga acccacttcc cacagtggag attgccatcc gaaataccgg agatgctgac |
| 1261 cagtggtgcc ccctgctgga gacactgact gatgccgaga tggagaaaaa gatccgggat |
| 1321 caagatagga acacaaggcg aatgaggcgt cttgccaaca ctgccccagc ctggtgatga |
| 1381 agacatccat gctcgacctc tacggagcat ctcagactgc ctttccttcc tctgtggaaa |
| 1441 gagaaaggca aagggacagc LggLgccaLc clgaggacLg gggLaggagc ctcctaggtg |
| 1501 cctcccttca gcacacattc catttgctaa accccaacac tgtcccccag agtctagagt |
| 1561 cggaagcagc ctcattttgg gttgtgtttt gtttttgtat aggagcccag gcagggctgg |
| 1621 taacactttt taaataaaaa gtaccatgtt caatttcaaa aaaaaaaaaa aaaa |
| SEQ ID NO: 10 Mouse SMARCB1 Amino Acid Sequence Isoform 1 (NP_035548.1) |
| 1 mmmmalsktf gqkpvkfqle ddgefymigs evgnylrmfr gslykrypsl wrrlatveer |
| 61 kkivasshgk ktkpntkdhg yttlatsvtl lkaseveeil dgndekykav sistepptyl |
| 121 reqkakrnsq wvptlpnssh hldavpcstt inrnrmgrdk krtfplcfdd hdpavihena |
| 181 sqpevlvpir ldmeidgqkl rdaftwnmne klmtpemfse ilcddldlnp ltfvpaiasa |
| 241 irqqiesypt dsiledqsdq rviiklnihv gnislvdqfe wdmsekensp ekfalklcse |
| 301 lglggefvtt iaysirgqls whqktyafse nplptveiai rntgdadqwc plletltdae |

TABLE 1-continued

| Representative SMARCB1 |
|---|
| 361 mekkirdqdr ntrrmrrlan tapaw |
| SEQ ID NO: 11 Mouse SMARCB1 cDNA Sequence Variant 2 (NM_001161853.1, CDS: 220-1350) |
| 1 gtcagcttct ccacgcatgc gcaccgaggg cggcctgctc gttgcagaga cggccaagga |
| 61 gcccagtagt gacacgagcg ctcgcccggt tcgcccggct tgccctgccc gaccttcacc |
| 121 tccaggcctc cgttcctttc ggtccgacgc gcctcggccc cgccctagcc caccggattc |
| 181 tttccagctc gaccccggct gccggtttcc cccgccgcca tgatgatgat ggcgttgagc |
| 241 aagaccttcg ggcagaagcc cgtcaagttt cagctggagg acgacgggga gttctacatg |
| 301 atcggctccg aggtgggaaa ctacctgcgt atgttccgag gttctctgta caagagatac |
| 361 ccctcactct ggcggcgact agccactgtg gaagaaagga agaaaatagt ggcatcgtca |
| 421 catgatcatg gatataccac cctggccacc agcgtgacac tcctgaaagc ctcagaggta |
| 481 gaagagatcc tggatggcaa tgacgagaag tacaaggctg tgtccatcag cacagagccc |
| 541 ccgacctacc tcagggagca gaaggccaag aggaacagcc agtgggtccc caccctgccc |
| 601 aacagctccc accacctgga tgctgtgccc tgttccacca ccatcaacag gaaccgcatg |
| 661 ggtcgggaca agaagagaac cttccccttg tgctttgatg accacgaccc agctgtgatc |
| 721 catgagaatg cgtcacagcc tgaggtgctg gtgcccatcc ggctcgacat ggagatcgac |
| 781 gggcagaagc tgcgagacgc ttttacctgg aacatgaatg agaagctaat gactcctgag |
| 841 atgttttcag aaatactttg tgatgacctg gatttgaatc cactgacttt tgtgccagct |
| 901 attgcctctg ccattcgaca gcagattgag tcctacccca cagacagcat cctagaggat |
| 961 caatccgacc agcgtgtcat catcaagctg aacatccacg tggggaacat ctccctggtg |
| 1021 gaccagtttg agtgggacat gtcagagaaa gagaactccc cagagaagtt tgccctgaag |
| 1081 ctgtgctcag agctgggctt gggcggggag tttgtcacca ccattgcata cagcatccga |
| 1141 ggacagctga gctggcacca gaagacctat gccttcagtg agaacccact tcccacagtg |
| 1201 gagattgcca tccgaaatac cggagatgct gaccagtggt gccccctgct ggagacactg |
| 1261 actgatgccg agatggagaa aaagatccgg gatcaagata ggaacacaag gcgaatgagg |
| 1321 cgtcttgcca acactgcccc agcctggtga tgaagacatc catgctcgac ctctacggag |
| 1381 catctcagac tgcctttcct tcctctgtgg aaagagaaag gcaaagggac agctggtgcc |
| 1441 atcctgagga ctggggtagg agcctcctag gtgcctccct tcagcacaca ttccatttgc |
| 1501 taaaccccaa cactgtcccc cagagtctag agtcggaagc agcctcattt tgggttgtgt |
| 1561 tttgtttttg tataggagcc caggcagggc tggtaacact ttttaaataa aaagtaccat |
| 1621 gttcaatttc aaaaaaaaaa aaaaaaa |
| SEQ ID NO: 12 Mouse SMARCB1 Amino Acid Sequence Isoform 2 (NP_001155325.1) |
| 1 mmmmalsktf gqkpvkfqle ddgefymigs evgnylrmfr gslykrypsl wrrlatveer |
| 61 kkivasshdh gyttlatsvt llkaseveei ldgndekyka vsisteppty lreqkakrns |
| 121 qwvptlpnss hhldavpcst tinrnrmgrd kkrtfplcfd dhdpavihen asqpevlvpi |
| 181 rldmeidgqk lrdaftwnmn eklmtpemfs eilcddldln pltfvpaias airqqiesyp |
| 241 tdsiledqsd qrviiklnih vgnislvdqf ewdmsekens pekfalklcs elglggefvt |

TABLE 1-continued

| Representative SMARCB1 | |
|---|---|
| 301 | tiaysirgql swhqktyafs enplptveia irntgdqdqw cplletltda emekkirdqd |
| 361 | rntrrmrrla ntapaw |

*Included in Table 1 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

*Included in Table 1 are protein variants comprising a SMARCB1 CC domain that can include 1, 2, 3, 4, 5, 6, 7, 8, 9, 10, or more, or any range in between, inclusive, such as 2-4, amino acid residue deletions and/or mutations as compared to the wild-type SMARCB1 CC domain.

TABLE 2

| Representative SMARCB1 Fragments |
|---|
| Primate SMARCB1 CC domain |
| Rodent SMARCB1 CC domain |
| Mammalian SMARCB1 CC domain |
| Human SMARCB1 CC domain |
| SEQ ID NO: 13 Human SMARCB1 Fragment (SMARCB1-CC_WT(A)) (residues 351-385) (35-mer) PLLETLTDAEMEKKIRDQDRNTRRMRRLANTAPAW |
| SEQ ID NO: 14 Human SMARCB1 Fragment (SMARCB1-CC_K364del (A)) (residues 351-385) (34-mer) PLLETLTDAEMEKIRDQDRNTRRMRRLANTAPAW |
| SEQ ID NO: 15 Human SMARCB1 Fragment (SMARCB1-CC_R377H) (residues 351-385) (35-mer) PLLETLTDAEMEKKIRDQDRNTRRMRHLANTAPAW |
| SEQ ID NO: 16 Human SMARCB1 Fragment (SMARCB1-CC_R366C) (residues 351-385) (35-mer) PLLETLTDAEMEKKICDQDRNTRRMRRLANTAPAW |
| SEQ ID NO: 17 Human SMARCB1 Fragment (SMARCB1-CC_K363N) (residues 351-385) (35-mer) PLLETLTDAEMENKIRDQDRNTRRMRRLANTAPAW |
| SEQ ID NO: 18 Human SMARCB1 Fragment (SMARCB1-CC_R374Q) (residues 351-385) (35-mer) PLLETLTDAEMEKKIRDQDRNTRQMRRLANTAPAW |
| SEQ ID NO: 19 Human SMARCB1 Fragment (SMARCB1-CC_K364A) (residues 351-385) (35-mer) PLLETLTDAEMEKAIRDQDRNTRRMRRLANTAPAW |
| SEQ ID NO: 20 Human SMARCB1 Fragment (SMARCB1-CC_K364E) (residues 351-385) (35-mer) PLLETLTDAEMEKEIRDQDRNTRRMRRLANTAPAW |
| SEQ ID NO: 21 Human SMARCB1 Fragment (SMARCB1-CC_K364R) (residues 351-385) (35-mer) PLLETLTDAEMEKRIRDQDRNTRRMRRLANTAPAW |

TABLE 2-continued

| Representative SMARCB1 Fragments |
|---|
| SEQ ID NO: 22 Human SMARCB1 Fragment (SMARCB1-CC_K364P) (residues 351-385) (35-mer)<br>PLLETLTDAEMEKPIRDQDRNTRRMRRLANTAPAW |
| SEQ ID NO: 23 Human SMARCB1 Fragment (SMARCB1-CC_I365A) (residues 351-385) (35-mer)<br>PLLETLTDAEMEKKARDQDRNTRRMRRLANTAPAW |
| SEQ ID NO: 24 Human SMARCB1 Fragment (SMARCB1-CC AA-363/364) (residues 351-385) (35-mer)<br>PLLETLTDAEMEAAIRDQDRNTRRMRRLANTAPAW |
| SEQ ID NO: 25 Human SMARCB1 Fragment (SMARCB1-CC EE-363/364) (residues 351-385) (35-mer)<br>PLLETLTDAEMEEEIRDQDRNTRRMRRLANTAPAW |
| SEP ID NO: 26 Human SMARCB1 Fragment (SMARCB1-CC K363A) (residues 351-385) (35-mer)<br>PLLETLTDAEMEAKIRDQDRNTRRMRRLANTAPAW |
| SEP ID NO: 27 Human SMARCB1 Fragment (SMARCB1-CC R370A) (residues 351-385) (35-mer)<br>PLLETLTDAEMEKKIRDQDANTRRMRRLANTAPAW |
| SEQ ID NO: 28 *S. cerevisae* SMARCB1 Fragment (*S.cerevisae*_SNF5CC) (residues 650-684) (35-mer)<br>PNLLQISAAELERLDKDKDRDTRRKRRQGRSNRRG |
| SEQ ID NO: 29 *S. cerevisae* SMARCB1 Fragment (*S.cerevisae*_SFH1CC) (residues 380-414) (35-mer)<br>PRVEILTKEEIQKREIEKERNLRRLKRETDRLSRR |
| SEQ ID NO: 30 *C. elegans* SMARCB1 Fragment (*C.elegans*_SNF5CC) (residues 347-381) (35-mer)<br>PFLETLTDAEIEKKMRDQDRNTRRMRRLVGGGFNY |
| SEQ ID NO: 31 *D. melanogaster* SMARCB1 Fragment (D.melanogaster SNR1CC) (residues 336-370) (35-mer)<br>PFLETLTDAEMEKKIRDQDRNTRRMRRLANTTTGW |
| SEQ ID NO: 32 Human SMARCB1 Fragment (SMARCB1-CC_WT(B)) (residues 351-382) (32-mer)<br>PLLETLTDAEMEKKIRDQDRNTRRMRRLANTA |
| SEQ ID NO: 33 Human SMARCB1 Fragment (SMARCB1-CC_K364del(B)) (residues 351-382) (31-mer)<br>PLLETLTDAEMEKIRDQDRNTRRMRRLANTA |
| SEQ ID NO: 34 Human SMARCB1 Fragment (SMARCB1-CC_R377H) (residues 351-382) (32-mer)<br>PLLETLTDAEMEKKIRDQDRNTRRMRHLANTA |
| SEQ ID NO: 35 Human SMARCB1 Fragment (SMARCB1-CC_R366C) (residues 351-382) (32-mer)<br>PLLETLTDAEMEKKICDQDRNTRRMRRLANTA |
| SEP ID NO: 36 Human SMARCB1 Fragment (SMARCB1-CC_K363N) (residues 351-382) (32-mer)<br>PLLETLTDAEMENKIRDQDRNTRRMRRLANTA |
| SEQ ID NO: 37 Human SMARCB1 Fragment (SMARCB1-CC_R3740) (residues 351-382) (32-mer)<br>PLLETLTDAEMEKKIRDQDRNTRQMRRLANTA |
| SEP ID NO: 38 Human SMARCB1 Fragment (SMARCB1-CC_WT) (residues 357-378) (22-mer)<br>TDAEMEKKIRDQDRNTRRMRRL |

TABLE 2-continued

| Representative SMARCB1 Fragments |
|---|
| SEP ID NO: 38 Human SMARCB1 Fragment (SMARCB1-CC_WT) (residues 357-377) (21-mer) TDAEMEKKIRDQDRNTRRMRR |

*Included in Table 2 are nucleic acids encoding the fragments, including RNA nucleic acid molecules (e.g., thymines replaced with uridines), nucleic acid molecules encoding orthologs of the encoded proteins, as well as DNA or RNA nucleic acid sequences comprising a nucleic acid sequence having at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 2, or a portion thereof. Such nucleic acid molecules can have a function of the full-length nucleic acid as described further herein.

*Included in Table 2 are orthologs of the proteins, as well as polypeptide molecules comprising an amino acid sequence having at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEP ID ND listed in Table 2, or a portion thereof, and have positively charged faces available for binding nucleosomes. Such polypeptides can have a function of the polypeptide as described further herein. For example, *S. cerevisiae* SFH1 and SNF5 CC sequences are 60% similar (31.5% to 37.1% identical) to *H. Sapiens* SMARCB1-CC and have positive charged faces believed to similarly bind nucleosomes (e.g., the sequence from D367-R373 is 100% conserved from yeast (except that T372 is a leucine residue in *S. cerevisiae* SNF5).

*Included in Table 2 are protein variants that can include 1, 2, 3, 4, 5, 6, 7, 8, 9, 10, or more, or any range in between, inclusive, such as 2-4, amino acid residue deletions and/or mutations as compared to the wild-type SMARCB1 CC domain.

*Included in Table 2 are the SMARCB1 C-terminal domain (e.g., region 335-385), as well as the alpha helical portions of the SMARCB1 CC region therein, which are demonstrated herein by NMR structural analyses to encompass residues 357-377 or 357- 378 of human SMARCB1, or a corresponding region in an ortholog thereof. It is believed that, in some embodiments, unstructured regions (residues 351-355/351-356 and 378-385) form a more ordered structure in the context of binding nucleosomes. It is further believed that residue T357 serves as an alpha helix capping residue. The threonine's hydroxyl can help form a hydrogen bond with the following backbone of residue 358 such that, in some embodiments, the residue functionally contributes to alpha helix structure.

II. Isolated Modified Polypeptides and Complexes

The present invention relates, in part, to an isolated polypeptide and/or a complex comprising same, such as those selected from the group consisting of polypeptides listed in Tables 1 and 2 and protein complexes listed in Table 3, wherein the isolated modified protein complex comprises at least one subunit (e.g., SMARCB1) that is modified.

Complexes for use according to the present invention can be single polypeptides (e.g., SMARCB1 polypeptide or fragment thereof) in association with another moiety, such as a nucleosome, or combinations of polypeptides (e.g., protein complexes comprising a SMARCB1 subunit) in association with each other and/or in association with another moiety, such as a nucleosome.

In certain embodiments, the isolated polypeptide is a SMARCB1 fragment comprising the SMARCB1 CC domain, or a sequence that is at least 30% identical to such a sequence and has a positively charged face capable of binding nucleosomes. In some embodiments, the isolated polypeptide is a SMARCB1 fragment that is modified relative to the wild-type sequence. Representative embodiments of such wild-type and modified SMARCB1 fragments are listed in Table 2. In some embodiments, the isolated modified SMARCB1 fragment has reduced nucleosome binding activity as compared to the wild-type SMARCB1 fragment. In some embodiments, the isolated modified SMARCB1 fragment has one or more of the following compared to the wild-type SMARCB1 fragment: a. replacement of at least one basic amino acid for a neutral or an acidic amino acid, optionally wherein the basic amino acid is an outward-facing residue of the alpha helix; b. deletion of at least one basic amino acid, optionally wherein the basic amino acid is an outward-facing residue of the alpha helix; c. reduced isoelectric point, reduced charge potential, and/or reduced net positive charge; d. reduced or eliminated interaction with the canonical nucleosome acidic patch, optionally wherein the interaction is with H2AE91, H4E52, H2AE64, and/or H2BE113; e. partial competitive binding with LANA peptide; and/or f. a deletion or missense mutation at residue K363, K364, R366, R370, R373, R374, R376, R377 and/or any residues within SMARCB1 residues 357-378 (e.g., the alpha helix) of human SMARCB1, or a corresponding residue in an ortholog thereof. In some embodiments, the isolated SMARCB1 fragment further comprises a heterologous amino acid sequence, such as an affinity tag or a label. Tags can include Glutathione-S-Transferase (GST), calmodulin binding protein (CBP), protein C tag, Myc tag, HaloTag, HA tag, Flag tag, His tag, biotin tag, and V5 tag. Labels can include a fluorescent protein.

In some embodiments, protein complexes comprising a modified SMARCB1 subunit that can be a fragment as described above or a full-length SMARCB1 polypeptide that is modified to have the functional properties of such a fragment, are provided. In some embodiments, a protein complex comprising such a modified SMARCB1 subunit has at least one of the following as compared to the protein complex comprising the wild-type SMARCB1 subunit rather than the modified SMARCB1 subunit: a. reduced nucleosome binding activity; b. reduced nucleosome remodeling activity; c. reduced nucleosome ATPase activity; d. reduced chromatin accessibility activity; or reduced gene expression at mSWI/SNF target genes.

For any embodiment described herein, SMARCB1 can be a subunit of a complex that is modified.

In certain embodiments, at least one subunit of a complex encompassed by the present invention (e.g., SMARCB1) is a homolog, a derivative, e.g., a functionally active derivative, a fragment, e.g., a functionally active fragment, of a protein subunit of a complex encompassed by the present invention. In certain embodiments encompassed by the present invention, a homolog/ortholog, derivative or fragment of a protein subunit of a complex encompassed by the present invention is still capable of forming a complex with the other subunit(s). Complex-formation can be tested by any method known to the skilled artisan. Such methods include, but are not limited to, non-denaturing PAGE, FRET, and Fluorescence Polarization Assay.

Homologs (e.g., nucleic acids encoding subunit proteins from other species) or other related sequences (e.g., paralogs) which are members of a native cellular protein complex can be identified and obtained by low, moderate or high stringency hybridization with all or a portion of the particular nucleic acid sequence as a probe, using methods well-known in the art for nucleic acid hybridization and cloning.

Exemplary moderately stringent hybridization conditions are as follows: prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 hours at 65° C. in prehybridization mixture containing 100 μg/ml denatured salmon sperm DNA and 5-20×$10^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 min before autoradiography. Alternatively, exemplary conditions of high stringency are as follows: e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, *Current Protocols in Molecular Biology*, Vol. I, Green Publishing Associates, Inc., and John Wiley & sons, Inc., New York, at p. 2.10.3). Other conditions of high stringency which may be used are well-known in the art. Exemplary low stringency hybridization conditions comprise hybridization in a buffer comprising 35% formamide, 5×SSC, 50 mM Tris-HCl (pH 7.5), 5 mM EDTA, 0.02% PVP, 0.02% Ficoll, 0.2% BSA, 100 μg/ml denatured salmon sperm DNA, and 10% (wt/vol) dextran sulfate for 18-20 hours at 40° C., washing in a buffer consisting of 2×SSC, 25 mM Tris-HCl (pH 7.4), 5 mM EDTA, and 0.1% SDS for 1.5 hours at 55° C., and washing in a buffer consisting of 2×SSC, 25 mM Tris-HCl (pH 7.4), 5 mM EDTA, and 0.1% SDS for 1.5 hours at 60° C.

In certain embodiments, a homolog of a subunit binds to the same proteins to which the subunit binds. In certain, more specific embodiments, a homolog of a subunit binds to the same proteins to which the subunit binds wherein the binding affinity between the homolog and the binding partner of the subunit is at least 10%, at least 20%, at least 30%, at least 40%, at least 50%, at least 60%, at least 70%, at least 80%, at least 90%, at least 95% or at least 98% of the binding affinity between the subunit and the binding partner. Binding affinities between proteins can be determined by any method known to the skilled artisan.

In certain embodiments, a fragment of a protein subunit of the complex consists of at least 6 (continuous) amino acids, of at least 10, at least 20 amino acids, at least 30 amino acids, at least 40 amino acids, at least 50 amino acids, at least 75 amino acids, at least 100 amino acids, at least 150 amino acids, at least 200 amino acids, at least 250 amino acids, at least 300 amino acids, at least 400 amino acids, or at least 500 amino acids of the protein subunit of the naturally occurring protein complex. In specific embodiments. Such fragments are not larger than 40 amino acids, 50 amino acids, 75 amino acids, 100 amino acids, 150 amino acids, 200 amino acids, 250 amino acids, 300 amino acids, 400 amino acids, or than 500 amino acids. In more specific embodiments, the functional fragment is capable of forming a complex encompassed by the present invention, i.e., the fragment can still bind to at least one other protein subunit to form a complex encompassed by the present invention. In some embodiments, the fragment comprises at least one SMARCB1 fragment comprising a CC domain, such as those provided in Table 2. In some embodiments, fragments are provided herein, which share an identical region of 30, 31, 32, 33, 34, 35, 36, 37, 38, 39, 40, 41, 42, 43, or 44 or more, or any range in between, inclusive, such as 31-35, contiguous amino acids of the CC domain of an SMARCB1 fragment comprising a CC domain, such as those provided in Table 2. In some embodiments, the SMARCB1 CC domain can include 1, 2, 3, 4, 5, 6, 7, 8, 9, 10, or more, or any range in between, inclusive, such as 2-4, amino acid residue deletions and/or mutations as compared to the wild-type SMARCB1 CC domain.

Derivatives or analogs of subunit proteins include, but are not limited, to molecules comprising regions that are substantially homologous to the subunit proteins, in various embodiments, by at least 30%, 40%, 50%, 60%, 70%, 80%, 90% or 95% identity over an amino acid sequence of identical size or when compared to an aligned sequence in which the alignment is done by a computer homology program known in the art, or whose encoding nucleic acid is capable of hybridizing to a sequence encoding the subunit protein under stringent, moderately stringent, or nonstringent conditions.

Derivatives of a protein subunit include, but are not limited to, fusion proteins of a protein subunit of a complex encompassed by the present invention to a heterologous amino acid sequence, mutant forms of a protein subunit of a complex encompassed by the present invention, and chemically modified forms of a protein subunit of a complex encompassed by the present invention. In a specific embodiment, the functional derivative of a protein subunit of a complex encompassed by the present invention is capable of forming a complex encompassed by the present invention, i.e., the derivative can still bind to at least one other protein subunit to form a complex encompassed by the present invention.

In certain embodiments encompassed by the present invention, at least two subunits of a complex encompassed by the present invention are linked to each other via at least one covalent bond. A covalent bond between subunits of a complex encompassed by the present invention increases the stability of the complex encompassed by the present invention because it prevents the dissociation of the subunits. Any method known to the skilled artisan can be used to achieve a covalent bond between at least two subunits encompassed by the present invention.

In specific embodiments, covalent cross-links are introduced between adjacent subunits. Such cross-links can be between the side chains of amino acids at opposing sides of the dimer interface. Any functional groups of amino acid residues at the dimer interface in combination with suitable cross-linking agents can be used to create covalent bonds between the protein subunits at the dimer interface. Existing amino acids at the dimer interface can be used or, alternatively, suitable amino acids can be introduced by site-directed mutagenesis.

In exemplary embodiments, cysteine residues at opposing sides of the dimer interface are oxidized to form disulfide bonds. See, e.g., Reznik et al., (1996) *Nat Bio Technol* 14:1007-1011, at page 1008. 1,3-dibromoacetone can also be used to create an irreversible covalent bond between two sulfhydryl groups at the dimer interface. In certain other embodiments, lysine residues at the dimer inter face are used to create a covalent bond between the protein subunits of the complex. Crosslinkers that can be used to create covalent bonds between the epsilon amino groups of lysine residues are, e.g., but are not limited to, bis(sulfosuccinimidyl)suberate; dimethyladipimidate-2HD1; disuccinimidyl glutarate; N-hydroxysuccinimidyl 2,3-dibromoproprionate.

In other specific embodiments, two or more interacting subunits, or homologues, derivatives or fragments thereof, are directly fused together, or covalently linked together through a peptide linker, forming a hybrid protein having a single unbranched polypeptide chain. Thus, the protein complex may be formed by "intramolecular interactions between two portions of the hybrid protein. In still another embodiment, at least one of the fused or linked interacting subunit in this protein complex is a homologue, derivative or fragment of a native protein.

In specific embodiments, at least one subunit, or a homologue, derivative or fragment thereof, may be expressed as fusion or chimeric protein comprising the subunit, homologue, derivative or fragment, joined via a peptide bond to a heterologous amino acid sequence.

As used herein, a "chimeric protein" or "fusion protein" comprises all or part (preferably a biologically active part) of a polypeptide corresponding to a subunit or a fragment, homologue or derivative thereof, operably linked to a heterologous polypeptide (i.e., a polypeptide other than the polypeptide corresponding to the subunit or a fragment, homologue or derivative thereof). Within the fusion protein, the term "operably linked" is intended to indicate that the polypeptide encompassed by the present invention and the heterologous polypeptide are fused in-frame to each other. The heterologous polypeptide can be fused to the amino-terminus or the carboxyl-terminus of the polypeptide encompassed by the present invention.

In one embodiment, the heterologous amino acid sequence comprises an affinity tag that can be used for affinity purification. In another embodiment, the heterologous amino acid sequence includes a fluorescent label. In still another embodiment, the fusion protein contains a heterologous signal sequence, immunoglobulin fusion protein, toxin, or other useful protein sequences.

A variety of peptide tags known in the art may be used to generate fusion proteins of the protein subunits of a complex encompassed by the present invention, such as but not limited to the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST: Smith, 1993, *Methods Mol. Cell Bio.* 4:220-229), the *E. coli* maltose binding protein (Guan et al., 1987, *Gene* 67:21-30), and various cellulose binding domains (U.S. Pat. Nos. 5,496, 934: 5,202,247; 5,137,819; Tomme et al., 1994, *Protein Eng.* 7:117-123), etc.

One possible peptide tags are short amino acid sequences to which monoclonal antibodies are available, such as but not limited to the following well-known examples, the FLAG epitope, the myc epitope at amino acids 408-439, the influenza virus hemaglutinin (HA) epitope. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

In certain embodiments, a combination of different peptide tags is used for the purification of the protein subunits of a complex encompassed by the present invention or for the purification of a complex. In certain embodiments, at least one subunit has at least two peptide tags, e.g., a FLAG tag and a His tag. The different tags can be fused together or can be fused in different positions to the protein subunit. In the purification procedure, the different peptide tags are used subsequently or concurrently for purification. In certain embodiments, at least two different subunits are fused to a peptide tag, wherein the peptide tags of the two subunits can be identical or different. Using different tagged subunits for the purification of the complex ensures that only complex will be purified and minimizes the amount of uncomplexed protein subunits, such as monomers or homodimers.

Various leader sequences known in the art can be used for the efficient secretion of a protein subunit of a complex encompassed by the present invention from bacterial and mammalian cells (von Heijne, 1985, J. Mol. Biol. 184:99-105). Leader peptides are selected based on the intended host cell, and may include bacterial, yeast, viral, animal, and mammalian sequences. For example, the herpes virus glycoprotein D leader peptide is suitable for use in a variety of mammalian cells. A preferred leader peptide for use in mammalian cells can be obtained from the V-J2-C region of the mouse immunoglobulin kappa chain (Bernard et al., 1981. *Proc. Natl. Acad. Sci.* 78:5812-5816).

DNA sequences encoding desired peptide tag or leader peptide which are known or readily available from libraries or commercial suppliers are suitable in the practice of this invention.

In certain embodiments, the protein subunits of a complex encompassed by the present invention are derived from the same species. In more specific embodiments, the protein subunits are all derived from human. In another specific embodiment, the protein subunits are all derived from a mammal.

In certain other embodiments, the protein subunits of a complex encompassed by the present invention are derived from a non-human species, such as, but not limited to, cow, pig, horse, cat, dog, rat, mouse, a primate (e.g., a chimpanzee, a monkey Such as a cynomolgous monkey). In certain embodiments, one or more subunits are derived from human and the other subunits are derived from a mammal other than a human to give rise to chimeric complexes.

Included within the scope encompassed by the present invention is an isolated modified protein complex in which the subunits, or homologs, derivatives, or fragments thereof, are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH4, acetylation, formylation, oxidation, reduction, metabolic synthesis in the presence of tunicamycin, etc. In still another embodiment, the protein sequences are modified to have a heterofunctional reagent; such heterofunctional reagents can be used to crosslink the members of the complex.

The protein complexes encompassed by the present invention can also be in a modified form. For example, an antibody selectively immunoreactive with the protein complex can be bound to the protein complex. In another example, a non-antibody modulator capable of enhancing the interaction between the interacting partners in the protein complex may be included.

The above-described protein complexes may further include any additional components, e.g., other proteins, nucleic acids, lipid molecules, monosaccharides or polysaccharides, ions, etc.

TABLE 3

Representative Complexes Containing SMARCB1

| Protein complex | Subunits of the protein complex |
|---|---|
| BAF | Subunit_1: SMARCC1 or SMARCC2 |
| | Subunit_2: SMARCC1 or SMARCC2 |
| | Subunit_3: SMARCD1, SMARCD2, or SMARCD3 |
| | Subunit_4: SMARCB1 |
| | Subunit_5: SMARCE1 |
| | Subunit_6: ARID1A or ARID1B |
| | Subunit_7: DPF1, DPF2, or DPF3 |
| | Subunit_8: ACTL6A |
| | Subunit_9: β-Actin |
| | Subunit_10: BCL7A, BCL7B, or BCL7C |
| | Subunit_11: SMARCA2 or SMARCA4 |
| | Subunit_12: SS18 or SS18L1 |
| PBAF | Subunit_1: SMARCC1 or SMARCC2 |
| | Subunit_2: SMARCC1 or SMARCC2 |
| | Subunit_3: SMARCD1, SMARCD2, or SMARCD3 |
| | Subunit_4: SMARCB1 |
| | Subunit_5: SMARCE1 |
| | Subunit_6: ARID2 |
| | Subunit_7: BRD7 |
| | Subunit_8: PHF10 |
| | Subunit_9: ACTL6A |
| | Subunit_10: β-Actin |
| | Subunit_11: BCL7A, BCL7B, or BCL7C |
| | Subunit_12: SMARCA2 or SMARCA4 |
| | Subunit_13: PBRM1 |
| | Subunit_14: PBRM1 |
| BAF Core | Subunit_1: SMARCC1 or SMARCC2 |
| | Subunit_2: SMARCC1 or SMARCC2 |
| | Subunit_3: SMARCD1, SMARCD2, or SMARCD3 |
| | Subunit_4: SMARCB1 |
| | Subunit_5: SMARCE1 |
| ARID/BAF | Subunit_1: SMARCC1 or SMARCC2 |
| Core | Subunit_2: SMARCC1 or SMARCC2 |
| intermediate_1 | Subunit_3: SMARCD1, SMARCD2, or SMARCD3 |
| | Subunit_4: SMARCB1 |
| | Subunit_5: SMARCE1 |
| | Subunit_6: ARID1A or ARID1B |
| ARID/BAF | Subunit_1: SMARCC1 or SMARCC2 |
| Core | Subunit_2: SMARCC1 or SMARCC2 |
| intermediate_2 | Subunit_3: SMARCD1, SMARCD2, or SMARCD3 |
| | Subunit_4: SMARCB1 |
| | Subunit_5: SMARCE1 |
| | Subunit_6: ARID1A or ARID1B |
| | Subunit_7: DPF1, DPF2, or DPF3 |
| ARID/PBAF | Subunit_1: SMARCC1 or SMARCC2 |
| Core | Subunit_2: SMARCC1 or SMARCC2 |
| intermediate_1 | Subunit_3: SMARCD1, SMARCD2, or SMARCD3 |
| | Subunit_4: SMARCB1 |
| | Subunit_5: SMARCE1 |
| | Subunit_6: ARID2 |
| | Subunit_7: BRD7 |
| ARID/PBAF | Subunit_1: SMARCC1 or SMARCC2 |
| Core | Subunit_2: SMARCC1 or SMARCC2 |
| intermediate_2 | Subunit_3: SMARCD1, SMARCD2, or SMARCD3 |
| | Subunit_4: SMARCB1 |
| | Subunit_5: SMARCE1 |
| | Subunit_6: ARID2 |
| | Subunit_7: BRD7 |
| | Subunit_8: PHF10 |

* Complexes encompassed by the present invention include any SMARCB1-containing protein complex in physical association with a nucleosome, as well as any SMARCB1 polypeptide, or fragment thereof, in physical association with a nucleosome. These include canonical BAF, PBAF, and core modules of each of these (SMARCC1, SMARCC2, SMARCD1, SMARCE1, SMARCB1 (WT or mutant variants), ARID1A/B (or ARID2 in PBAF), and DPF2 (or PHF10 in PBAF)).

III. Methods of Preparing Polypeptides and Protein Complexes

The polypeptides and protein complexes encompassed by the present invention can be obtained by methods well-known in the art for protein purification and recombinant protein expression, as well as the methods described in details in the Examples. For example, the polypeptides and protein complexes encompassed by the present invention can be isolated using the TAP method described in Section 5, infra, and in WO 00/09716 and Rigaut et al., 1999, *Nature Biotechnol.* 17:1030-1032, which are each incorporated by reference in their entirety. Additionally, the polypeptides and protein complexes can be isolated by immunoprecipitation of subunit proteins and combining the immunoprecipitated proteins. The protein complexes can also be produced by recombinantly expressing the subunit proteins and combining the expressed proteins.

In certain embodiments, the complexes can be generated by co-expressing the subunits of the complex in a cell and subsequently purifying the complex. In certain, more specific embodiments, the cell expresses at least one subunit of the complex by recombinant DNA technology. In other embodiments, the cells normally express the subunits of the complex. In certain other embodiments, the subunits of the complex are expressed separately, wherein the subunits can be expressed using recombinant DNA technology or wherein at least one subunit is purified from a cell that normally expresses the subunit. The individual subunits of the complex are incubated in vitro under conditions conducive to the binding of the subunits of a complex encompassed by the present invention to each other to generate a complex encompassed by the present invention.

If one or more of the subunits is expressed by recombinant DNA technology, any method known to the skilled artisan can be used to produce the recombinant protein. The nucleic and amino acid sequences of the subunit proteins of the protein complexes encompassed by the present invention are provided herein, such as in Table 1, and can be obtained by any method known in the art, e.g., by PCR amplification using synthetic primers hybridizable to the 3' and 5' ends of each sequence, and/or by cloning from a cDNA or genomic library using an oligonucleotide specific for each nucleotide sequence.

For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter of the subunit protein gene, and/or flanking regions.

A variety of host-vector systems may be utilized to express the protein coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In a preferred embodiment, a complex encompassed by the present invention is obtained by expressing the entire coding sequences of the subunit proteins in the same cell, either under the control of the same promoter or separate promoters. In yet another embodiment, a derivative, fragment or homologue of a subunit protein is recombinantly expressed. Preferably the derivative, fragment or homologue of the protein forms a complex with the other subunits of the complex, and more preferably forms a complex that binds to an anti-complex antibody.

Any method available in the art can be used for the insertion of DNA fragments into a vector to construct expression vectors containing a chimeric gene consisting of appropriate transcriptional/translational control signals and protein coding sequences. These methods may include in vitro recombinant DNA and synthetic techniques and in vivo recombinant techniques (genetic recombination). Expression of nucleic acid sequences encoding a subunit protein, or a derivative, fragment or homologue thereof, may be regulated by a second nucleic acid sequence so that the gene or fragment thereof is expressed in a host transformed with the recombinant DNA molecule(s). For example, expression of the proteins may be controlled by any promoter/enhancer known in the art. In a specific embodiment, the promoter is not native to the gene for the subunit protein. Promoters that may be used can be selected from among the many known in the art, and are chosen so as to be operative in the selected host cell.

In a specific embodiment, a vector is used that comprises a promoter operably linked to nucleic acid sequences encoding a subunit protein, or a fragment, derivative or homologue thereof, one or more origins of replication, and optionally, one or more selectable markers (e.g., an antibiotic resistance gene).

In another specific embodiment, an expression vector containing the coding sequence, or a portion thereof, of a subunit protein, either together or separately, is made by subcloning the gene sequences into the EcoRI restriction site of each of the three pGEX vectors (glutathione S-transferase expression vectors; Smith and Johnson, 1988, Gene 7:31-40). This allows for the expression of products in the correct reading frame.

Expression vectors containing the sequences of interest can be identified by three general approaches: (a) nucleic acid hybridization, (b) presence or absence of "marker" gene function, and (c) expression of the inserted sequences. In the first approach, coding sequences can be detected by nucleic acid hybridization to probes comprising sequences homologous and complementary to the inserted sequences. In the second approach, the recombinant vector/host system can be identified and selected based upon the presence or absence of certain "marker" functions (e.g., resistance to antibiotics, occlusion body formation in baculovirus, etc.) caused by insertion of the sequences of interest in the vector. For example, if a subunit protein gene, or portion thereof, is inserted within the marker gene sequence of the vector, recombinants containing the encoded protein or portion will be identified by the absence of the marker gene function (e.g., loss of β-galactosidase activity). In the third approach, recombinant expression vectors can be identified by assaying for the subunit protein expressed by the recombinant vector. Such assays can be based, for example, on the physical or functional properties of the interacting species in in vitro assay systems, e.g., formation of a complex comprising the protein or binding to an anti-complex antibody.

Once recombinant subunit protein molecules are identified and the complexes or individual proteins isolated, several methods known in the art can be used to propagate them. Using a suitable host system and growth conditions, recombinant expression vectors can be propagated and amplified in quantity. As previously described, the expression vectors or derivatives which can be used include, but are not limited to, human or animal viruses such as vaccinia virus or adenovirus; insect viruses such as baculovirus, yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered subunit proteins may be controlled. Furthermore, different host cells have characteristic and specific mechanisms for the translational and post-translational processing and modification (e.g., glycosylation, phosphorylation, etc.) of proteins. Appropriate cell lines or host systems can be chosen to ensure that the desired modification and processing of the foreign protein is achieved. For example, expression in a bacterial system can be used to produce an unglycosylated core protein, while expression in mammalian cells ensures"native" glycosylation of a heterologous protein. Furthermore, different vector/host expression systems may effect processing reactions to different extents.

In other specific embodiments, a subunit protein or a fragment, homologue or derivative thereof, may be expressed as fusion or chimeric protein product comprising the protein, fragment, homologue, or derivative joined via a peptide bond to a heterologous protein sequence of a different protein. Such chimeric products can be made by ligating the appropriate nucleic acid sequences encoding the desired amino acids to each other by methods known in the art, in the proper coding frame, and expressing the chimeric products in a suitable host by methods commonly known in the art. Alternatively, such a chimeric product can be made by protein synthetic techniques, e.g., by use of a peptide synthesizer. Chimeric genes comprising a portion of a subunit protein fused to any heterologous protein-encoding sequences may be constructed.

In particular, protein subunit derivatives can be made by altering their sequences by substitutions, additions or deletions that provide for functionally equivalent molecules. Due to the degeneracy of nucleotide coding sequences, other DNA sequences that encode substantially the same amino acid sequence as a subunit gene or cDNA can be used in the practice encompassed by the present invention. These include but are not limited to nucleotide sequences comprising all or portions of the subunit protein gene that are altered by the substitution of different codons that encode a functionally equivalent amino acid residue within the sequence, thus producing a silent change. Likewise, the derivatives encompassed by the present invention include, but are not limited to, those containing, as a primary amino acid sequence, all or part of the amino acid sequence of a subunit protein, including altered sequences in which functionally equivalent amino acid residues are substituted for residues within the sequence resulting in a silent change. For example, one or more amino acid residues within the sequence can be substituted by another amino acid of a similar polarity that acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment, up to 1%, 2%, 5%, 10%, 15% or 20% of the total number of amino acids in the wild-type protein are substituted or deleted; or 1, 2, 3, 4, 5, or 6 or up to 10 or up to 20 amino acids are inserted, substituted or deleted relative to the wild-type protein.

The protein subunit derivatives and analogs encompassed by the present invention can be produced by various methods known in the art. The manipulations which result in their production can occur at the gene or protein level. For example, the cloned gene sequences can be modified by any of numerous strategies known in the art (Sambrook et al., 1989, Molecular Cloning, A Laboratory Manual, 2d Ed., Cold Spring Harbor Laboratory Press, Cold Spring Harbor, New York). The sequences can be cleaved at appropriate sites with restriction endonuclease(s), followed by further enzymatic modification if desired, isolated, and ligated in vitro. In the production of the gene encoding a derivative, homologue or analog of a subunit protein, care should be taken to ensure that the modified gene retains the original translational reading frame, uninterrupted by translational stop signals, in the gene region where the desired activity is encoded.

Additionally, the encoding nucleic acid sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used, including but not limited to, chemical mutagenesis and in vitro site-directed mutagenesis (Hutchinson et al., 1978, *J. Bioi. Chern.* 253:6551-6558), amplification with PCR primers containing a mutation, etc.

Once a recombinant cell expressing a subunit protein, or fragment or derivative thereof, is identified, the individual gene product or complex can be isolated and analyzed. This is achieved by assays based on the physical and/or functional properties of the protein or complex, including, but not limited to, radioactive labeling of the product followed by analysis by gel electrophoresis, immunoassay, cross-linking to marker-labeled product, etc.

The subunit proteins and complexes may be isolated and purified by standard methods known in the art (either from natural sources or recombinant host cells expressing the complexes or proteins) or methods described in the examples herein, including but not restricted to column chromatography (e.g., ion exchange, affinity, gel exclusion, reversed-phase high pressure, fast protein liquid, etc.), differential centrifugation, differential solubility, or by any other standard technique used for the purification of proteins. In some embodiment, the isolation methods include the density sedimentation-based approaches. Functional properties may be evaluated using any suitable assay known in the art.

Alternatively, once a subunit protein or its derivative, is identified, the amino acid sequence of the protein can be deduced from the nucleic acid sequence of the chimeric gene from which it was encoded. As a result, the protein or its derivative can be synthesized by standard chemical methods known in the art (e.g., Hunkapiller et al., 1984, *Nature* 310:105-111).

In addition, complexes of analogs and derivatives of subunit proteins can be chemically synthesized. For example, a peptide corresponding to a portion of a subunit protein, which comprises the desired domain or mediates the desired activity in vitro (e.g., complex formation) can be synthesized by use of a peptide synthesizer.

Furthermore, if desired, non-classical amino acids or chemical amino acid analogs can be introduced as a substitution or addition into the protein sequence. Non-classical amino acids include but are not limited to the D-isomers of the common amino acids, α-amino isobutyric acid, 4-aminobutyric acid (4-Abu), 2-aminobutyric acid (2-Abu), 6-amino hexanoic acid (Ahk), 2-amino isobutyric acid (2-Aib), 3-amino propionic acid, ornithine, norleucine, norvaline, hydroxyproline, sarcosine, citrulline, cysteic acid. t-butylglycine, t-butylalanine, phenylglycine, cyclohexylalanine, β-alanine, fluoro-amino acids, designer amino acids such as β-methyl amino acids, Ca-methyl amino acids. Na-methylamino acids, and amino acid analogs in general. Furthermore, the amino acid can be D (dextrorotary) or L (levorotary).

In cases where natural products are suspected of being mutant or are purified from new species, the amino acid sequence of a subunit protein purified from the natural Source. as well as those expressed in vitro, or from synthesized expression vectors in vVivo or in vitro, can be determined from analysis of the DNA sequence, or alternatively, by direct sequencing of the purified protein. Such analysis can be per formed by manual sequencing or through use of an automated amino acid sequenator.

The complexes can also be analyzed by hydrophilicity analysis (Hopp and Woods, 1981, Proc. Natl. Acad. Sci. USA 78:3824-3828). A hydrophilicity profile can be used to identify the hydrophobic and hydrophilic regions of the proteins, and help predict their orientation in designing substrates for experimental manipulation, such as in binding experiments, antibody synthesis, etc. Secondary structural analysis can also be done to identify regions of the subunit proteins, or their derivatives, that assume specific structures (Chou and Fasman, 1974, Biochemistry 13:222-23). Manipulation, translation, secondary structure prediction, hydrophilicity and hydrophobicity profile predictions, open reading frame prediction and plotting, and determination of sequence homologies, etc., can be accomplished using computer software programs available in the art.

Other methods of structural analysis including but not limited to X-ray crystallography (Engstrom, 1974, Biochem. Exp. Bioi. 11:7-13), mass spectroscopy and gas chromatography (Methods in Protein Science, J. Wiley and Sons, New York, 1997), and computer modeling (Fietterick and Zoller, eds., 1986, Computer Graphics and Molecular Modeling, In: Current Communications in Molecular Biology, Cold Spring Harbor Laboratory, Cold Spring Harbor Press, New York) can also be employed.

In certain embodiments, at least one subunit of the complex is generated by recombinant DNA technology and is a derivative of the naturally occurring protein. In certain embodiments, the derivative is a fusion protein, wherein the amino acid sequence of the naturally occurring protein is fused to a second amino acid sequence. The second amino acid sequence can be a peptide tag that facilitates the purification, immunological detection and identification as well as visualization of the protein. A variety of peptide tags with different functions and affinities can be used in the invention to facilitate the purification of the subunit or the complex comprising the subunit by affinity chromatography. A specific peptide tag comprises the constant regions of an immunoglobulin. In other embodiments, the subunit is fused to a leader sequence to promote secretion of the protein subunit from the cell that expresses the protein subunit.

Other peptide tags that can be used with the invention include, but are not limited to, FLAG epitope or HA tag.

If the subunits of the complex are co-expressed, the complex can be purified by any method known to the skilled artisan, including immunoprecipitation, ammonium Sulfate precipitation, acid extraction, anion or cation exchange chromatography, phosphocellulose chromatography, immunoaffinity chromatography, hydroxyapatite chromatography, and lectin chromatography.

The methods described herein can be used to purify the individual subunits of the complex encompassed by the present invention. The methods can also be used to purify the entire complex. Generally, the purification conditions as well as the dissociation constant of the complex will determine whether the complex remains intact during the purification procedure. Such conditions include, but are not limited to, salt concentration, detergent concentration, pH and redox-potential.

If at least one polypeptide, or subunit of the complex, comprises a peptide tag, the invention the invention also contemplates methods for the purification of the complexes encompassed by the present invention which are based on the properties of the peptide tag. One approach is based on specific molecular interactions between a tag and its binding partner. The other approach relies on the immunospecific binding of an antibody to an epitope present on the tag. The principle of affinity chromatography well-known in the art is generally applicable to both of these approaches. In another embodiment, the complex is purified using immunoprecipitation.

In certain embodiments, the individual subunits of a complex encompassed by the present invention are expressed separately. The subunits are subsequently incubated under conditions conducive to the binding of the subunits of the complex to each other to generate the complex. In certain, more specific embodiments, the subunits are purified before complex formation. In other embodiments the supernatants of cells that express the subunit (if the subunit is secreted) or cell lysates of cells that express the subunit (if the subunit is not secreted) are combined first to give rise to the complex, and the complex is purified subsequently. Parameters affecting the ability of the subunits encompassed by the present invention to bind to each other include, but are not limited to, salt concentration, detergent concentration, pH, and redox-potential. Once the complex has formed, the complex can be purified or concentrated by any method known to the skilled artisan. In certain embodiments, the complex is separated from the remaining individual subunits by filtration. The pore size of the filter should be such that the individual subunits can still pass through the filter, but the complex does not pass through the filter. Other methods for enriching the complex include sucrose gradient centrifugation and chromatography.

IV. Screening Methods a. Modulators of Complex Formation

A complex encompassed by the present invention, the component proteins of the complex and nucleic acids encoding the component proteins, as well as derivatives and fragments of the amino and nucleic acids, can be used to screen for compounds that bind to, or modulate the amount of, activity of, formation of, or stability of, said complex, and thus, have potential use as modulators, i.e., agonists or antagonists, of complex activity, complex stability, and/or complex formation, i.e., the amount of complex formed, and/or protein component composition of the complex.

As described above, complexes for use according to the present invention can be single polypeptides (e.g., SMARCB1 polypeptide or fragment thereof) in association with another moiety, such as a nucleosome, or combinations of polypeptides (e.g., protein complexes comprising a SMARCB1 subunit) in association with each other and/or in association with another moiety, such as a nucleosome.

Thus, the present invention is also directed to methods for screening for molecules that bind to, or modulate the amount of activity of, or protein component composition of a complex encompassed by the present invention. In one embodiment encompassed by the present invention, the method for screening for a molecule that modulates directly or indirectly the function, activity or formation of a complex encompassed by the present invention comprises exposing said complex, or a cell or organism containing the complex machinery, to one or more test agents under conditions conducive to modulation; and determining the amount of activity of or identities of the protein components of said complex, wherein a change in said amount, activity, or identities relative to said amount, activity or identities in the absence of the test agents indicates that the test agents modulate function, activity or formation of said complex. Such screening assays can be carried out using cell-free and cell-based methods that are commonly known in the art.

In one embodiment, the method for screening for molecules that bind to, or modulate the amount of, activity of, formation of, or stability of, a complex encompassed by the present invention further comprises incubating subunits of the isolated modified protein complex in the presence of a test agent under conditions conductive to form the modified protein complex prior to step of contacting described above. In another embodiment, the method further comprises a step of determining the presence and/or amount of the individual subunits in the isolated modified protein complex.

The present invention is further directed to methods for screening for molecules that modulate the expression of a subunit of a complex encompassed by the present invention. In one embodiment encompassed by the present invention, the method for screening for a molecule that modulates the expression of a subunit of a complex encompassed by the present invention comprises exposing a cell or organism containing the nucleic acid encoding the component, to one or more compounds under conditions conducive to modulation; and determining the amount of activity of, or identities of the protein components of said complex, wherein a change in said amount, activity, or identities relative to said amount, activity or identities in the absence of said compounds indicates that the compounds modulate expression of said complex. Such screening assays can be carried out using cell-free and cell based methods that are commonly known in the art. If activity of the complex or component is used as read-out of the assay, subsequent assays, such as western blot analysis or northern blot analysis, may be performed to verify that the modulated expression levels of the component are responsible for the modulated activity.

In a further specific embodiment, a modulation of the formation or stability of a complex can be determined. In some embodiment, the agent modulates (inhibits or promotes) the formation or stability of the isolated modified protein complex. In specific embodiments, the agent inhibits the formation or stability of the isolated modified protein complex by inhibiting the interaction between at least one interaction between SMARCB1 and another subunit listed in Table 3. The agent may be, e.g., a small molecule inhibitor, a small molecule degrader, CRISPR guide RNA (gRNA), RNA interfering agent, oligonucleotide, peptide or peptidomimetic inhibitor, aptamer, antibody, or intrabody. In a specific embodiment, the agent comprises an antibody and/or intrabody, or an antigen binding fragment thereof, which specifically binds to at least one subunit of the isolated modified protein complex. In some other embodiments, the agent enhances the formation or stability of the isolated modified protein complex. In specific embodiments, the agent enhances the formation or stability of the protein complex by stabilizing the interaction between at least one interaction between SMARCB1 and another subunit listed in Table 3. The agent may be a small molecule compound, e.g., a small molecule stabilizer.

Such a modulation can either be a change in the typical time course of its formation or a change in the typical steps leading to the formation of the complete complex. Such changes can for example be detected by analyzing and comparing the process of complex formation in untreated wild-type cells of a particular type and/or cells showing or having the predisposition to develop a certain disease phenotype and/or cells which have been treated with particular conditions and/or particular agents in a particular situation. Methods to study such changes in time course are well-known in the art and include for example Western blot analysis of the proteins in the complex isolated at different steps of its formation.

In a specific embodiment, fragments and/or analogs of protein components of a complex, especially peptidomimetics, are screened for activity as competitive or non-competitive inhibitors of complex formation, which thereby inhibit complex activity or formation.

In another embodiment, the present invention is directed to a method for screening for a molecule that binds a protein complex encompassed by the present invention comprising exposing said complex, or a cell or organism containing the complex machinery, to one or more candidate molecules; and determining whether said complex is bound by any of said candidate molecules.

Screening the libraries can be accomplished by any of a variety of commonly known methods. See, e.g., the following references, which disclose screening of peptide libraries: Parmley and Smith, 1989, *Adv. Exp. Med. Biol.* 251:215-218: Scott and Smith, 1990, *Science* 249:386-390; Fowlkes et al., 1992, *BioTechniques* 13:422-427; Oldenburg et al., 1992, *Proc. Natl. Acad. Sci. USA* 89:5393-5397: Yu et al., 1994, *Cell* 76:933-945; Staudt et al., 1988, *Science* 241:577-580; Bock et al., 1992, *Nature* 355:564-566: Tuerk et al., 1992, *Proc. Natl. Acad. Sci. USA* 89:6988-6992: Ellington et al., 1992, *Nature* 355:850-852; U.S. Pat. Nos. 5,096,815, 5,223,409, and 5,198,346, all to Ladner et al.; Rebar and Pabo, 1993, *Science* 263:671-673; and International Patent Publication No. WO 94/18318.

In a specific embodiment, screening can be carried out by contacting the library members with a complex immobilized on a solid phase, and harvesting those library members that bind to the protein (or encoding nucleic acid or derivative). Examples of such screening methods, termed "panning" techniques, are described by way of example in Parmley and Smith, 1988, *Gene* 73:305-318; Fowlkes et al., 1992, *BioTechniques* 13:422-427; International Patent Publication No. WO 94/18318; and in references cited herein above.

In a specific embodiment, fragments and/or analogs of protein components of a complex, especially peptidomimetics, are screened for activity as competitive or non-competitive inhibitors of complex formation (amount of complex or composition of complex) or activity in the cell, which thereby inhibit complex activity or formation in the cell.

In one embodiment, agents that modulate (i.e., antagonize or agonize) complex activity or formation can be screened for using a binding inhibition assay, wherein agents are screened for their ability to modulate formation of a complex under aqueous, or physiological, binding conditions in which complex formation occurs in the absence of the agent to be tested. Agents that interfere with the formation of complexes encompassed by the present invention are identified as antagonists of complex formation. Agents that promote the formation of complexes are identified as agonists of complex formation. Agents that completely block the formation of complexes are identified as inhibitors of complex formation.

Methods for screening may involve labeling the component proteins of the complex with radioligands (e.g., $^{125}I$ or $^{3}H$), magnetic ligands (e.g., paramagnetic beads covalently attached to photobiotin acetate), fluorescent ligands (e.g., fluorescein or rhodamine), or enzyme ligands (e.g., luciferase or β-galactosidase). The reactants that bind in solution can then be isolated by one of many techniques known in the art, including but not restricted to, co-immunoprecipitation of the labeled complex moiety using antisera against the unlabeled binding partner (or labeled binding partner with a distinguishable marker from that used on the second labeled complex moiety), immunoaffinity chromatography, size exclusion chromatography, and gradient density centrifugation. In a preferred embodiment, the labeled binding partner is a small fragment or peptidomimetic that is not retained by a commercially available filter. Upon binding, the labeled species is then unable to pass through the filter, providing for a simple assay of complex formation.

In certain embodiments, the protein components of a complex encompassed by the present invention are labeled with different fluorophores such that binding of the components to each other results in FRET (Fluorescence Resonance Energy Transfer). If the addition of a compound results in a difference in FRET compared to FRET in the absence of the compound, the compound is identified as a modulator of complex formation. If FRET in the presence of the compound is decreased in comparison to FRET in the absence of the compound, the compound is identified as an inhibitor of complex formation. If FRET in the presence of the compound is increased in comparison to FRET in the absence of the compound, the compound is identified as an activator of complex formation.

In certain other embodiments, a protein component of a complex encompassed by the present invention is labeled with a fluorophore such that binding of the component to another protein component to form a complex encompassed by the present invention results in FP (Fluorescence Polarization). If the addition of a compound results in a difference in FP compared to FP in the absence of the compound, the compound is identified as a modulator of complex formation.

Methods commonly known in the art are used to label at least one of the component members of the complex. Suitable labeling methods include, but are not limited to, radiolabeling by incorporation of radiolabeled amino acids, e.g., $^{3}H$-leucine or $^{35}S$-methionine, radiolabeling by post-translational iodination with $^{125}I$ or $^{131}I$ using the chloramine T method, Bolton-Hunter reagents, etc., or labeling with $^{32}P$ using phosphorylase and inorganic radiolabeled phosphorous, biotin labeling with photobiotin-acetate and sunlamp exposure, etc. In cases where one of the members of the complex is immobilized, e.g., as described infra, the free species is labeled. Where neither of the interacting species is immobilized, each can be labeled with a distinguishable marker such that isolation of both moieties can be followed to provide for more accurate quantification, and to distinguish the formation of homomeric from heteromeric complexes. Methods that utilize accessory proteins that bind to one of the modified interactants to improve the sensitivity of detection, increase the stability of the complex, etc., are provided.

The physical parameters of complex formation can be analyzed by quantification of complex formation using assay methods specific for the label used, e.g., liquid scintillation counting for radioactivity detection, enzyme activity for enzyme-labeled moieties, etc. The reaction results are then analyzed utilizing Scatchard analysis, Hill analysis, and other methods commonly known in the arts (see, e.g., Proteins, Structures, and Molecular Principles, 2nd Edition (1993) Creighton, Ed., W.H. Freeman and Company, New York).

Agents/molecules (candidate molecules) to be screened can be provided as mixtures of a limited number of specified compounds, or as compound libraries, peptide libraries and the like. Agents/molecules to be screened may also include all forms of antisera, antisense nucleic acids, etc., that can modulate complex activity or formation. Exemplary candidate molecules and libraries for screening are set forth below.

In certain embodiments, the compounds are screened in pools. Once a positive pool has been identified, the individual molecules of that pool are tested separately. In certain embodiments, the pool size is at least 2, at least 5, at least 10, at least 25, at least 50, at least 75, at least 100, at least 150, at least 200, at least 250, or at least 500 compounds.

In certain embodiments encompassed by the present invention, the screening method further comprises determining the structure of the candidate molecule. The structure of a candidate molecule can be determined by any technique known to the skilled artisan.

i. Test Agents

Any molecule known in the art can be tested for its ability to modulate (increase or decrease) the amount of, activity of, or protein component composition of a complex encompassed by the present invention as detected by a change in the amount of, activity of, or protein component composition of said complex. By way of example, a change in the amount of the complex can be detected by detecting a change in the amount of the complex that can be isolated from a cell expressing the complex machinery. In other embodiments, a change in signal intensity (e.g., when using FRET or FP) in the presence of a compound compare to the absence of the compound indicates that the compound is a modulator of complex formation. For identifying a molecule that modulates complex activity, candidate molecules can be directly provided to a cell expressing the complex, or, in the case of candidate proteins, can be provided by providing their encoding nucleic acids under conditions in which the nucleic acids are recombinantly expressed to produce the candidate proteins within the cell expressing the complex machinery, the complex is then purified from the cell and the purified complex is assayed for activity using methods well-known in the art, not limited to those described, Supra.

In certain embodiments, the invention provides screening assays using chemical libraries for molecules which modulate, e.g., inhibit, antagonize, or agonize, the amount of, activity of, or protein component composition of the complex. The chemical libraries can be peptide libraries, peptidomimetic libraries, chemically synthesized libraries, recombinant, e.g., phage display libraries, and in vitro translation-based libraries, other non-peptide synthetic organic libraries, etc.

Exemplary libraries are commercially available from several sources (ArOule, Tripos/PanLabs, ChemDesign, and Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, Smaller and Smaller pools of interacting pairs can be assayed for the modulation activity. By Such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome based libraries are exemplary types of libraries that can be used.

The libraries can be constrained or semirigid (having some degree of structural rigidity), or linear or non-constrained. The library can be a cDNA or genomic expression library, random peptide expression library or a chemically synthesized random peptide library, or non-peptide library. Expression libraries are introduced into the cells in which the assay occurs, where the nucleic acids of the library are expressed to produce their encoded proteins.

In one embodiment, peptide libraries that can be used in the present invention may be libraries that are chemically synthesized in vitro. Examples of such libraries are given in Houghten et al., 1991, *Nature* 354:84-86, which describes mixtures of free hexapeptides in which the first and second residues in each peptide were individually and specifically defined; Lam et al., 1991, *Nature* 354:82-84, which describes a "one bead, one peptide' approach in which a solid phase split synthesis scheme produced a library of peptides in which each bead in the collection had immobilized thereon a single, random sequence of amino acid residues; Medynski, 1994, *Bio/Technology* 12:709-710, which describes split synthesis and T-bag synthesis methods; and Gallop et al., 1994, *J. Medicinal Chemistry* 37(9): 1233-1251. Simply by way of other examples, a combinatorial library may be prepared for use, according to the methods of Ohlmeyer et al., 1993, *Proc. Natl. Acad Sci. USA* 90:10922-10926; Erb et al., 1994, *Proc. Natl. Acad Sci. USA* 91:11422-11426; Houghten et al., 1992, Biotechniques 13:412; Jayawickreme et al., 1994, *Proc. Natl. Acad Sci. USA* 91:1614-1618; or Salmon et al., 1993. *Proc. Natl. Acad Sci. USA* 90:11708-11712. PCT Publication No. WO 93/20242 and Brenner and Lerner. 1992, *Proc. Natl. Acad Sci. USA* 89:5381-5383 describe "encoded combinatorial chemical libraries," that contain oligonucleotide identifiers for each chemical polymer library member.

In a preferred embodiment, the library screened is a biological expression library that is a random peptide phage display library, where the random peptides are constrained (e.g., by virtue of having disulfide bonding).

Further, more general, structurally constrained, organic diversity (e.g., nonpeptide) libraries, can also be used.

Conformationally constrained libraries that can be used include but are not limited to those containing invariant cysteine residues which, in an oxidizing environment, cross link by disulfide bonds to form cysteines, modified peptides (e.g., incorporating fluorine, metals, isotopic labels, are phosphorylated, etc.), peptides containing one or more non-naturally occurring amino acids, non-peptide structures, and peptides containing a significant fraction of Y-carboxyglutamic acid.

Libraries of non-peptides, e.g., peptide derivatives (for example that contain one or more non-naturally occurring amino acids) can also be used. One example of these are peptoid libraries (Simon et al., 1992, *Proc. Natl. Acad Sci. USA* 89:9367-9371). Peptoids are polymers of non-natural amino acids that have naturally occurring side chains attached not to the alpha carbon but to the backbone amino nitrogen.

Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, *Proc. Natl. Acad. Sci. USA* 91:11138-11142).

The members of the peptide libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γ-Abu, ε-Ahk, 6-amino hexanoic acid; Aib, 2-amino isobutyric acid: 3-amino propionic acid: ornithine; norleucine: norvaline, hydroxyproline, sarcosine, citrulline, cysteic acid, t-butylglycine, t-butylalanine, phenylglycine, cyclohexylalanine, β-alanine, designer amino acids such as β-methyl amino acids, Ca-methyl amino acids, Na-methyl amino acids, fluoro-amino acids and amino acid analogs in general. Furthermore, the amino acid can be D (dextrorotary) or L (levorotary).

In a specific embodiment, fragments and/or analogs of protein components of complexes encompassed by the present invention, especially peptidomimetics, are screened for activity as competitive or non-competitive inhibitors of complex activity or formation.

In another embodiment encompassed by the present invention, combinatorial chemistry can be used to identify modulators of the complexes. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See, e.g., Matter, 1997, *Journal of Medicinal Chemistry* 40:1219-1229).

One method of combinatorial chemistry, affinity fingerprinting, has previously been used to test a discrete library of small molecules for binding affinities for a defined panel of proteins. The fingerprints obtained by the Screen are used to predict the affinity of the individual library members for other proteins or receptors of interest (in the instant invention, the protein complexes encompassed by the present invention and protein components thereof) The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, *Chemistry and Biology* 2:107-118; Kauvar, 1995, *Affinity finger printing, Pharmaceutical Manufacturing International.* 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Kay et al., 1993, Gene 128:59-65 (Kay) discloses a method of constructing peptide libraries that encode peptides of totally random sequence that are longer than those of any prior conventional libraries. The libraries disclosed in Kay encode totally synthetic random peptides of greater than about 20 amino acids in length. Such libraries can be advantageously screened to identify complex modulators. (See also U.S. Pat. No. 5,498,538 dated Mar. 12, 1996; and PCT Publication No. WO 94/18318 dated Aug. 18, 1994).

A comprehensive review of various types of peptide libraries can be found in Gallop et al., 1994, *J. Med. Chem.* 37:1233-1251.

Libraries screened using the methods encompassed by the present invention can comprise a variety of types of compounds. Examples of libraries that can be screened in accordance with the methods encompassed by the present invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as α-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays encompassed by the present invention.

In a preferred embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods encompassed by the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries encompassed by the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries.

The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides.

In contrast to solid phase synthesize of combinatorial compound libraries, liquid phase synthesis does not require the use of specialized protocols for monitoring the individual steps of a multistep solid phase synthesis (Egner et al., 1995, *J Org. Chem.* 60:2652; Anderson et al., 1995, *J. Org. Chem.* 60:2650; Fitch et al., 1994, *J. Org. Chem.* 59:7955; Look et al., 1994, *J. Org. Chem.* 49:7588; Metzger et al., 1993, *Angew. Chem.*, Int. Ed. Engl. 32:894; Youngquist et al., 1994, *Rapid Commun. Mass Spect.* 8:77; Chu et al., 1995, *J. Am. Chern. Soc.* 117:5419; Brummel et al., 1994, *Science* 264:399; and Stevanovic et al., 1993, *Bioorg. Med. Chern. Lett.* 3:431).

Combinatorial compound libraries useful for the methods encompassed by the present invention can be synthesized on solid supports. In one embodiment, a split synthesis method, a protocol of separating and mixing solid supports during the synthesis, is used to synthesize a library of compounds on solid supports (see e.g., Lam et al., 1997. *Chem. Rev.* 97:41-448; Ohlmeyer et al., 1993, *Proc. Nat. Acad. Sci. USA* 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi eta!., 1997, *Chem. Rev.* 97:449-472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments encompassed by the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high throughput screening of the compounds.

In certain embodiments encompassed by the present invention, the agent is a small molecule.

ii. Cell-Free Assays

In certain embodiments, the method for identifying a modulator of the formation or stability of a complex encompassed by the present invention can be carried out in vitro, particularly in a cell-free system. In certain, more specific embodiments, the complex is purified. In certain embodiments the candidate molecule is purified.

In a specific embodiment, screening can be carried out by contacting the library members with a complex immobilized on a solid phase, and harvesting those library members that bind to the protein (or encoding nucleic acid or derivative). Examples of such screening methods, termed "panning techniques, are described by way of example in Parmley and Smith, 1988, Gene 73:305-318: Fowlkes et al., 1992, *BioTechniques* 13:422-427: International Patent Publication No. WO 94/18318; and in references cited herein above.

In one embodiment, agents that modulate (i.e., antagonize or agonize) complex activity or formation can be screened for using a binding inhibition assay, wherein agents are screened for their ability to modulate formation of a complex under aqueous, or physiological, binding conditions in which complex formation occurs in the absence of the agent to be tested. Agents that interfere with the formation of complexes encompassed by the present invention are identified as antagonists of complex formation. Agents that promote the formation of complexes are identified as agonists of complex formation. Agents that completely block the formation of complexes are identified as inhibitors of complex formation. In an exemplary embodiment, the binding conditions are, for example, but not by way of limitation, in an aqueous salt solution of 10-250 mM NaCl, 5-50 mM Tris-HCl, pH 5-8, and 0.5% Triton X-100 or other detergent that improves specificity of interaction. Metal chelators and/or divalent cations may be added to improve binding and/or reduce proteolysis. Reaction temperatures may include 4, 10, 15, 22, 25, 35, or 42 degrees Celsius, and time of incubation is typically at least 15 seconds, but longer times are preferred to allow binding equilibrium to occur. Particular complexes can be assayed using routine protein binding assays to determine optimal binding conditions for reproducible binding.

Determining the interaction between two molecules can be accomplished using standard binding or enzymatic analysis assays. These assays may include thermal shift assays (measure of variation of the melting temperature of the protein alone and in the presence of a molecule) (R. Zhang, F. Monsma, (2010) *Curr. Opin. Drug Discov. Devel.,* 13:389-402), SPR (surface plasmon resonance) (T. Neumann, et al. (2007), *Curr. Top Med. Chem.,* 7: 1630-1642), FRET/BRET (Fluorescence or Bioluminescence Resonance Excitation Transfer) (A. L. Mattheyses, A. I. Marcus, (2015), *Methods Mol. Biol.,* 1278:329-339; J. Bacart, et al. (2008), *Biotechnol. J.,* 3: 311-324), Elisa (Enzyme-linked immunosorbent assay) (Z. Weng, Q. Zhao, (2015), *Methods Mol. Biol.,* 1278:341-352), fluorescence polarization (Y. Du, (2015), *Methods Mol. Biol.,* 1278:529-544), and Far western (U. Mahlknecht, O. G. Ottmann, D. Hoelzer J. (2001), *Biotechnol.,* 88: 89-94) or other techniques. More sophisticated (and lower throughput) biophysical methods that provide structural or thermodynamic details of the molecule binding mode (using isothermal calorimetry (ITC), Nuclear Magnetic Resonance (NMR), and X-ray crystallography) may also be needed for further validation and characterization of potential hits.

For example, in a direct binding assay, one subunit (or their respective binding partners) can be coupled with a radioisotope or enzymatic label such that binding can be determined by detecting the labeled subunit in a complex. For example, the subunits can be labeled with $^{125}I$, $^{35}S$, $^{14}C$, or $^{3}H$, either directly or indirectly, and the radioisotope detected by direct counting of radioemmission or by scintillation counting. Alternatively, the subunits can be enzymatically labeled with, for example, horseradish peroxidase, alkaline phosphatase, or luciferase, and the enzymatic label detected by determination of conversion of an appropriate substrate to product.

In certain embodiments, another common approach to in vitro binding assays is used. In this assay, one of the binding species is immobilized on a filter, in a microtiter plate well, in a test tube, to a chromatography matrix, etc., either covalently or non-covalently. Proteins can be covalently immobilized using any method well-known in the art, for example, but not limited to the method of Kadonaga and Tjian, 1986, *Proc. Natl. Acad. Sci. USA* 83:5889-5893, i.e., linkage to a cyanogen-bromide derivatized substrate such as CNBr-Sepharose 48 (Pharmacia). Where needed, the use of spacers can reduce steric hindrance by the substrate. Non-covalent attachment of proteins to a substrate include, but are not limited to, attachment of a protein to a charged surface, binding with specific antibodies, binding to a third unrelated interacting protein, etc.

Assays of agents (including cell extracts or a library pool) for competition for binding of one member of a complex (or derivatives thereof) with another member of the complex labeled by any means (e.g., those means described above) are provided to screen for competitors or enhancers of complex formation. In specific embodiments, blocking agents to inhibit non-specific binding of reagents to other protein components, or absorptive losses of reagents to plastics, immobilization matrices, etc., are included in the assay mixture. Blocking agents include, but are not restricted to bovine serum albumin, 13-casein, nonfat dried milk, Denhardt's reagent, Ficoll, polyvinylpyrolidine, nonionic detergents (NP40, Triton X-100, Tween 20, Tween 80, etc.), ionic detergents (e.g., SDS, LOS, etc.), polyethylene glycol, etc. Appropriate blocking agent concentrations allow complex formation.

After binding is performed, unbound, labeled protein is removed in the supernatant, and the immobilized protein retaining any bound, labeled protein is washed extensively. The amount of bound label is then quantified using standard methods in the art to detect the label.

In preferred embodiments, polypeptide derivatives that have superior stabilities but retain the ability to form a complex (e.g., one or more component proteins modified to be resistant to proteolytic degradation in the binding assay buffers, or to be resistant to oxidative degradation), are used to screen for modulators of complex activity or formation.

Such resistant molecules can be generated, e.g., by substitution of amino acids at proteolytic cleavage sites, the use of chemically derivatized amino acids at proteolytic susceptible sites, and the replacement of amino acid residues subject to oxidation, i.e. methionine and cysteine.

iii. Cell-Based Assays

In certain embodiments, assays can be carried out using recombinant cells expressing the protein components of a complex, to screen for molecules that bind to, or interfere with, or promote complex activity or formation. In certain embodiments, at least one of the protein components expressed in the recombinant cell as fusion protein, wherein the protein component is fused to a peptide tag to facilitate purification and subsequent quantification and/or immunological visualization and quantification.

A particular aspect encompassed by the present invention relates to identifying molecules that inhibit or promote formation or degradation of a complex encompassed by the present invention, e.g., using the method described for isolating the complex and identifying members of the complex using the TAP assay described in Section 4, infra, and in WO 00/09716 and Rigaut et al., 1999, Nature Biotechnol. 17:1030-1032, which are each incorporated by reference in their entirety.

In another embodiment encompassed by the present invention, a modulator is identified by administering a test agent to a transgenic non-human animal expressing the recombinant component proteins of a complex encompassed by the present invention. In certain embodiments, the complex components are distinguishable from the homologous endogenous protein components. In certain embodiments, the recombinant component proteins are fusion proteins, wherein the protein component is fused to a peptide tag. In certain embodiments, the amino acid sequence of the recombinant protein component is different from the amino acid sequence of the endogenous protein component such that antibodies specific to the recombinant protein component can be used to determine the level of the protein component or the complex formed with the component. In certain embodiments, the recombinant protein component is expressed from promoters that are not the native promoters of the respective proteins. In a specific embodiment, the recombinant protein component is expressed in tissues where it is normally not expressed. In a specific embodiment, the compound is also recombinantly expressed in the transgenic non-human animal.

In certain embodiments, a mutant form of a protein component of a complex encompassed by the present invention is expressed in a cell, wherein the mutant form of the protein component has a binding affinity that is lower than the binding affinity of the naturally occurring protein to the other protein component of a complex encompassed by the present invention. In a specific embodiment, a dominant negative mutant form of a protein component is expressed in a cell. A dominant negative form can be the domain of the protein component that binds to the other protein component, i.e., the binding domain. Without being bound by theory, the binding domain will compete with the naturally occurring protein component for binding to the other protein component of the complex thereby preventing the formation of complex that contains full length protein components. Instead, with increasing level of the dominant negative form in the cell, an increasing amount of complex lacks those domains that are normally provided to the complex by the protein component which is expressed as dominant negative.

The binding domain of a protein component can be identified by any standard technique known to the skilled artisan. In a non-limiting example, alanine-scanning mutagenesis (Cunningham and Wells, (1989) *Science* 244: 1081-1085) is conducted to identify the region(s) of the protein that is/are required for dimerization with another protein component. In other embodiments, different deletion mutants of the protein component are generated Such that the combined deleted regions would span the entire protein. In a specific embodiment, the different deletions overlap with each other. Once mutant forms of a protein component are generated, they are tested for their ability to form a dimer with another protein component. If a particular mutant fails to form a dimer with another protein component or binds the other protein component with reduced affinity compared to the naturally occurring form, the mutation of this mutant form is identified as being in a region of the protein that is involved in the dimer formation. To exclude that the mutation simply interfered with proper folding of the protein, any structural analysis known to the skilled artisan can be performed to determine the three-dimensional conformation of the protein. Such techniques include, but are not limited to, circular dichroism (CD), NMR, and X-ray crystallography.

In certain embodiments, a mutated form of a component of a complex encompassed by the present invention can be expressed in a cell under an inducible promoter. Any method known to the skilled artisan can be used to mutate the nucleotide sequence encoding the component. Any inducible promoter known to the skilled artisan can be used. In particular, the mutated form of the component of a complex encompassed by the present invention has reduced activity, e.g., reduced RNA-nucleolytic activity and/or reduced affinity to the other components of the complex.

In certain embodiments, the assays encompassed by the present invention are performed in high-throughput format. For example, high throughput cellular screens measuring the loss of interaction using reverse two hybrid or BRET may be used and offer the advantage of selecting only cell penetrable molecules (A. R. Horswill, S. N. Savinov, S. J. Benkovic (2004), *Proc. Natl. Acad. Sci. USA,* 101: 15591-15596; A. Hamdi, P. Colas (2012), *Trends Pharmacol. Sci.,* 33: 109-118). The latter approaches require further validation to assess the "on target" effect. In one or more embodiments of the above described assay methods, it may be desirable to immobilize polypeptides or molecules to facilitate separation of complexed from uncomplexed forms of one or both of the proteins or molecules, as well as to accommodate automation of the assay.

b. Use of Complexes to Identify New Binding Partners

In certain embodiments encompassed by the present invention, a complex encompassed by the present invention is used to identify new components the complex. In certain embodiments, new binding partners of a complex encompassed by the present invention are identified and thereby implicated in chromatin remodeling processing. Any technique known to the skilled artisan can be used to identify such new binding partners. In certain embodiments, a binding partner of a complex encompassed by the present invention binds to a complex encompassed by the present invention but not to an individual protein component of a complex encompassed by the present invention. In a specific embodiment, immunoprecipitation is used to identify binding partners of a complex encompassed by the present invention.

In certain embodiments, the assays encompassed by the present invention are performed in high-throughput format.

The screening methods encompassed by the present invention can also use other cell-free or cell-based assays known in the art, e.g., those disclosed in WO 2004/009622, US 2002/0177692 A1, US 2010/0136710 A1, all of which are incorporated herein by reference.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

V. Protein Microchip

In accordance with another embodiment encompassed by the present invention, a protein microchip or microarray is provided having one or more of the polypeptides, complexes, and/or antibodies selectively immunoreactive with the complexes encompassed by the present invention. Protein microarrays are becoming increasingly important in both proteomics research and protein based detection and diagnosis of diseases. The protein microarrays in accordance with this embodiment encompassed by the present invention will be useful in a variety of applications including, e.g., large-scale or high throughput screening for compounds capable of binding to the protein complexes or modulating the interactions between the interacting protein members in the protein complexes.

The protein microarray encompassed by the present invention can be prepared in a number of methods known in the art. An example of a suitable method is that disclosed in MacBeath and Schreiber, (2000) Science, 289: 1760-1763. Essentially, glass microscope slides are treated with an aldehyde-containing Silane reagent (Super Aldehyde substrates purchased from TeleChem International, Cupertino, CA). Nanoliter volumes of protein samples in a phosphate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer that functions to prevent non-specific protein binding in subsequent applications of the microchip. Alternatively, as disclosed in MacBeath and Schreiber, proteins or protein complexes encompassed by the present invention can be attached to a BSA-NHS slide by covalent linkages. BSA-NHS slides are fabricated by first attaching a molecular layer of BSA to the surface of glass slides and then activating the BSA with N, N'-disuccinimidyl carbonate. As a result, the amino groups of the lysine, aspartate, and glutamate residues on the BSA are activated and can form covalent urea or amide linkages with protein Samples Spotted on the slides. See MacBeath and Schreiber, (2000) *Science,* 289:1760-1763.

Another example of a useful method for preparing the protein microchip encompassed by the present invention is that disclosed in PCT Publication Nos. WO 00/4389A2 and WO 00/04382, both of which are assigned to Zyomyx and are incorporated herein by reference. First, a substrate or chip base is covered with one or more layers of thin organic film to eliminate any Surface defects, insulate proteins from the base materials, and to ensure uniform protein array. Next, a plurality of protein-capturing agents (e.g., antibodies, pep tides, etc.) are arrayed and attached to the base that is covered with the thin film. Proteins or protein complexes can then be bound to the capturing agents forming a protein microarray. The protein microchips are kept in flow chambers with an aqueous Solution.

The protein microarray encompassed by the present invention can also be made by the method disclosed in PCT Publication No. WO 99/36576 assigned to Packard Bioscience Company, which is incorporated herein by reference. For example, a three-dimensional hydrophilic polymer matrix, i.e., a gel, is first dispensed on a Solid Substrate Such as a glass slide. The polymer matrix gel is capable of expanding or contracting and contains a coupling reagent that reacts with amine groups. Thus, proteins and protein complexes can be contacted with the matrix gel in an expanded aqueous and porous State to allow reactions between the amine groups on the protein or protein complexes with the coupling reagents thus immobilizing the proteins and protein complexes on the Substrate. Thereafter, the gel is contracted to embed the attached proteins and protein complexes in the matrix gel.

Alternatively, the proteins and protein complexes encompassed by the present invention can be incorporated into a commercially available protein microchip, e.g., the ProteinChip System from Ciphergen Biosystems Inc., Palo Alto, Calif. The ProteinChip System comprises metal chips having a treated Surface, which interact with proteins. Basically, a metal chip Surface is coated with a Silicon dioxide film. The molecules of interest Such as proteins and protein complexes can then be attached covalently to the chip Surface via a silane coupling agent.

The preparation of such an array containing different types of proteins is well-known in the art and is apparent to a person skilled in the art (see e.g. Ekins et al., 1989, *J. Pharm. Biomed. Anal.* 7:155-168; Mitchell et al. 2002, *Nature Biotechnol.* 20:225-229; Petricoin et al., 2002, Lancet 359:572-577; Templin et al., 2001, *Trends Biotechnol.* 20:160-166; Wilson and Nock, 2001, *Curr. Opin. Chern. Biol.* 6:81-85; Lee et al., 2002 Science 295:1702-1705; MacBeath and Schreiber, 2000, *Science* 289:1760; Blawas and Reichert, 1998, Biomaterials 19:595; Kane et al., 1999, *Biomaterials* 20:2363; Chen et al., 1997, *Science* 276:1425; Vaugham et al., 1996, *Nature Biotechnol.* 14:309-314; Mahler et al., 1997, *Immunotechnology* 3:31-43; Roberts et al., 1999, *Curr. Opin. Chern. Biol.* 3:268-273; Nord et al., 1997, *Nature Biotechnol.* 15:772-777; Nord et al., 2001, *Eur. J. Biochem.* 268:4269-4277; Brody and Gold, 2000, *Rev. Mol. Biotechnol.* 74:5-13; Karlstroem and Nygren, 2001, *Anal. Biochem.* 295:22-30; Nelson et al., 2000, *Electrophoresis* 21:1155-1163; Honore et al., 2001, *Expert Rev. Mol. Diagn.* 3:265-274; Albala, 2001, *Expert Rev. Mol. Diagn.* 2:145-152, Figeys and Pinto, 2001, *Electrophoresis* 2:208-216 and references in the publications listed here).

The protein microchips encompassed by the present invention can also be prepared with other methods known in the art, e.g., those disclosed in U.S. Pat. Nos. 6,087,102, 6,139,831, 6,087,103; PCT Publication Nos. WO 99/60156, WO 99/39210, WO 00/54046, WO 00/53625, WO 99/51773,
WO 99/35289, WO 97/42507, WO 01/01142, WO 00/63694, WO 00/61806, WO 99/61148, WO 99/40434, US 2002/0177692 A1, WO 2004/009622, all of which are incorporated herein by reference.

Complexes can be attached to an array by different means as will be apparent to a person skilled in the art. Complexes can for example be added to the array via a TAP-tag (as described in WO/0009716 and in Rigaut et al., 1999, *Nature Biotechnol.* 10:1030-1032) after the purification step or by another suitable purification scheme as will be apparent to a person skilled in the art.

Optionally, the proteins of the complex can be cross-linked to enhance the stability of the complex. Different methods to cross-link proteins are well-known in the art. Reactive end-groups of cross-linking agents include but are not limited to —COOH, —SH, —NH2 or N-oxy-succinamate. The spacer of the cross-linking agent should be chosen with respect to the size of the complex to be cross-linked. For small protein complexes, comprising only a few proteins, relatively short spacers are preferable in order to reduce the likelihood of cross-linking separate complexes in the reaction mixture. For larger protein complexes, additional use of larger spacers is preferable in order to facilitate cross-linking between proteins within the complex.

It is preferable to check the success-rate of cross-linking before linking the complex to the carrier. As will be apparent to a person skilled in the art, the optimal rate of cross-linking need to be determined on a case by case basis. This can be achieved by methods well-known in the art, some of which are exemplary described below.

A sufficient rate of cross-linking can be checked for example by analysing the cross-linked complex vs. a non-cross-linked complex on a denaturating protein gel. If cross-linking has been performed successfully, the proteins of the complex are expected to be found in the same lane, whereas the proteins of the non-cross-linked complex are expected to be separated according to their individual characteristics. Optionally the presence of all proteins of the complex can be further checked by peptide-sequencing of proteins in the respective bands using methods well-known in the art such as mass spectrometry and/or Edman degradation.

In addition, a rate of crosslinking which is too high should also be avoided. If cross-linking has been carried out too extensively, there will be an increasing amount of cross-linking of the individual protein complex, which potentially interferes with a screening for potential binding partners and/or modulators etc. using the arrays.

The presence of such structures can be determined by methods well-known in the art and include e.g., gel-filtration experiments comparing the gel filtration profile solutions containing cross-linked complexes vs. uncross-linked complexes.

Optionally, functional assays as will be apparent to a person skilled in the art, some of which are exemplarily provided herein, can be performed to check the integrity of the complex.

Alternatively, members of the protein complex can be expressed as a single fusion protein and coupled to the matrix as will be apparent to a person skilled in the art.

Optionally, the attachment of the complex or proteins as outlined above can be further monitored by various methods apparent to a person skilled in the art. Those include, but are not limited to surface plasmon resonance (see e.g., McDannel, 2001, *Curr. Opin. Chern. Biol.* 5:572-577; Lee, 2001, *Trends Biotechnol.* 19:217-222; Weinberger et al., 2000, 1:395-416; Pearson et al., 2000, *Ann. Clin. Biochem.* 37:119-145; Vely et al., 2000, *Methods Mol. Biol.* 121:313-321; Slepak, 2000, *J. Mol Recognit.* 13:20-26.)

VI. Pharmaceutical Compositions

In another aspect, the present invention provides pharmaceutically acceptable compositions which comprise an isolated polypeptide and/or a complex comprising same, such as those selected from the group consisting of polypeptides listed in Tables 1 and 2 and protein complexes listed in Table 3, wherein the isolated modified protein complex comprises at least one subunit (e.g., SMARCB1) that is modified, formulated together with one or more pharmaceutically acceptable carriers (additives) and/or diluents.

As described in detail below, the pharmaceutical compositions encompassed by the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits or enhances) protein complex formation and/or activity which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) protein complex expression and/or activity. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods encompassed by the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a polypeptide subunit of an isolated modified protein complex encompassed by the present invention. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods encompassed by the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an isolated modified protein complex encompassed by the present invention, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an isolated modified protein complexes encompassed by the present invention include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an isolated modified protein complex, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The isolated modified protein complex, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions encompassed by the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an isolated modified protein complex, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents encompassed by the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods encompassed by the present invention so as to obtain an amount of the active ingredient, which is effective to achieve the desired therapeutic response for a particular subject, composition, and mode of administration, without being toxic to the subject.

The nucleic acid molecules encompassed by the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VII. Kits

In addition, the present invention also encompasses kits comprising one or more containers filled with one or more isolated polypeptides and/or a complexes comprising same, such as those selected from the group consisting of polypeptides listed in Tables 1 and 2 and protein complexes listed in Table 3, wherein the isolated modified protein complex comprises at least one subunit (e.g., SMARCB1) that is modified. Alternatively, the kit can comprise in one or more containers, all protein subunits, homologs, derivatives, or fragments thereof, of an isolated modified protein complex selected from the group of protein complexes listed in Table 2 and Table 3. The kit encompassed by the present invention can also contain expression vectors encoding the essential components of the complex machinery, which components after being expressed can be reconstituted in order to form a biology active protein complex. Such a kit preferably also contains the required buffers and reagents.

The kit encompassed by the present invention can further contain substrates of the isolated modified protein complexes encompassed by the present invention. The kit may further contain reagents that specifically detect the isolated modified protein complex. For example, the kit can comprise a labeled compound or agent capable of detecting an isolated modified protein complex in a biological sample; means for determining the amount of the isolated modified protein complex in the sample; and means for comparing the amount of the isolated modified protein complex in the sample with a standard. The compound or agent can be packaged in a suitable container. For example, the present invention provides kits comprising at least one antibody that binds to the isolated modified protein complex. Kits encompassed by the present invention can contain an antibody coupled to a solid support, e.g., a tissue culture plate or beads (e.g., sepharose beads).

A kit can include additional components to facilitate the particular application for which the kit is designed. For example, kits can be provided which contain antibodies for detection and quantification of an isolated modified protein complex in vitro, e.g. in an ELISA or a Western blot. Additional, exemplary agents that kits can contain include means of detecting the label (e.g., enzyme substrates for enzymatic labels, filter sets to detect fluorescent labels, appropriate secondary labels such as a sheep anti-mouse-H1RP, etc.) and reagents necessary for controls (e.g., control biological samples or an isolated modified protein standards). A kit may additionally include buffers and other reagents recognized for use in a method of the disclosed invention. Non-limiting examples include agents to reduce non-specific binding, such as a carrier protein or a detergent. A kit encompassed by the present invention can also include instructional materials disclosing or describing the use of the kit or an isolated modified protein complex of the disclosed invention in a method of the disclosed invention as provided herein.

This invention is further illustrated by the following examples which should not be construed as limiting. The contents of all references, patents and published patent applications cited throughout this application, as well as the Figures, are incorporated herein by reference.

EXAMPLES

Example 1: Materials and Methods for Examples 2-6 a. Cell Lines and Culture Conditions

The TTC1240 malignant rhabdoid tumor (MRT) cell line was a generous gift from Dr. T. J. Triche (Children's Hospital of Los Angeles). The G401 MRT cell line was purchased from ATCC. The SMARCB1 knockout cell line ($293T^{SMARCB1\Delta/\Delta}$) from Nakayama et al. (2017) *Nat. Genet.* 49:1613-1623 was also used in the examples. MRT and $293T^{SMARCB1\Delta/\Delta}$ cells were grown in DMEM (Gibco), supplemented with 10% FBS (Omega), 1× GlutaMAX™ (Gibco), 100 U/mL penicillin-streptomycin (Gibco), 1 mM sodium pyruvate (Gibco), 1×MEM NEAA (Gibco), 10 mM HEPES (Gibco), 1×2-mercaptoethanol (Gibco) and maintained in a humidified incubator at 37° C. with 5% C02.

The SAH (SAH0047-02) induced-pluripotent stem cell (iPSC) line was generated in Dr. M. Sahin's laboratory at Boston Children's Hospital (Ebrahimi-Fakhari et al. (2016) *Cell Rep.* 17:1053-1070) and a generous gift from Dr. Clifford Wolf's laboratory at Boston Children's Hospital. The wild-type and mutant SAH iPSCs were maintained in StemFlex Medium (Gibco) prior to differentiation.

b. SMARCB1 CRISPR-Cas9 Genome Editing

The $293T^{SMARCB1\Delta/\Delta}$ cell line was generated using the Ini1 CRISPR/Cas9 KO and Ini1 HDR plasmids (Santa Cruz Biotechnology, sc-423027; sc-423027-HDR) following the manufacturer's protocol as previously described in Nakayama et al. (2017) *Nat. Genet.* 49:1613-1623.

The SAH iPSC line underwent CRISPR/Cas9 mediated genome editing with a short-guide RNA (sgRNA, 5'-GGAGAAGAAGATCCGCGACC AGG-3') targeting exon 8 of the SMARCB1 gene and a single-stranded oligodeoxynucleotide (ssODN, 5'-CCGGAACACG GGCGATGCGG ACCAGTGGTG CCCACTGCTG GAGACTCTGA CAGACGCTGA GATGGAA-AAAATACGCG ATCAAGACAG GAACACGAGG TACCCCTGGC CCTGTGGTCC TGGGCTCTGC CCACAGGCAC CTGGCTTTCC-3'; silent mutations emphasized in red) donor strand encoding for the SMARCB1 K364del in-frame deletion. Specifically, cells were nucleofected with a ssODN donor and CRISPR/Cas9 plasmid (px458) that was constructed with hSMARCB1 distinct sgRNA using Amaxa 4D-Nucleofector™. Forty-eight hours after nucleofection, cells were single cell sorted by FACS, genotyped by PCR, and then confirmed via standard TA-cloning procedures to obtain a SMARCB1+/+ wild-type control, a SMARCB1^K364del/+ heterozygous mutant, and a SMARCB1 exon 8 indel mutant (SMARCB1^p.(I349Lfs*)/+).

c. Nuclear Extract

Nuclear extracts for TTC1240 and 293T SMARCB1 knockout cells were prepared as described in (Mashtalir et al., 2018). Specifically, cells were scraped from plates, washed with cold PBS, pelleted at 1,200 rpm for 5 min at 4° C., and resuspended in EBO hypotonic buffer (50 mM Tris, pH 7.5, 0.1% NP-40, 1 mM EDTA, 1 mM $MgCl_2$ supplemented with protease inhibitor (Roche), and 1 mM phenylmethylsulfonyl fluoride (PMSF)). Lysates were pelleted at 5,000 rpm for 5 min at 4° C. Supernatants were discarded, and nuclei were resuspended in EB300 high salt buffer (50 mM Tris, pH 7.5, 300 mM NaCl, 1% NP-40, 1 mM EDTA, 1 mM $MgCl_2$ supplemented with protease inhibitor and 1 mM PMSF). Lysates were incubated on ice for 10 min with occasional vortexing. Lysates were then pelleted at 21,000×g for 10 min at 4° C. Supernatants were collected, and protein concentrations were quantified via bicinchonic acid (BCA) assay (Pierce). Finally, samples were supplemented with 1 mM DTT.

d. Co-Immunoprecipitation

For immunoprecipitation of $293T^{SMARCB1\Delta/\Delta}$ nuclear extracts, 700 μg of nuclear extract (at 1 μg/μL) were incubated with 2-5 μg of antibody (Table 4) overnight at 4° C. Dynabeads® (Pierce Protein G Magnetic Beads, Thermo Scientific) were then added, rotated for 2 hours at 4° C., and washed 3-5 times with EB300. Beads were eluted with sample buffer (2× NuPAGE™ LDS Buffer (Invitrogen) and 200 mM DTT) to load onto an SDS-PAGE gel.

For immunoprecipitation of G401 nuclear extracts, 200 μg of nuclear extract were incubated with 2 μg of antibody in IP Buffer rotating overnight at 4° C. Samples were then incubated with Dynabeads® (Pierce Protein G Magnetic Beads, Thermo Scientific) rotating for 2 hours at 4° C. Beads were washed 3 times in IP Buffer, once with BC100 (20 mM HEPES, 100 mM KCl, 0.2 mM EDTA, 10% glycerol), and eluted with 20 μL of sample buffer (1× NuPAGE™ LDS Buffer (Invitrogen) and 100 mM DTT) to load onto an SDS PAGE gel.

TABLE 4

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| | Antibodies | |
| Mouse Anti-SMARCC2 (BAF170) (G-12) (WB) | Santa Cruz | Cat# sc-166237, Lot: G1310; RRID: AB_2192013 |
| Mouse Anti-SMARCD1 (BAF60A) (23) (WB) | Santa Cruz | Cat# sc-135843, Lot: A2616; RRID: AB_2192137 |
| Rabbit Anti-PBRM1 (BAF180) (WB) | Millipore | Cat#ABE70, Lot: A2616; RRID: AB_10807561 |
| Rabbit Anti-SMARCE1 (BAF57) (WB) | Bethyl | Cat# A300-810A, Lot: 2; RRID: AB_577243 |
| Mouse Anti-TATA binding protein (TBP) (WB) | Abeam | Cat# ab51841, Lot: GR297600-4; RRID: AB_945758 |
| Rabbit Anti-Histone H3 (WB) | Abeam | Cat# ab1791, Lot: GR3236377-1; RRID: AB_302613 |
| Rabbit Anti-Histone H2B (D2H6) (WB) | Cell Signaling Technology | Cat# 12364, RRID: AB_2714167 |
| Rabbit Anti-PARP (WB) | Cell Signaling Technology | Cat# 9532, Lot: 9; RRID: AB_659884 |
| Rabbit Anti-Cleaved PARP (Asp214) XP (WB) | Cell Signaling Technology | Cat# 5625, Lot: 13; RRID: AB_10699459 |
| Mouse Anti-IgG (IP) | Santa Cruz | Cat# sc-2025, Lot: H0615; RRID: AB_737182 |
| Rabbit Anti-ARID1 A (BAF250A) (D2A8U) (IP/WB) | Cell Signaling Technology | Cat# 12354, Lot: 1; RRID: AB_2637010 |
| Mouse Anti-Anti-INH (BAF47) (A-5) (IP/WB) (IP/WB) | Santa Cruz | Cat# sc-166165, Lot: K0515; RRID: AB_2270651 |
| Mouse Anti-Anti-BRG1 (SMARCA4) (G-7) (IP/WB) | Santa Cruz | Cat# sc-17796, Lot: G0115; RRID: AB_626762 |
| Rabbit Anti-HA-Tag (C29F4) (IP/WB) (ChIP/B) | Cell Signaling Technology | Cat# 3724S, Lot: 8; RRID: AB_1549585 |
| Rabbit Anti-SMARCB1 (BAF47) (D8M1X) (ChIP/WB) | Cell Signaling Technology | Cat# 91735, Lot: 1; RRID: AB_2800172 |
| Rabbit Anti-SMARCC1 (BAF155) (D7F8S) (ChIP/WB) | Cell Signaling Technology | Cat# 11956, Lot: 2; RRID: AB_2797776 |
| Rabbit Anti-SMARCA4 (BRG1) (EPNCIR111 A) (ChIP) | Abeam | Cat# ab110641, Lot: GR150844-37*, Lot: GR3208604-7**; RRID: AB_10861578 |
| Rabbit Anti-Histone H3 (acetyl K27)-ChIP Grade (ChIP) | Abeam | Cat# ab4729, Lot: GR238071-2*, Lot: GR144577-1**; RRID: AB_2118291 |
| Mouse Anti-RNA Pol II monoclonal antibody-Classic (ChIP) | Diagenode | Cat# C15200004, Lot: 001-11; RRID: AB_2728744 |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| Rabbit Anti-SUZ12 (D39F6) XP (ChIP) | Cell Signaling | Cat# 3737, Lot: 6; RRID: AB_2196850 |
| Rabbit Anti-H3K27me3 (trimethyl Histone H3 (Lys27)) (ChIP) | Millipore | Cat# 07-449, Lot: 2275589; RRID: AB_310624 |
| Mouse Anti-Beta-Tubulin III (TUJ1) (IF) | Sigma-Aldrich | Cat# T8660, RRID: AB_477590 |
| Goat Anti-Mouse IgG Antibody, IRDye 680RD Conjugated | LI-COR Biosciences | Cat# 926-68070, RRID: AB_10956588 |
| Goat Anti-Rabbit IgG Antibody, IRDye 800CW Conjugated | LI-COR Biosciences | Cat# 926-32211, RRID: AB_621843 |
| Note: Asterisks denote whether antibody was used for ChIP for either *-TTC1240 or **-SAH iPSC cell line. | | |
| **Bacterial and Virus Strains** | | |
| One-Shot Stbl 3 chemically competent cells | Invitrogen | Cat# C7373-03 |
| Rosetta (DE3) Competent Cells | Novagen | Cat# 70954 |
| BL21 (DE3) Competent *E. coli* | New England Biolabs | Cat# C2527H |
| **Biological Samples** | | |
| MNase-digested purified mononucleosomes from 293T cells | This study, protocol adapted from Masthalir et al., Mol Cell 2014 | N/A |
| HeLa Polynucleosomes Purified | EpiCypher | Cat# 16-0003 |
| **Chemicals, Peptides, and Recombinant Proteins** | | |
| Peptide: Biotin-SMARCB1_SCRM (351-385): Bio-TENTKLDLMRIPENKLARATRWRQTDLEARPMDAR (35-mer) | KE Biochem | N/A |
| Peptide: Biotin-SMARCB1_WT (351-385): Bio-PLLETLTDAEMEKKIRDQDRNTRRMRRLANTAPAW (35-mer) | KE Biochem | N/A |
| Peptide: Biotin-SMARCB1_K364del (351-385): Bio-PLLETLTDAEMEKIRDQDRNTRRMRRLANTAPAW (34-mer) | KE Biochem | N/A |
| Peptide: Biotin-SMARCB1_R377H (351-385): Bio-PLLETLTDAEMEKKIRDQDRNTRRMRHLANTAPAW (35-mer) | KE Biochem | N/A |
| Peptide: Biotin-SMARCB1_R366C (351-385): Bio-PLLETLTDAEMEKKICDQDRNTRRMRRLANTAPAW (35-mer) | KE Biochem | N/A |
| Peptide: Biotin-SMARCB1_K363N (351-385): Bio-PLLETLTDAEMENKIRDQDRNTRRMRRLANTAPAW (35-mer) | KE Biochem | N/A |
| Peptide: Biotin-SMARCB1_R374Q (351-385): Bio-PLLETLTDAEMEKKIRDQDRNTRQMRRLANTAPAW (35-mer) | KE Biochem | N/A |
| Peptide: Biotin-SMARCB1_K364A (351-385): Bio-PLLETLTDAEMEKAIRDQDRNTRRMRRLANTAPAW (35-mer) | KE Biochem | N/A |
| Peptide: Biotin-SMARCB1_K364E (351-385): Bio-PLLETLTDAEMEKEIRDQDRNTRRMRRLANTAPAW (35-mer) | KE Biochem | N/A |
| Peptide: Biotin-SMARCB1_K364R (351-385): Bio-PLLETLTDAEMEKRIRDQDRNTRRMRRLANTAPAW (35-mer) | KE Biochem | N/A |
| Peptide: Biotin-SMARCB1_K364P (351-385): Bio-PLLETLTDAEMEKPIRDQDRNTRRMRRLANTAPAW (35-mer) | KE Biochem | N/A |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| Peptide: Biotin-SMARCB1_I365A (351-385): Bio-PLLETLTDAEMEKKARDQDRNTRRMRRLANTAPAW (35-mer) | KE Biochem | N/A |
| Peptide: Biotin-SMARCB1_AA-363/4 (351-385): Bio-PLLETLTDAEMEAAIRDQDRNTRRMRRLANTAPAW (35-mer) | KE Biochem | N/A |
| Peptide: Biotin-SMARCB1_EE-363/4 (351-385): Bio-PLLETLTDAEMEEEIRDQDRNTRRMRRLANTAPAW (35-mer) | KE Biochem | N/A |
| Peptide: Biotin-SMARCB1_K363A (351-385): Bio-PLLETLTDAEMEAKIRDQDRNTRRMRRLANTAPAW (35-mer) | KE Biochem | N/A |
| Peptide: Biotin-SMARCB1_R370A (351-385): Bio-PLLETLTDAEMEKKIRDQDANTRRMRRLANTAPAW (35-mer) | KE Biochem | N/A |
| Peptide: Biotin-*S.cerevisae*_SNF5_WT (650-684): Bio-PNLLQISAAELERLDKDKDRDTRRKRRQGRSNRRG (35-mer) | KE Biochem | N/A |
| Peptide: Biotin-*S.cerevisae*_SFH1_WT (380-414): Bio-PRVEILTKEEIQKREIEKERNLRRLKRETDRLSRR (35-mer) | KE Biochem | N/A |
| Peptide: Biotin-*C.elegans*_SNF5_WT (347-381): Bio-PFLETLTDAEIEKKMRDQDRNTRRMRRLVGGGFNY (35-mer) | KE Biochem | N/A |
| Peptide: Biotin-*D.melanogaster*_SNR1_WT (336-370): Bio-PFLETLTDAEMEKKIRDQDRNTRRMRRLANTTTGW (35-mer) | KE Biochem | N/A |
| Peptide: Biotin-SMARCB1_WT (351-382): Bio-PLLETLTDAEMEKKIRDQDRNTRRMRRLANTA (32-mer) | KE Biochem | N/A |
| Peptide: Biotin-SMARCB1_K364del (351-382): Bio-PLLETLTDAEMEKIRDQDRNTRRMRRLANTA (31-mer) | KE Biochem | N/A |
| Peptide: SMARCB1_WT (351-382): PLLETLTDAEMEKKIRDQDRNTRRMRRLANTA (32-mer) (CD) | KE Biochem | N/A |
| Peptide: SMARCB1_K364del (351-382): PLLETLTDAEMEKIRDQDRNTRRMRRLANTA (31-mer) (CD) | KE Biochem | N/A |
| Peptide: SMARCB1_R377H (351-382): PLLETLTDAEMEKKIRDQDRNTRRMRHLANTA (32-mer) (CD) | KE Biochem | N/A |
| Peptide: SMARCB1_R366C (351-382): PLLETLTDAEMEKKICDQDRNTRRMRRLANTA (32-mer) (CD) | KE Biochem | N/A |
| Peptide: SMARCB1_K363N (351-382): PLLETLTDAEMENKIRDQDRNTRRMRRLANTA (32-mer) (CD) | KE Biochem | N/A |
| Peptide: SMARCB1_R374Q (351-382): PLLETLTDAEMEKKIRDQDRNTRQMRRLANTA (32-mer) (CD) | KE Biochem | N/A |
| Peptide: LANA Peptide (1-23): MAPPGMRLRSGRSTGAPLTRGSC (23-mer) | KE Biochem | N/A |
| 15N-Ammonium Chloride | Cambridge Isotope | Cat# NLM-467-1 |
| 13C-glucose | Cambridge Isotope | Cat# CLM-1396-2 |
| Ponceau S Staining Solution | Sigma Aldrich | Cat#P7170 |
| Dynabeads Streptavidin | Thermo Fisher Scientific | Cat# 88817 |
| Dynabeads Protein G | Thermo Fisher Scientific | Cat# 10004D |
| Pierce Anti-HA Magnetic Beads | Thermo Fisher Scientific | Cat# 88837 |
| Puromycin | Sigma-Aldrich | Cat# P8833-25MG |
| Blasticidin | Life Technologies | Cat# R210-01 |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| Dimethyl sulfoxide (DMSO) | Sigma-Aldrich | Cat# D2650 |
| PBS, pH 7.4 | Thermo Fisher Scientific/ Gibco | Cat# 10010049 |
| Trypsin EDTA (0.25%), phenol red | Thermo Fisher Scientific/ Gibco | Cat# 25200-114 |
| DMEM, high glucose, no glutamine | Thermo Fisher Scientific/ Gibco | Cat# 11960-044 |
| GlutaMAX | Thermo Fisher Scientific/ Gibco | Cat# 35050-079 |
| Sodium Pyruvate | Thermo Fisher Scientific/ Gibco | Cat# 11360-070 |
| Penicillin-Streptomycin | Thermo Fisher Scientific/ Gibco | Cat# 15140-163 |
| MEM Non-Essential Amino Acids Solution | Thermo Fisher Scientific/ Gibco | Cat# 11140-050 |
| HEPES | Thermo Fisher Scientific/ Gibco | Cat# 15630-080 |
| 2-mercaptoethanoi | Thermo Fisher Scientific/ Gibco | Cat# 21985023 |
| Fetal Bovine Serum (FBS) | Omega Scientific, Inc. | Cat# FB-11 |
| Polybrene | Santa Cruz Biotechnology | Cat# sc-134220 |
| Polyethylenimine (PEI) (MW 40,000) | Polysciences | Cat# 24765 |
| NuPage LDS Sample Buffer (4X) | Life Technologies | Cat# NP0007 |
| Formaldehyde | Sigma-Aldrich | Cat# F8775 |
| Glycine | Sigma-Aldrich | Cat# G7126 |
| RNase | Roche | Cat# 11119915001 |
| Proteinase K Solution | Thermo Fisher Scientific | Cat# AM2546 |
| MNase | Sigma-Aldrich | Cat# N3755 |
| Agencourt AMPure XP Beads | Beckman Coulter | Cat# A63882 |
| High Sensitivity D1000 ScreenTape & Reagents | Agilent | Cat# 5067-5584/5585 |
| High Sensitivity D5000 ScreenTape & Reagents | Agilent | Cat# 5067-5592/5593 |
| Recombinant mononucleosome with diazirine photocrosslinker at Histone H4E52 | Laboratory of Dr. Thomas W. Muir, Princeton University | N/A |
| Recombinant mononucleosome with diazirine photocrosslinker at Histone H2BE113 | Laboratory of Dr. Thomas W. Muir, Princeton University | N/A |
| Recombinant mononucleosome with diazirine photocrosslinker at Histone H2BE105 | Laboratory of Dr. Thomas W. Muir, Princeton University | N/A |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| Recombinant mononucleosome with diazirine photocrosslinker at Histone H2AE91 | Laboratory of Dr. Thomas W. Muir, Princeton University | N/A |
| Recombinant mononucleosome with diazirine photocrosslinker at Histone H2AD90 | Laboratory of Dr. Thomas W. Muir, Princeton University | N/A |
| Recombinant mononucleosome with diazirine photocrosslinker at Histone H2AE64 | Laboratory of Dr. Thomas W. Muir, Princeton University | N/A |
| Recombinant mononucleosome with diazirine photocrosslinker at Histone H2AE61 | Laboratory of Dr. Thomas W. Muir, Princeton University | N/A |
| Recombinant mononucleosome with diazirine photocrosslinker at Histone H2AE56 | Laboratory of Dr. Thomas W. Muir, Princeton University | N/A |
| Recombinant Mononucleosome: Wild-type | Laboratory of Dr. Thomas W. Muir, Princeton University | N/A |
| Recombinant Mononucleosome: Mutant-Histone H2AD90N | Laboratory of Dr. Thomas W. Muir, Princeton University | N/A |
| Recombinant Mononucleosome: Mutant-Histone H2AE92K | Laboratory of Dr. Thomas W. Muir, Princeton University | N/A |
| Recombinant Mononucleosome: Mutant-Histone H2BE113K | Laboratory of Dr. Thomas W. Muir, Princeton University | N/A |
| EpiDyne Nucleosome Remodeling Assay Substrate ST601-GATC1 | EpiCypher | Cat# 16-4101 |
| Recombinant tetranucleosomes | Reaction Biology | Cat# HMT-15-369 |
| Recombinant histone octamer | EpiCypher | Cat# 16-0001 |
| 6X GelPilot Loading Dye | QIAGEN | Cat# 239901 |
| DpnII Restriction Enzyme | New England Biolabs | Cat# R0543L |
| Ultrapure ATP (provided in ADP Glo Max Assay kit) | Promega | Cat# V7001 |
| Recombinant $^{15}N/^{13}C$ doubly-labeled SMARCB1-C-terminal protein (aa 351-385) | This study, Dana-Faber Cancer Institute Structural Biology Core | N/A |
| Recombinant SMARCB1-WH DNA binding domain | Purification adapted from Allen at al., Structure 2015 | N/A |
| Cycloheximide | Sigma-Aldrich | Cat# C1988-1G |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| SYBR-Gold Nucleic Acid Gel Stain | Thermo Fisher Scientific/ Invitrogen | Cat# S11494 |
| SYBR-Safe Nucleic Acid Gel Stain | Thermo Fisher Scientific/ Invitrogen | Cat# S33102 |
| Syto-60 Red Fluorescent Nucleic Acid Stain | Thermo Fisher Scientific/ Invitrogen | Cat# S11342 |
| IRDye 800CW Streptavidin for Biotin Detection | LI-COR Biosciences | Cat# 926-32230 |
| StemFlex ™ Medium | Thermo Fisher Scientific/Gibco | Cat# A3349401 |
| ReLeSR ™ Enzyme-free human ES and iPS cell selection and passaging reagent | Stem Cell Technologies | Cat# 05872 |
| CryoStor ® CS1 Freeze Media | Bio Life Solutions | Cat# 210102 |
| Critical Commercial Assays | | |
| NEBNext Ultra II DNA Library Prep Kit for Illumina | New England Biolabs | Cat# E7645 |
| NextSeq 500/550 High Output Kit v2.5 (75 Cycles) | Illumina | Cat# 20024906 |
| NovaSeq 6000 SP Reagent Kit (100 cycles) | Illumina | Cat# 20027464 |
| EZ Nucleosomal DNA Prep Kit | Zymo Research | Cat# D5220 |
| RNEasy Mini Kit | Qiagen | Cat# 74136 |
| MinElute PCR Purification Kit | Qiagen | Cat# 28006 |
| ADP-Glo Max Assay | Promega | Cat# V7001 |
| 2% Agarose w/ external markers, Pippin Prep. 100-600 bp | Sage Science | Cat# CSD2010 |
| BCA Protein Assay Kit | Pierce/Thermo Scientific | Cat# 23225 |
| SilverQuest Silver Staining Kit | Invitrogen | Cat# LC6070 |
| Annexin V-CF Blue 7-AAD Apoptosis Staining/ Detection Kit | Abeam | Cat# ab214663 |
| Deposited Data | | |
| ChlP-seq, RNA-seq, ATAC-seq, MNase-seq | This study | GEO: GSE124903 |
| TTC1240 SS18, ARID2, H3K4me1, and H3K4me3 ChIP-seq | Nakayama et al., Nat. Gen. 2017 | GEO: GSE90634 |
| HUES64 OCT4, NANOG, and SOX2 ChlP-seq data | Tsankov et al., Nature 2015 | GEO: GSE61475 |
| NMR Structure of SMARCB1 C-Terminal Alpha Helix | This study | PDB: 6UCH |
| a. X-Ray Structure of the Nucleosome Core Particle | Davey et al., J. Mol. Biol. 2002 | PDB: 1KX5 |
| b. X-ray Structure of a Kaposi's sarcoma herpesvirus LANA peptide bound to the nucleosomal core | Chodaparambil et al., Science 2006 | PDB: 1ZLA |
| c. Complex of Snf2-Nucleosome complex with Snf2 bound to positions | Liu et al., Nature 2017 | PDB: 5X0X; 5XOY |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| SHL2 and SHL6 of the nucleosome | | |
| **Experimental Models: Cell Lines** | | |
| Lenti-X 293T cell line | Clontech | Cat# 632180; RRID: CVCL_4401 |
| HEK293T$^{SMARCB1\Delta/\Delta}$(293T BAF47KO (29.1)) cell line | Nakayama et al., Nat. Gen. 2017 | N/A |
| TTC1240 | Gift from laboratory of Dr. T.J. Triche, Children's Hospital Los Angeles (CHLA) | RRID: CVCL_8002 |
| G401 | ATCC | RRID: CVCL_0270 |
| SAH (SAH0047-2) | Ebrahimi-Fakhari et al., Cell Rep. 2016 | N/A |
| SAH$^{SMARCB1_K364del/+}$ | This study | N/A |
| SAH$^{SMARCB1_Indel/+}$ | This study | N/A |
| **Experimental Models: Organisms/Strains** | | |
| N/A | N/A | N/A |
| **Oligonucleotides** | | |
| SMARCB1-K364del sgRNA, 5'-GGAGAAGAAGATCCGCGACC **AGG**-3' | Integrated DNA Technologies | N/A |
| SMARCB1-K364del ssODN, 5'-CCGGAACACG GGCGATGCGG ACCAGTGGTG CCCACTGCTG GAGACTCTGA CAGACGCTGA GATGGAA-A-AAATACGCG ATCAAGACAG GAACACGAGG TACCCCTGGC CCTGTGGTCC TGGGCTCTGC CCACAGGCAC CTGGCTTTCC-3'; | Integrated DNA Technologies | N/A |
| INI1 Winged Helix DNA Binding DNA (5' IRDye700-GGAATTGTGAGCGCTCACAATTCC-3') | Integrated DNA Technologies, Adapted from Allen et al., 2015 | N/A |
| INI1 Winged Helix DNA Binding DNA (unlabeled reverse complement) (5'-GGAATTGTGAGCGCTCACAATTCC-3') | Integrated DNA Technologies, Allen et al., 2015 | N/A |
| **Recombinant DNA** | | |
| EF-1a-MCS-PGK-Blast (Empty Vector) | Clonetech, Kadoch & Crabtree (2013) | N/A |
| EF-1a-MCS-PGK-Blast-SMARCB1-V5 WT | Nakayama et al., 2017 | N/A |
| EF-1a-MCS-PGK-Blast-SMARCB1-V5 K364del | This study | N/A |
| EF-1a-MCS-PGK-Blast-SMARCB1-V5 R377H | This study | N/A |
| EF-1a-MCS-PGK-Blast-SMARCB1-V5 delCC (Y326*) | This study | N/A |
| EF-1a-MCS-PGK-Blast-SMARCB1-V5 delN-term (deletion of aa 1-176) | This study | N/A |
| EF-1a-MCS-PGK-Blast-SMARCB1-V5 delC-term (deletion of aa 177-385) | This study | N/A |
| EF-1a-MCS-PGK-Blast-SMARCB1-V5 delRpt1 (deletion of aa 186-245) | This study | N/A |

TABLE 4-continued

| Reatents and resources, including antibodies used for Western blot (WB), co-immunoprecipitation (IP), immunofluorescence, and chromatin-immunoprecipitation (ChIP) | | |
|---|---|---|
| REAGENT or RESOURCE | SOURCE | IDENTIFIER |
| EF-1a-MCS-PGK-Blast-SMARCB1-V5 delRpt2 (deletion of aa 259-319) | This study | N/A |
| EF-1a-MCS-PGK-Blast-SMARCB1-V5 delRpt1-2 (deletion of aa 186-319) | This study | N/A |
| EF-1a-MCS-PGK-Puro (Empty Vector) | Clonetech, Kadoch & Crabtree (2013) | N/A |
| EF-1a-MCS-PGK-Puro-SMARCB1-HA WT | This study | N/A |
| EF-1a-MCS-PGK-Blast-SMARCB1-HA R37H | This study | N/A |
| EF-1a-MCS-PGK-Blast-SMARCB1-HA K364del | This study | N/A |
| EF-1a-MCS-PGK-Blast-SMARCB1-HA K363N | This study | N/A |
| EF-1a-MCS-PGK-Blast-SMARCB1-HA R366C | This study | N/A |
| psPAX2 | Tiscornia et al., 2006 | RRID: Addgene_12260 |
| pMD2.G | Tiscornia et al., 2006 | RRID: Addgene_12259 |
| Ini1 (BAF47) CRISPR/Cas9 KO Plasmid | Santa Cruz Biotechnology | Cat# sc-423027 |
| Ini1 (BAF47) HDR Plasmid | Santa Cruz Biotechnology | Cat# sc-423027-HDR |
| pSpCas9(BB)-2A-GFP (PX458) CRISPR/Cas9 Plasmid constructed with hSMARCB1 distinct sgRNA (see Olignonucleotides above) | Ran et al., 2013 | RRID: Addgene_48138 |
| pGEX-6P-2-SMARCB1CC (aa 351-385) | This study | N/A |
| pGST-SMARCB1WH (aa 1-115) | This study adapted from Allen at al., Structure 2015 | N/A |
| Software and Algorithms | | |
| Bowtie2 v2.29 | Langmead and Sialzberg, 2012 | bowtie-bio.sourceforge.net/bowtie2/index.shtml; RRID:SCR_005476 |
| STAR v2.5.2b | Dobin et al., 2013 | github.com/alexdobin/STAR; RRID:SCR_015899 |
| MAC2 V2.1.1 | Zhang et al., 2008 | github.com/taoliu/MACS; RRID:SCR_013291 |
| GSEA | Subramanian et al., 2005 | software.broadinstitute.org/gsea/index.js; RRID:SCR_003199 |
| BEDTools | Quinlan and Hall, 2010 | bedtools.readthedocs.io/en/latest/; RRID:SCR_006646 |
| Picard v2.8.0 | Broad Institute | broadinstitute.github.io/picard; RRID:SCR_006525 |
| Trimmomatic v0.36 | Bolger et al., 2014 | usadellab.org/cms/?page=trimmomatic; RRID:SCR_011848 |
| GREAT | McLean et al., 2010 | great.stanford.edu/public/html/; RRID:SCR_005807 |
| ngsplot v2.63 | Shen et al., 2014 | github.com/shenlab-sinai/ngsplot; RRID:SCR_011795 |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| LOLA v1.12.0 | Sheffield and Bock, 2016 | bioconductor.org/packages/ release/bioc/html/LOLA.html |
| HOMER v4.9 | Heinz et al., 2010 | homer.ucsd.edu/homer/; RRID:SCR_010881 |
| deepTools v2.5.3 | Ramirez et al., 2016 | deeptools.readth edocs.io/ en/develop/content/api.html; RRID:SCR_016366 |
| edgeR V3.12.1 | Robinson et al., 2010 | bioconductor.org/packages/ release/bioc/html/edgeR.html; RRID:SCR_012802 |
| Metascape | Tripathi et al., 2015 | metascape, org/gp/index. html#/main/step1; RRID:SCR_016620 |
| UCSC Utilities | Kuhn etal., 2013 | hgdownload.soe.ucsc.edu/ downloads.html#utilities_ downloads |
| SAMtools v0.1.19 | Li et al., 2009 | samtools.sourceforge.net/; RRID:SCR_002105 |
| ChIPpeakAnno v3.17.0 | Zhu etal., 2010 | bioconductor.org/packages/ release/bioc/html/ ChIPpeakAnno.html; RRID:SCR_012828 |
| Principal components analysis (PCA) | Schafer and Strimmer, 2005/ Opgen-Rhein and Strimmer, 2007 | strimmerlab.org/software/ corpcor/ |
| ZDOCK Server v.3.0.2 | Pierce et al., 2014 | zdock.umassmed.edu/ |
| FloJo software v.10.4.1 | TreeStar | flowjo.com |
| ConSurf Database | Ashkenazy et al., 2016 | consurf.tau.ac.il/; RRID:SCR_002320 |
| CYANA software | Guntert et al., 2009 | cyana.org; RRID:SCR_014229 |
| TALOS+ Sofware | Shen et al., 2009 | N/A |
| NMRPipe | Delaglio et al., 19995 | ibbr.umd.edu/nmrpipe/install. html |
| Iterative Soft Thresholding (istHMS) | Hyberts etal., 2012 | N/A |
| CARA | Kelleretal., 2004 | cara.nmr.ch/doku.php |
| SonoLab Software | Covaris | covaris.com/instruments/ sonolab-software/; RRID:SCR_016302 |
| Integrative Genomics Viewer (IGV) | Broad Institute | broadinstitute.org/igv/; RRID:SCR_011793 |
| HCS Studio Cell Analysis Software | Thermo Fisher Scientific | RRID:SCR_016787 |
| Image Studio Lite | LI-COR | licor.com/bio/products/ software/image_studio_lite/; RRID:SCR_013715 |
| Geneious Prime v.2019.0.3 | Geneious | geneious.com/; RRID:SCR_010519 |

TABLE 4-continued

Reatents and resources, including antibodies used for Western blot (WB), co-immunoprecipitation (IP), immunofluorescence, and chromatin-immunoprecipitation (ChIP)

| REAGENT or RESOURCE | SOURCE | IDENTIFIER |
|---|---|---|
| Other | | |
| Odyssey CLx Imaging System | LI-COR | RRID:SCR_014579 |
| NextSeq 500 Sequencing System | Illumina | RRID:SCR_014983 |
| NovaSeq 6000 Sequencing System | Illumina | RRID:SCR_016387 |
| 2200 TapeStation Instrument | Agilent | RRID:SCR_014994 |
| E220 focused-ultrasonicator | Covaris | N/A |
| AKTA Pure chromatography system | GE Healthcare | N/A |
| 700 MHz Agilent DD2 NMR Spectrometer equipped with a cryogenic probe | Agilent | N/A |
| ImageXpress Micro Confocal High Content Imaging System | Molecular Devices | N/A |
| Arrayscan XTI | Thermo Fisher Scientific | N/A |
| Aviv Model 430 CD spectrometer | Aviv Biomedical Inc. | N/A |
| Advantec Grade QR200 Quartz Fiber Filters | Cole-Parmer | EW-06658-10 |
| Epson-Perfection V600 Photo Scanner | Epson | Model: B11B198011 |
| NuPage 4-12% Bis-Tris gels, 12 and 15 well | Thermo Fisher Scientific/ Invitrogen | Cat# NP0322BOX Cat# NP0336BOX |
| Novex 8% TBE gels, 15 well | Thermo Fisher Scientific/ Invitrogen | Cat# EC62155BOX |
| Novex 10-20% Tricine gels | Thermo Fisher Scientific/ Invitrogen | Cat# EC66252BOX |
| DNA Retardation Gels (6%) | Thermo Fisher Scientific/ Invitrogen | Cat# EC63655BOX |
| Immobilon-FL PVDF membrane | EMD Millipore | Cat# 05317 |
| Immobilon-PSQ PVDF membrane | EMD Millipore | Cat# ISEQ00010 |
| Amicon Ultra-15 Centrifugal Filter Unit (30 KDa MWCO) | EMD Millipore | Cat# UFC903024 |
| Slide-A-Lyzer MINI dialysis unit (10 kDa MWCO) | Thermo Fisher Scientific | Cat# 69570 |
| Slide-A-Lyzer MINI dialysis unit (3.5 kDa MWCO) | Thermo Fisher Scientific | Cat# 69550 |
| Pierce Peptide Desalting Spin Columns | Thermo Fisher Scientific | Cat# 89851 |

e. Western Blotting

Western blot analysis was performed using standard procedures. For Western blots visualizing mSWI/SNF complex subunits, samples were separated using a 4-12% Bis-Tris PAGE gel (NuPAGE™ 4-12%0 Bis-Tris Protein Gel, Invitrogen), and transferred onto a PVDF membrane (Immobilon®-FL, EMD Millipore). For Western blots visualizing histones, samples were separated using a 1020 tricine gel (Novex™ 1-0% Tricine Protein Gel, Thermo Scientific), and transferred onto a PVDF membrane (Immobilon®-PSQ, EMD Millipore). Membranes were blocked with 50% milk in PBST and incubated with primary antibody (Table 4) for 3 hours at RT or overnight at 4° C. Membranes were washed 3 times with PBST and then incubated with near-infrared fluorophore-conjugated species-specific secondary antibodies (LI-COR) for 1 hour at RT. Following secondary, membranes were washed 3 times with PBST, once with PBS, and then imaged using a Li-Cor Odyssey® CLx imaging system (LI-COR).

f. Purification of mSWI/SNF Complexes mSW/SNF complex purification was performed essentially as described in Mashtalir et al. (2018) *Cell* 175:1272-1288. Briefly, stable $293T^{SMARCB1\Delta/\Delta}$ cell lines infected with HA-tagged SMARCB1 variants or full-length SMARCE1 were expanded to obtain necessary bait expression levels. Cells were scraped from plates, washed with cold PBS, and centrifuged at 5,000 rpm for 5 min at 4° C. Pellets were resuspended in hypotonic buffer (HB: 10 mM Tris HCl, pH 7.5, 10 mM KCl, 1.5 mM $MgCl_2$, supplemented with 1 mM DTT and 1 mM PMSF) and incubated for 5 min. on ice. The suspension was centrifuged at 5,000 rpm for 5 min at 4° C., and pellets were resuspended in 5 volumes of HB containing protease inhibitor cocktail. The suspension was then homogenized using a glass Dounce homogenizer (Kimble Kontes). Suspension was layered onto HB sucrose cushion containing 30% sucrose (w/v) and centrifuged at 5,000 rpm for 1 hour at 4° C. The nuclear pellets were resuspended in high salt buffer (HSB: 50 mM Tris HCl, pH 7.5, 300 mM KCl, 1 mM $MgCl_2$, 1 mM EDTA, 1% NP40 supplemented with 1 mM DTT, 1 mM PMSF, and protease inhibitor cocktail). Homogenate was incubated on rotator for 1 hour at 4° C. The supernatant was then centrifuged at 20,000 rpm (30,000×g) for 1 hour at 4° C. using a SW32Ti rotor. The high salt nuclear extract supernatant was filtered through a 25 mm quartz filter (Advantec QR-200 Quartz Fiber Filter, Cole-Parmer) and incubated with Pierce™ Anti-HA Magnetic Beads (Thermo Fisher) overnight at 4° C. HA beads were washed 6 times in HSB and eluted with HSB containing 1 mg/mL of HA peptide (GenScript) for 4×1.5 hours each. Eluted proteins were then subjected to dialysis (Slide-A-Lyzer™ MINI Dialysis Device, 10K MWCO, Thermo Scientific) using Dialysis Buffer (25 mM HEPES, pH 8.0, 0.1 mM EDTA, 100 mM KCl, 1 mM $MgCl_2$, 15% glycerol, and 1 mM DTT) overnight at 4° C., and finally concentrated using Amicon® Ultra centrifugal filters (30 kDa MWCO, EMD Millipore).

g. Silver Stain

SMARCB1-HA WT- and mutant variant-containing mSWI/SNF complexes were purified via HA-epitope dependent complex purification. Samples were run on a 4-12% Bis-Tris SDS PAGE gel, stained using the SilverQuest™ Silver Staining Kit (Invitrogen), and imaged using an Epson-Perfection V600 Photo scanner.

h. Restriction Enzyme Accessibility Assay (REAA) Nucleosome Remodeling Assay

SMARCA4 (BRG1) levels of the HA-purified mSWI/SNF complex purifications were normalized via BCA protein quantification and Silver Stain analyses. Purified mSWI/SNF complexes were diluted for final reaction concentration of 10 ng/μL in REAA buffer (20 mM HEPES, pH 8.0, 50 mM KCl, 5 mM $MgCl_2$) containing 0.1 mg/mL BSA, 1 μM DTT, 20 nM nucleosomes (EpiDyne Nucleosome Remodeling Assay Substrate ST601-GATC1, EpiCypher®). The REAA mixture was incubated at 30 or 37° C. for 10 min, and the reaction was initiated using 1-2 mM ATP (Ultrapure ATP, Promega) and 0.005 U/μL DpnII Restriction Enzyme (New England Biolabs). The REAA reaction mixture was quenched with 20-24 mM EDTA and placed on ice. Proteinase K (Ambion) was added at (100 μg/mL) for 30-60 min, followed by either AMPure bead DNA purification and D1000 HS DNA ScreenTape Analysis (Agilent) or mixing with GelPilot® Loading Dye (QIAGEN) and loading onto 8% TBE gel (Novex® 8% TBE Gels, Thermo Fisher). TBE gels were stained with either SYBR™-Safe (Invitrogen) or Syto-60 Red Fluorescent Nucleic Acid Stain (Invitrogen), followed by imaging with UV light on an Alpha Innotech Alphalmager 2200 and/or with 652 nm light excitation on a Li-Cor Odyssey® CLx imaging system (LI-COR).

i. ATPase Assay (ADP Glo Kinase Assay)

ATPase consumption assays were performed using the ADP-Glo™ Kinase Assay kit (Promega). The same conditions as the REAA nucleosome remodeling assay described above were used, excluding the DpnII restriction enzyme. Following incubation with desired substrates for 60-90 min at either 30° C., 1× volume of ADP-Glo™ Reagent was used to quench the reaction and incubated at RT for 40 min. 2× volume of the Kinase Detection Reagent was then added and incubated at RT for 1 hour. Luminescence readout was recorded. Substrates used for this assay were purified 601 NCP DNA, recombinant histone octamer (EpiCypher®, Cat #16-0001), recombinant mononucleosome (EpiDyne® Nucleosome Remodeling Assay Substrate ST601-GATC1, EpiCypher®, Cat #16-4101), recombinant tetranucleosomes (Reaction Biology, Cat #HMT-15-369), and HeLa polynucleosomes (EpiCypher®, Cat #16-0003). HA-purified mSWI/SNF complexes were used at 10 ng/μL and 200 μg of material was used for each ARID1A-IP nuclear extract using ARID1A antibody (Cell Signaling, Cat #12354S).

j. SNF5 Homology Protein Conservation Analysis Across Species

ConSurf conservation analysis was performed. Briefly, canonical (aa 1-385) and coiled coil (aa 332-385) SMARCB1 (Uniprot ID: Q12824) sequences were run through ConSurf (Ashkenazy et al. (2016) *Nucl. Acids Res.* 44:W344-W350) conservation analysis using UNIREF90 and MAFFT running parameters. Phylogenetic trees were created using Geneious with built alignment options for building distance matrix (Alignment type: global alignment with free end gaps, Cost Matrix: Blosum62) and Tree Builder Options (Genetics Distance Model: Jukes-Cantor, and Tree Build Method: UPGMA). Similarity analyses were conducted using the Geneious pairwise/multiple alignment tool to determine identity and similarity between SMARCB1 and other SNF5 homology proteins and their respective domains.

k. Peptide Pull-Down Experiments

N-terminal biotin-labeled SNF5 homology coiled-coil peptide variants (including SMARCB1 variants) were obtained from KE Biochem (Table 5). Lyophilized peptides were diluted to 10 mM in DMSO and subsequently diluted to 1 mM in EB150 (50 mM Tris, pH 7.5, 150 mM NaCl, 0.1% NP-40, 1 mM EDTA, 1 mM MgCl2 supplemented with 1 mM DTT, and 1 mM PMSF). Biotin-labeled peptides were diluted to 10 μM in EB150 and bound to Streptavidin Dynabeads® (Pierce™ Streptavidin Magnetic Beads, Thermo Scientific) overnight at 4° C. Beads were washed 3 times in EB150, and 1-1.6 μg of mononucleosomes were added. The suspension was rotated for 5-7 hours at 4° C. The beads were washed 3-5 times in EB150, and eluted in Sample Buffer (2×LDS with 200 mM DTT) to load onto 10-20% Tricine gels. Following electrophoresis and PVDF membrane transfer, membranes were subjected to Ponceau Staining for peptide detection and/or Western blotting for detecting the presence of nucleosome components.

TABLE 5

Peptides used for nucleosome binding studies and circular dichroism

| PEPTIDE ID | PROTEIN SEQUENCE | PEPTIDE SEQUENCE (N->C) | LENGTH (aa) |
|---|---|---|---|
| Biotin-labeled peptides | | | |
| Bio-SMARCB1-CC_SCRM | 351-385 | Bio-TENTKLDLMRIPENKLARATRWRQTDLEARPMDAR | 35-mer |
| Bio-SMARCB1-CC_WT(A) | 351-385 | Bio-PLLETLTDAEMEKKIRDQDRNTRRMRRLANTAPAW | 35-mer |
| Bio-SMARCB1-CC_K364del (A) | 351-385 | Bio-PLLETLTDAEMEKIRDQDRNTRRMRRLANTAPAW | 34-mer |
| Bio-SMARCB1-CC_R377H | 351-385 | Bio-PLLETLTDAEMEKKIRDQDRNTRRMRHLANTAPAW | 35-mer |
| Bio-SMARCB1-CC_R366C | 351-385 | Bio-PLLETLTDAEMEKKICDQDRNTRRMRRLANTAPAW | 35-mer |
| Bio-SMARCB1-CC_K363N | 351-385 | Bio-PLLETLTDAEMENKIRDQDRNTRRMRRLANTAPAW | 35-mer |
| Bio-SMARCB1-CC_R374Q | 351-385 | Bio-PLLETLTDAEMEKKIRDQDRNTRQMRRLANTAPAW | 35-mer |
| Bio-SMARCB1-CC_K364A | 351-385 | Bio-PLLETLTDAEMEKAIRDQDRNTRRMRRLANTAPAW | 35-mer |
| Bio-SMARCB1-CC_K364E | 351-385 | Bio-PLLETLTDAEMEKEIRDQDRNTRRMRRLANTAPAW | 35-mer |
| Bio-SMARCB1-CC_K364R | 351-385 | Bio-PLLETLTDAEMEKRIRDQDRNTRRMRRLANTAPAW | 35-mer |
| Bio-SMARCB1-CC_K364P | 351-385 | Bio-PLLETLTDAEMEKPIRDQDRNTRRMRRLANTAPAW | 35-mer |
| Bio-SMARCB1-CC_I365A | 351-385 | Bio-PLLETLTDAEMEKKARDQDRNTRRMRRLANTAPAW | 35-mer |
| Bio-SMARCB1-CC_AA-363/4 | 351-385 | Bio-PLLETLTDAEMEAAIRDQDRNTRRMRRLANTAPAW | 35-mer |
| Bio-SMARCB1-CC_EE-363/4 | 351-385 | Bio-PLLETLTDAEMEEEIRDQDRNTRRMRRLANTAPAW | 35-mer |
| Bio-SMARCB1-CC_K363A | 351-385 | Bio-PLLETLTDAEMEAKIRDQDRNTRRMRRLANTAPAW | 35-mer |
| Bio-SMARCB1-CC_R370A | 351-385 | Bio-PLLETLTDAEMEKKIRDQDANTRRMRRLANTAPAW | 35-mer |
| Bio-*S.cerevisae*_SNF5CC | 650-684 | Bio-PNLLQISAAELERLDKDKDRDTRRKRRQGRSNRRG | 35-mer |
| Bio-*S.cerevisae*_SFH1CC | 380-414 | Bio-PRVEILTKEEIQKREIEKERNLRRLKRETDRLSRR | 35-mer |
| Bio-*C.elegans*_SNF5CC | 347-381 | Bio-PFLETLTDAEIEKKMRDQDRNTRRMRRLVGGGFNY | 35-mer |
| Bio-*D.melanogaster* SNRICC | 336-370 | Bio-PFLETLTDAEMEKKIRDQDRNTRRMRRLANTTTGW | 35-mer |
| Bio-SMARCB1-CC_WT(B) | 351-382 | Bio-PLLETLTDAEMEKKIRDQDRNTRRMRRLANTA | 32-mer |
| Bio-SMARCB1-CC_K364del(B) | 351-382 | Bio-PLLETLTDAEMEKIRDQDRNTRRMRRLANTA | 31-mer |
| Unlabeled variant peptides (used for Circular Dichroism) | | | |
| SMARCB1-CC_WT (B) | 351-382 | PLLETLTDAEMEKKIRDQDRNTRRMRRLANTA | 32-mer |
| SMARCB1-CC_K364del (B) | 351-382 | PLLETLTDAEMEKIRDQDRNTRRMRRLANTA | 31-mer |
| SMARCB1-CC_R377H | 351-382 | PLLETLTDAEMEKKIRDQDRNTRRMRHLANTA | 32-mer |
| SMARCB1-CC_R366C | 351-382 | PLLETLTDAEMEKKICDQDRNTRRMRRLANTA | 32-mer |
| SMARCB1-CC_K363N | 351-382 | PLLETLTDAEMENKIRDQDRNTRRMRRLANTA | 32-mer |
| SMARCB1-CC_R374Q | 351-382 | PLLETLTDAEMEKKIRDQDRNTRQMRRLANTA | 32-mer |
| LANA Peptide | 1-23 | MAPPGMRLRSGRSTGAPLTRGSC | 23-mer |

l. LANA Peptide Competition

The LANA peptide competition was set up in a similar manner as the peptide pull-down experiments with the following exceptions: SMARCB1-CC (aa 351-385) biotin-labeled peptides at 10 μM in EB150 were bound to Streptavidin Dynabeads® (Pierce™ Streptavidin Magnetic Beads, Thermo Scientific) in parallel to 1-1.6 ag of mononucleosomes incubated with LANA peptide (KE Biochem) at varying concentrations ranging from 0-30 μM overnight at 4° C. Beads were washed 3 times in EB150, and resuspended with the mononucleosome/LANA peptide solutions. The suspension was rotated for 3-5 hours at 4° C. The beads were washed 3-5 times in EB150, and eluted in Sample Buffer (2×LDS with 200 mM DTT) to load onto 1020 Tricine gels.

m. Ponceau Stain

Immediately following transfer onto a PVDF membrane, the membrane was rinsed in PBST and stained using Ponceau-S solution (Sigma-Aldrich) for 1 hour at RT. The membrane was washed 3 times in milliQ $H_2O$ and imaged on an Epson-Perfection V600 Photo scanner.

n. Cycloheximide Chase Experiments to Assess Protein Stability

Seven days following lentiviral infection of TTC1240 cells with Empty vector or SMARCB1 WT or c-terminal mutant constructs as described above, cells were plated at 400K cells/well in 24 well. On Day 9, cycloheximide was added (10 μM) sequentially at 6, 3, 1, and 0 (negative control) hours prior to cell lysis with 100 μL of SDS Lysis Buffer (1.5% SDS, 25 mM Tris, pH 7.5). Whole cell lysates were sonicated and protein concentrations were quantified by BCA and prepared for Western blot analysis as described above.

o. Mammalian Mononucleosomes Purification

Mammalian mononucleosomes were purified from HEK293T cells similar to as described in Mashtalir et al. (2014) *Mol. Cell* 54:392-406. Cells were scraped from plates, washed with cold PBS, and centrifuged at 5,000 rpm for 5 min at 4° C. Pellets were resuspended in hypotonic buffer (EBO: 50 mM Tris HCl, pH 7.5, 1 mM EDTA, 1 mM $MgCl_2$, 0.1% NP40 supplemented with 1 mM DTT, 1 mM PMSF, and protease inhibitor cocktail and incubated for 5 min on ice. The suspension was centrifuged at 5,000 rpm for 5 min at 4° C., and pellets were resuspended in 5 volumes of EB420 (EBO: 50 mM Tris HCl, pH 7.5, 420 mM NaCl, 1 mM $MgCl_2$, 0.1% NP40 with supplemented with 1 mM DTT and 1 mM PMSF containing protease inhibitor cocktail. The homogenate was incubated on rotator for 1 hour at 4° C. The supernatant was then centrifuged at 20,000 rpm (30,000×g) for 1 hour at 4° C. using a SW32Ti rotor. Supernatant was then discarded and the chromatin pellet was washed in MNAse buffer (20 mM Tris-HCl pH 7.5, 100 mM KCl, 2 mM $MgCl_2$, 1 mM $CaCl_2$), 0.3 M sucrose, 0.1% NP-40, and protease inhibitor cocktail) 3 times. Following MNase treatment (3 U/mL for 30 min at room temperature, Sigma-Aldrich), the reaction was quenched with 5 mM of EGTA and 5 mM of EDTA. The samples were then centrifuged at 20,000×g for 1 hour at 4° C. to obtain the soluble chromatin fraction. The soluble chromatin fraction was loaded onto a 10-30% glycerol gradient (Mashtalir et al. (2018) *Cell* 175:1272-1288) and fractions containing mononucleosomes were isolated and concentrated using centrifugal filter (Amicon, EMD Millipore).

p. Vectors

Constitutive expression of C-terminal HA-tagged SMARCB1 (BAF47) variants (i.e., full-length, R37H, K363N, K364del, R366C, or ΔCC (aa 1-325) or N-terminal HA-tagged full-length SMARCE1 (BAF57) in the $293T^{SMARCB1\Delta/\Delta}$ cell line was achieved using lentiviral infection of an EF1α-driven expression vector (modified pTight vector from Clontech, dual promoter EF-1a-MCS-PGK-Puro), selected with puromycin (2 μg/μL, Sigma-Aldrich).

Constitutive expression C-terminal V5-tagged BAF47 (SMARCB1) variants (i.e. full-length, K364del, R377H, ΔCC (aa 1-325), ΔN-term (aa 177-385), ΔC-term (aa 1-176), ΔRPT1 (deletion of aa 186-245), ΔRPT2 (deletion of aa 259-319), ΔRPT1-2 (deletion of aa 186-319) in MRT and iPS cell lines was achieved using lentiviral infection of an EF1α-driven expression vector (modified pTight vector from Clontech, dual promoter EF-1a-MCS-PGK-Blast), selected with blasticidin (10 μg/μl, Thermo Fisher).

q. Lentiviral Generation

Lentiviral particles were prepared using Lenti-X™ HEK293T packaging cells (Clontech) via polyethylenimine-mediated transfection (PEI, Polysciences Inc.) of gene delivery vector co-transfected with packaging vectors pspax2 and pMD2.G as previously described in Tiscornia et al. (2006) *Nat. Protoc.* 1:241-245. Supernatants were harvested 72 hours after transfection and centrifuged at 20,000 rpm for 2.5 hours at 4° C. Virus containing pellets were resuspended in PBS, pH 7.4 (Gibco) and placed on cells dropwise.

r. Infection and Selection

TTC1240 cells and were lentivirally infected with either Empty vector, or one of four c-terminal V5-tagged SMARCB1 variant constructs (full length, K364del, R377H, or ΔDCC construct) for 48 h and then selected with blasticidin (10 μg/mL) split at 72 hour and continued with selection for 5 days. Cells were harvested for biochemical, ChIP-seq, RNA-seq, and ATAC-seq experiments 7 days post-infection. For TTC1240 cells lentivirally infected with the ΔN-term (aa 177-385) or ΔC-term (aa 1-176) constructs, cells were harvested for ATAC-seq 9 days post-infection.

The $293T^{SMARCB1\Delta/\Delta}$ cells were made into stable lines via lentiviral infection of either c-terminal HA-tagged full length, R37H, K363N, K364del, R366C, or ΔCC SMARCB1 constructs followed by puromycin selection (2 μg/mL). The SAH $SMARCB1^{+/+}$, $SMARCB1^{K364del/+}$, and $SMARCB1^{p.(I340Lfs*)/+}$ iPS cells were made into stable lines via lentiviral infection with either Empty vector or C-terminal V5-tagged full-length SMARCB1 followed by blasticidin selection (10 μg/mL).

s. Cortical Neuron Differentiation of iPSCs

Ngn2-induced cortical neuron differentiation protocol was adapted and slightly modified from Zhang et al. (2013) *Neuron* 78:785-798. On Day −2 (D-2), SAH cells were split and plated at 2K/well in Geltrex™-coated 96-well plates. On Day −1 (D-1), cells were transduced with lentivirus expressing rtTA, Ngn2 conjugated with puromycin resistant gene and EGFP. To induce NGN2-mediated differentiation, 2 μg/ml Doxycycline (Clontech) was added to the DMEM/F12/NEAA/N2 medium (Gibco) supplemented with 10 ng/ml human BDNF, 10 ng/ml NT-3 and 0.2 μg/ml mouse laminin on D0. Following 24 h puromycin (1 μg/ml, InvivoGen) selection on D1, mouse glia or glia conditioned medium was added to the culture, and the medium was switched to Neurobasal/B27 containing BDNF, NT-3, laminin and 2 μM Arc-C(Sigma) on D2. Half of the media was changed every other day on D3-6. 2.5% FBS (Gibco) was added to the medium from D7 to support glia viability. During differentiation, images were acquired by ArrayScan™ XTI (ThermoFisher) high content imaging system periodically. The differentiated NGN2 neurons were also fixed at DIV 6, 8 and 10 of differentiation and imaged for FITC (NGN2) and stained with DAPI and TUJ1 antibody for automatic quantification of total neuronal counts, average neuron length, and total cell count using ImageXpress® Micro Confocal High Content Imaging System and HCS Studio cell analysis software (ThermoFisher).

t. Photo-Crosslinking Methods

Diazirine-containing recombinant nucleosomes (0.5 uM) were incubated with biotinylated CC peptides (12.5 uM) in binding buffer (20 mM HEPES, pH 7.9, 4 mM Tris, pH 7.5, 150 mM KCl, 10 mM $MgCl_2$, 10% glycerol, and 0.02% (v/v) IGEPAL CA-630) at 30° C. for 30 mins, and cooled on ice for 5 mins. The reaction mixtures were then irradiated at 365 nm for 10 minutes. Reactions were then analyzed by western blotting employing IRDye® 800CW streptavidin on a LI-COR Odyssey® Infrared Imager.

u. Recombinant Nucleosome Preparation

Unmodified recombinant human histones (H2A, Uniprot ID: Q6FI13; H2B, Uniprot ID: 060814; H3C96A, C110A, Uniprot ID: P68431; H4, Uniprot ID: P62805), and histone mutants were produced in and purified from *E. coli* (Dann et al. (2017) *Nature* 548:607-611). Histone octamers were prepared using established protocols (Luger et al. (1997) *J. Mol. Biol.* 272:301-311). Nucleosomes were assembled as previously described with minor modifications (Luger et al. (1997) *J. Mol. Biol.* 272:301-311). Briefly, a 601 DNA fragment was mixed with a similar volume of KCl (4M) to make a 2 M KCl mixture. Then, a histone octamer was added, and octamer refolding buffer (2 M NaCl, 10 mM Tris, 0.5 mM EDTA, 1 mM DTT, pH 7.8 at 4° C.) was used to adjusted final concentration of nucleosome to 0.5-1 μM. The mixture was placed in a Slide-A-Lyzer™ MINI dialysis unit (3.5 kDa MW cutoff, ThermoFisher Scientific) and dialyzed at 4° C. against 150 ml nucleosome assembly start buffer (10 mM Tris, 2 M KCl, 0.1 mM EDTA, 1 mM DTT, pH 7.5 at 4° C.) for 5 min at 4° C. Subsequently, 450 ml nucleosome assembly end buffer (10 mM Tris, 10 mM KCl, 0.1 mM EDTA, 1 mM DTT, pH 7.5 at 4° C.) was added at a rate of 0.8 ml/min using a peristaltic pump to bring the overall KCl concentration to about 0.5 M. The dialysis mixture was then transferred to a microcentrifuge tube, incubated at 37° C. for 15 min, and centrifuged at 17,000×g for 10 min. The supernatant was then transferred to a new dialysis unit and the mixture was dialyzed against nucleosome assembly end buffer twice (4 h each). After that, the dialysis mixture was transferred to a microcentrifuge tube, and centrifuged at 17,000×g for 10 min. The final nucleosome concentration was quantified by UV spectroscopy at 260 nm. The quality of individual nucleosomes was assessed by native polyacrylamide gel electrophoresis (5-6% acrylamide gel, 0.5×TBE, 150 V, 1 h), followed by SYBR® Gold DNA gel staining.

v. Circular Dichroism (CD)

Biotinylated peptides for analysis by CD were desalted using Pierce™ Peptide Desalting Spin Columns (ThermoFisher) following the manufacturer protocol. Peptides were eluted in 0.1% Trifluoroacetic acid (TFA) in 50% acetonitrile, lyophilized overnight, and re-dissolved in CD buffer (20 mM $PO_4^-$, pH 8) at 200 mM. Unbiotinylated peptides were dissolved directly in CD buffer at 200 mM. Single point CD measurements were performed on an Aviv Model 430 CD Spectrometer using a 0.1 cm path length cell. Spectra were acquired at 25° C. with a bandwidth of 1.0 nm, a scan rate of 100 nm/min, and averaging spectra over 10 scans.

w. NMR Methods $^{15}N$ and $^{13}C$ doubly-labeled SMARCB1CC domain protein were expressed from *E. coli* in M9 minimal medium containing $^{15}NH_4Cl$ and $^{13}C$-glucose as the sole nitrogen and carbon sources and purified as described above. Non-uniformly-sampled (NUS) triple resonance experiments, HNCA, HN(CO)CA, HNCO, HN(CA)CO, HN(CA)CB, C(CO)NH, H(CCO)NH and 15N-edited 3D-NOESY, using 0.3 mM $^{15}N/^{13}C$-SMARCB1CC protein in PBS buffer, pH 6.5 with 10% D20, were performed at 15° C. on a 700 MHz Agilent DD2 spectrometer equipped with a cryogenic probe. 2D-NOESY and TOCSY spectra were acquired using an unlabeled sample in same buffer and 100% D20 on the same NMR spectrometer. The data were processed using NMRPipe (Delaglio et al. (1995) *J. Biomol. NMR* 6:277-293) and Iterative Soft Thresholding reconstruction approach (istHMS) (Hyberts et al. (2012) *J. Biomol. NMR* 52:315-327) and analyzed by CARA (Keller (2004) *Swiss FedInst Technol* Dissertation ETH NO. 15947). Backbone dihedral angle restraints and secondary structure predications based on assigned chemical shifts were obtained using the TALOS+ software (Shen et al. (2009) *J. Biomol. NMR* 44:213-23). Fifty structural model with 422 NOE distance restraints and 15 identified hydrogen-bonds were calculated using XPLOR-NIH software (Schwieters et al. (2003) *J. Magn. Res.* 160:66-74), from which 10 lowest energy conformers are selected for deposition in the PDB database.

x. Proteomics

A 10 μL aliquot of concentrated HA-purified mSWI/SNF complexes described above were run on a 4-12% Bis-Tris SDS PAGE gel and stained with Colloidal Blue (Colloidal Blue Staining Kit, Invitrogen) following the NuPAGE™ Novex™ Bis-Tris gel staining kit protocol. mSWI/SNF gel bands were excised from the gel and submitted Harvard Univeristy's Taplin Mass Spectrometry Facility for processing.

y. Flow Cytometry

Cells were analyzed following the protocol for the Abcam Annexin V-CF Blue 7-AAD Apoptosis Staining/Detection Kit (ab214663). Briefly, 100,000 cells were washed twice in room temperature PBS and resuspended in 1× Binding Solution. 5 uL of Annexin V-CF Blue conjugate and 5 uL of 7-AAD staining solution were added and incubated for 15 minutes at room temperature, at which time 400 uL of 1× Binding Solution was added. Cells were analyzed on a LSR Fortessa™ (BD biosciences). Data was analyzed using FlowJo software (v.10.4.1, TreeStar).

z. ChIP Preparation and Protocol

ChIP-seq was performed using standard protocols (Millipore, Billerica, MA). Specifically, cells were fixed in 1% formaldehyde (Sigma Aldrich, F8775) for 10 min at 37° C. and quenched with 125 mM glycine for 5 min at 37° C. After washing, nuclei were sonicated using a Covaris sonicator, and the supernatant was used for immunoprecipitation with the indicated antibody (Table 4). ChIP-sequencing libraries were prepared with Illumina's NEBNext® Ultra™ II DNA library Prep Kit using standard protocols. All ChIP-seq was sequenced on an Illumina NextSeq® 500 using 75 bp single-end sequencing parameters.

aa. RNA Isolation and Preparation

All RNA was collected in duplicate and isolated using the RNeasy® Mini Kit (QIAGEN) according to the manufacturer's protocol. RNA-seq libraries were prepared with Illumina's TruSeq® standard mRNA Sample Prep Kit using standard protocols. All RNA was sequenced on Illumina NextSeq® 500 (Illumina) using 75 bp single-end sequencing parameters through Dana-Farber Cancer Institute's Molecular Biology Core Genomics Facility.

ab. ATAC-Seq Protocol

ATAC-seq libraries were prepared using 50,000 cells per sample following a standard protocol (Buenrostro et al. (2015) *Curr. Prot. Mol. Biol.* 21.29.1-21.29.9) with 12 cycles of amplification. ATAC-seq samples were sequenced on a NextSeq® 500 (Illumina) using 37 bp pair-end sequencing parameters.

ac. MNase-Seq Preparation

One million cells per condition were treated with 0.5 U of Micrococcal Nuclease (MNase, Zymo, Cat #D5220-1) using the EZ Nucleosomal DNA Prep Kit (Zymo, Cat #D5220) following the kit protocol. Size fractionation of MNase-digested DNA was performed using a 2% Agarose gel cassette (Sage Science, Cat #CSD2010) and run on a Pippin Prep machine (Sage Science) to obtain DNA between 120-180 bps. Appropriate size distribution of MNase-digested DNA was confirmed using a D1000 Screentape (Agilent Technologies) run on a 2200 TapeStation System (Agilent Technologies). Library preparation of MNase-digested DNA was carried using the NEBNext® Ultra™ II DNA Library Prep Kit for Illumina (New England Biolabs, Cat #E7645). Paired-End 50 next generation sequencing was performed using a NovaSeq 6000 (Illumina) through Dana-Farber Cancer Institute's Molecular Biology Core Genomics Facility.

ad. Sequence Data Processing and Acquisition

RNAseq, ChIPseq, and ATACseq samples were sequenced with the Illumina NextSeq® 500 technology, and MNase-seq samples were sequenced with the Illumina NovaSeq technology. Output data were demultiplexed using the bcl2fastq software tool. RNAseq reads were aligned to the hg19 genome with STAR v2.5.2b (Dobin et al. (2013) *Bioinformatics* 29:15-21), and ChIPseq reads were aligned with Bowtie2 v2.29 in the –k 1 reporting mode (Langmead and Salzberg (2012) *Nat. Meth.* 9:357-359). For the ATACseq data and MNase-seq, quality read trimming was performed by Trimmmomatic v0.36 (Bolger et al. (2014) *Bioinformatics* 30:2114-2120), followed by alignment, duplicate read removal, and read quality filtering using Bowtie2 v2.29, Picard v2.8.0 (Picard; available at broadinstitute.github.io/picard/; accessed: 15 Feb. 2019)), and SAMtools v0.1.19 (Vissers et al. (2016) *Nat. Rev. Genet.* 17:9-18), respectively. For the ChIPseq and ATACseq data, output BAM files were converted into BigWig track files using BEDTools (Quinlan and Hall (2010) *Bioinform.* 26:841-842) and UCSC utilities (Kuhn et al. (2013) *Brief Bioinform.* 14:144-161) in order to display coverage throughout the genome. For the RNAseq data, tracks were generated using the deepTools v2.5.3 bamCoverage function (Ramirez et al. (2016) *Nucl. Acids Res.* 44:W160-W165). These data have been deposited at NCBI's Gene Expression Omnibus under accession number GSE124903. TTC1240 SS18, ARID2, H3K4me1, and H3K4me3 ChIP-seq data were acquired from GSE90634 (Nakayama et al. (2017) *Nat. Genet.* 49:1613-1623). HUES64 OCT4, NANOG, and SOX2 ChiP-seq data were obtained from GSE61475 (Tsankov et al. (2015) *Nature* 518:344-349).

ae. RNA-Seq Data Analysis

For the RNA-seq data, output gene count tables from STAR based on alignments to the hg19 reflat annotation were used as input into edgeR v3.12.1 (Robinson et al. (2010) *Bioinform.* 26:139-140) to evaluate differential gene expression. Log 2 fold change values from edgeR were used as input into GSEA (Subramanian et al. (2005) *Proc. Natl. Acad.* Sci. USA 102:15545-15550), and the GseaPreranked tool was run with default settings to measure gene set enrichment. In order to analyze gene ontology and pathway enrichment for select subsets of genes, Metascape was used (Tripathi et al. (2015) *Cell Host Microbe* 18:723-735). RPKM values were quantified using median length isoforms and total mapped read counts computed by the Samtools idxstats function. Principle Components Analysis (PCA) was performed using the wt.scale and fast.svd functions from the corpcor R package on RPKM values (Schäfer and Strimmer (2005) *Stat. Appl. Genet. Mol. Biol.* 4:Article 32; Opgen-Rhein and Strimmer (2007) *Stat. Appl. Genet. Mol. Biol.* 6:Article 9).

af. ATAC-Seq, MNase-Seq, and ChIP-Seq Data Analysis

For the ChIP-seq data, narrow peaks were called with the MACS2 v2.1.1 software (Zhang et al. (2008) *Genome Biol.* 9:R137) using input as controls and a q-value cutoff of 0.001, and for the ATAC-seq data, broad peaks were called with MACs using the BAMPE option with a broad peak cutoff of 0.001. The R package, ChIPpeakAnno v3.17.0, was used to perform peak overlap analyses, and cis-regulatory function was assessed by GREAT (McLean et al. (2010) *Nat. Biotechnol.* 28:495-501). To evaluate differential accessibility between the WT and K364del conditions, raw read counts from ATAC-seq samples within ATAC-seq peaks were computed using the BEDTools intersect function, and these counts were used as input into edgeR. For the MNase-seq data, fragment length distributions were derived from properly-paired read alignments in output SAM files. Metaplots and heat maps were generated using ngsplot v2.63 (Shen et al. (2014) *BMC Genom.* 15:284). Transcription factor enrichment and motif analysis were carried out by the LOLA v1.12.0 (Sheffield and Bock (2016) *Bioinform.* 32:587-589) and HOMER v4.9 (Heinz et al. (2010) *Mol. Cell* 38:576-589) software packages, respectively.

ag. Data Submission

All data are deposited under Gene Expression Omnibus GSE124903 (available at ncbi.nlm.nih.gov/geo/query/acc.cgi?acc=GSE124903 under reviewer token: wvozasiwbxwxhul)

Example 2: CSS-Associated Mutations in the SMARCB1 CC Domain Inhibit mSWI/SNF Nucleosome Remodeling and ATPase Activity on Nucleosomes Coffin-Siris syndrome (CSS)-associated mutations occur across several mSWI/SNF subunit genes, largely those previously characterized to encode subunits within a 'core functional module' (Pan et al. (2018) *Cell Systems* 6:555-568.e557) and in genes specific for the canonical BA (cBAF) subcomplex within the mSWI/SNF complex family (Mashtalir et a. (2018) *Cell* 175:1272-1288; Michel et al. (2018) *Nat. Cell Biol.* 154:490-1420; Pan et al. (2018) *Cell Systems* 6:555-568.e557) (FIG. 1B-FIG. C). The most recurrent CSS-associated mutation is an in-frame deletion of a single lysine, K364de (identified in 9 independent CSS cases), in the C-terminal putative CC domain of SMARCB1, followed by a variety of missense mutations, including R377H, K363N, R366C, and R374Q (4 cases in independent families) also in this region (FIG. 2A)). Notably, single amino-acid mutations within the C-terminal region of SMARCB1 (located on chromosome 22) also occur in cancers (FIG. 1A; Table 6; PanCan, COSMIC databases).

TABLE 6

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheritance | Reference | Note: |
|---|---|---|---|---|---|---|---|
| CSS-01 | CSS | c.1091_1093del | p.Lys364del | Inframe-shift | de novo | Tsurusaki et al. (2012) Nat. Genet. 44-376-378 | |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| CSS-02 | CSS | c.1091_ 1093del | p.Lys364del | Inframe-shift | Unknown | Tsurusaki et al. (2012) Nat. Genet. 44-376-378 | |
| CSS-03 | CSS | c.1091_ 1093del | p.Lys364del | Inframe-shift | Unknown | Tsurusaki et al. (2012) Nat. Genet. 44-376-378 | |
| CSS-04 | CSS | c. 1130G > A | p.Arg377His | Missense | de novo | Tsurusaki et al. (2012) Nat. Genet. 44-376-378 | |
| CSS-05 | CSS | c. 1089G > T | p.Lys363Asn | Missense | de novo | Santen et al. (2013) Hum. Mut. 34:1519-1528 | |
| CSS-06 | CSS | c.1091_ 1093del | p.Lys364del | Inframe-shift | de novo | Santen et al. (2013) Hum. Mut. 34:1519-1528 | |
| CSS-07 | CSS | c.1091_ 1093del | p.Lys364del | Inframe-shift | Unknown | Santen et al. (2013) Hum. Mut. 34:1519-1528 | |
| CSS-08 | CSS | c.1091_ 1093del | p.Lys364del | Inframe-shift | de novo | Santen et al. (2013) Hum. Mut. 34:1519-1528 | |
| CSS-09 | CSS | c.1091_ 1093del | p.Lys364del | Inframe-shift | de novo | Tsurusaki et al. (2013) Clin. Genet. 85:548-554 | |
| CSS-10 | CSS | c.1091_ 1093del | p.Lys364del | Inframe-shift | de novo | Tsurusaki et al. (2013) Clin. Genet. 85:548-554 | |
| CSS-11 | CSS | c.1091_ 1093del | p.Lys364del | Inframe-shift | de novo | Tsurusaki et al. (2013) Clin. Genet. 85:548-554 | |
| CSS-12 | CSS | c. 1121G.A | p.Arg374Gln | Missense | de novo | Wieczorek et al. (2013) Hum. Mol. Genet. 22:5121-5135 | |
| CSS-13 | CSS* | c. 1096C.T | p.Arg366Cys | Missense | de novo | Wieczorek et al. (2013) Hum. Mol. Genet. 22:5121-5135 | *- re-classi-fied to CSS from original diagnosis ofNBS (K2588) |
| ID-01 | Severe ID-KSS | c. 110G > A | p.Arg37His | Missense | de novo | Kleefstra et al. (2012) Am. J. Hum. Genet. 91:73-82 | |
| see note | Severe ID-KSS | c. 110G > A | p.Arg37His | Missense | de novo | Diets et al, (2019) Genet. Med. 21572-579 | Origi-nally Published in Kleefstra et al., AJHG (2012) |
| ID-02 | Severe ID | c. 110G > A | p.Arg37His | Missense | de novo | Diets et al. (2019) Genet. Med. 21:572-579 | |
| ID-03 | Severe ID | c. 110G > A | p.Arg37His | Missense | de novo | Diets et al. (2019) Genet. Med. 21:572-579 | |
| ID-04 | Severe ID | c. 110G > A | p.Arg37His | Missense | de novo | Diets et al. (2019) Genet. Med. 21:572-579 | |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|

| AA Position | CDS Mutation | AA Mutation | Mutation ID (COSM) | Count | Type |
|---|---|---|---|---|---|
| 1 | c.1_*del | p.0 | 24619 | 142 | Whole gene deletion |
| 4 | c.12_13insATG | p.M4_A5insM | 26409 | 1 | Insertion-In frame |
| 5 | c.13G > A | p.A5T | 6784972 | 1 | Substitution-Missense |
| 8 | c.23A > G | p.K8R | 6854785 | 1 | Substitution-Missense |
| 8 | c.24G > C | p.K8N | 3800073 | 1 | Substitution-Missense |
| 10 | c.30c > T | p.F10F | 5984512 | 1 | Substitution-coding silent |
| 12 | c.36G > A | p.Q12Q | 5443776 | 1 | Substitution-coding silent |
| 18 | C.52c < T | p.Q18* | 4832131 | 1 | Substitution-Nonsense |
| 22 | c.64G > A | p.D22N | 6969152 | 1 | Substitution-Missense |
| 22 | c.65A > G | p.D22G | 1714197 | 1 | Substitution-Missense |
| 24 | c.56_57ins10 | p.E24fs*50 | 6934046 | 1 | Insertion-Frameshift |
| 24 | c.70G > C | p.E24Q | 6094957 | 1 | Substitution-Missense |
| 24 | c.72G > T | p.E24D | 6944423 | 1 | Substitution-Missense |
| 25 | c.75C > A | p.F25L | 6952402 | 2 | Substitution-Missense |
| 29 | c.86G > A | p.G29D | 4728314 | 2 | Substitution-Missense |
| 31 | c.91G > A | p.E31K | 3842289 | 1 | Substitution-Missense |
| 33 | c.96delG | p.G33fs*22 | 6922621 | 1 | Deletion-Frameshift |
| 36 | c.108_126del19 | p.L36fs*13 | 1067 | 1 | Deletion-Frameshift |
| 36 | c.107T > C | p.L36P | 6845503 | 1 | Substitution-Missense |
| 38 | c.114G > A | p.M38I | 6909238 | 1 | Substitution-Missense |
| 38 | c.? | p.M38I | 6495567 | 1 | Substitution-Missense |
| 39 | c.115_117delTTC | p.F39delF | 300998 | 1 | Deletion-In frame |
| 40 | c.118delC | p.R40fs*15 | 21423 | 1 | Deletion-Frameshift |
| 40 | c.119G > A | p.R40Q | 3740370 | 2 | Substitution-Missense |
| 40 | c.118C > T | p.R40* | 1002 | 20 | Substitution-Nonsense |
| 40 | c.? | p.R40* | 4127678 | 2 | Substitution-Nonsense |
| 41 | c.121G > T | p.G41C | 6410478 | 2 | Substitution-Missense |
| 42 | c.123delT | p.S42fs*13 | 6922954 | 1 | Deletion-Frameshift |
| 43 | c.127C > T | p.L43L | 4991480 | 1 | Substitution-coding silent |
| 45 | c.132_133insTGTAC | p.K45fs*12 | 27946 | 1 | Insertion-Frameshift |
| 45 | c.133A > G | p.K45E | 6905200 | 1 | Substitution-Missense |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 45 | | c.135G > C | p.K45N | 7339854 | | 1 | Substitution-Missense |
| 46 | | c.138_139insTACC | p.R46fs*25 | 995 | | 1 | Insertion-Frameshift |
| 47 | | c.139_143delTACCC | p.Y47fs*22 | 1062 | | 1 | Deletion-Frameshift |
| 47 | | c.140A > C | p.Y47S | 5887144 | | 1 | Substitution-Missense |
| 47 | | C.141C > A | p.Y47* | 991 | | 7 | Substitution-Nonsense |
| 48 | | c.142C > T | p.P48S | 1072 | | 1 | Substitution-Missense |
| 49 | | c.146C > A | p.S49* | 1053 | | 2 | Substitution-Nonsense |
| 49 | | c.146C > G | p.S49* | 5731551 | | 1 | Substitution-Nonsense |
| 50 | | c.147_150delACTC | p.L50fs*4 | 4766062 | | 1 | Deletion-Frameshift |
| 51 | | c.153C > A | p.W51* | 1078 | | 1 | Substitution-Nonsense |
| 53 | | c.157delC | p.R53fs*2 | 4582244 | | 1 | Deletion-Frameshift |
| 53 | | c.158C > A | p.R53Q | 1415161 | | 1 | Substitution-Missense |
| 53 | | c.157C > T | p.R53* | 24595 | | 14 | Substitution-Nonsense |
| 54 | | c.161T > C | p.L54P | 6997536 | | 1 | Substitution-Missense |
| 56 | | c.167C > T | p.T56I | 6191582 | | 2 | Substitution-Missense |
| 58 | | c.174_175delAG | p.E58fs*12 | 1010 | | 1 | Deletion-Frameshift |
| 59 | | c.177_178ins28 | p.E59fs*20 | 1082 | | 1 | Insertion-Frameshift |
| 59 | | c.177G > C | p.E59D | 6963944 | | 1 | Substitution-Missense |
| 60 | | c.178_179delAG | p.R60fs*10 | 4766061 | | 1 | Deletion-Frameshift |
| 62 | | c.184A > C | p.K62Q | 6958277 | | 1 | Substitution-Missense |
| 63 | | c.189_196delAGTTGCAT | p.I63fs*5 | 1063 | | 1 | Deletion-Frameshift |
| 66 | | c.197C > T | p.S66L | 1415163 | | 2 | Substitution-Missense |
| 67 | | c.197_198insA | p.S67fs*4 | 255201 | | 1 | Insertion-Frameshift |
| 68 | | c.202_203insG | p.H68fs*3 | 24615 | | 1 | Insertion-Frameshift |
| 69 | | c.206G > A | p.G69D | 3939577 | | 1 | Substitution-Missense |
| 72 | | c.208delA | p.T72fs*13 | 3309692 | | 1 | Deletion-Frameshift |
| 72 | | c.207_208insA | p.T72fs*4 | 6978820 | | 1 | Insertion-Frameshift |
| 76 | | c.226A > G | p.T76A | 3785510 | | 1 | Substitution-Missense |
| 79 | | c.237C > T | p.H79H | 183186 | | 3 | Substitution-coding silent |
| 79 | | c.235C > T | p.H79Y | 5750873 | | 1 | Substitution-Missense |
| 80 | | c.238G > A | p.G80R | 4103003 | | 2 | Substitution-Missense |
| 80 | | c.239G > A | p.G80E | 5610644 | | 1 | Substitution-Missense |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 81 | | c.243C > G | p.Y81* | | 1169663 | 1 | Substitution-Nonsense |
| 82 | | c.243_278del36 | p.T82_A93del12 | | 6919152 | 1 | Deletion-In frame |
| 82 | | c.246G > C | p.T82T | | 369675 | 1 | Substitution-coding silent |
| 82 | | c.246G > T | p.T82T | | 6056315 | 1 | Substitution-coding silent |
| 82 | | c.245C > T | p.T82M | | 6915963 | 1 | Substitution-Missense |
| 84 | | c.252_253insA | p.L84fs*21 | | 1056 | 1 | Insertion-Frameshift |
| 85 | | c.253G > T | p.A85S | | 6908769 | 1 | Substitution-Missense |
| 92 | | c.276A > C | p.K92N | | 4952317 | 1 | Substitution-Missense |
| 93 | | c.273delA | p.A93fs*50 | | 4172275 | 1 | Deletion-Frameshift |
| 94 | | c.281C > T | p.S94L | | 1032616 | 1 | Substitution-Missense |
| 96 | | c.286_287insC | p.V96fs*10 | | 24614 | 1 | Insertion-Frameshift |
| 98 | | c.291_292delAG | p.E98fs*7 | | 6972587 | 1 | Deletion-Frameshift |
| 98 | | c.292C > A | p.E98K | | 6929110 | 2 | Substitution-Missense |
| 98 | | c.292G > C | p.E98Q | | 6921816 | 1 | Substitution-Missense |
| 100 | | c.298_299delCT | p.L100fs*5 | | 33986 | 1 | Deletion-Frameshift |
| 100 | | c.298C > T | p.L100L | | 4991482 | 1 | Substitution-coding silent |
| 103 | | c.309C > T | p.N103N | | 7321764 | 1 | Substitution-coding silent |
| 104 | | c.310C > A | p.D104N | | 285203 | 1 | Substitution-Missense |
| 107 | | c.320A > G | p.Y107C | | 4767768 | 2 | Substitution-Missense |
| 108 | | c.323_323delA | p.K108fs*35 | | 53294 | 1 | Deletion-Frameshift |
| 108 | | c.324G > A | p.K108K | | 1032618 | 1 | Substitution-coding silent |
| 108 | | c.322A > C | p.K108Q | | 5452880 | 1 | Substitution-Missense |
| 109 | | c.324_325insG | p.A109fs*61 | | 36388 | 1 | Insertion-Frameshift |
| 109 | | c.325G > A | p.A109T | | 140296 | 1 | Substitution-Missense |
| 109 | | c.326_327CT > GA | p.A109G | | 5452947 | 1 | Substitution-Missense |
| 110 | | c.329T > G | p.V110G | | 5452882 | 1 | Substitution-Missense |
| 111 | | c.331_332insGT | p.S111fs*33 | | 6006426 | 1 | Insertion-Frameshift |
| 112 | | c.332delC | p.I112fs*31 | | 24597 | 1 | Deletion-Frameshift |
| 116 | | c.346C > A | p.P116T | | 21959 | 1 | Substitution-Missense |
| 116 | | c.346C > T | p.P116S | | 6784974 | 1 | Substitution-Missense |
| 117 | | c.351delC | p.P117fs*26 | | 1064 | 1 | Deletion-Frameshift |
| 118 | | c.346_346delC | p.T118fs*25 | | 53301 | 1 | Deletion-Frameshift |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 118 | | c.346delC | p.T118fs*25 | 6918085 | | 2 | Deletion-Frameshift |
| 118 | | c.354delC | p.T118fs*25 | 1068 | | 1 | Deletion-Frameshift |
| 118 | | c.345_346insC | p.T118fs*52 | 6927545 | | 1 | Insertion-Frameshift |
| 118 | | c.351_352insC | p.T118fs*52 | 5967279 | | 1 | Insertion-Frameshift |
| 118 | | c.352_353insA | p.T118fs*52 | 1061 | | 1 | Insertion-Frameshift |
| 119 | | c.356_360delACCTC | p.Y119fs*1 | 29384 | | 1 | Deletion-Frameshift |
| 119 | | c.357C > T | p.Y119Y | 4103005 | | 1 | Substitution-coding silent |
| 123 | | c.367C > T | p.Q123* | 6928313 | | 1 | Substitution-Nonsense |
| 125 | | c.375C > T | p.A125A | 5610646 | | 1 | Substitution-coding silent |
| 126 | | c.378G > C | p.K126N | 1032620 | | 2 | Substitution-Missense |
| 127 | | c.379A > G | p.R127G | 1076 | | 1 | Substitution-Missense |
| 129 | | c.385_398del14 | p.S129fs*36 | 27276 | | 1 | Deletion-Frameshift |
| 133 | | c.397C > A | p.P133T | 1130490 | | 1 | Substitution-Missense |
| 133 | | c.398C > T | p.P133L | 6928315 | | 1 | Substitution-Missense |
| 136 | | c.406C > T | p.P136S | 6933484 | | 1 | Substitution-Missense |
| 141 | | c.422A > G | p.H141R | 6958830 | | 1 | Substitution-Missense |
| 141 | | c.422A > T | p.H141L | 6961579 | | 1 | Substitution-Missense |
| 142 | | c.424T > A | p.L142I | 478789 | | 1 | Substitution-Missense |
| 142 | | c.425T > G | p.L142* | 29385 | | 1 | Substitution-Nonsense |
| 144 | | c.430delG | p.A144fs*32 | 27976 | | 1 | Deletion-Frameshift |
| 144 | | c.432C > T | p.A144A | 3552565 | | 1 | Substitution-coding silent |
| 146 | | c.436C > G | p.P146A | 6928317 | | 1 | Substitution-Missense |
| 148 | | c.443C > T | p.S148F | 5610648 | | 1 | Substitution-Missense |
| 149 | | c.446C > A | p.T149K | 726164 | | 2 | Substitution-Missense |
| 152 | | c.454A > G | p.N152D | 1008 | | 1 | Substitution-Missense |
| 152 | | c.455A > G | p.N152S | 6932819 | | 1 | Substitution-Missense |
| 155 | | c.463C > T | p.R155C | 6006363 | | 2 | Substitution-Missense |
| 155 | | c.464G >A | p.R155H | 1032622 | | 3 | Substitution-Missense |
| 155 | | c.464_465GC > TT | p.R155L | 6962465 | | 1 | Substitution-Missense |
| 156 | | c.468G > A | p.M156I | 7325453 | | 1 | Substitution-Missense |
| 157 | | c.469G > A | p.G157S | 5991516 | | 1 | Substitution-Missense |
| 158 | | c.473G > A | p.R158Q | 3693968 | | 4 | Substitution-Missense |
| 158 | | c.473G > T | p.R158L | 6202754 | | 1 | Substitution-Missense |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 158 | | c.472C > T | p.R158* | 992 | | 14 | Substitution-Nonsense |
| 159 | | c.475G > A | p.D159N | 4849613 | | 1 | Substitution-Missense |
| 160 | | c.480G > A | p.K160K | 4851443 | | 1 | Substitution-coding silent |
| 160 | | c.478A > C | p.K160Q | 6008884 | | 1 | Substitution-Missense |
| 165 | | c.491_492insCCTT | p.P165fs*6 | 1666914 | | 2 | Insertion-Frameshift |
| 165 | | c.494C > T | p.P165L | 5393245 | | 2 | Substitution-Missense |
| 166 | | c.492delC | p.L166fs*10 | 6912818 | | 2 | Deletion-Frameshift |
| 166 | | c.498T > C | p.L166L | 3390128 | | 1 | Substitution-coding silent |
| 169 | | c.505G > C | p.D169H | 6928592 | | 1 | Substitution-Missense |
| 170 | | c.510C > T | p.D170D | 3309709 | | 1 | Substitution-coding silent |
| 170 | | c.508G > T | p.D170Y | 6964909 | | 1 | Substitution-Missense |
| 171 | | c.511_512insC | p.H171fs*2 | 674182 | | 1 | Insertion-Frameshift |
| 172 | | c.? | p.D172G | 6506620 | | 1 | Substitution-Missense |
| 173 | | c.517C > T | p.P173S | 1001 | | 1 | Substitution-Missense |
| 177 | | c.528_528delC | p.H177fs*32 | 4774845 | | 1 | Deletion-Frameshift |
| 178 | | c.532G > A | p.E178K | 6191375 | | 1 | Substitution-Missense |
| 179 | | c.537C > T | p.N179N | 1415171 | | 3 | Substitution-coding silent |
| 179 | | c.536A > C | p.N179T | 7325473 | | 1 | Substitution-Missense |
| 180 | | c.538G > A | p.A180T | 7281925 | | 1 | Substitution-Missense |
| 181 | | c.543_544delTC | p.S181fs*29 | 1007 | | 1 | Deletion-Frameshift |
| 182 | | c.545delA | p.Q182fs*27 | 1077 | | 1 | Deletion-Frameshift |
| 183 | | c.546_547insCATCTCAG | p.P183fs*29 | 29383 | | 1 | Insertion-Frameshift |
| 183 | | c.549C > T | p.P183P | 108464 | | 1 | Substitution-coding silent |
| 183 | | c.548C > T | p.P183L | 108375 | | 1 | Substitution-Missense |
| 184 | | c.550G > A | p.E184K | 1664271 | | 2 | Substitution-Missense |
| 185 | | c.553_579del27 | p.V185_M193del | 1005 | | 1 | Deletion-In frame |
| 185 | | c.553G > A | p.V185M | 6057052 | | 1 | Substitution-Missense |
| 186 | | c.556_557insGAGGTGC | p.L186fs*27 | 53300 | | 1 | Insertion-Frameshift |
| 187 | | c.559_560ins11 | p.V187fs*26 | 6006423 | | 1 | Insertion-Frameshift |
| 188 | | c.564_565insATCCGGC | p.P188fs*24 | 1074 | | 1 | Insertion-Frameshift |
| 188 | | c.562C > T | p.P188S | 107362 | | 1 | Substitution-Missense |
| 188 | | c.563C > T | p.P188L | 110414 | | 4 | Substitution-Missense |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 189 | | c.564_565ins14 | p.I189fs*25 | | 27949 | 1 | Insertion-Frameshift |
| 189 | | c.564_565insGGTCCCC | p.I189fs*24 | | 27948 | 1 | Insertion-Frameshift |
| 189 | | c.565_566ins13 | p.I189fs*26 | | 53297 | 2 | Insertion-Frameshift |
| 190 | | c.568C > T | p.R190W | | 4500563 | 3 | Substitution-Missense |
| 190 | | c.569G > A | p.R190Q | | 6918311 | 1 | Substitution-Missense |
| 190 | | c.569C > T | p.R190L | | 6161714 | 1 | Substitution-Missense |
| 191 | | c.566_567ins19 | p.L191fs*26 | | 51386 | 2 | Insertion-Frameshift |
| 191 | | c.? | p.L191L | | 6506621 | 1 | Substitution-coding silent |
| 191 | | c.571C > A | p.L191M | | 6191350 | 1 | Substitution-Missense |
| 192 | | c.575A > G | p.D192G | | 1632538 | 2 | Substitution-Missense |
| 195 | | c.582_583ins13 | p.H95fs*20 | | 6006424 | 1 | Insertion-Frameshift |
| 195 | | c.584_585insCGATGGG | p.I195fs*18 | | 1081 | 1 | Insertion-Frameshift |
| 196 | | c.586delG | p.D196fs*13 | | 6972589 | 1 | Deletion-Frameshift |
| 196 | | c.585_586ins17 | p.D196fs*19 | | 27950 | 1 | Insertion-Frameshift |
| 196 | | c.585_586ins43 | p.D196fs*29 | | 6006425 | 1 | Insertion-Frameshift |
| 196 | | c.586_587ins17 | p.D196fs*19 | | 1066 | 1 | Insertion-Frameshift |
| 198 | | c.592C > T | p.Q198* | | 6953484 | 1 | Substitution-Nonsense |
| 199 | | c.597_597delG | p.K199fs*10 | | 6438249 | 1 | Deletion-Frameshift |
| 201 | | c.602G > A | p.R201Q | | 3309715 | 1 | Substitution-Missense |
| 201 | | c.602G > T | p.R201L | | 217231 | 1 | Substitution-Missense |
| 201 | | c.601C > T | p.R201* | | 993 | 22 | Substitution-Nonsense |
| 202 | | c.606C > T | p.D202D | | 1415176 | 1 | Substitution-coding silent |
| 202 | | c.604C > T | p.D202Y | | 6438248 | 1 | Substitution-Missense |
| 202 | | c.605A > G | p.D202G | | 6438247 | 1 | Substitution-Missense |
| 202 | | c.606C > A | p.D202E | | 1130488 | 1 | Substitution-Missense |
| 203 | | c.606_607ins20 | p.A203fs*13 | | 27947 | 1 | Insertion-Frameshift |
| 203 | | c.607G > A | p.A203T | | 999 | 2 | Substitution-Missense |
| 205 | | c.614C > T | p.T205I | | 5991514 | 1 | Substitution-Missense |
| 206 | | c.617G > A | p.W206* | | 1075 | 2 | Substitution-Nonsense |
| 206 | | c.618G > A | p.W206* | | 994 | 2 | Substitution-Nonsense |
| 207 | | c.620A > G | p.N207S | | 3552567 | 1 | Substitution-Missense |
| 209 | | c.625_625delA | p.N209fs*4 | | 6438250 | 1 | Deletion-Frameshift |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 210 | | c.629_795del167 | p.E210fs*15 | 13445 | | 1 | Deletion-Frameshift |
| 210 | | c.628G > A | p.E210K | 6912808 | | 1 | Substitution-Missense |
| 211 | | c.631A > T | p.K211* | 1070 | | 1 | Substitution-Nonsense |
| 213 | | c.639G > A | p.M213I | 6935730 | | 1 | Substitution-Missense |
| 214 | | c.641C > T | p.T214M | 4618174 | | 1 | Substitution-Missense |
| 215 | | c.644C > T | p.P215L | 6929112 | | 1 | Substitution-Missense |
| 216 | | c.646G > T | p.E216* | 1004 | | 6 | Substitution-Nonsense |
| 221 | | c.663C > T | p.I221I | 4991484 | | 1 | Substitution-coding silent |
| 222 | | c.664C > A | p.L222I | 6948995 | | 1 | Substitution-Missense |
| 222 | | c.664C > T | p.L222F | 4991486 | | 1 | Substitution-Missense |
| 223 | | c.669_670delTG | p.C223fs*1 | 1069 | | 1 | Deletion-Frameshift |
| 230 | | c.689C > A | p.P230Q | 5610642 | | 1 | Substitution-Missense |
| 230 | | c.689C > T | p.P230L | 4766058 | | 2 | Substitution-Missense |
| 231 | | c.691_692ins19 | p.L231fs*56 | 1079 | | 1 | Insertion-Frameshift |
| 232 | | c.696G > A | p.T232T | 298967 | | 1 | Substitution-coding silent |
| 232 | | c.695C > G | p.T232R | 5569528 | | 1 | Substitution-Missense |
| 232 | | c.695C > T | p.T232M | 1266243 | | 3 | Substitution-Missense |
| 237 | | c.711delC | p.I237fs*30 | 24598 | | 2 | Deletion-Frameshift |
| 238 | | c.712G > A | p.A238T | 5046903 | | 2 | Substitution-Missense |
| 238 | | c.713C > A | p.A238D | 6912837 | | 1 | Substitution-Missense |
| 242 | | c.726_729delACAG | p.R242fs*24 | 4971706 | | 1 | Deletion-Frameshift |
| 242 | | c.725G > A | p.R242K | 26906 | | 1 | Substitution-Missense |
| 243 | | c.726_727delAC | p.Q243fs*37 | 6006422 | | 1 | Deletion-Frameshift |
| 243 | | c.727C > T | p.Q243* | 996 | | 3 | Substitution-Nonsense |
| 244 | | c.730C > T | p.Q244* | 5352274 | | 1 | Substitution-Nonsense |
| 247 | | c.740C > G | p.S247C | 4825337 | | 1 | Substitution-Missense |
| 250 | | c.744delC | p.T250fs*17 | 4728316 | | 1 | Deletion-Frameshift |
| 250 | | c.749C > T | p.T250M | 5393247 | | 3 | Substitution-Missense |
| 251 | | c.749_750insC | p.D251fs*30 | 24599 | | 1 | Insertion-Frameshift |
| 252 | | c.755G > T | p.S252I | 1032624 | | 1 | Substitution-Missense |
| 254 | | c.760C > T | p.L254L | 5393249 | | 1 | Substitution-coding silent |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 257 | | c.769C > T | p.Q257* | 33806 | | 1 | Substitution-Nonsense |
| 259 | | c.775_778delGACC | p.D259fs*7 | 6922956 | | 1 | Deletion-Frameshift |
| 259 | | c.774_775ins13 | p.D259fs*26 | 53296 | | 1 | Insertion-Frameshift |
| 259 | | c.775G > A | p.D259N | 1307999 | | 1 | Substitution-Missense |
| 260 | | c.778C > T | p.Q260* | 990 | | 3 | Substitution-Nonsense |
| 261 | | c.783C > T | p.R261R | 4728318 | | 2 | Substitution-coding silent |
| 261 | | c.781C > T | p.R261C | 1032626 | | 3 | Substitution-Missense |
| 261 | | c.782G > A | p.R261H | 5004225 | | 1 | Substitution-Missense |
| 262 | | c.786C > A | p.V262V | 3363573 | | 1 | Substitution-coding silent |
| 262 | | c.784G > A | p.V262I | 76526 | | 2 | Substitution-Missense |
| 265 | | c.793A > T | p.K265* | 1055 | | 1 | Substitution-Nonsense |
| 266 | | c.796_1158del363 | p.L266_*386del | 29493 | | 2 | Deletion-In frame |
| 268 | | c.804C > T | p.I268I | 5151215 | | 1 | Substitution-coding silent |
| 274 | | c.822C > T | p.S274S | 3552571 | | 1 | Substitution-coding silent |
| 274 | | c.821C > T | p.S274F | 3552569 | | 1 | Substitution-Missense |
| 277 | | c.825_838del14 | p.D277fs*79 | 674183 | | 1 | Deletion-Frameshift |
| 279 | | c.836T > G | p.F279C | 292094 | | 1 | Substitution-Missense |
| 280 | | c.838G > A | p.E280K | 6928390 | | 1 | Substitution-Missense |
| 280 | | c.838C > T | p.E280* | 1071 | | 1 | Substitution-Nonsense |
| 281 | | c.842G > A | p.W281* | 53303 | | 1 | Substitution-Nonsense |
| 281 | | c.843G > A | p.W281* | 1058 | | 2 | Substitution-Nonsense |
| 283 | | c.847_848delAT | p.M283fs*77 | 53302 | | 1 | Deletion-Frameshift |
| 284 | | c.851C > T | p.S284L | 1073 | | 1 | Substitution-Missense |
| 284 | | c.851C > G | p.S284* | 6921364 | | 1 | Substitution-Nonsense |
| 285 | | c.855G > C | p.E285D | 3964140 | | 2 | Substitution-Missense |
| 288 | | c.864C > A | p.N288K | 327307 | | 1 | Substitution-Missense |
| 290 | | c.869delC | p.P290fs*6 | 1054 | | 1 | Deletion-Frameshift |
| 290 | | c.868_869CC > TT | p.P290L | 6951295 | | 1 | Substitution-Missense |
| 294 | | c.881C > T | p.A294V | 6935871 | | 1 | Substitution-Missense |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 295 | | c.885G > A | p.L295L | | 3552573 | 1 | Substitution-coding silent |
| 299 | | c.897G > A | p.S299S | | 1009 | 13 | Substitution-coding silent |
| 299 | | c.896C > T | p.S299L | | 6784969 | 1 | Substitution-Missense |
| 302 | | c.906G > A | p.G302G | | 4766059 | 1 | Substitution-coding silent |
| 305 | | c.913C > A | p.G305R | | 5393251 | 1 | Substitution-Missense |
| 306 | | c.916G > T | p.E306* | | 1059 | 1 | Substitution-Nonsense |
| 307 | | c.919T > G | p.F307V | | 4103007 | 1 | Substitution-Missense |
| 312 | | c.933_934insAT | p.A312fs*9 | | 36389 | 1 | Insertion-Frameshift |
| 312 | | c.934G > A | p.A312T | | 1226776 | 7 | Substitution-Missense |
| 312 | | c.934G > T | p.A312S | | 6946818 | 1 | Substitution-Missense |
| 314 | | c.941G > A | p.S314N | | 6938073 | 1 | Substitution-Missense |
| 316 | | c.946C > T | p.R316W | | 5859022 | 1 | Substitution-Missense |
| 317 | | c.950delG | p.G317fs*3 | | 1065 | 3 | Deletion-Frameshift |
| 318 | | c.952C > T | p.Q318* | | 6784967 | 1 | Substitution-Nonsense |
| 320 | | c.960C > G | p.S320R | | 6784964 | 1 | Substitution-Missense |
| 321 | | c.961T > A | p.W321R | | 4766060 | 1 | Substitution-Missense |
| 323 | | c.967_969CAG > TTAA | p.Q323fs*38 | | 6933028 | 1 | Complex-frameshift |
| 325 | | c.974C > T | p.T325I | | 6963250 | 1 | Substitution-Missense |
| 326 | | c.978C > A | p.Y326* | | 24596 | 3 | Substitution-Nonsense |
| 327 | | c.979G > A | p.A327T | | 95256 | 1 | Substitution-Missense |
| 329 | | c.985A > T | p.S329C | | 7426119 | 1 | Substitution-Missense |
| 330 | | c.988G > A | p.E330K | | 3424066 | 1 | Substitution-Missense |
| 337 | | c.1009G > C | p.E337Q | | 6944843 | 1 | Substitution-Missense |
| 340 | | c.1018_1019delAT | p.I340fs*20 | | 7335464 | 2 | Deletion-Frameshift |
| 341 | | c.1023G > A | p.R341R | | 5642102 | 1 | Substitution-coding silent |
| 341 | | c.1021C > T | p.R341W | | 6912630 | 1 | Substitution-Missense |
| 341 | | c.1022C > T | p.R341L | | 1000 | 1 | Substitution-Missense |
| 343 | | c.1029G > A | p.T343T | | 1032628 | 1 | Substitution-coding silent |
| 344 | | c.1029delG | p.G344fs*13 | | 1665760 | 1 | Deletion-Frameshift |
| 344 | | c.1030C > A | p.G344S | | 6948815 | 1 | Substitution-Missense |
| 347 | | c.1039C > C | p.D347H | | 6983956 | 1 | Substitution-Missense |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 348 | | c.1041delC | p.Q348fs*9 | 1578552 | | 1 | Deletion-Frameshift |
| 351 | | c.1051_1054delCCAC | p.P351fs*5 | 26410 | | 1 | Deletion-Frameshift |
| 351 | | c.1051C > T | p.P351S | 116157 | | 1 | Substitution-Missense |
| 356 | | c.1064_1065delCT | p.L356fs*4 | 6921804 | | 2 | Deletion-Frameshift |
| 356 | | c.1066_1067delCT | p.L356fs*4 | 5967280 | | 1 | Deletion-Frameshift |
| 356 | | c.1067T > C | p.L356P | 4798555 | | 1 | Substitution-Missense |
| 357 | | c.1066_1067insT | p.T357fs*4 | 6950300 | | 1 | Insertion-Frameshift |
| 363 | | c.1089G > C | p.K363N | 3309726 | | 1 | Substitution-Missense |
| 363 | | c.1087A > T | p.K363* | 5707608 | | 1 | Substitution-Nonsense |
| 364 | | c.1085_1087delAGA | p.K364delK | 1180929 | | 5 | Deletion-In frame |
| 364 | | c.1090A > T | p.K364* | 5015713 | | 1 | Substitution-Nonsense |
| 366 | | c.1096C > T | p.R366C | 4728320 | | 3 | Substitution-Missense |
| 366 | | c.1097G > C | p.R366P | 215858 | | 1 | Substitution-Missense |
| 367 | | c.1101C > A | p.D367E | 6930149 | | 1 | Substitution-Missense |
| 368 | | c.1103A > G | p.Q368R | 78546 | | 1 | Substitution-Missense |
| 368 | | c.1102C > T | p.Q368* | 997 | | 6 | Substitution-Nonsense |
| 370 | | c.1109G > C | p.R370T | 6929540 | | 1 | Substitution-Missense |
| 370 | | c.1109G > T | p.R370M | 3309728 | | 1 | Substitution-Missense |
| 370 | | c.1110G > T | p.R370S | 1308001 | | 2 | Substitution-Missense |
| 371 | | c.1112A > G | p.N371S | 478792 | | 1 | Substitution-Missense |
| 372 | | c.1116G > A | p.T372T | 1003 | | 2 | Substitution-coding silent |
| 372 | | c.1115C > T | p.T372M | 5057721 | | 1 | Substitution-Missense |
| 373 | | c.1117A > G | p.R373G | 327305 | | 2 | Substitution-Missense |
| 373 | | c.1117A > T | p.R373W | 1740720 | | 1 | Substitution-Missense |
| 373 | | c.? | p.R373W | 6904500 | | 1 | Substitution-Missense |
| 374 | | c.1120C > A | p.R374R | 3363575 | | 1 | Substitution-coding silent |
| 374 | | c.1120C > T | p.R374W | 1226778 | | 3 | Substitution-Missense |
| 374 | | c.1121G > A | p.R374Q | 998 | | 10 | Substitution-Missense |
| 374 | | c.1121G > C | p.R374P | 7219565 | | 1 | Substitution-Missense |
| 374 | | c.? | p.R374Q | 6022465 | | 1 | Substitution-Missense |
| 375 | | c. 1124_1125insGAGGCGTC | p.M375fs*14 | 1080 | | 1 | Insertion-Frameshift |
| 375 | | c.1125_1126insG | p.M375fs*12 | 1006 | | 1 | Insertion-Frameshift |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| 375 | | c.1125G > C | p.M375I | | 7339204 | 1 | Substitution-Missense |
| 376 | | c.1126A > G | p.R376G | | 1161417 | 1 | Substitution-Missense |
| 377 | | c.1130delG | p.R377fs*10 | | 27977 | 1 | Deletion-Frameshift |
| 377 | | c.1129C > T | p.R377C | | 3972885 | 10 | Substitution-Missense |
| 377 | | c.1130G > A | p.R377H | | 989 | 27 | Substitution-Missense |
| 377 | | c.1130C > T | p.R377L | | 4596765 | 4 | Substitution-Missense |
| 377 | | c.? | p.R377H | | 4166186 | 2 | Substitution-Missense |
| 378 | | c.1132C > T | p.L378F | | 5991515 | 2 | Substitution-Missense |
| 378 | | c.1133T > C | p.L378P | | 6945086 | 2 | Substitution-Missense |
| 379 | | c.1135C > A | p.A379T | | 6904737 | 1 | Substitution-Missense |
| 381 | | c.1141A > G | p.T381A | | 4624608 | 1 | Substitution-Missense |
| 381 | | c.1142C > G | p.T381R | | 5574330 | 1 | Substitution-Missense |
| 382 | | c.1143delG | p.A382fs*5 | | 29382 | 11 | Deletion-Frameshift |
| 382 | | c.1144delG | p.A382fs*4 | | 1060 | 4 | Deletion-Frameshift |
| 382 | | c.1145C > T | p.A382V | | 6438246 | 1 | Substitution-Missense |
| 383 | | c.1145delC | p.P383fs*4 | | 29495 | 13 | Deletion-Frameshift |
| 383 | | c.1147_1147delC | p.P383fs | | 144160 | 1 | Deletion-Frameshift |
| 383 | | c.1148delC | p.P383fs*>3 | | 1057 | 16 | Deletion-Frameshift |
| 383 | | c.1148C > T | p.P383L | | 5991513 | 2 | Substitution-Missense |
| | | c.363_628del266 | p.? | | 13446 | 3 | Deletion-Frameshift |
| | | c.?del? | p.?fs | | 1087 | 2 | Deletion-Frameshift |
| | | c.?del? | p.?fs | | 1097 | 1 | Deletion-Frameshift |
| | | c.?del? | p.?fs | | 1098 | 1 | Deletion-Frameshift |
| | | c.987_1118del | p.? | | 1102 | 1 | Deletion-In frame |
| | | c.146_147ins25 | p.?fs | | 53304 | 1 | Insertion-Frameshift |
| | | c.243_244ins? | p.?fs | | 27978 | 1 | Insertion-Frameshift |
| | | c.1-?_93+?del5006 | p.? | | 6006428 | 1 | Unknown |
| | | c.1_362del362 | p.? | | 1169665 | 2 | Unknown |
| | | c.1_628del628 | p.? | | 24617 | 4 | Unknown |
| | | c.1_628del628 | p.? | | 53295 | 2 | Unknown |
| | | c.1_795del | p? | | 24616 | 2 | Unknown |
| | | c.1_93del | p? | | 1083 | 13 | Unknown |
| | | c.1_986del986 | p? | | 1133056 | 1 | Unknown |
| | | c.233_1158del926 | p? | | 4774843 | 1 | Unknown |
| | | c.363-?_628+?del | p? | | 674155 | 1 | Unknown |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| | | c.363_500del | p? | 1103 | | 22 | Unknown |
| | | c.500_500+1GG>TT | p? | 6912416 | | 1 | Unknown |
| | | c.501_628del128 | p? | 1133055 | | 1 | Unknown |
| | | c.569_570ins18 | p? | 36391 | | 1 | Unknown |
| | | c.628_629ins? | p? | 33667 | | 1 | Unknown |
| | | c.629-?_1158+?del | p? | 674156 | | 1 | Unknown |
| | | c.629_1158del530 | p? | 29387 | | 2 | Unknown |
| | | c.629_795del | p? | 1101 | | 3 | Unknown |
| | | c.629_986del358 | p? | 53293 | | 1 | Unknown |
| | | c.796-?_1118+?del | p? | 5576339 | | 1 | Unknown |
| | | c.796_986del191 | p.? | 29386 | | 2 | Unknown |
| | | c.796_986del191 | p.? | 51387 | | 1 | Unknown |
| | | c.986_987ins? | p.? | 33666 | | 1 | Unknown |
| | | c.987_1158del172 | p.? | 4774844 | | 1 | Unknown |
| | | c.1-126A > C | p.? | 1106 | | 1 | Unknown |
| | | c.1-405C > A | p.? | 1105 | | 1 | Unknown |
| | | c.1-65C > T | p.? | 1088 | | 1 | Unknown |
| | | c.1119-38insA | p.? | 1091 | | 1 | Unknown |
| | | c.1119-41C > A | p.? | 1090 | | 4 | Unknown |
| | | c.1158+116insG | p.? | 1093 | | 3 | Unknown |
| | | c.1158+145C > A | p.? | 1094 | | 1 | Unknown |
| | | c.1158+17C > T | p.? | 6503273 | | 1 | Unknown |
| | | c.1158+1delC | p.? | 1107 | | 1 | Unknown |
| | | c.1158+26C > T | p.? | 1092 | | 1 | Unknown |
| | | c.232+4C > T | p.? | 6438253 | | 1 | Unknown |
| | | c.233-1G > C | p.? | 1104 | | 1 | Unknown |
| | | c.363-1C > T | p.? | 6924581 | | 1 | Unknown |
| | | c.363-2_363-1delAG | p.? | 6910120 | | 1 | Unknown |
| | | c.500+1G > T | p.? | 6972182 | | 1 | Unknown |
| | | c.501-1G > C | p.? | 53298 | | 1 | Unknown |
| | | c.628+13C > T | p.? | 1099 | | 2 | Unknown |
| | | c.628+2T > G | p.? | 5731549 | | 1 | Unknown |
| | | c.628+4C > T | p.? | 6438251 | | 1 | Unknown |
| | | c.629-1G > A | p.? | 1085 | | 1 | Unknown |
| | | c.629-27G > A | p.? | 1086 | | 1 | Unknown |

TABLE 6-continued

SMARCB1 mutations identified in Coffin-Siris Syndrome (MIM 135900), Kleefstra Syndrome (KSS), and Generalized Intellectual Disability (ID), and SMARCB1 mutations from COSMIC database

| Subject ID (for this study) | Referral Diagnosis (from original study) | DNA | Protein | Shift | Inheri-tance | Reference | Note: |
|---|---|---|---|---|---|---|---|
| | | c.629-2A > G | p.? | | 1100 | 1 | Unknown |
| | | c.629-3C > T | p.? | | 4849576 | 1 | Unknown |
| | | c.795+2T > ATGA | p.? | | 36390 | 1 | Unknown |
| | | c.986+1C > T | p.? | | 1666667 | 1 | Unknown |
| | | c.986+57insAA | p.? | | 1089 | 3 | Unknown |
| | | c.987-2A > T | p.? | | 6964939 | 1 | Unknown |
| | | c.987-4G > A | p.? | | 6301086 | 1 | Unknown |
| | | c.? | p.? | | 1108 | 13 | Unknown |
| | | c.?_?del? | p.? | | 29855 | 1 | Unknown |
| | | c.?_?del? | p.? | | 308350 | 1 | Unknown |
| | | c.?_?del? | p.? | | 1133057 | 2 | Unknown |
| | | c.?_?del? | p.? | | 6904522 | 5 | Unknown |

To biochemically evaluate the effects of these mutations on mSWI/SNF protein complex assembly and integrity, SMARCB1 wild-type (WT) and mutant variants were introduced into SMARCB1-knockout HEK-293T cells (FIG. 1D-FIG. 1E). WT and CSS-associated mutant SMARCB1 variants were stable at the total nuclear protein levels and stably incorporated into mSWI/SNF complexes irrespective of SMARCB1 mutation status, as indicated by immunoprecipitation studies followed by immunoblot, proteomic mass spectrometry and silver staining (FIG. 1F-FIG. 1G and FIG. 2B-FIG. 2D, Table 4). These data are consistent with the fact that tandem repeat domains within the SNF5 homology region (RPT1 and RPT2) were identified as essential for SMARCB1-mSWI/SNF complex binding (FIG. 1H), and indicate that CSS-associated point mutations in the SMARCB1 CC domain do not affect BAF complex integrity or assembly, pointing toward alternative functional consequences.

To assess possible changes in mSWI/SNF complex function, endogenous, fully-formed mSWI/SNF complexes containing either WT SMARCB1 or CSS-associated SMARCB1 variants, as well as a Kleefstra syndrome-associated SMARCB1 mutant variant containing the R37H mutation in the Winged-helix (WH) DNA binding domain (Diets et al. (2018) *Genetics in Medicine* 69:1; Kleefstra et al. (2012) *Am. J. Human Genet.* 91:73-82), were purified (FIG. 2D). Purified complexes were subjected to DpnII-mediated 601 mononucleosome restriction enzyme accessibility assays (REAA) to evaluate nucleosome remodeling activity (FIG. 2E). Intriguingly, complexes containing CSS-associated SMARCB1 CC mutant variants were determined to exhibit significant attenuation in nucleosome remodeling activity compared to those containing WT SMARCB1 or R37H DNA-binding domain mutant SMARCB1 (FIG. 1I-FIG. 1J and FIG. 2F-FIG. 2G). In addition, a significant reduction in ATPase activity of SMARCB1 CC domain mutant mSWI/SNF complexes relative to WT complexes when bound to nucleosome substrates (recombinant tetrameric polynucleosomes, and HeLa cell polynucleosomes), but no differences were detected when in solution with free 601 Widom DNA without the histone octamer, suggesting decreased mSWI/SNF remodeling activity and ATP consumption in the context of a complete nucleosome substrate (FIG. 1K-FIG. 1L and FIG. 2H-FIG. 2J). Taken together, these data unmask a specific compromise to the hallmark function of mSWI/SNF chromatin remodeling complexes rendered by single residue CSS-associated SMARCB1 CC domain mutations (but not by mutations in the N-terminal DNA binding domain).

Figure 4:
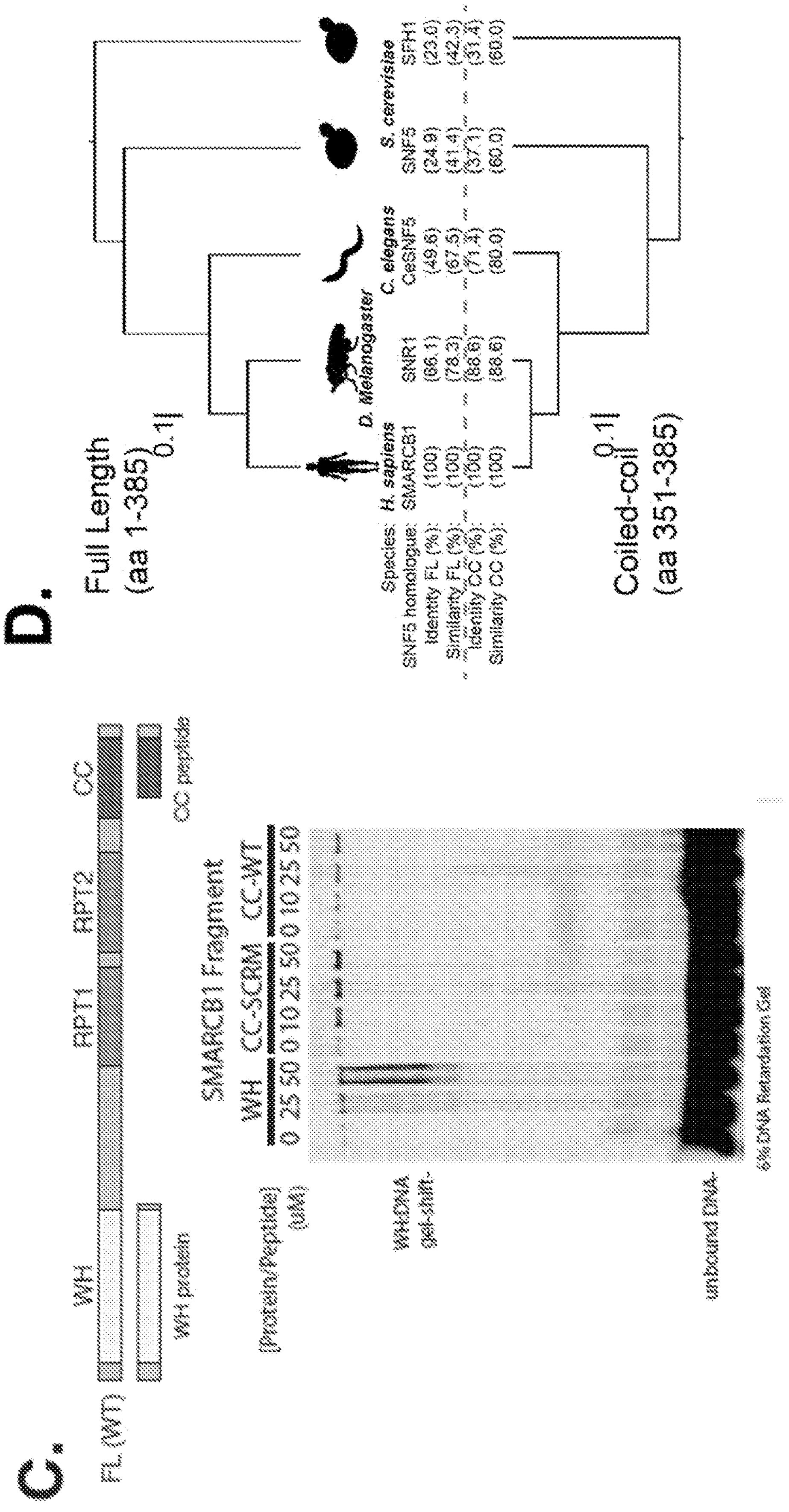
FIG. 4A-FIG. 4N show evolutionary, biophysical, and structural properties of the WT and mutant SMARCB1 CC domain.
FIG. 4B shows a schematic for peptide pull-down of mononucleosomes incubated with biotinylated CC peptides, followed by immunoblot for histone H3 or histone H2B.
FIG. 4C shows the results of a DNA binding assay (EMSA) performed with WT SMARCB1 CC domain and SMARCB1 Winged-helix DNA binding domain as control.
FIG. 4D shows phylogenetic trees demonstrating evolutionary conservation across full-length SMARCB1 protein (top panel) and C-terminal domain (aa 351-385) across SNF5-like homologues (bottom panel).
FIG. 4E shows an immunoblot of *H. sapiens* SMARCB1 CC WT and K363, K364, 1365, and R370 mutant biotin-tagged peptide pull downs of mammalian mononucleosomes.
FIG. 4F shows that circular dichroism (CD) performed on SMARCB1 C-terminal domain peptides (aa 351-382) resulted in no significant changes in alpha-helical signature across WT and mutant variants.
FIG. 4G shows a HPLC chromatogram and accompanying Coomassie® stained gels demonstrating expression and purification of SMARCB1 C-terminal domain potein (GST-SMARCB1 CC aa 351-385; pGEX6-P-2) used in HSQC NMR experiments.
FIG. 4H (left panel) shows transverse relaxation times (T2) of 15N-labeled SMARCB1-CC protein (351-385) and FIG. 4H (right panel) shows a secondary structure prediction plot of combined probability of Helix (red)/Coil (grey)/Strand (cyan) of SMARCB1-CC secondary structures.
FIG. 4I shows side view and barrel view superpositions of all positively charged residues (left) and CSS-mutated SMARCB1 residues (aa 357-378) (right). CSS mutated Arg/Lys residues colored dark blue and other Arg/Lys residues colored light blue.
FIG. 4J shows a Consurf Conservation overlay on structurally-predicted NMR structure of SMARCB1-CC alpha helix.
FIG. 4K shows that all CSS-associated SMARCB1 mutations reduce the isoelectric point and net positive charge of the SMARCB1-C-terminus.
FIG. 4L-FIG. 4M show side (FIG. 4L) and barrel (FIG. 4M) views of the SMARCB1-CC in WT and CSS-associated mutant forms (in orange) are structurally predicted to disrupt the positively-charged residue cluster. Positive residues (Arg/Lys) are colored blue and negative residues (Glu/Asp) are colored red. Structural mutagenesis was carried out in Pymol.
Figure 4:
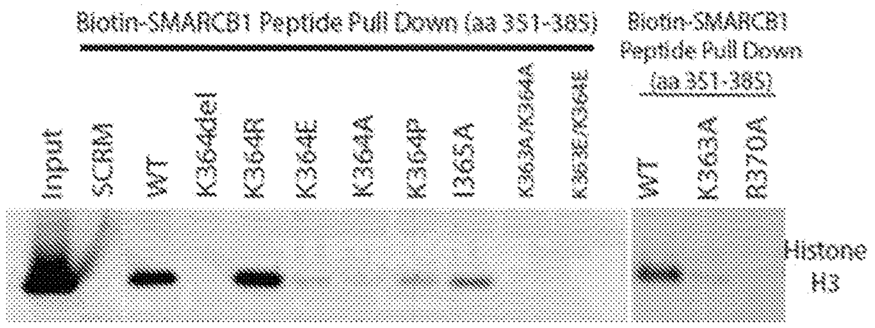
Figure 4:
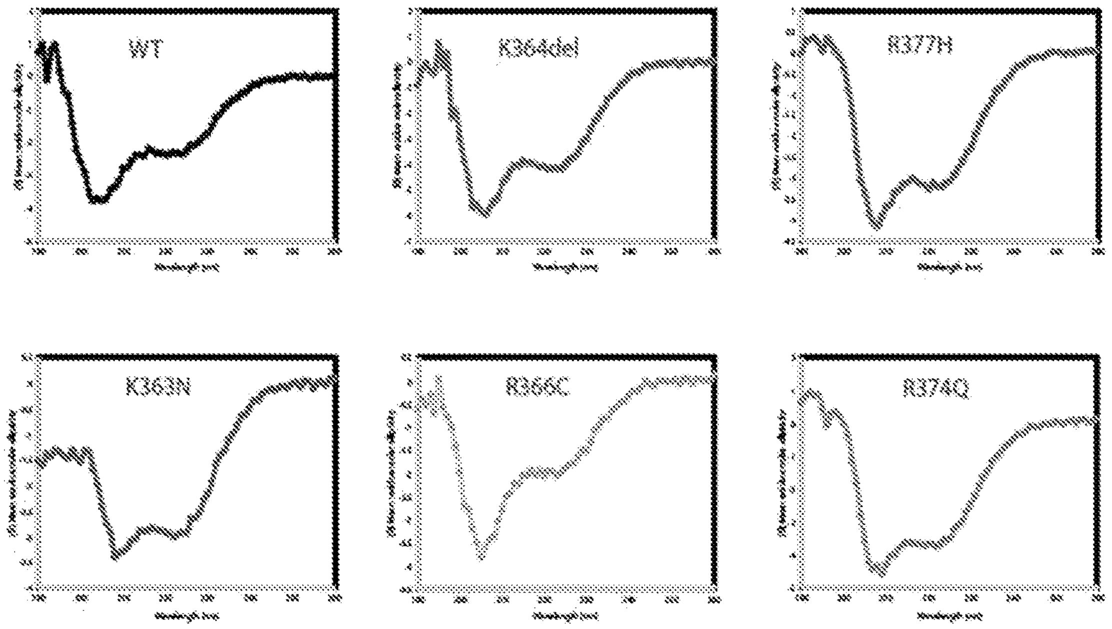
Figure 4:
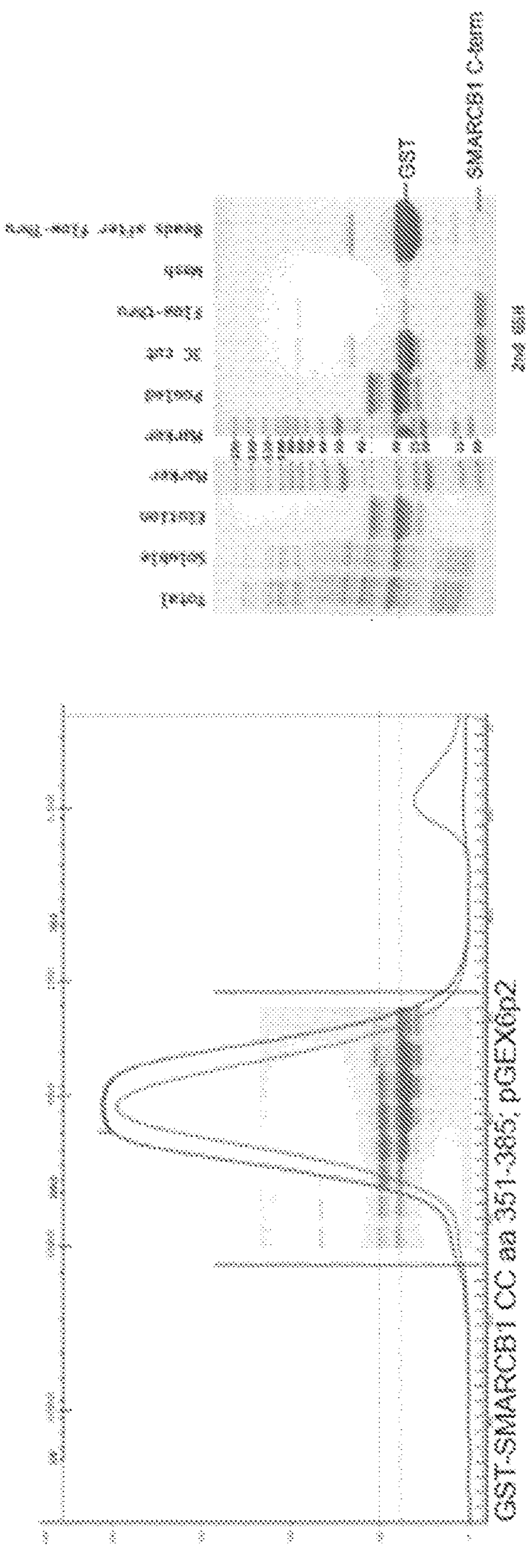
Figure 4:
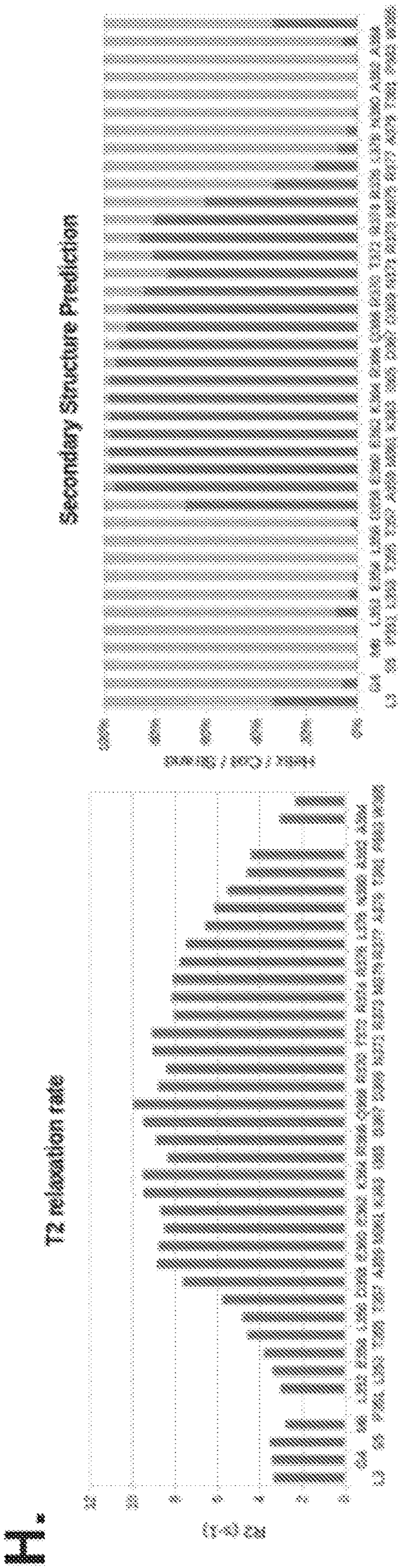
Figure 4:
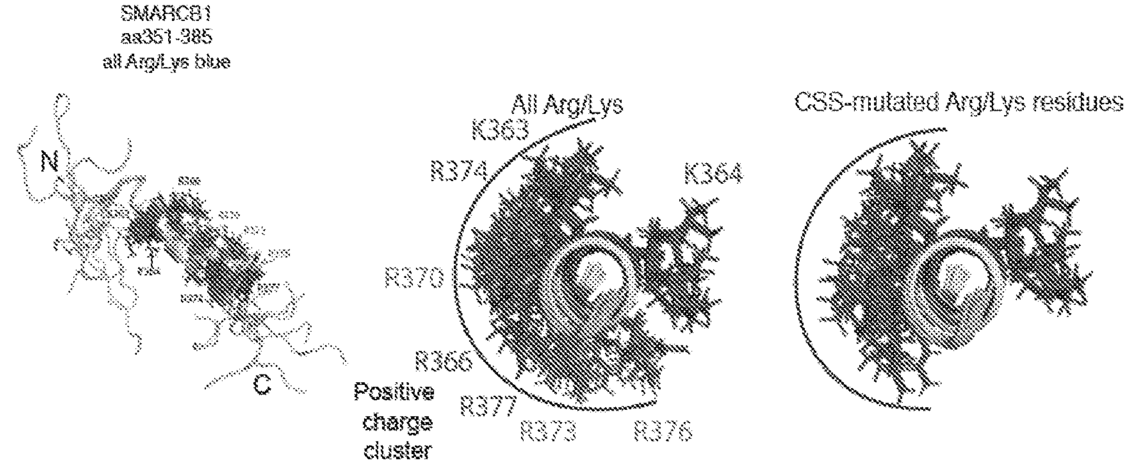
Figure 4:
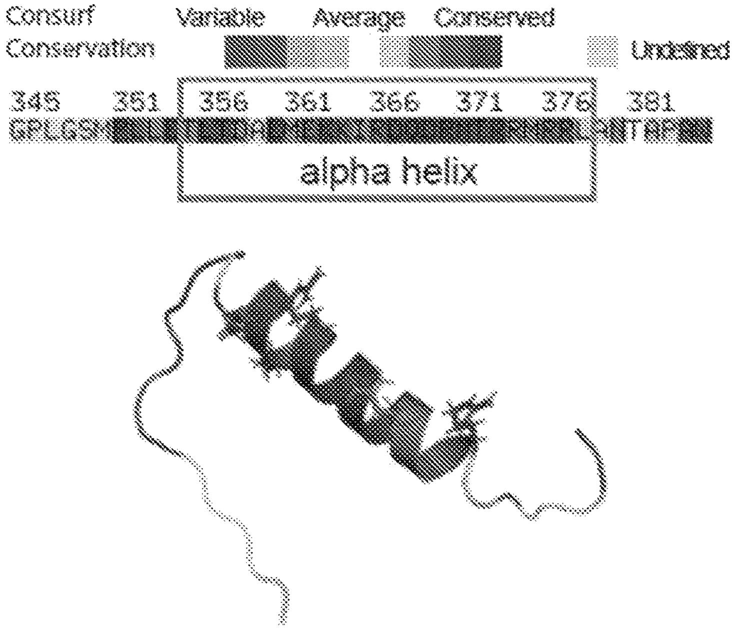
Figure 4:
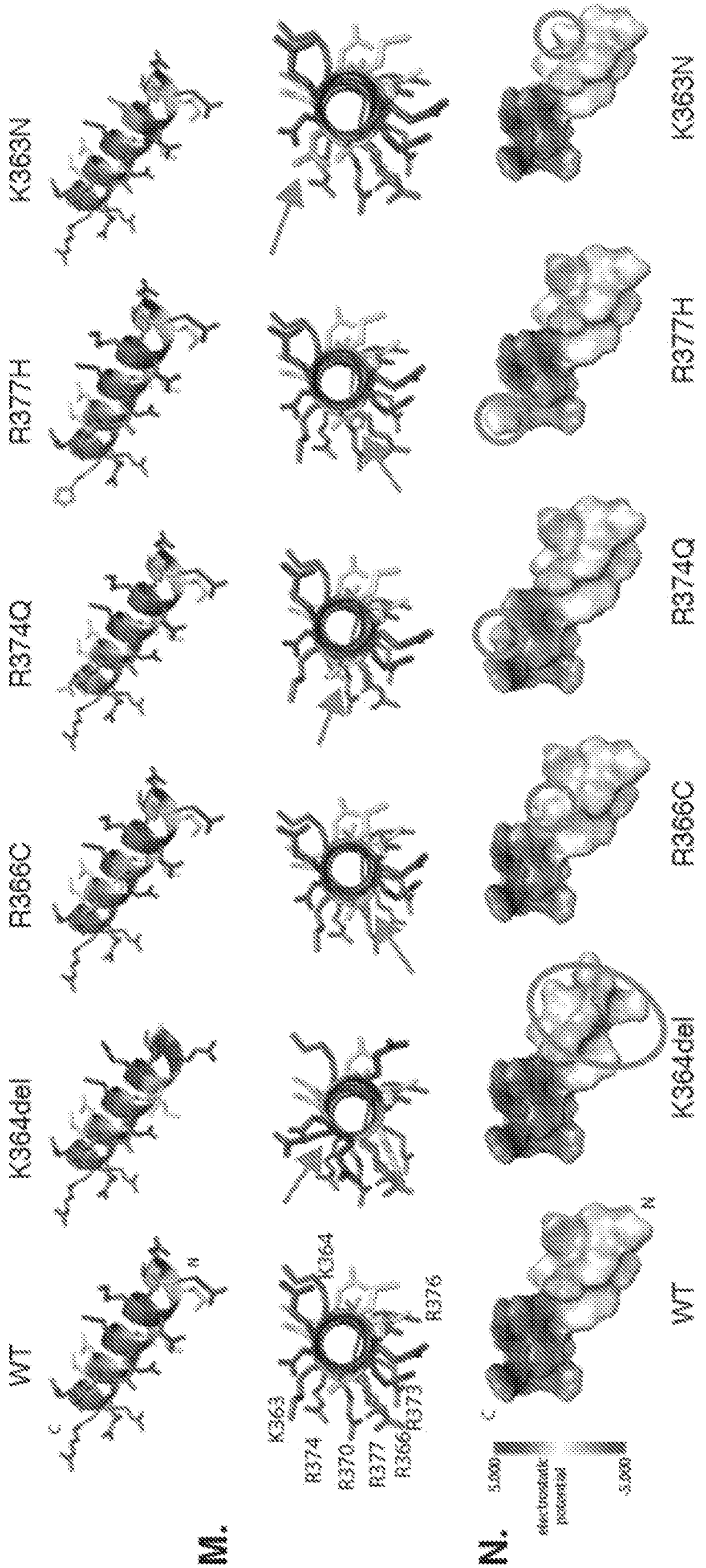

Example 3: SMARCB1 CC Domain Binds Directly to Nucleosomes, Mediated by a Basic, Alpha-Helical Amino Acid Cluster Given these results, it was next sought to determine whether the remodeling defect observed upon mutation of the SMARCB1-CC could be due to altered interactions between mSWI/SNF complexes and their nucleosome substrates. Of note, while nucleosomes are well-established to be the key substrates of mSWI/SNF complexes, the specific interaction surfaces among the ~11-15 mSWI/SNF subunits with nucleosomes remains unknown with the exception of the recently-characterized yeast Snf2 helicase domain solved with nucleosomal DNA (Liu et al. (2017) *Nature* 544:440-445). To this end, biotinylated peptides corresponding to amino acids 351-385 of SMARCB1 (minimal putative CC domain and the most highly conserved region within the c-terminal region of SMARCB1), in either WT or CSS-associated mutant forms, were generated (FIG. 3A and FIG. 4A). Strikingly, it was determined that this 35-aa minimal region of the WT SMARCB1 c-terminal domain was sufficient to bind mammalian mononucleosomes (FIG. 3B and FIG. 4B) and that all CSS-associated CC domain mutations completely disrupted this binding interaction (FIG. 3B). Importantly, incubation of CC domain peptides with DNA did not produce changes in gel-shift assays (EMSA) relative to WH DNA-binding domain protein, further confirming this as a protein-protein interaction with the histone octamer of the nucleosome rather than a protein-DNA interaction (FIG. 4C).

Considering that SMARCB1 is one of the most conserved members of the SWI/SNF family, with high degrees of conservation back to yeast SNF5 (FIG. 4D) and has been shown to play important roles in ATP-dependent chromatin remodeling in yeast (Dutta et al. (2017) *Cell Reports* 18:2124-2134; Sen et al. (2017) *Cell Reports* 18:2135-2147) and other systems (Nakayama et al. (2017) *Nat. Genet.* 49:1613-1623; Phelan et al. (1999) *Mol. Cell* 3:247-253; Wang et al. (2017) *Nat. Genet.* 49:289-295), it was sought to determine whether the minimal 35 aa C-terminal putative CC domains across species similarly bound nucleosomes. Indeed, all SNF5-like C-terminal putative CC domains exhibited clear binding to mononucleosomes, indicating conservation of this critical interaction throughout evolution (FIG. 3C). Additional point mutations within the *H. sapiens* SMARCB1 CC domain, including changes of lysine 364 to glutamine, alanine, proline residues, but not to a similarly charged arginine residue, also resulted in attenuated or completely abrogated SMARCB1 CC domain-nucleosome binding (FIG. 4E).

To characterize the effect of these mutations on SMARCB1 CC domain secondary structure, circular dichroism (CD) spectroscopy was used. This revealed that the CC domain is alpha-helical in nature and that CSS-associated mutations do not grossly disrupt this secondary structure (FIG. 4F). SMARCB1 C-terminal domain protein (aa 351-385) was recombinantly expressed in heavy-labeled media ($^{13}C$, $^{15}N$) for structural determination by nuclear magnetic resonance (NMR) spectroscopy (FIG. 4G). T2 relaxation and secondary structure prediction of $^{15}N$ labeled SMARCB1-CC provided evidence that the SMARCB1 C-terminal domain contains an alpha-helix (aa 357-377) flanked by residues that appear to be in highly dynamic random coil state (FIG. 4H). Chemical shift assignments and backbone resonances were obtained using a set of seven triple-resonance experiments (the assigned $^{15}N$-HSQC fingerprint spectrum is shown in FIG. 3D). Ultimately, fifty structural models with 422 NOE distance restraints and 15 identified hydrogen-bonds were calculated using the XPLOR-NIH (Schwieters et al. (2003) *J. Magn. Res.* 160: 66-74). A high resolution structure of the alpha helical region of the SMARCB1-C terminus (aa 358-377) was obtained (0.15−/+0.04 Å backbone root mean squared deviation for the top 10 determined structures) (FIG. 3E; Table 5). Strikingly, the structures reveal an outward-facing positive charge (basic, K (Lys), R (Arg)) cluster of amino acids (FIG. 3F and FIG. 4I), several of which are those specifically mutated in CSS (FIG. 1A). Analysis of the alpha helical structure (barrel view) further identified a dense cluster of 6+, highly conserved basic residues (FIG. 3F and FIG. 4J). Moreover, electrostatic calculations using ABPS indicate that this arrangement leads to a positive charge cluster in the domain with the highest electrostatic potential calculation relative to the remainder of this region (FIG. 3G), with all CSS-associated mutations predicted to significantly alter the isoelectric point (pI), net charge, or charge orientation of this region (FIGS. 4K-4N). While the K364del mutation disrupts the ordered register of the helix, hence repositioning acidic residues within the CC domain to the same face as the basic charge cluster, the missense mutations decrease the charge potential and abrogate association to the acidic nucleosome residues. These data collectively highlight distinct mechanisms of structural disruption to the SMARCB1 C-terminal alpha helical region, which uniformly perturb a critical mSWI/SNF: nucleosome interface.

Figure 2:
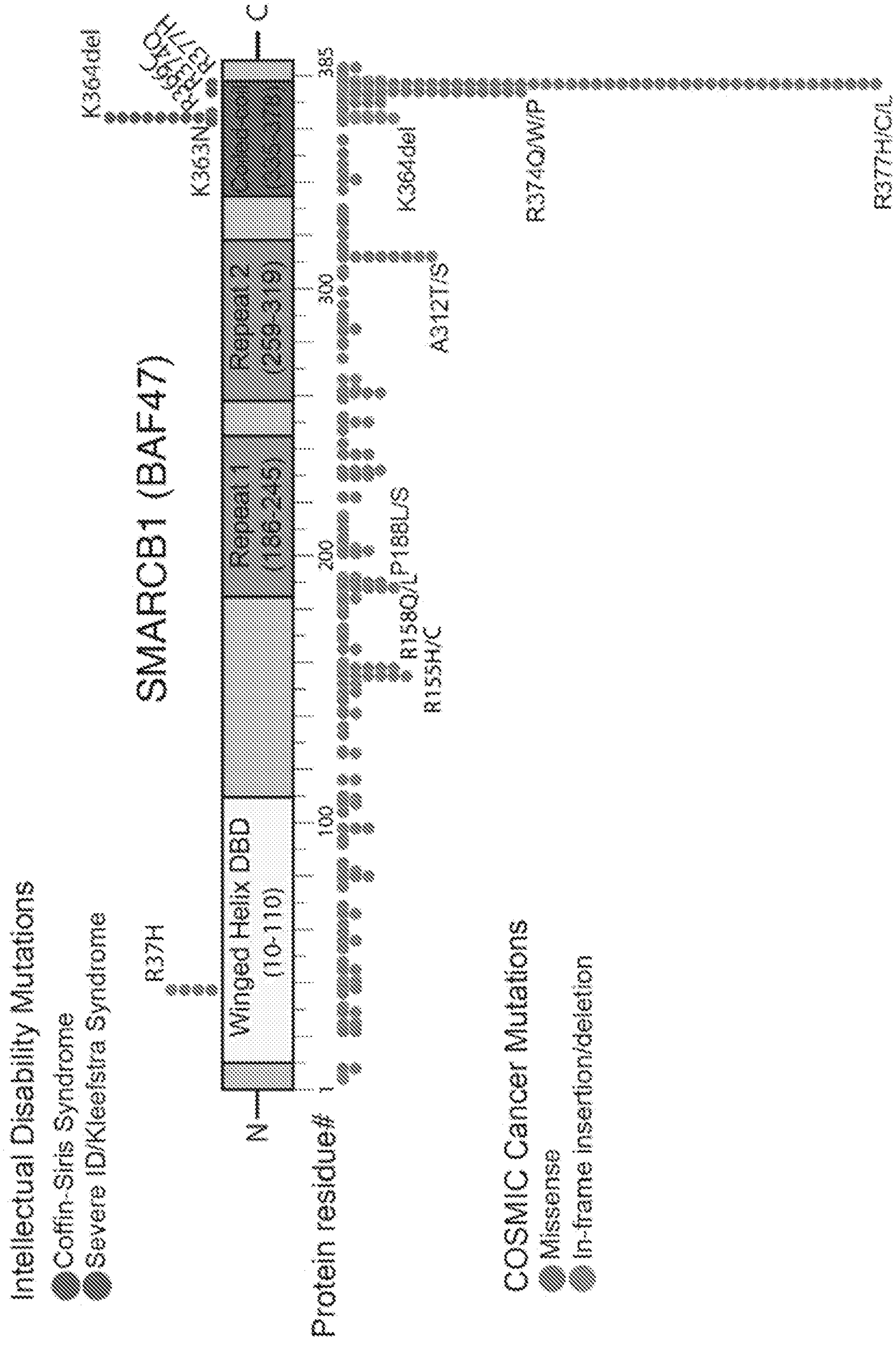
FIG. 2A-FIG. 2J show that CSS-associated mutations in the SMARCB1 C-terminal CC domain inhibit mSWI/SNF nucleosome remodeling and ATPase activity on nucleosomes.
Figure 2:
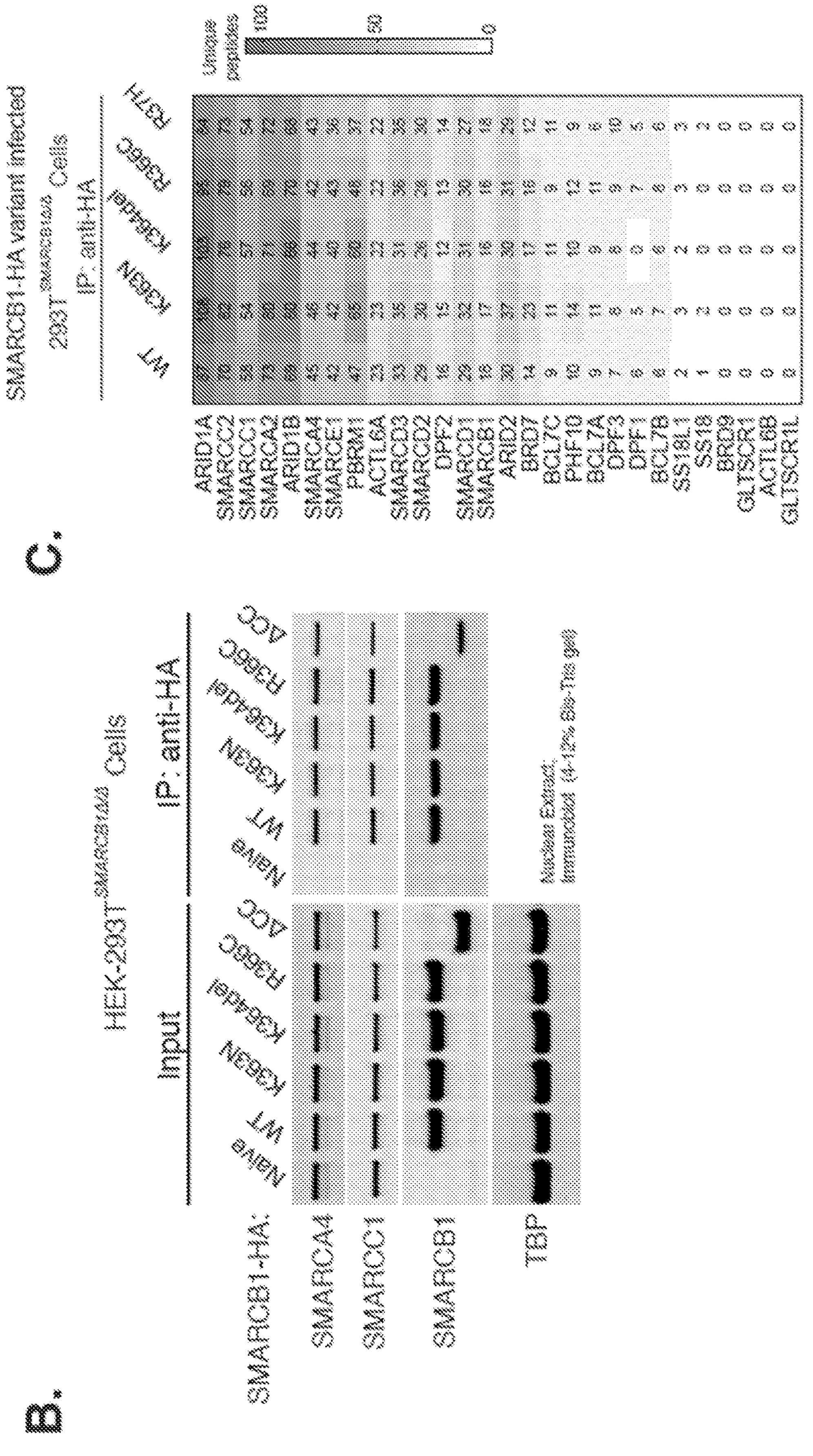
Figure 2:
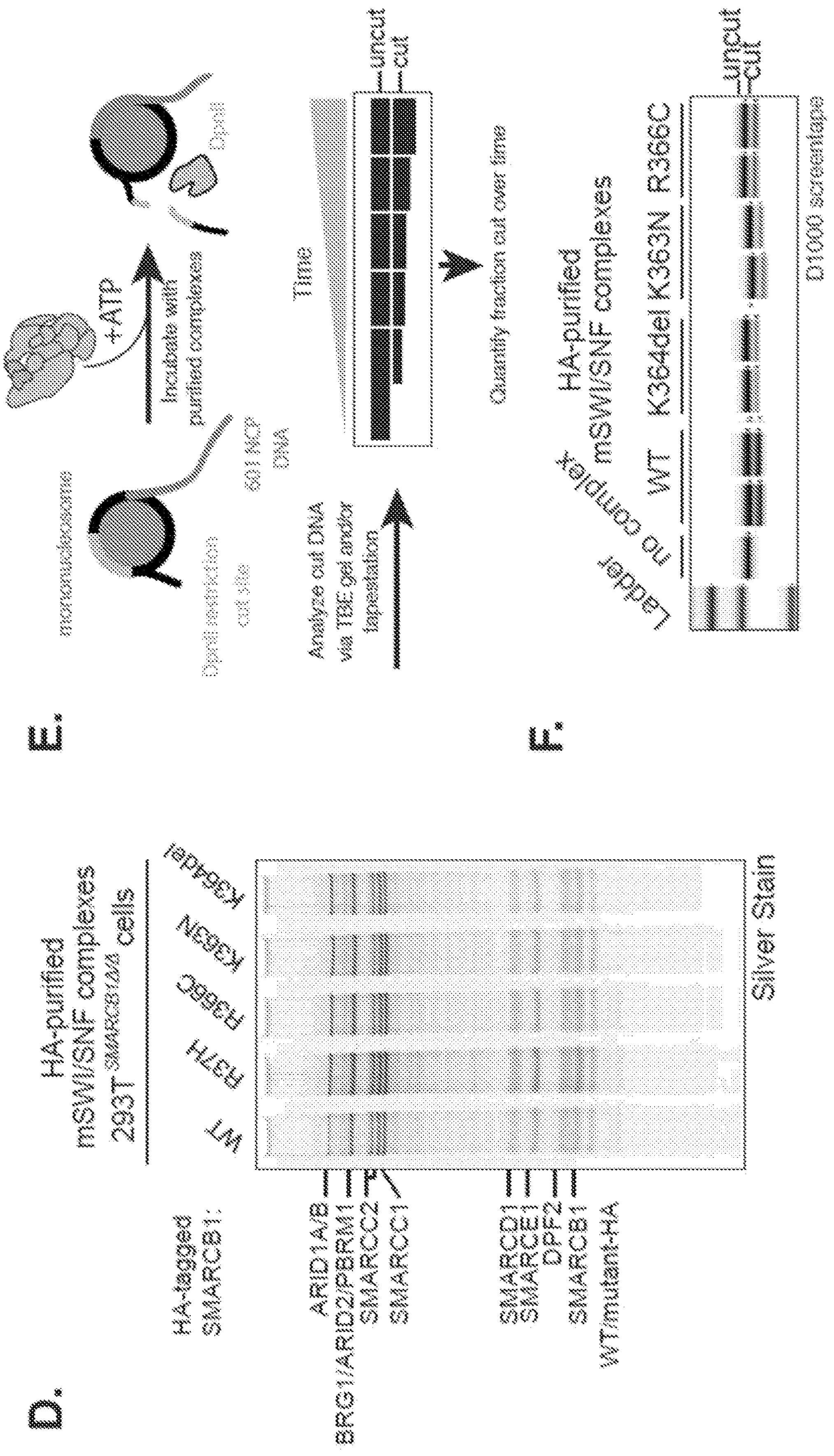
Figure 2:
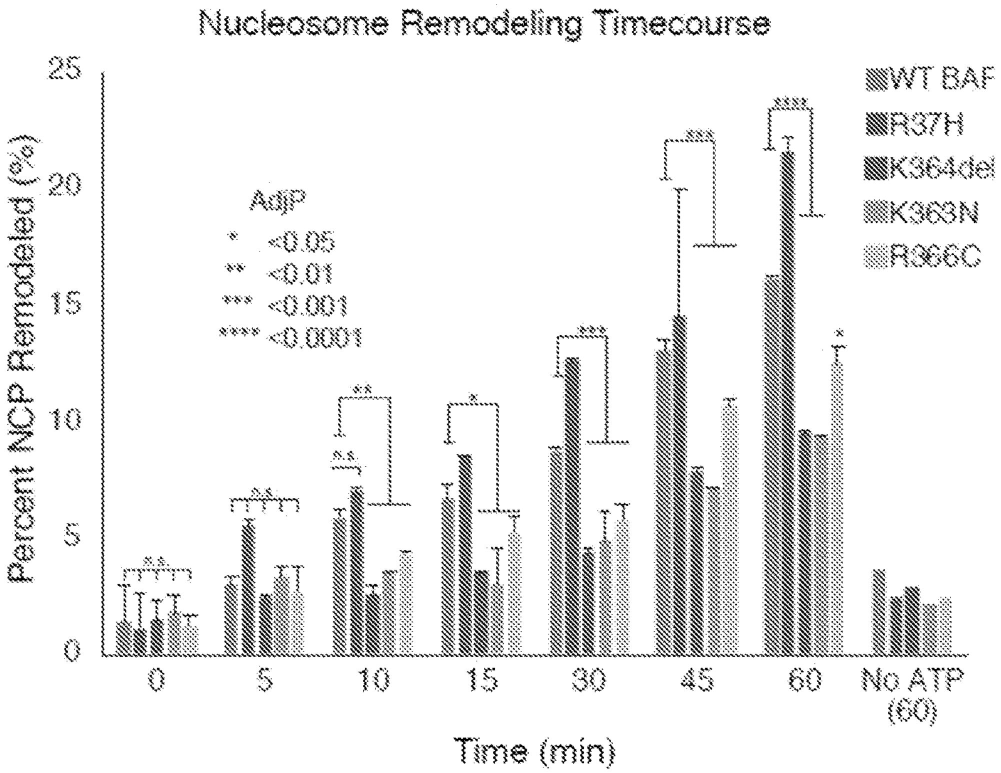
Figure 2:
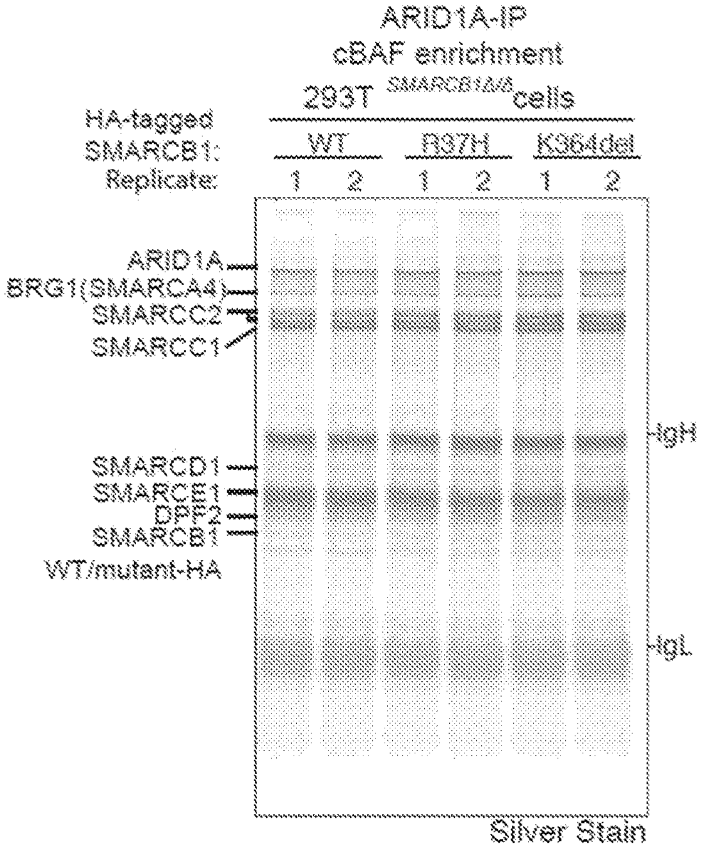
Figure 2:
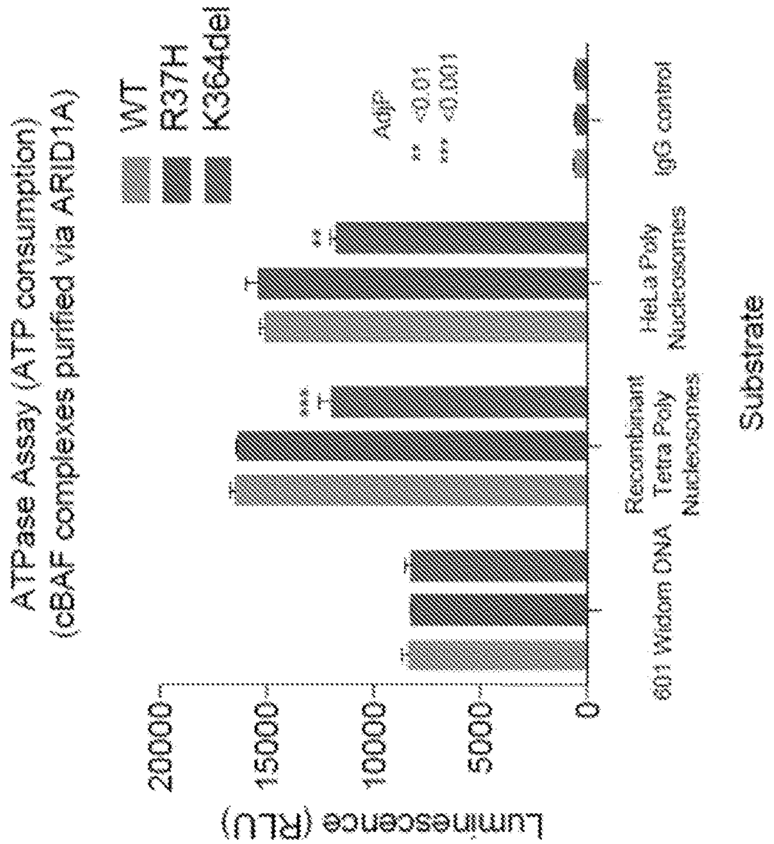
Figure 2:
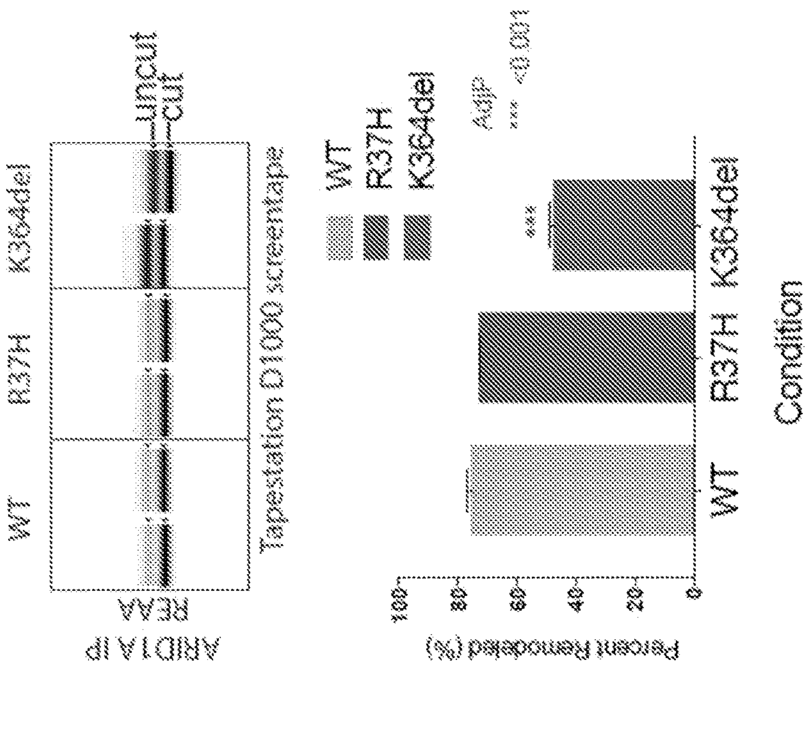
Figure 5:
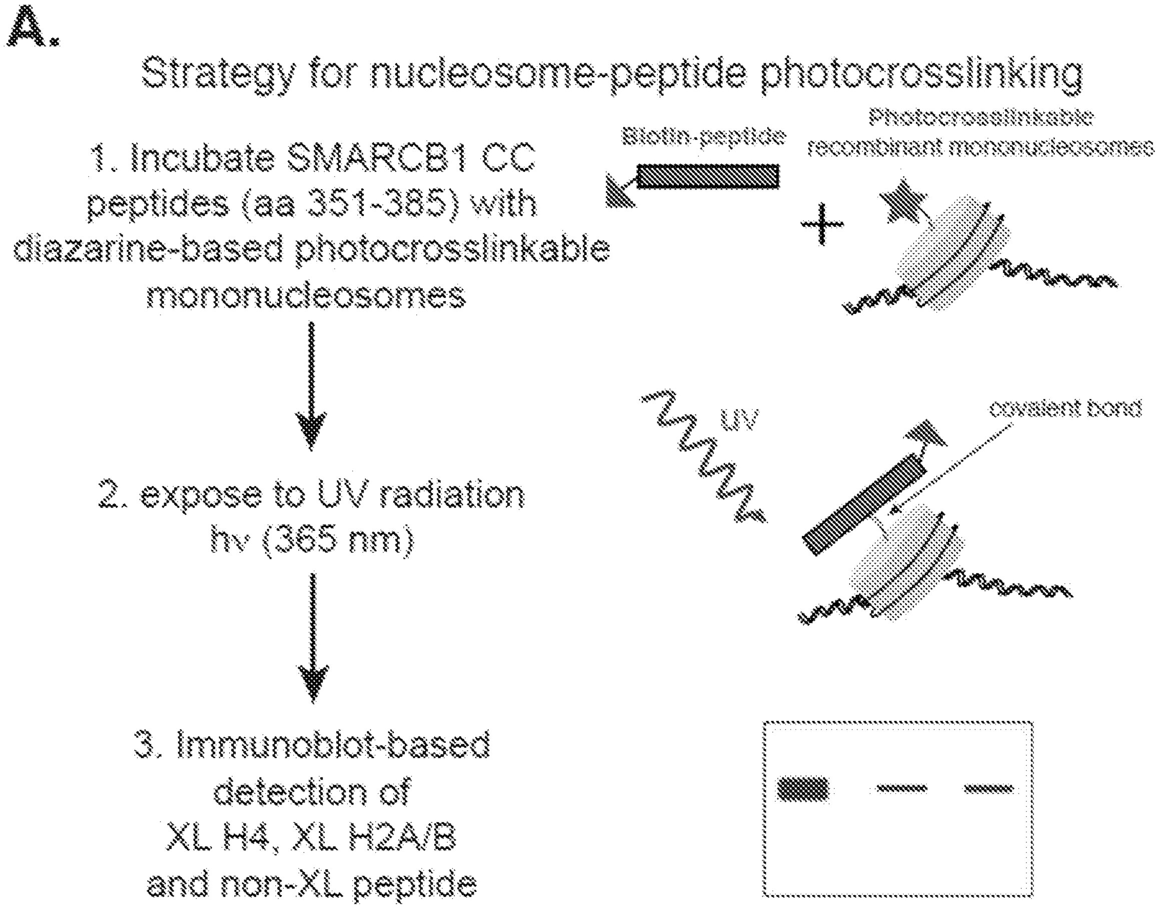
FIG. 5A-FIG. 5F show that the SMARCB1 C-terminal domain binds to the nucleosome acidic patch, which is disrupted by CSS-associated missense mutations.
Figure 5:
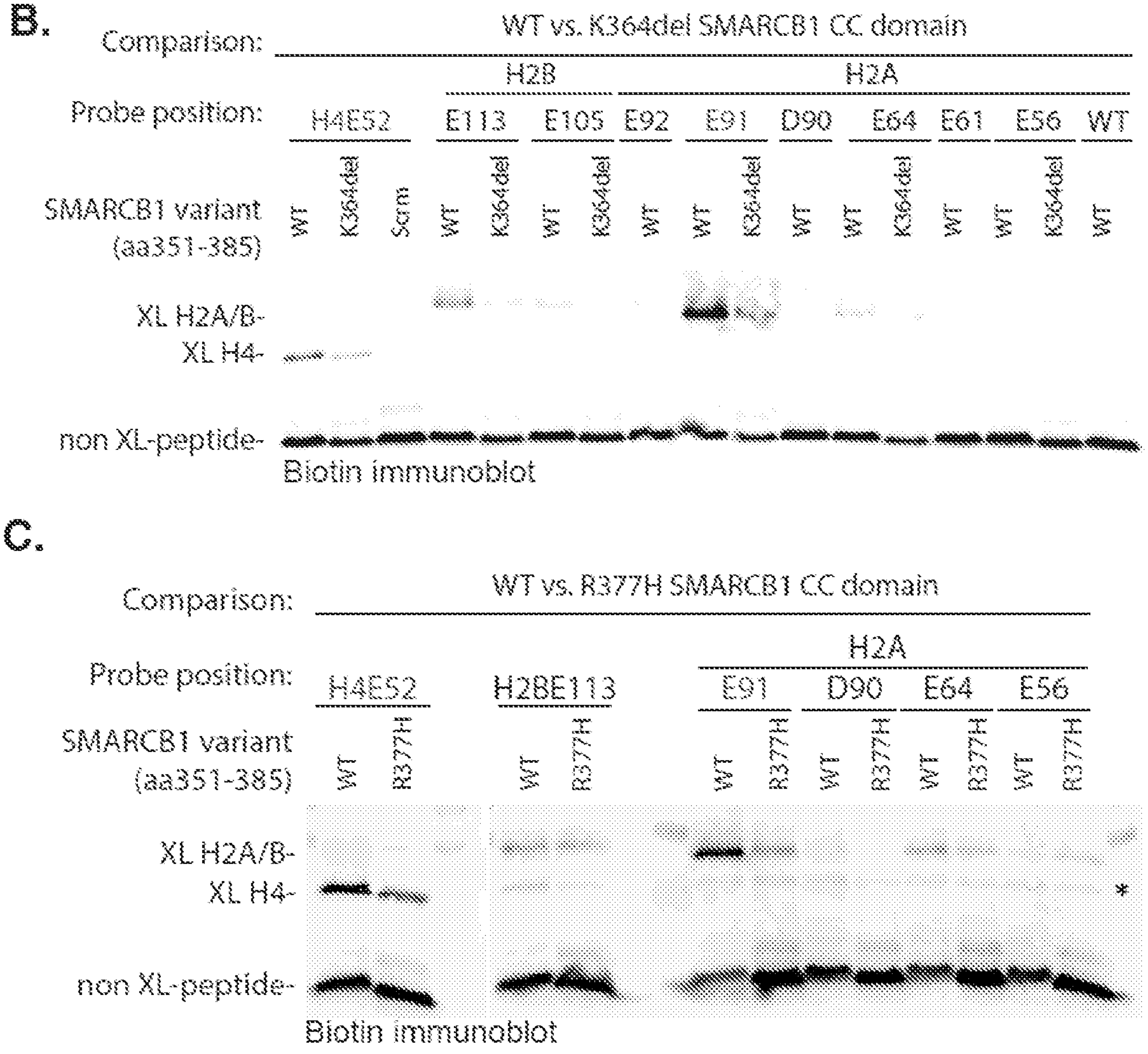
Figure 5:
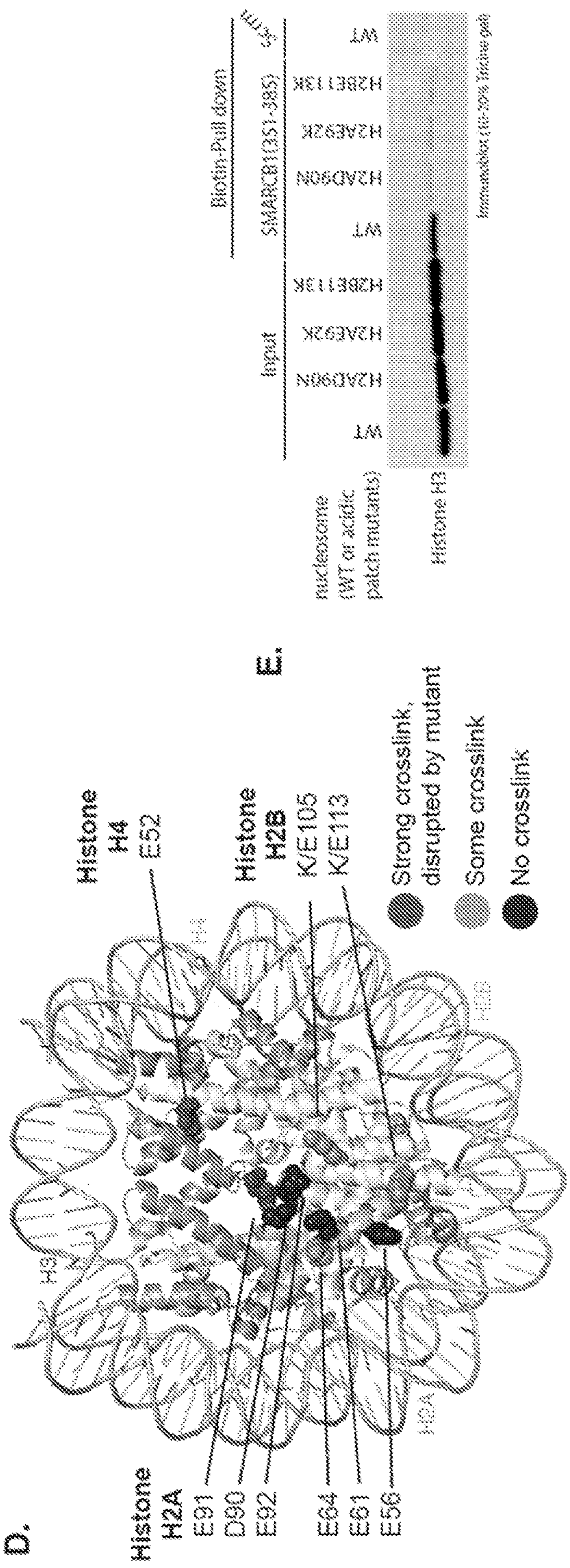
Figure 5:
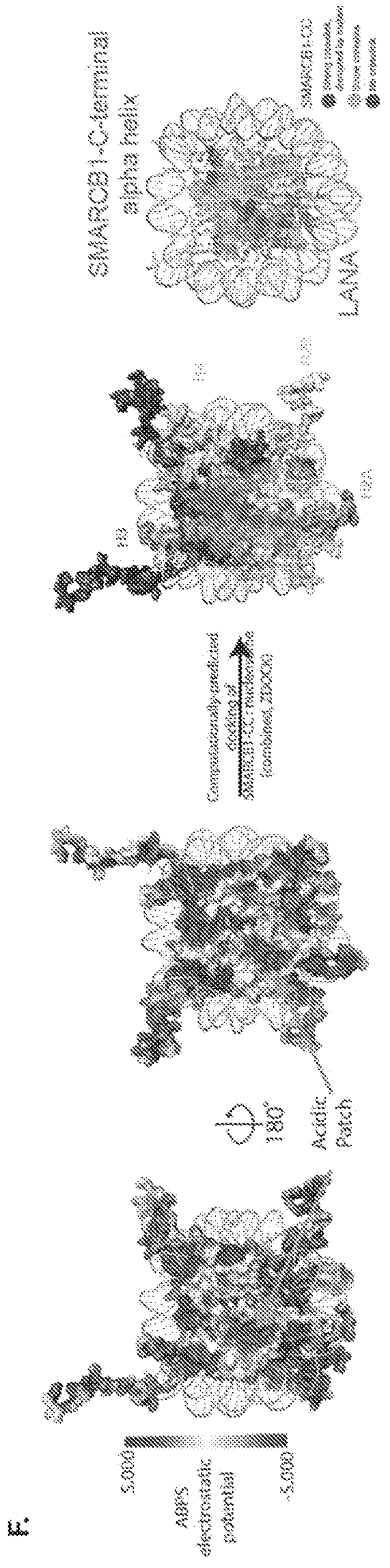
Figure 6:
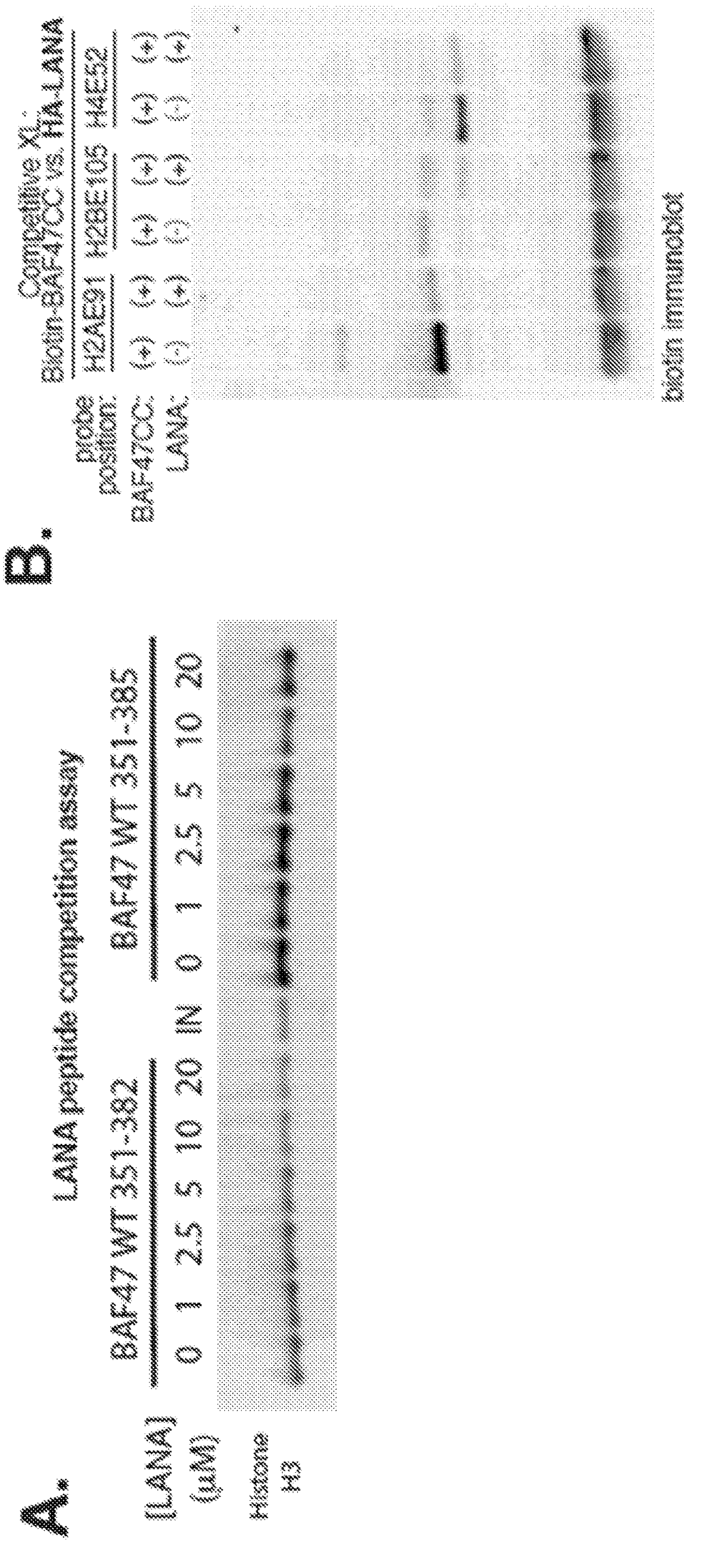
FIG. 6A-FIG. 6H show characterization of the SMARCB1-C-terminal domain:nucleosome acidic patch interaction surface.
Figure 6:
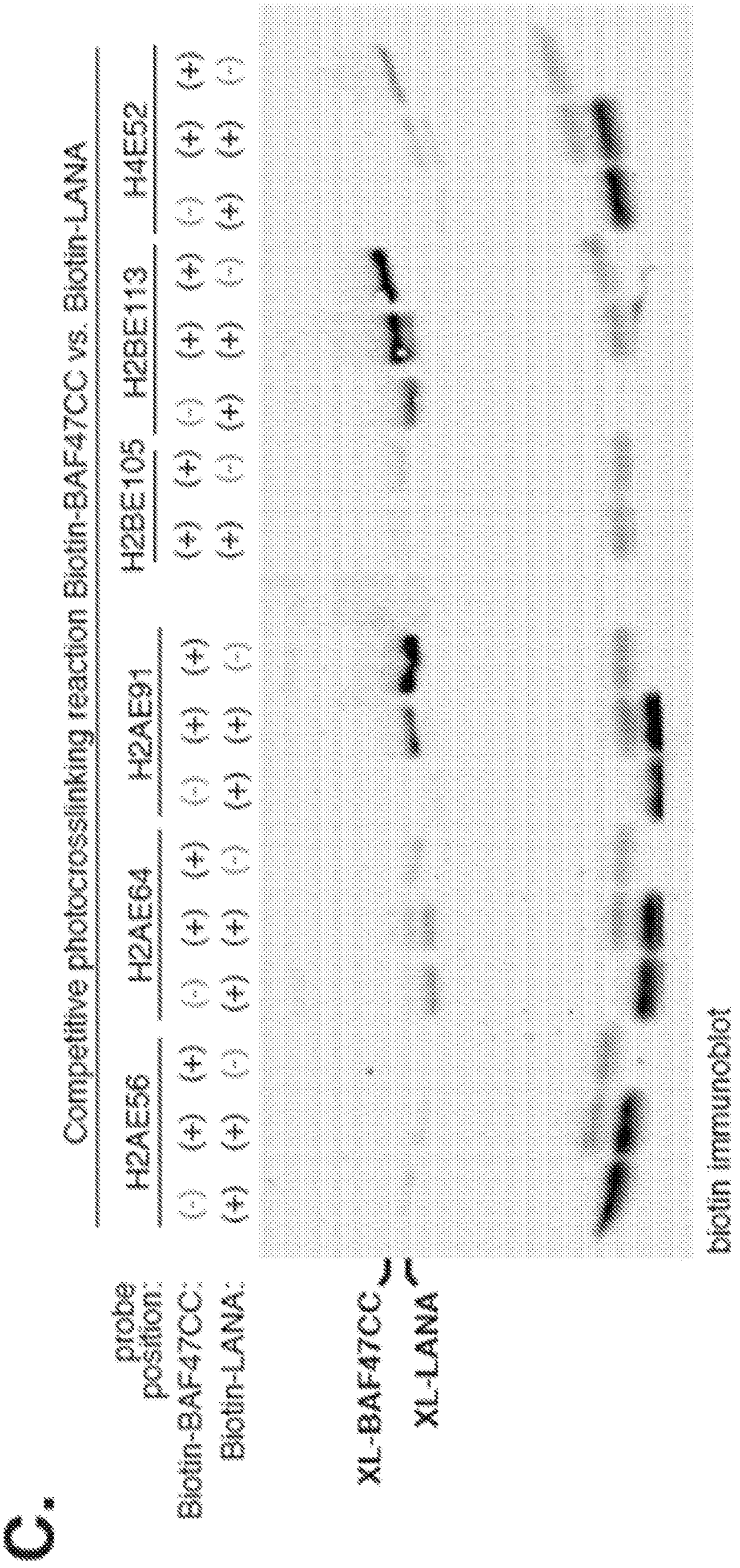
Figure 6:
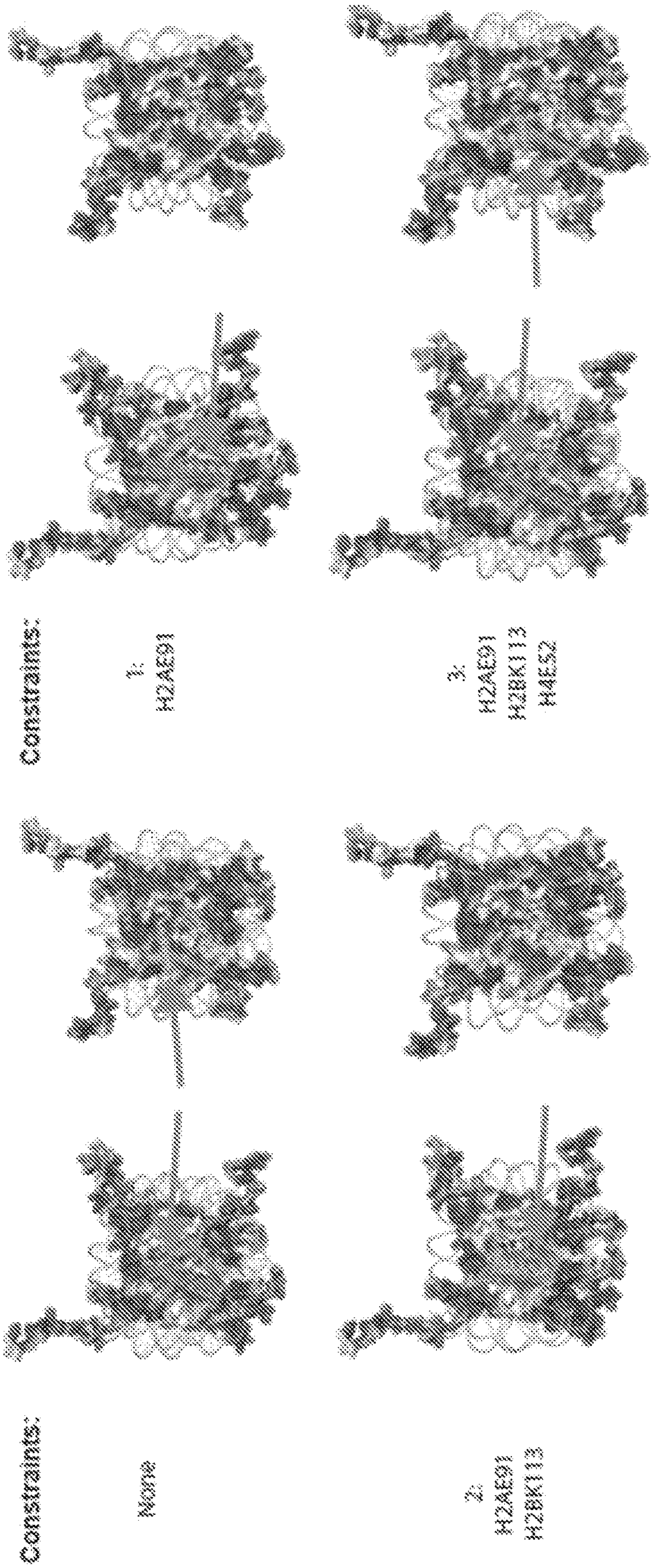
Figure 6:
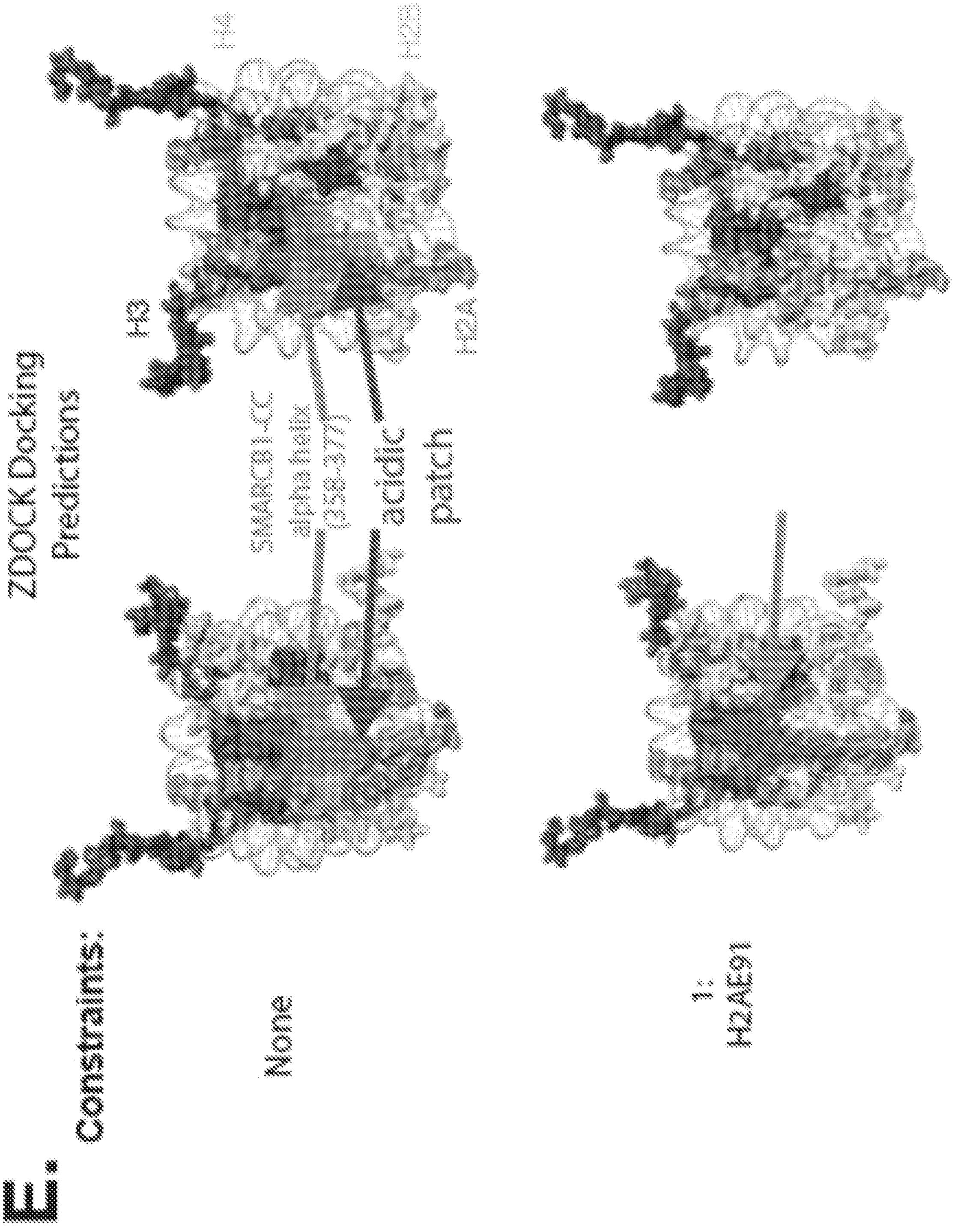
Figure 6:
Figure 6:
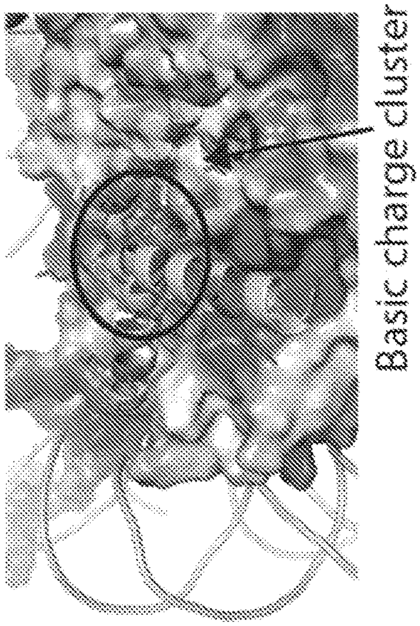
Figure 6:
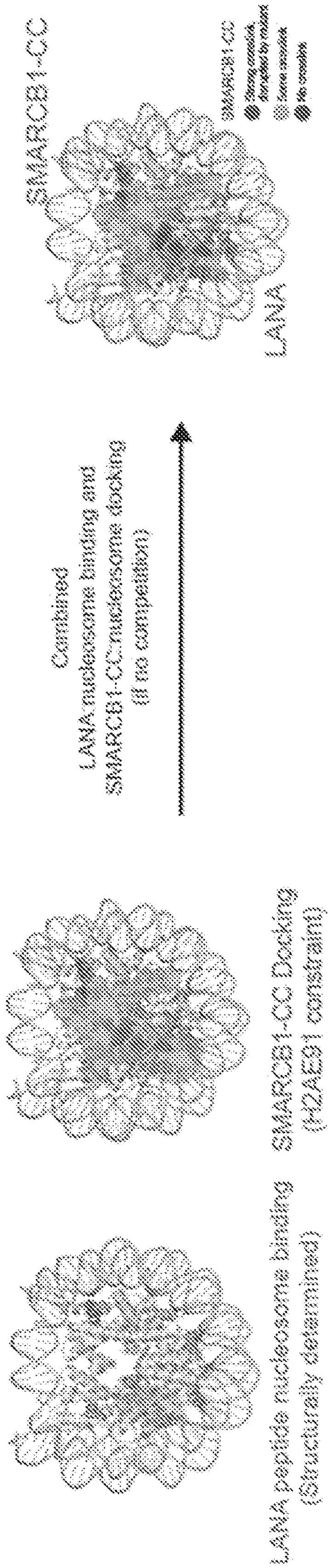

Example 4: The SMARCB1 CC Domain Binds to the Nucleosome Acidic Patch, which is Disrupted by CSS-Associated Missense Mutations To determine the region of the nucleosome to which the SMARCB1 CC domain interacts, a photocrosslinking strategy in which a reactive diazirine probe was incorporated at various locations on the nucleosome surface was adopted (FIG. 5A). This ‘photoscanning’ approach indicated that the SMARCB1 CC domain interacts with an extended region of the nucleosome that includes the canonical acidic patch, a key binding epitope on the nucleosome surface (Dann et al. (2017) *Nature* 548:607-611) (interaction sites H2AE91 and H4E52, and to a lesser extent H2AE64 and H2BE113) (FIGS. 5B-5C). Notably, both K364del and R377H mutations led to a reduction in crosslinking across-experiments (FIGS. 5B-5D). In agreement with the crosslinking results, it was found that mutations known to disrupt the integrity of the acidic patch significantly reduced binding of the SMARCB1 CC domain (FIG. 5E). Interestingly, the interaction was only partially antagonized in competition experiments employing LANA peptide, which is known to engage the canonical acidic patch region (FIGS. 6A-6C), consistent with the idea that the SMARCB1 CC domain interacts with a nucleosome surface epitope that extends beyond the canonical acidic patch region bound by LANA, which was further computationally predicted using ZDOCK (FIG. 5F and FIG. 6D-6H). Taken together, these studies establish that the SMARCB1 CC domain (aa 351-385) binds the nucleosome acidic patch, explaining the critical role for this minimal region in endogenous mSWI/SNF complex-mediated nucleosome remodeling, and the consequent impact of its disruption in intellectual disability syndromes and cancer (FIG. 2).

Figure 7:
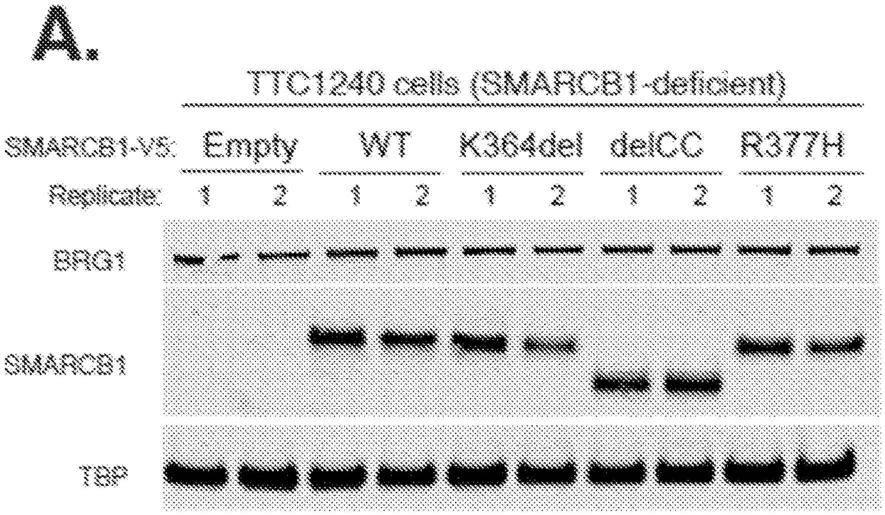
FIG. 7A-FIG. 7H show that CSS-associated mutations in SMARCB1 disrupt genome-wide enhancer DNA accessibility without affecting mSWI/SNF complex targeting.
Figure 7:
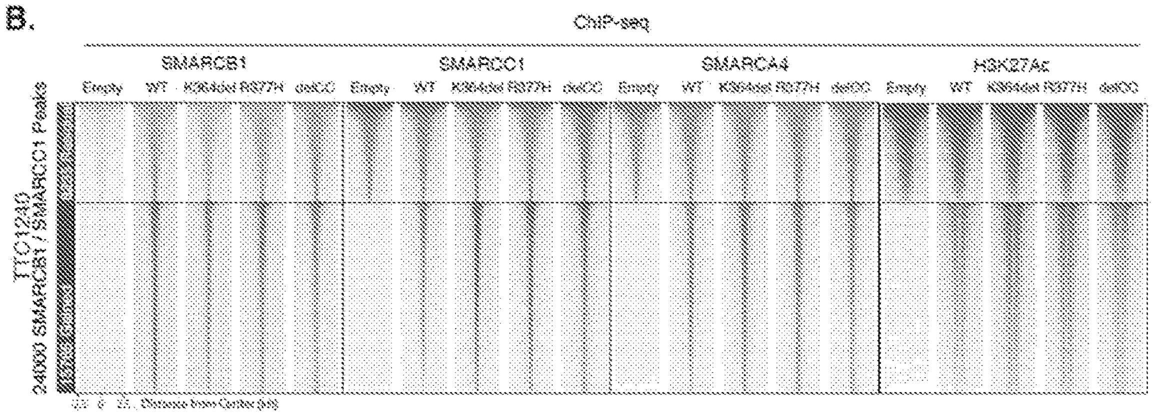
Figure 7:
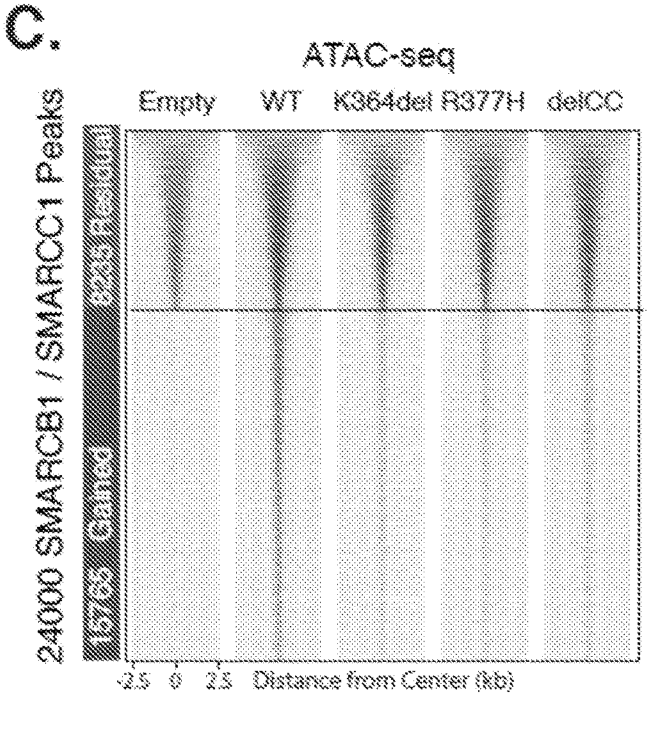
Figure 7:
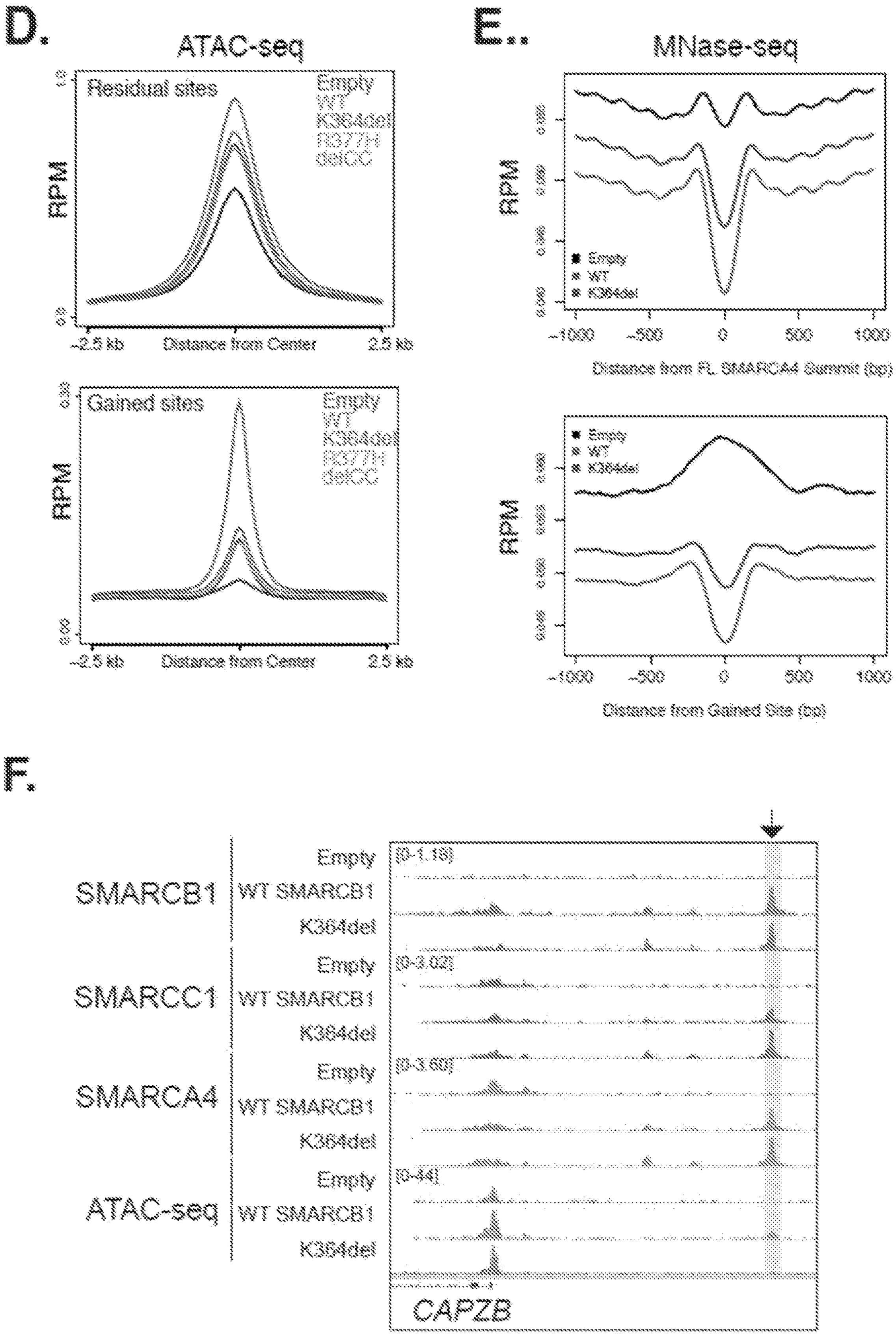
Figure 7:
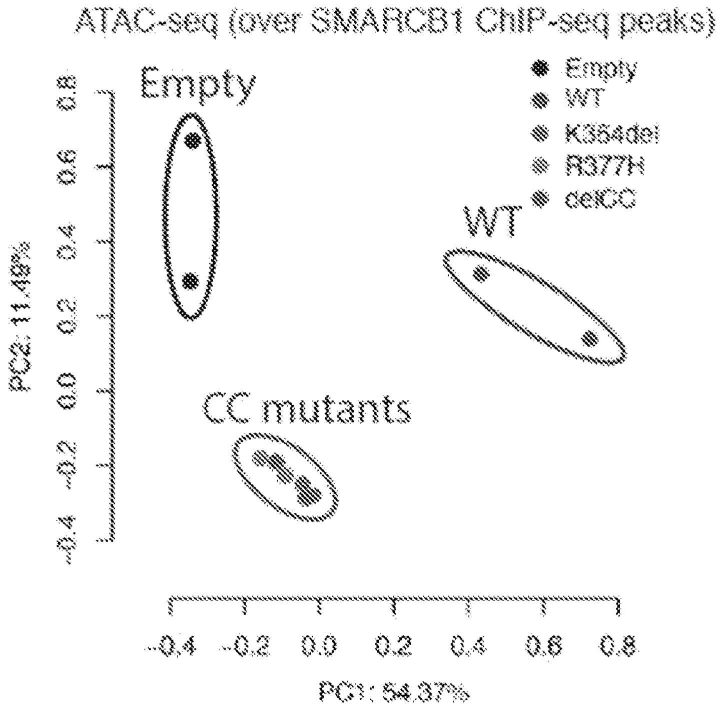
Figure 7:
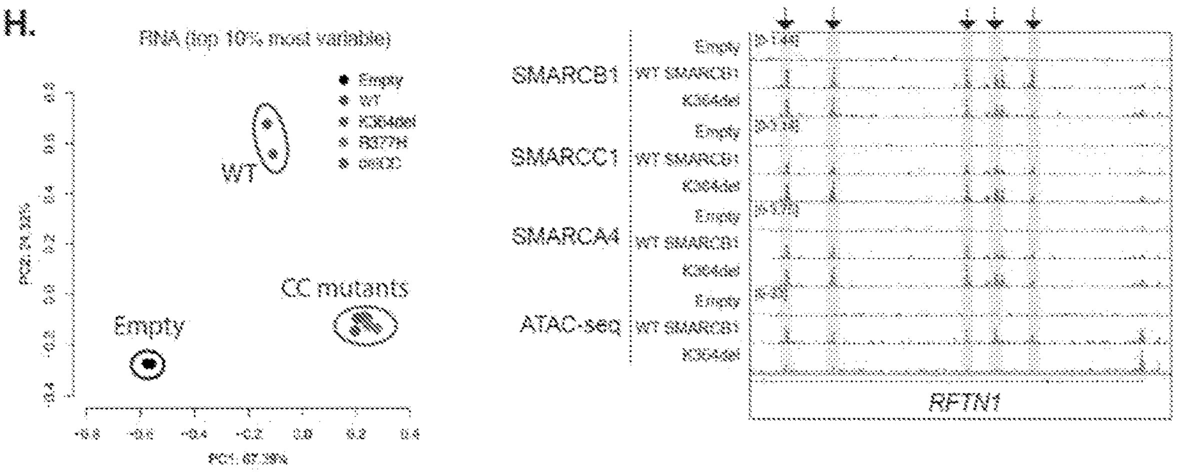
Figure 8:
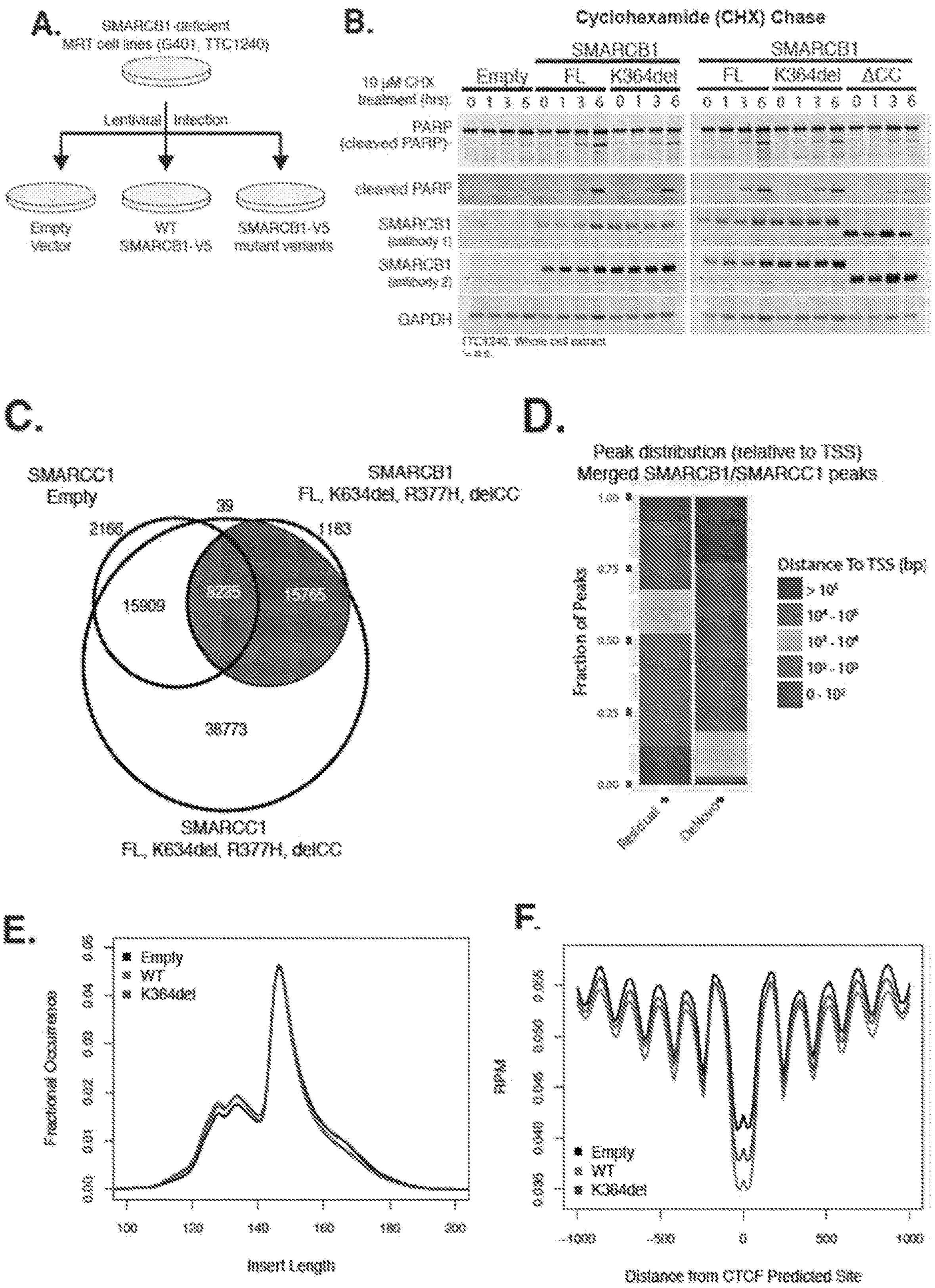
FIG. 8A-FIG. 8P show the results of genome-wide studies of SMARCB1 WT and CC domain mutant variants for chromatin binding and accessibility.
FIG. 8B shows results of a Western blot of TTC1240 whole cell extracts infected with C-terminal SMARCB1 constructs following cyclohexamide (CHX) chase experiment to assess protein degradation (cleaved PARP is the positive control and GAPDH is the loading control).
FIG. 8C shows the overlap of SMARCC1 sites in empty condition with SMARCC1 sites in merged FL, K364del, R377H, and delCC conditions, overlapped with SMARCB1 sites in merged FL, K364del, R377H, and delCC conditions. Blue indicates residual sites used in figures and red indicates gained sites.
FIG. 8D shows the distance to TSS distribution of residual versus de novo peaks merged for all conditions.
FIG. 8E and FIG. 8F show TTC1240 MNase-seq fragment length distribution (FIG. 8E) and a metaplot (FIG. 8F) over CTCF-predicted binding sites for empty, WT, and K364del conditions.
FIG. 8G-FIG. 8H show example ChIP-seq and ATAC-seq data (FIG. 8G), and MNase-seq tracks (FIG. 8H) over the RTFN1 and CAPZB loci with empty, WT SMARCB1, and SMARCB1 mutants.
FIG. 8I shows a summary of results in (FIG. 7F) by log 2FC>0/<0 or log 2FC>1/<−1, with adj p-value<0.01. Bar graphs show RNA RPKM levels for RFTN1 and CAPZB for all conditions shown in FIG. 8G.
FIG. 8J shows a scatter plot reflecting changes in accessibility between WT and mutant SMARCB1 conditions at all ATAC-seq merged peaks; blue represents downregulated sites, and red represents upregulated sites, in the mutant SMARCB1 conditions.
FIG. 8K shows a Venn diagrams of ATAC-seq sites comparing FL versus Empty over all merged mutants versus FL peaks.
FIG. 8L shows the results of an immunoblot analysis of G401 nuclear extracts infected with Empty vector and SMARCB1 variants shown.
FIG. 8M shows the results of PCA performed on the top 10% most variable genes as assessed by RNA-seq experimental replicates for empty vector, SMARCB1 WT, and all SMARCB1 mutant conditions.
FIG. 8N shows an ATAC-seq and RNA-seq heatmap over merged SMARCC1-peaks reveals a subset of nearest genes downregulated in mutant versus WT (FL) conditions.
FIG. 8O shows metascape analysis results of genes downregulated in mutant versus FL condition from FIG. 8N.
Figure 8:
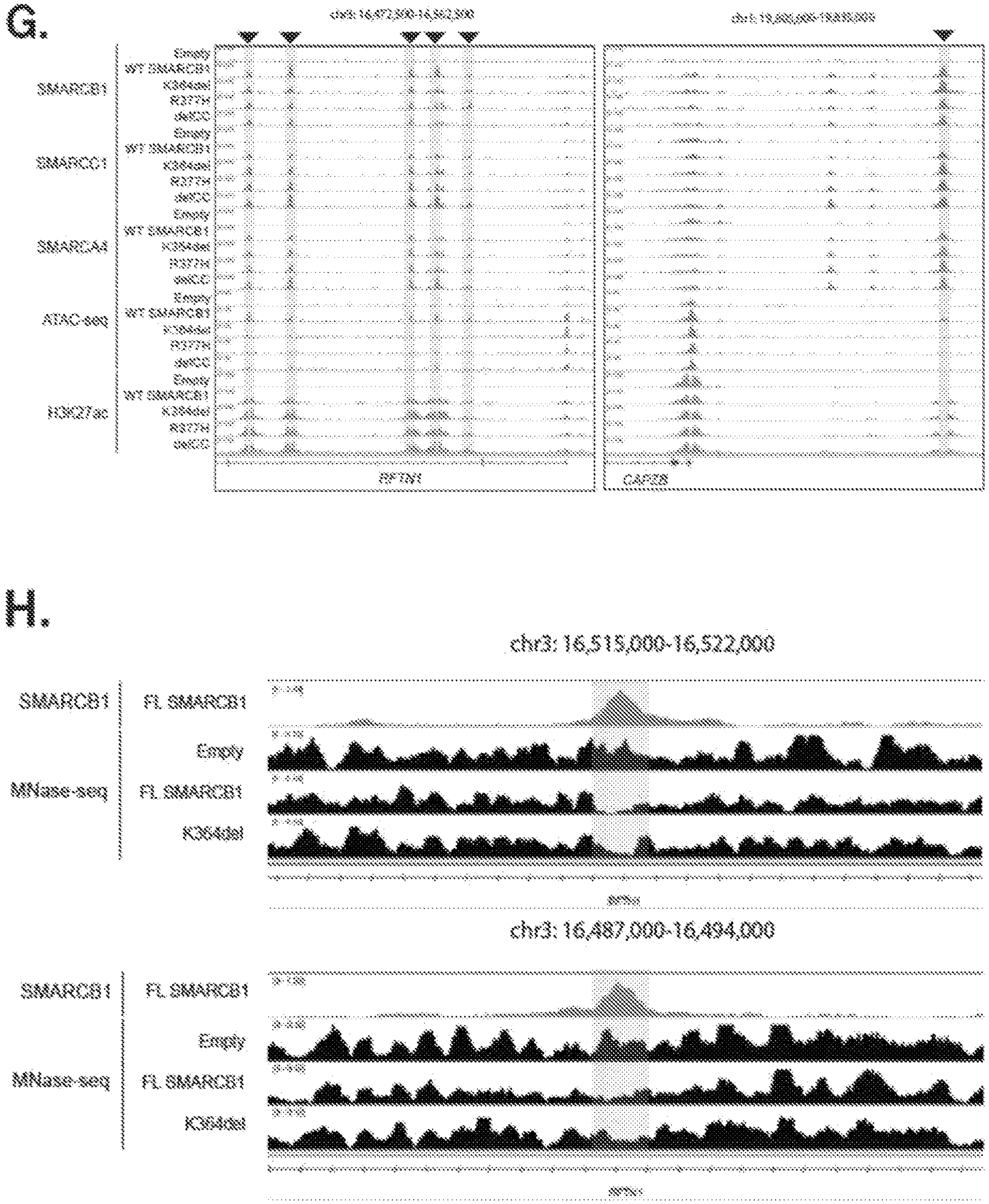
Figure 8:
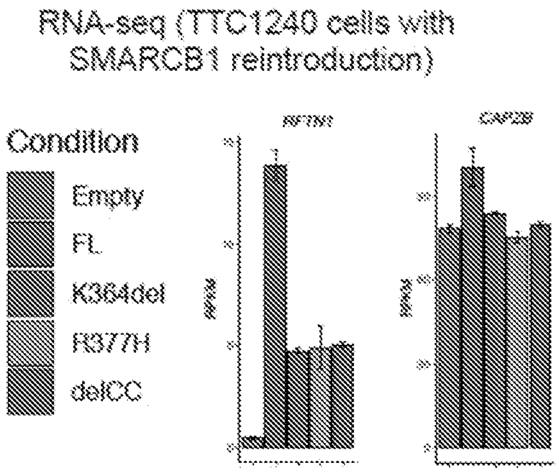
Figure 8:
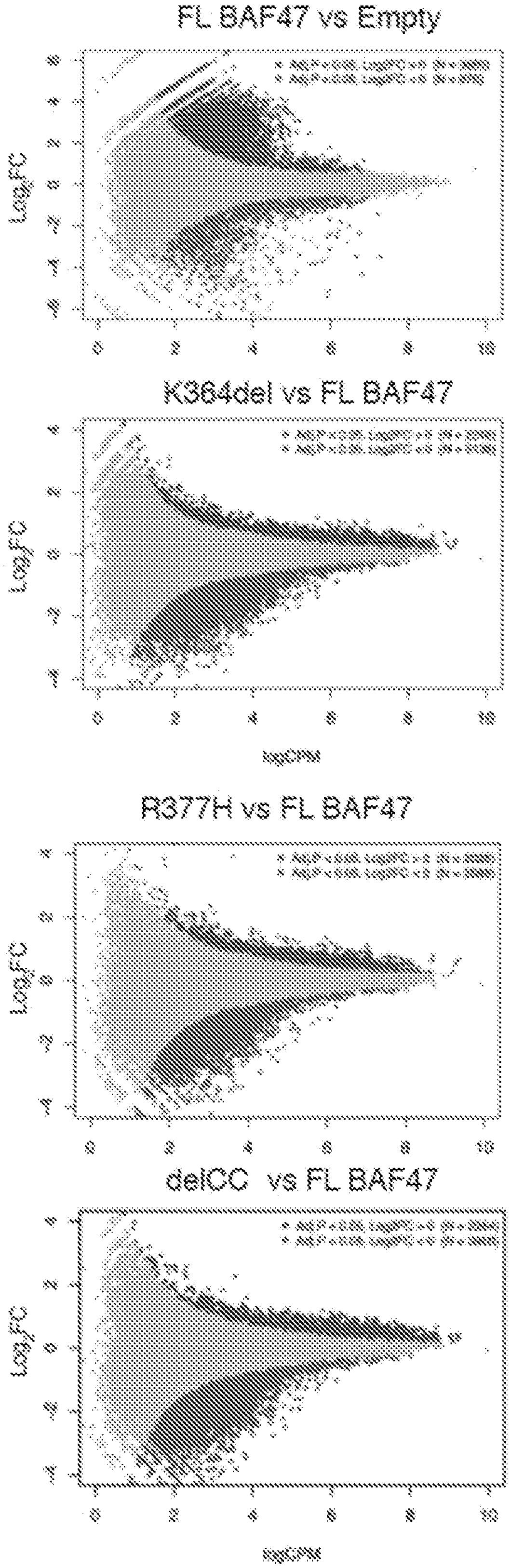
Figure 8:
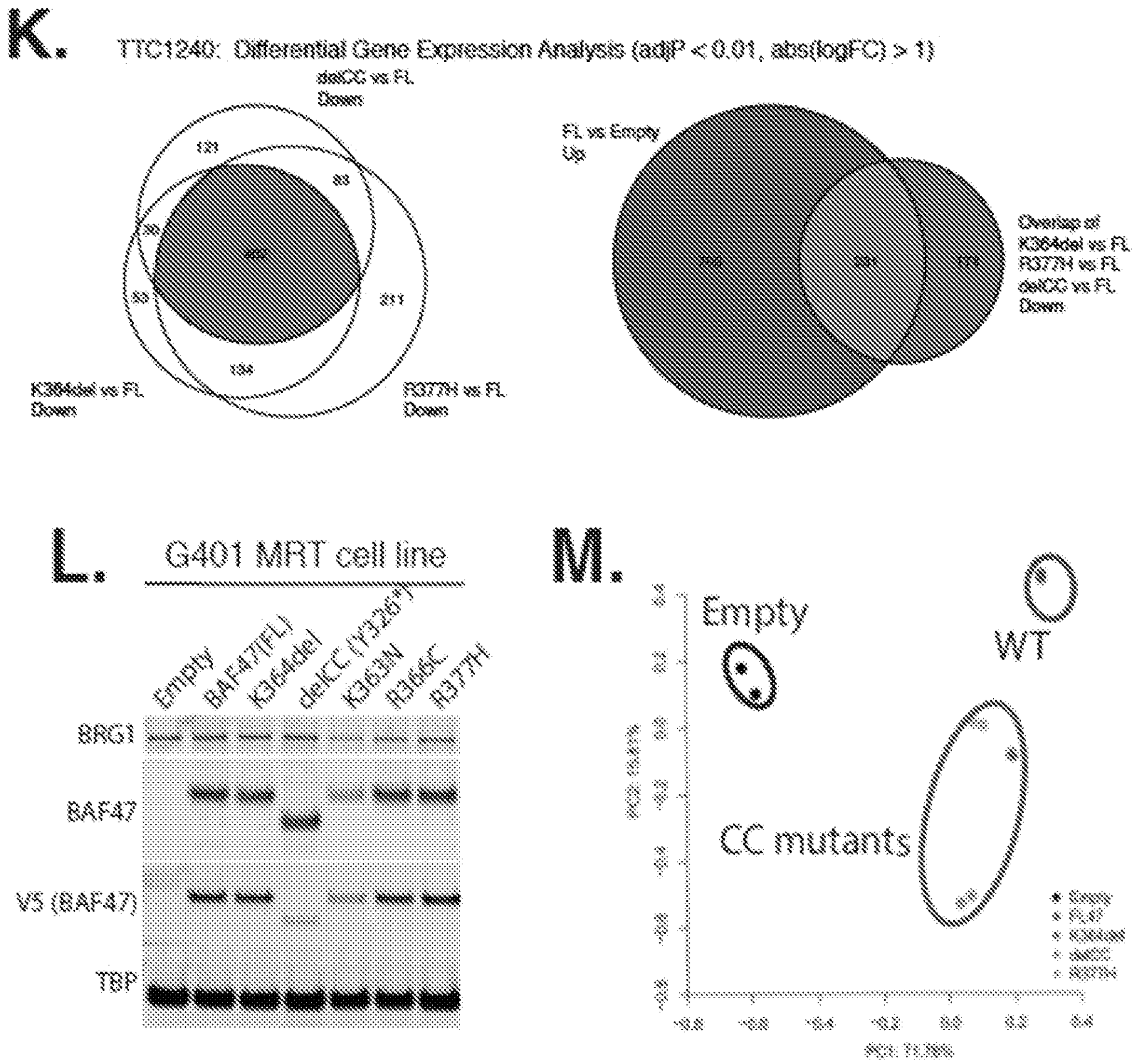
Figure 8:
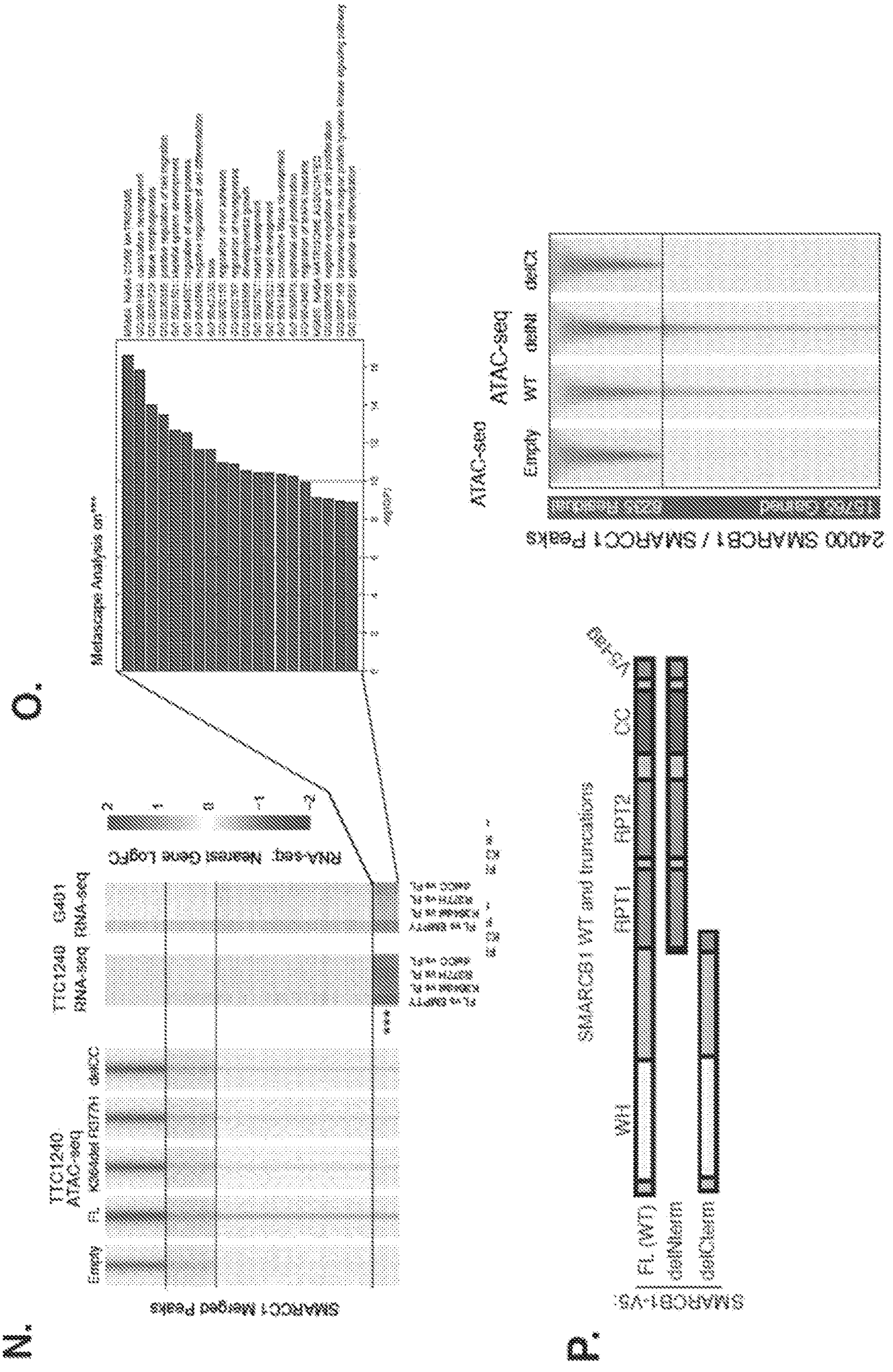

Example 5: CSS-Associated Mutations in SMARCB1 Disrupt Genome-Wide Enhancer DNA Accessibility without Affecting mSWI/SNF Complex Targeting To assess functions of these mutations in the context of human cell lines and at a genome-wide level, the SMARCB1-deficient TTC1240 and G401 malignant rhabdoid tumor (MRT) cell lines was leveraged to perform rescue experiments with either WT SMARCB1 or a series of CSS-associated SMARCB1 mutants, including deletion of the entire putative CC domain (FIG. 7A and FIG. 8A). Treatment of these cells with the protein synthesis inhibitor, cycloheximide (CHX) demonstrated that FL and mutant SMARCB1 variants were stable across the 6-hour time course in TTC1240 (FIG. 8B), in agreement with biochemical findings indicating complex integrity and abundance are not compromised with SMARCB1 mutants (FIGS. 2B-D). Previously, it was identified that rescue of MRT cell lines with WT SMARCB1 resulted in genome-wide increases in mSWI/SNF complex occupancy, particularly at TSS-distal enhancer sites, and that restoration of complex occupancy over these sites correlated with an increase in enhancer activation as assessed by presence of the H3K27 acetylation mark (Nakayama et al. (2017) *Nat. Genet.* 49:1613-1623;

Wang et al. (2017) *Nat. Genet.* 49:289-295). Surprisingly, in comparing the genome-wide targeting of BAF complexes in SMARCB1 WT and CSS-associated mutant conditions, it was found that WT and mutant variants exhibited nearly identical genome-wide targeting (FIG. 7B and FIG. 8C-8D). Moreover, expression of both WT and mutant SMARCB1 variants resulted in similar increases in H3K27ac occupancy over gained SMARCB1/SMARCC1-bound distal sites, indicative of enhancer activation (FIG. 7B). However, when DNA accessibility over these gained BAF complex sites was examined using ATAC-seq, it was found that CSS-associated SMARCB1 mutants generated substantially diminished accessibility relative to WT SMARCB1 (FIG. 7C-7D). This was also true at residual, promoter-proximal sites (sites to which BAF complexes were targeted irrespective of SMARCB1 status) (FIG. 7D). To assess more directly whether the diminished DNA accessibility correlated with reduced nucleosome occupancy, MNase-seq was performed in the empty vector control, WT SMARCB1, and K364del mutant conditions. MNase-seq fragment length distribution analysis confirmed the majority of reads were of mononucleosomal length (FIG. 8E).

Mapping MNase-seq reads over CTCF sites demonstrated no differences in nucleosome phasing between Empty, WT, or K364del mutant conditions, as recently demonstrated in mouse ES cells in the presence or absence of Smarca4 (Brg1) (Barisic et al. (2019) *Nature* 569:136-140) (FIG. 8F). Interestingly, however, MNase-seq metaplot analysis at the SMARCA4 ChIP-seq peaks showed decreased nucleosome occupancy (greater nucleosome eviction) for the WT compared to K36del mutant or Empty conditions (FIG. 7E). Furthermore, in line with ATAC-seq results, it was found that the K364del exhibited reduced nucleosome eviction at the gained BAF complex sites, as indicated by a depletion of MNase-seq signal at the center of the SMARCA4-gained peaks (FIG. 7E). These results (both ATAC-seq and MNase-seq) are exemplified at the RFTN1 and CAPZB loci (FIG. 7F and FIGS. 8G-8I) and differences between conditions are captured by principle component analysis (PCA) of ATAC-seq signals over SMARCB1 peaks (FIG. 7G). Comparing differential accessibility between SMARCB1 variant conditions revealed that the majority of significantly changed sites exhibited decreases in accessibility in the mutant SMARCB1 conditions relative to WT (FIG. 8J). Finally, it was observed that these changes in chromatin accessibility were manifested globally at the mRNA level (FIG. 8K), with PCA of corresponding RNA-seq showing marked separation between empty vector, SMARCB1 WT, and CSS-associated CC domain mutant conditions (FIG. 7H). These results were recapitulated in the G401 SMARCB1-deficient MRT cell line (FIG. 8L-M). Finally, clustering of ATAC-seq and RNA-seq datasets revealed a subset of ATAC-seq sites gained in the WT SMARCB1 rescue setting that showed decreased gene expression in the mutant conditions relative to WT in both TTC1240 and G401 cell lines (FIG. 8N). Metascape analysis of these sites revealed a number of developmental processes such as vasculature development, heart development, skeletal system development, regulation of neurogenesis, among others (FIG. 8O).

These results establish a role for the SMARCB1 CC domain in mediating mSWI/SNF driven DNA accessibility rather than genome-wide complex targeting. These genome-wide findings closely align with results of in vitro ATPase activity and nucleosome remodeling assays performed in vitro with endogenously-purified complexes (FIG. 2), pointing to a specific mechanism that is coopted via mutations in the CC domain of SMARCB1 in CSS, a neurodevelopmental condition that has enabled the uncoupling of mSWI/SNF remodeling activity and targeting on chromatin. Mutations in the SMARCB1 CC domain stand in stark contrast to mutations or deletion of the winged-helix DNA binding domain (N-terminus) that were determined not to disrupt mSWI/SNF-mediated nucleosome remodeling in vitro (FIG. 2G-2J), or alter DNA accessibility in cells (FIG. 8P), furthering the concept that mSWI/SNF activities can be disrupted at distinct functional axes.

Figure 10:
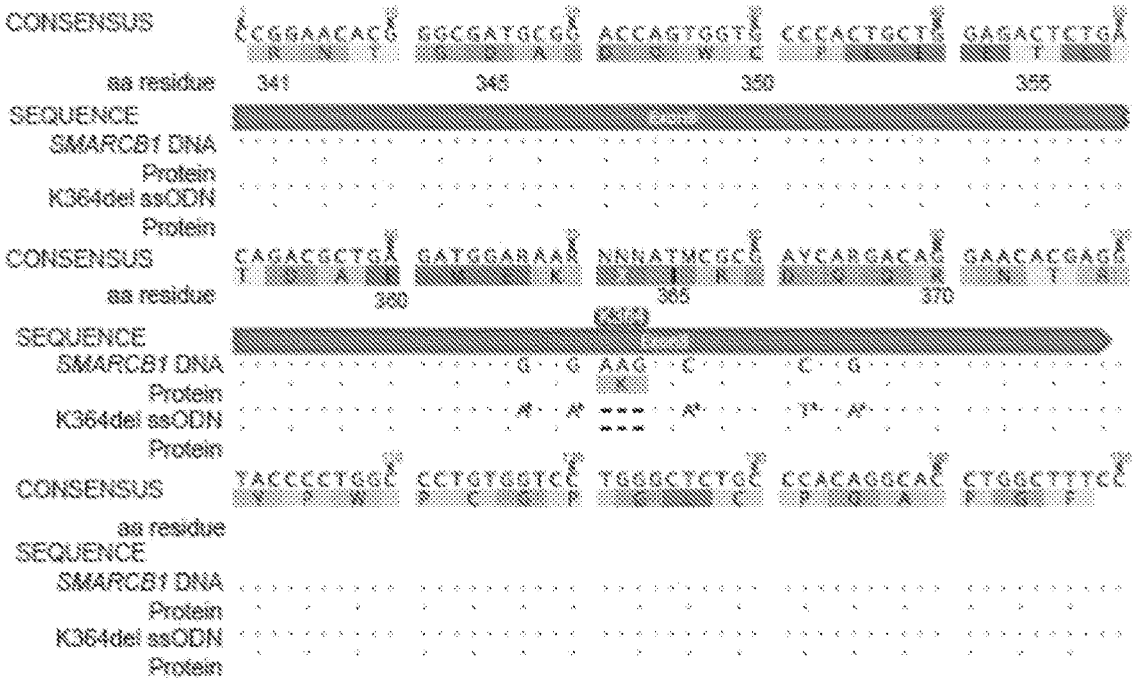
FIG. 10A-FIG. 10O show the results of CRISPR-Cas9-mediated introduction of heterozygous SMARCB1 mutations in human iPSCs.
FIG. 10B shows sequencing confirmation of capture WT, K364del, and indel SAH iPSCs following CRISPR-Cas9 treatment.
FIG. 10C shows the Flow analysis of WT and K364del/+ mutant cell lines infected with empty vector or FL SMARCB1 staining for CF-Blue (Annexin V) and 7-AAD to assess apoptosis.
FIG. 10D shows the metaplots (Top panel) and Box plots (bottom panel) of mSWI/SNF (SMARCB1, SMARCC1, SMARCA4) and H3K27ac ChIP-seq, and ATAC-seq over merged SAH WT and K364del mutant SMARCA4 peaks.
FIG. 10E shows the results of transcription factor enrichment analysis by LOLA of the top 40 most enriched ChIP-seq datasets in database [REF] (n=6092) within reduced (top) or enriched (bottom) ATAC-seq peaks in mutant versus WT condition.
FIG. 10F shows representative example ChIP-seq and ATAC-seq tracks at the ANKRD1 locus demonstrating decreased accessibility of a NANOG, SOX2, and OCT4 marked site in the K364del SAH iPSC line.
FIG. 10G-FIG. 10H show results of gene set enrichment analyses (GSEA) performed on changed genes between WT and K364del iPSC conditions.
FIG. 10I shows a heatmap of SMARCB1 WT and heterozygous K364del and Indel SAH iPSCs expression profiles along differentiation timecourse (days 0, 2, 4, 8).
FIG. 10J shows results of Gene Ontology (Metascape) analysis of clusters 6 and 5, highlighting differentially upregulated versus downregulated genes in K364del mutant iPSC versus wild-type iPSCs at Day 8 of differentiation.
FIG. 10K shows a heatmap of Day 0 and Day 4 ATAC-seq signals for WT and K364del mutant SAH cells separated into 3 clusters.
FIG. 10L shows a distribution of ATAC-seq peaks relative to transcription start sites (TSSs) for clusters 1-3 from FIG. 10K.
FIG. 10M shows gene ontology (metascape) analysis results of clusters 1 and 2 from FIG. 10K enriched for neurodevelopmental GO processes.
FIG. 10N show bar graphs of neurite outgrowth at Days 6 and 8 of NGN2-mediated cortical neuron differentiation. Empty vector control and SMARCB1 rescue conditions are indicated.
Figure 10:
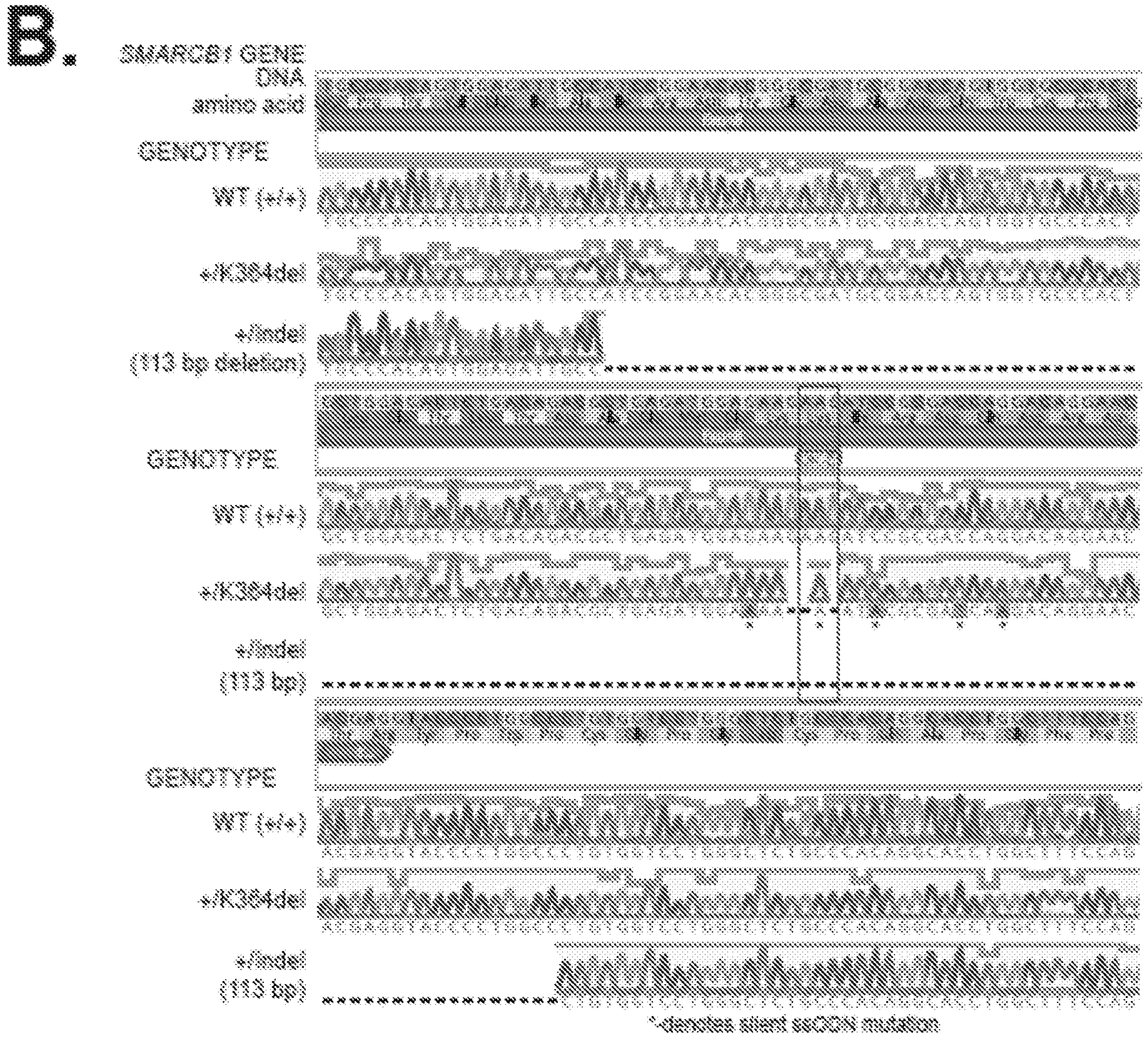
Figure 10:
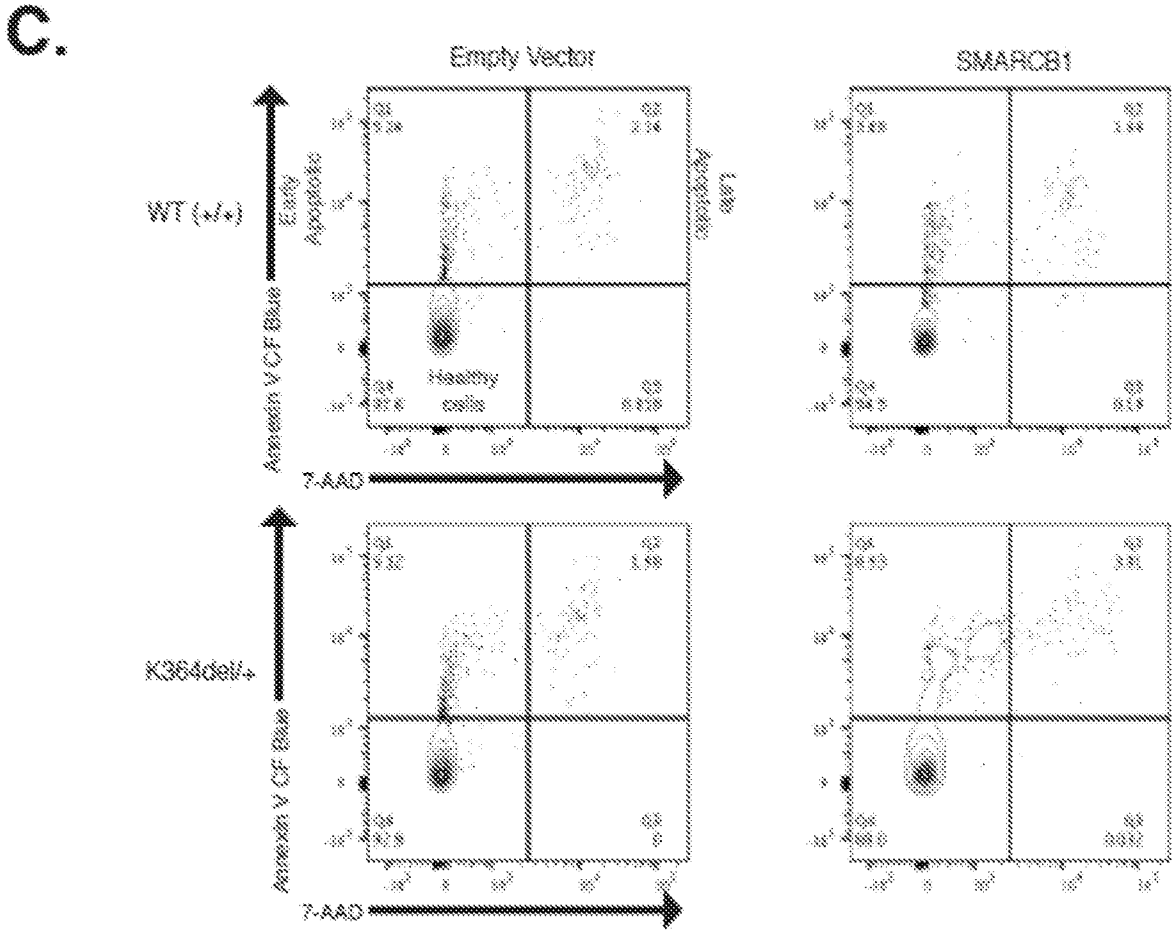
Figure 10:
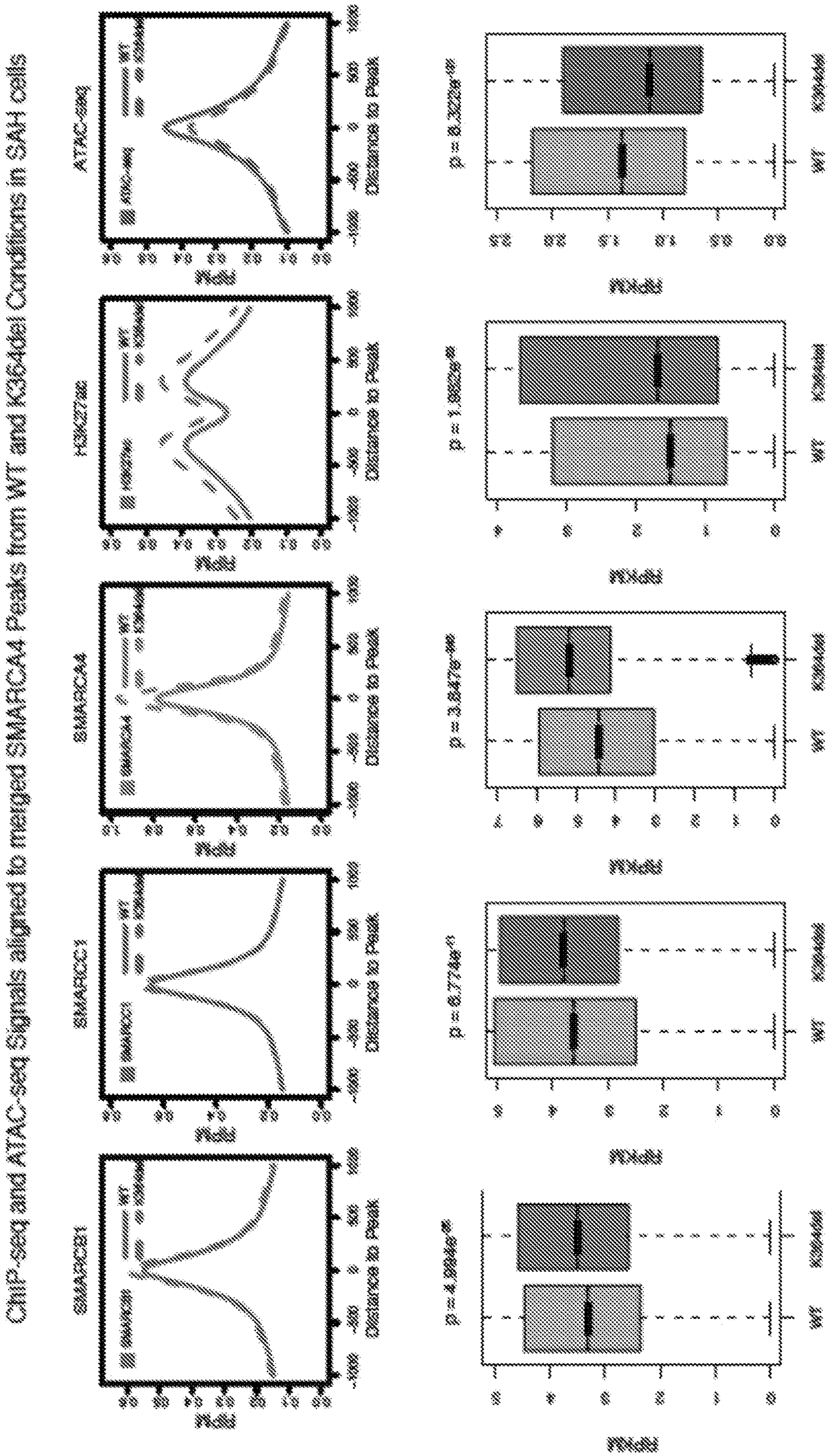
Figure 10:
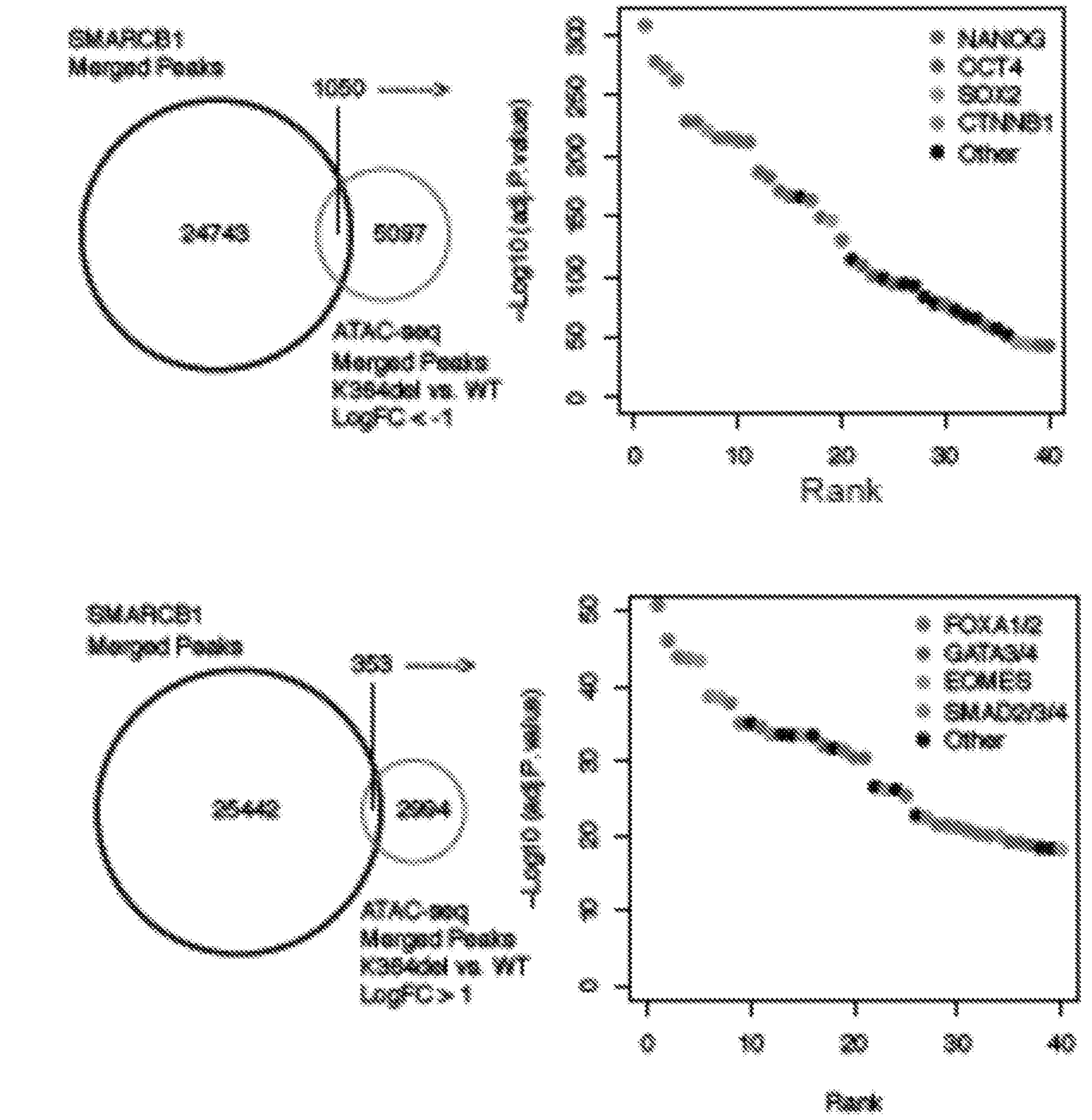
Figure 10:
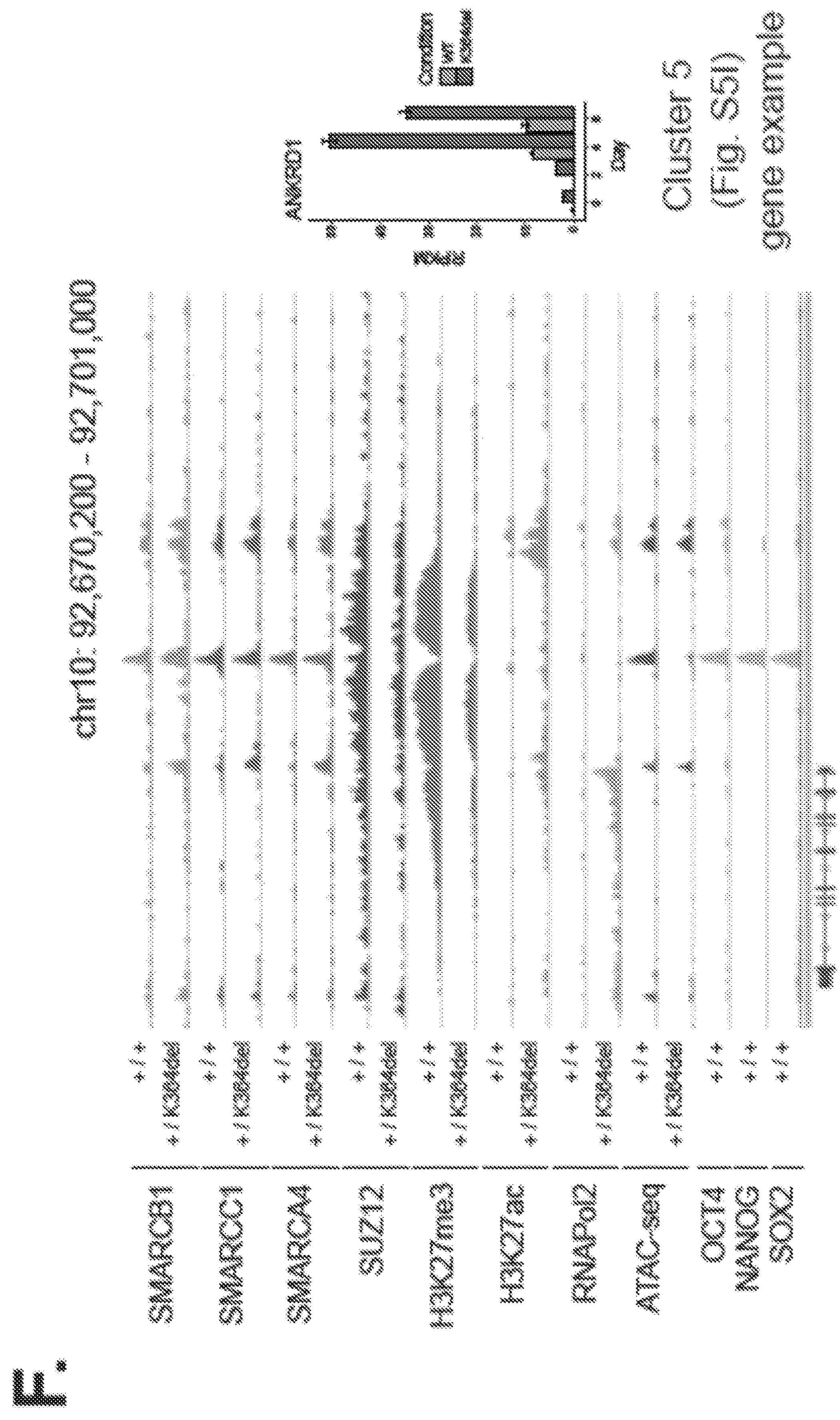
Figure 10:
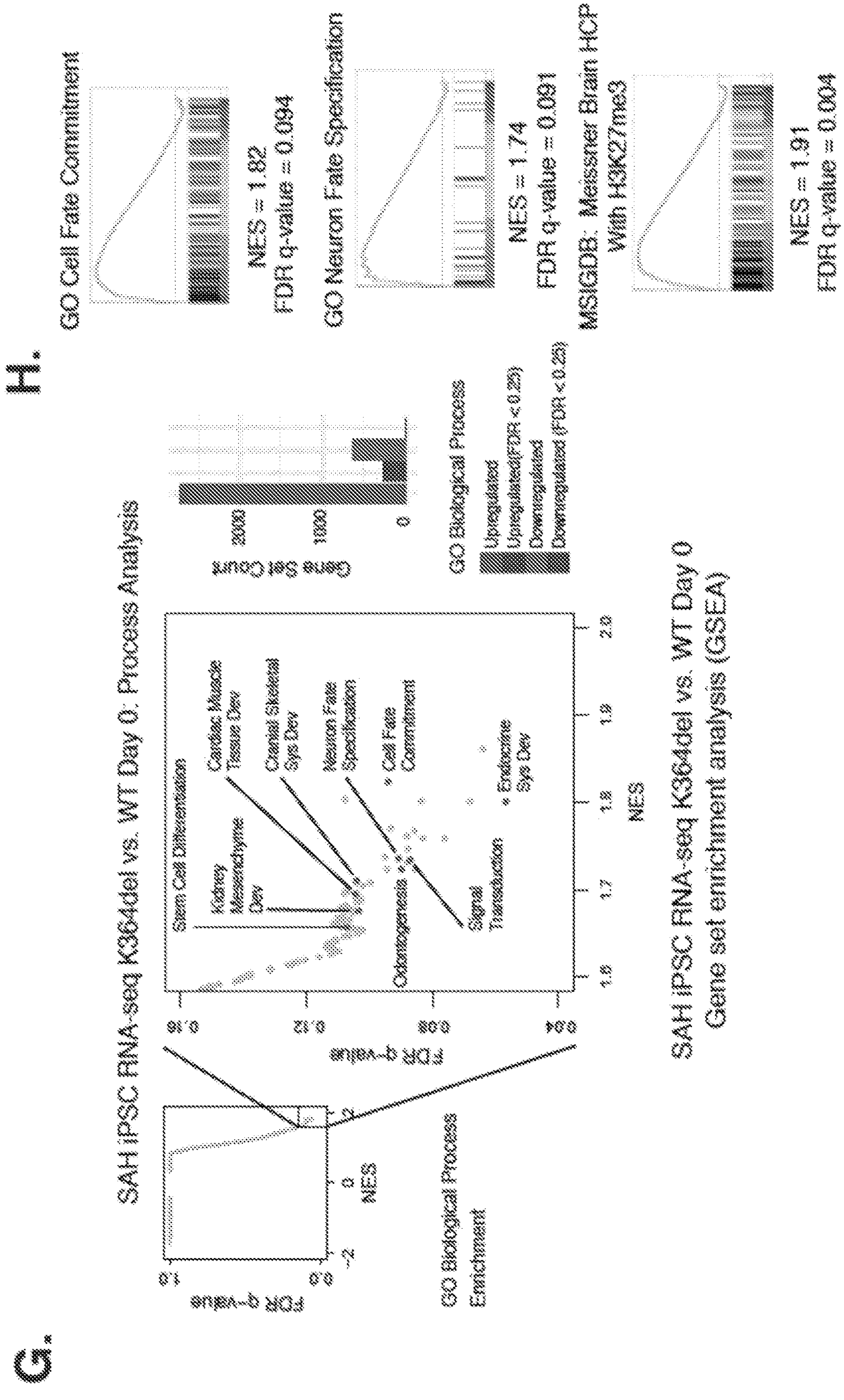
Figure 10:
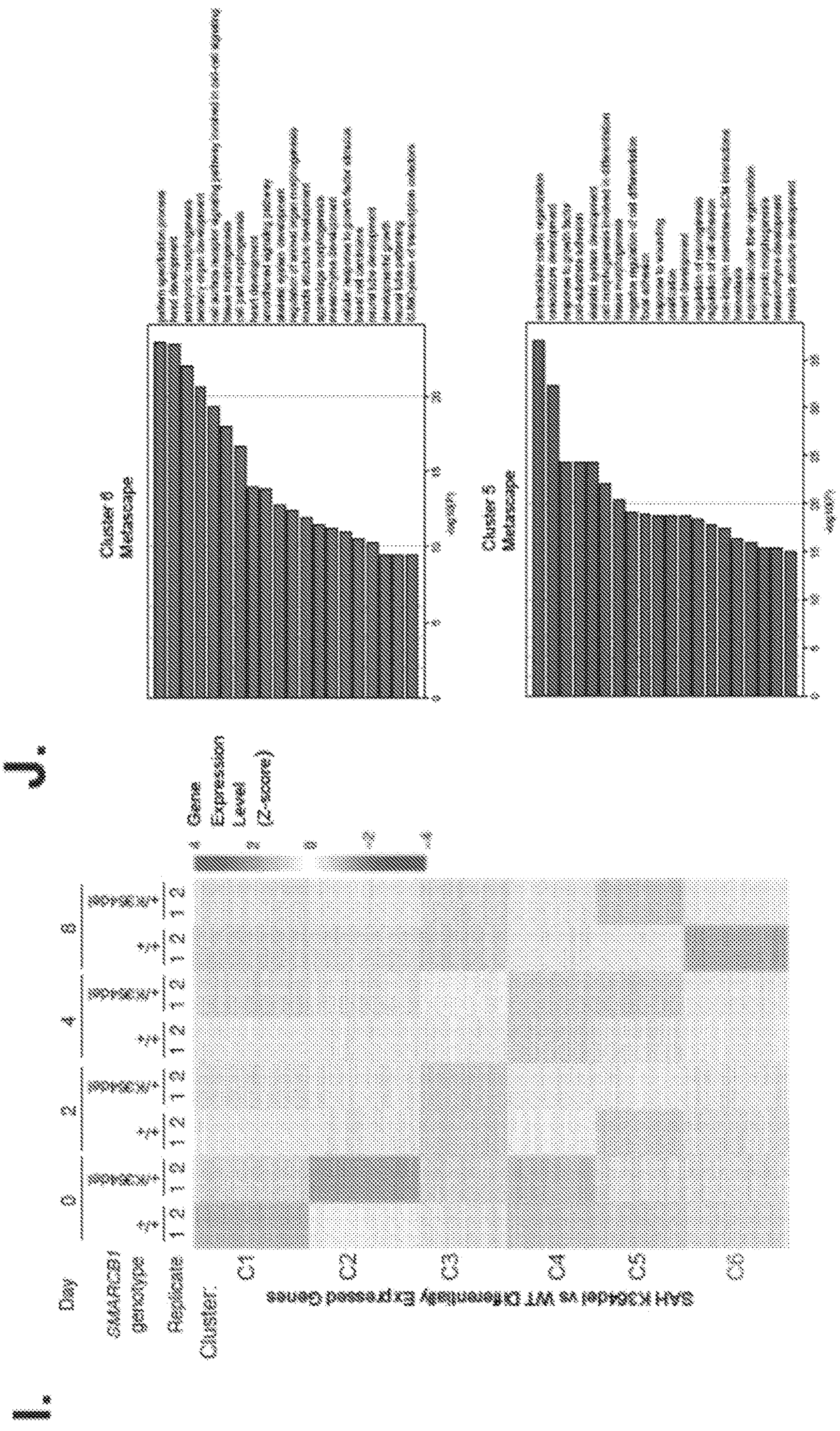
Figure 10:
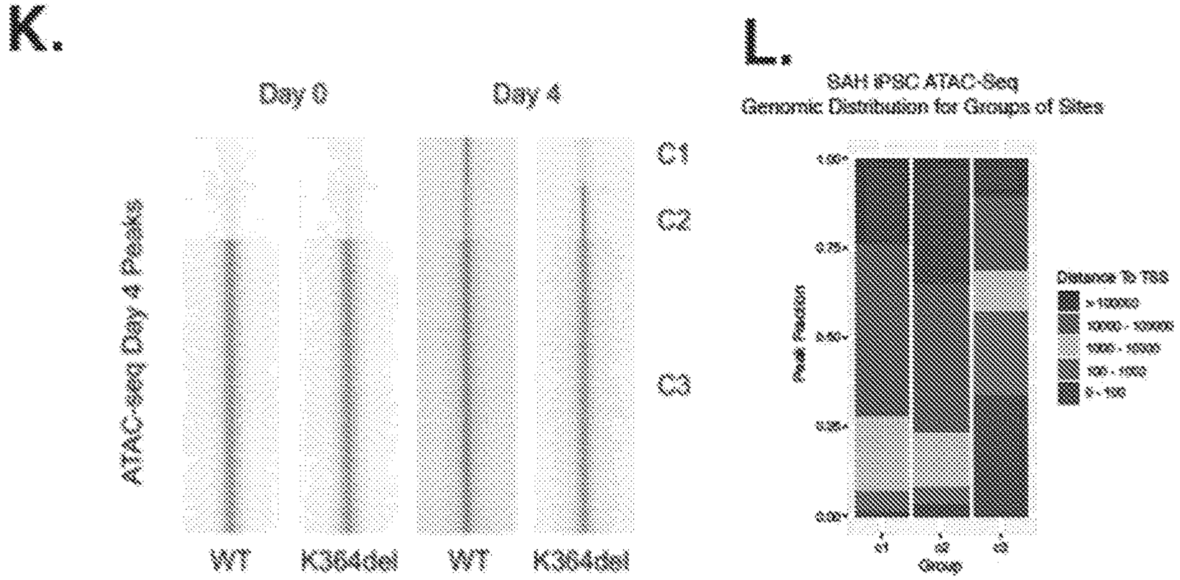
Figure 10:
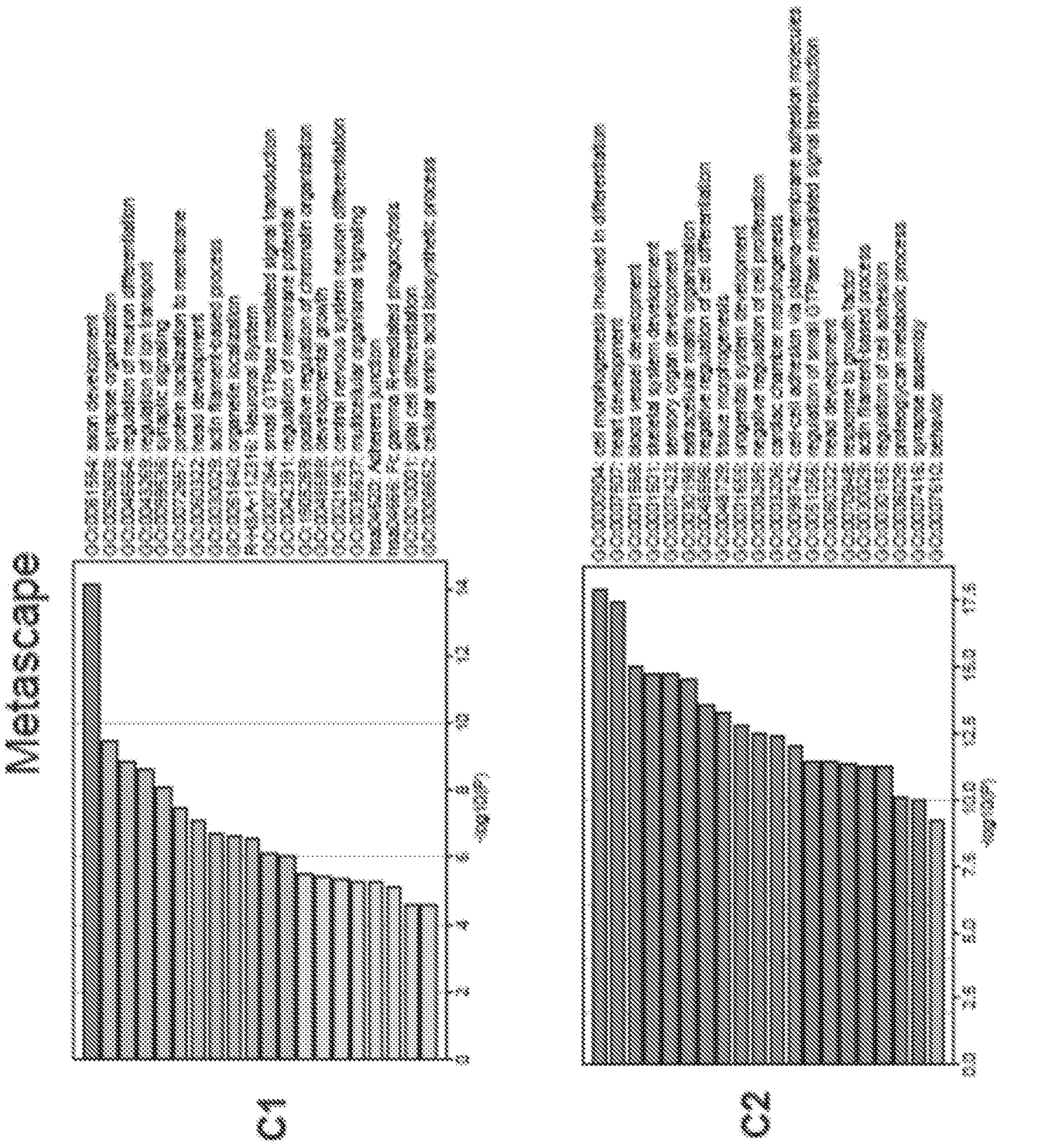
Figure 10:
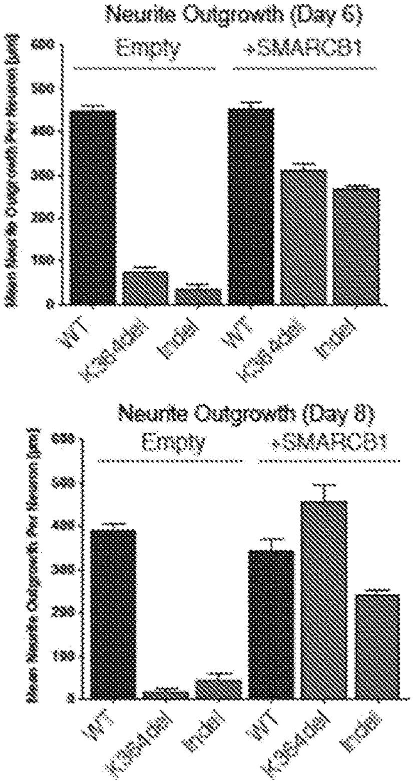
Figure 10:
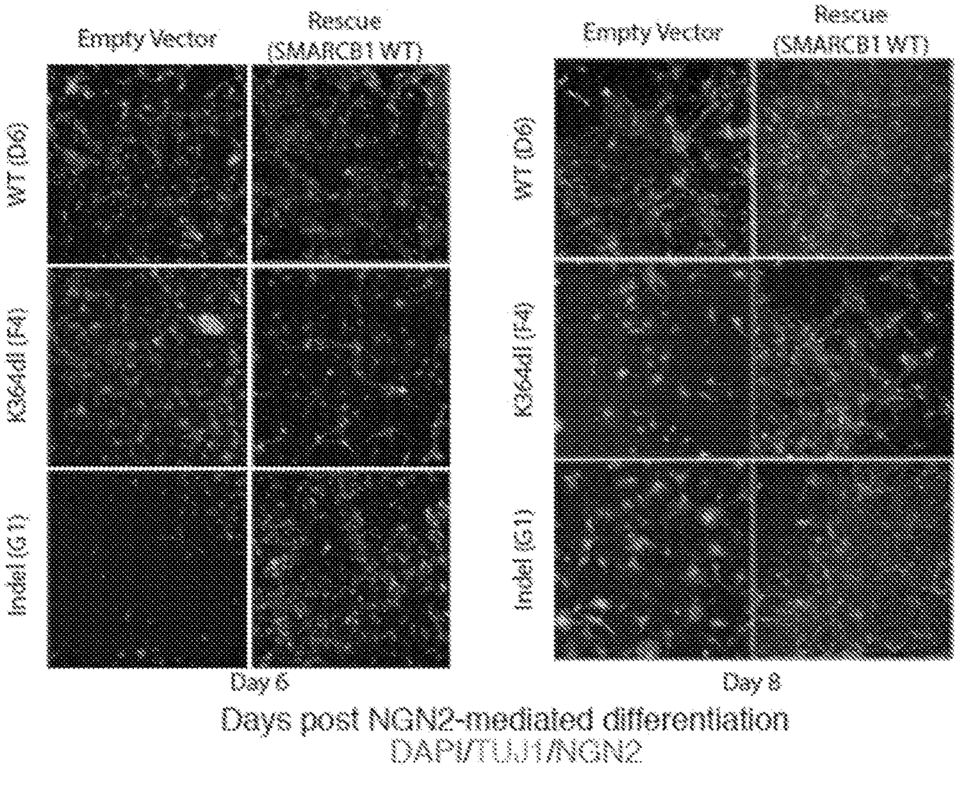

Example 6: CSS-Associated Heterozygous SMARCB1 Mutations in iPSCs Block Neuronal Differentiation To assess the phenotypic consequences of SMARCB1 C-terminal domain mutations in a heterozygous setting (mimicking the gene status of individuals with CSS), human induced pluripotent stem cells (iPSCs) were genetically modified to harbor heterozygous SMARCB1 c-terminal mutations, particularly K364del (FIG. 9A) which could then be differentiated toward neuronal lineage using a neurogenin (Ngn2)-based neuronal differentiation protocol (Zhang et al. (2013) *Neuron* 78:785-798). Briefly, heterozygous SMARCB1 mutant SAH iPSCs were generated using homology directed repair (HDR) with a mutant single-stranded oligodeoxynucleotide (ssODN) donor template introduced with CRISPR-Cas9 reagents targeting the SMARCB1 gene 3'-end (FIG. 10A). Mutations were confirmed by sequencing of the SMARCB1 gene (FIG. 10B). Baseline WT and mutant iPSCs exhibited similar cell health profiles as assessed by flow cytometry-based analysis of early (Annexin-V (V CF Blue)), and late (7-AAD) stage apoptosis markers (FIG. 10C). In undifferentiated SAH iPSCs, genome-wide BAF complex targeting, as well as H3K27ac occupancy, was comparable between WT and the SMARCB1 K364del mutant settings, however, nearly 25% of sites exhibited statistically significant decreases in DNA accessibility in the K364del mutant relative to WT, as measured by ATAC-seq (FIG. 9B). Interestingly, while all analyzed ChIP-seq signals were comparable or increased in the K364del/+ versus WT condition over merged SMARCA4 peaks, ATAC-seq signal decreased (FIG. 9C and FIG. 10D). HOMER and LOLA motif analysis of sites with reduced DNA accessibility in the K364del mutant condition were enriched for OCT, SOX, and NANOG motifs, indicating decreased accessibility at pluripotent factor gene loci, as exemplified also at the ANKRD1 locus (FIG. 9D and FIGS. 10E-10F). At baseline, differential gene expression analysis and GSEA studies performed on Day 0 (undifferentiated) iPSCs comparing wild-type versus K364del iPSCs indicated a range of processes affected in beyond nervous system processes, including cardiac muscle development, kidney and mesenchyme development, endocrine system development, and cell fate commitment, in agreement with physiologic findings in CSS individuals (FIGS. 10G-10H). In order to visualize transcriptional changes between the SMARCB1 WT and K364del conditions during differentiation, expression levels of differentially expressed genes derived from days 0, 2, 4, and 8 were partitioned into 6 groups by k-means clustering and displayed in heatmap form (FIG. 10I). A substantial divergence in transcription was observed at day 8, as shown in clusters 5 and 6. Intriguingly, cluster 6 genes, which appeared less activated in the mutant condition, were enriched for developmental processes (FIG. 9E and FIG. 10J) and overlapped with nearly 100 genes (n=91) that are mutated in intellectual disability syndromes (Vissers et al. (2016) *Nat. Rev. Genet.*

17:9-18) and those normally upregulated during Ngn-2 induced differentiation (Zhang et al. (2013) *Neuron* 78:785-798) (n=749 total), indicating a convergence between the consequences of individual mutations of these genes and the effect of mSWI/SNF master regulatory complex perturbations (FIG. 9F and Table 7). Through a similar approach examining ATAC-seq on Day 4 versus 0 of the Ngn2-differentiation protocol, increases in DNA accessibility were observed at a number of enhancers (C1 and C2) in the WT condition, which did not increase in the K36del mutant condition (C1) (FIGS. 10K-10L). Metascape analysis performed on clusters C1 and C2 showed that both clusters enriched for neurodevelopmental processes, suggesting that the mutant condition was unable to appropriately open and thereby activate appropriate neurodevelopmental processes (FIG. 10M). Indeed, TD-associated genes, such as ASCL1, FGFR2, GLC3, PAX6, SOX10 and others, exhibited significant blocks in activation during the neurogenin-induced differentiation time course in SMARCB1 K364del mutant iPSCs (FIG. 9G).

TABLE 7

Downregulated genes in K364del heterozygous iPSCs at day 8 of NGN2-differentiation and related disorders and phenotypes (FIG. 9E and 10L, C6, LofFC < −0.75)

| GENE NAME | ASSOCIATED PHENOTYPE(S) OR DISORDER(S) | OMIM ID |
|---|---|---|
| AHDC1 | Xia-Gibbs syndrome | 615829 |
| ALX4 | Potocki-Shaffer syndrome | 601224 |
| | Frontonasal dysplasia 2 (FND2) | 613451 |
| | Parietal foramina 2 (PFM2) | 609597 |
| | Craniosynostosis 5, susceptibility to (CRS5) | 615529 |
| ASCL1 | Central hypoventilation syndrome, congenital (CCHS) | 209880 |
| | Haddad syndrome | 209880 |
| CDON | Holoprosencephaly 11 | 614226 |
| CNTNAP2 | Cortical dysplasia-focal epilepsy syndrome | 610042 |
| | Pitt-Hopkins like syndrome 1 | 610042 |
| | Autism susceptibility 15 | 612100 |
| DOCK8 | Hyper-IgE recurrent infection syndrome, autosomal recessive | 243700 |
| DPP6 | Mental retardation, autosomal dominant 33 | 616311 |
| | Ventricular fibrillation, paroxysmal familial, 2 | 612956 |
| EMX2 | Schizencephaly | 269160 |
| FGFR2 | Antley-Bixler syndrome without genital anomalies or disordered steroidogenesis | 207410 |
| | Apert syndrome | 101200 |
| | Beare-Stevenson cutis gyrata syndrome | 123790 |
| | Bent bone dysplasia syndrome | 614592 |
| | Craniofacial-skeletal-dermatologic dysplasia | 101600 |
| | Craniosynostosis, nonspecific | — |
| | Crouzon syndrome | 123500 |
| | Gastric cancer, somatic | 613659 |
| | Jackson-Weiss syndrome | 123150 |
| | LADD syndrome | 149730 |
| | Pfeiffer syndrome | 101600 |
| | Saethre-Chotzen syndrome | 101400 |
| | Scaphocephaly and Axenfeld-Rieger anomaly | — |
| | Scaphocephaly, maxillary retrusion. and mental retardation | 609579 |
| GAD1 | Cerebral palsy, spastic quadriplegic, 1 | 603513 |
| | Greig cephalopolysyndactyly syndrome | 175700 |
| | Pallister-Hall syndrome | 146510 |
| GLI3 | Polydactyly, postaxial, types A1 and B | 174200 |
| | Polydactyly, preaxial, type IV | 174700 |
| | Hypothalamic hamartomas, somatic | 241800 |
| GPC3 | Simpson-Golabi-Behmel syndrome, type 1 | 312870 |
| | Wilms tumor, somatic | 194070 |
| HOXA1 | Athabaskan brainstem dysgenesis syndrome | 601536 |
| | Bosley-Salih-Alorainy syndrome | 601536 |
| IL1RAPL1 | Mental retardation, X-linked 21/34 | 300143 |
| KCNC3 | Spinocerebellar ataxia 13 | 605259 |
| | Microphthalmia, syndromic 5 | 610125 |
| OTX2 | Pituitary hormone deficiency, combined, 6 | 613986 |
| | Retinal dystrophy, early-onset, with or without pituitary dysfunction | 610125 |
| | Coloboma of optic nerve | 120430 |
| | Coloboma, ocular | 120200 |
| | Morning glory disc anomaly | 120430 |
| | Aniridia | 106210 |
| PAX6 | Anterior segment dysgenesis 5, multiple subtypes | 604229 |
| | Cataract with late-onset corneal dystrophy | 106210 |
| | Foveal hypoplasia 1 | 136520 |
| | Keratitis | 148190 |
| | Optic nerve hypoplasia | 165550 |
| | Infantile neuroaxonal dystrophy 1 | 256600 |
| PLA2G6 | Neurodegeneration with brain iron accumulation 2B | 610217 |
| | Parkinson disease 14, autosomal recessive | 612953 |
| PLCB1 | Epileptic encephalopathy, early infantile, 12 | 613722 |
| ROGDI | Kohlschutter-Tonz syndrome | 226750 |
| | PCWH syndrome | 609136 |
| SOX10 | Waardenburg syndrome, type 2E, with or without neurologic involvement | 611584 |
| | Waardenburg syndrome, type 4C | 613266 |
| | Mental retardation, X-linked, with isolated growth hormone deficiency | 300123 |

TABLE 7-continued

| Downregulated genes in K364del heterozygous iPSCs at day 8 of NGN2-differentiation and related disorders and phenotypes (FIG. 9E and 10L, C6, LofFC < −0.75) | | |
|---|---|---|
| GENE NAME | ASSOCIATED PHENOTYPE(S) OR DISORDER(S) | OMIM ID |
| | Panhypopituitarism, X-linked | 312000 |
| | Microphthalmia, isolated, with coloboma 8 | 601186 |
| STRA6 | Microphthalmia, syndromic 9 | 601186 |
| TFAP2A | Branchiooculofacial syndrome | 113620 |

The morphologic properties of differentiated neurons derived from WT SMARCB1 versus SMARCB1 K364del and heterozygous KO (indel) mutant iPSCs was also explored. Significantly diminished neurite outgrowth (length) and neuron counts (at days 6, 8 and 10) in SMARCB1 CSS mutant cells (either K364del or indel) relative to WT control cells was found (FIGS. 9H-9I and FIGS. 10N-10O). Notably, rescue of WT SMARCB1 in heterozygous K364 or indel iPSCs resulted in substantial rescue of both neurite outgrowth and neuron counts (Adj p<0.0001) (FIG. 9H-9J and FIG. 10N). Further, using NGN2 (FITC) fluorescence imaging to confirm NGN2 (neuronal differentiation marker) expression as well as microtubule-associated TUJ1 (neuron-specific class III beta tubulin) immunofluorescence staining to visualize neuronal projections. Through this, it was found that K364del and heterozygous KO cells developed significantly fewer neuronal projections compared to WT control cells upon neurogenin differentiation, phenotypes which were rescued by restoration of WT SMARCB1 (FIG. 9J and FIG. 10O). These data highlight the role for mSWI/SNF-mediated chromatin remodeling facilitated by the SMARCB1 C-terminal domain during neuronal differentiation and provide a mechanistic rationalization for the neurodevelopmental features of CSS.

Taken together, a critical structural and functional role for the SMARCB1 C-terminal putative CC domain in nucleosome remodeling and enhancer DNA accessibility by interrogating point mutations found in individuals with the intellectual disability, Coffin-Siris Syndrome, was identified. Unexpectedly, it was found that mSWI/SNF complexes containing domain single-residue point mutations in the SMARCB1-C-terminal alpha helical domain exhibit similar targeting on chromatin genome-wide, but are defective in generating DNA accessibility and in activating critical target genes, marking the finding that mSWI/SNF targeting and DNA accessibility do not mirror one another. For example, these data present an interesting contrast to recent studies examining ATPase-active versus-inactive BAF complexes, in that complexes lacking ATPase catalytic activity (via point mutations in the ATPase/helicase domain of SMARCA4/SMARCA2) are both unable to target to and open and activate distal sites (Pan et al. (2019) *Nat. Genet.* 51:618-626). Here it was shown that CSS-associated SMARCB1 mutations result in a retained ability of mSWI/SNF complexes to target to distal enhancer sites (and to recruit H3K27ac), but an inability to create DNA accessibility to the levels of wild-type complexes. These complementary investigations provide an opportunity to uncouple the roles of proper nucleosome remodeling and mSWI/SNF complex localization, as well as recruitment of other complexes (i.e. P300) to place activating histone marks (i.e. H3K27Ac) at differentially poised chromatin landscapes. These results further highlight a fundamental difference between focused point mutations in the CC domain and complete loss of the SMARCB1 subunit (biallelic deletion) in MRT (Nakayama et al. (2017) *Nat. Genet.* 49:1613-1623), again which shows complete loss of targeting to distal enhancer sites genome-wide. Of note, it was found that SMARCB1 C-terminal mutant mSWI/SNF complexes, which exhibited decreased remodeling activity and decreased ATP consumption on nucleosome substrates in vitro, trended toward increased chromatin occupancy compared to complexes with WT SMARCB1, indicating longer residence times and potential "stalling" of mSWI/SNF movement (FIG. 7F and FIG. 8G). This was further complemented by MNase-seq studies which indicated genome-wide increased occupancy of flanking nucleosomes on either side of the BAF complex peaks in the CSS-associated mutant versus SMARCB1 WT conditions.

Figure 11:
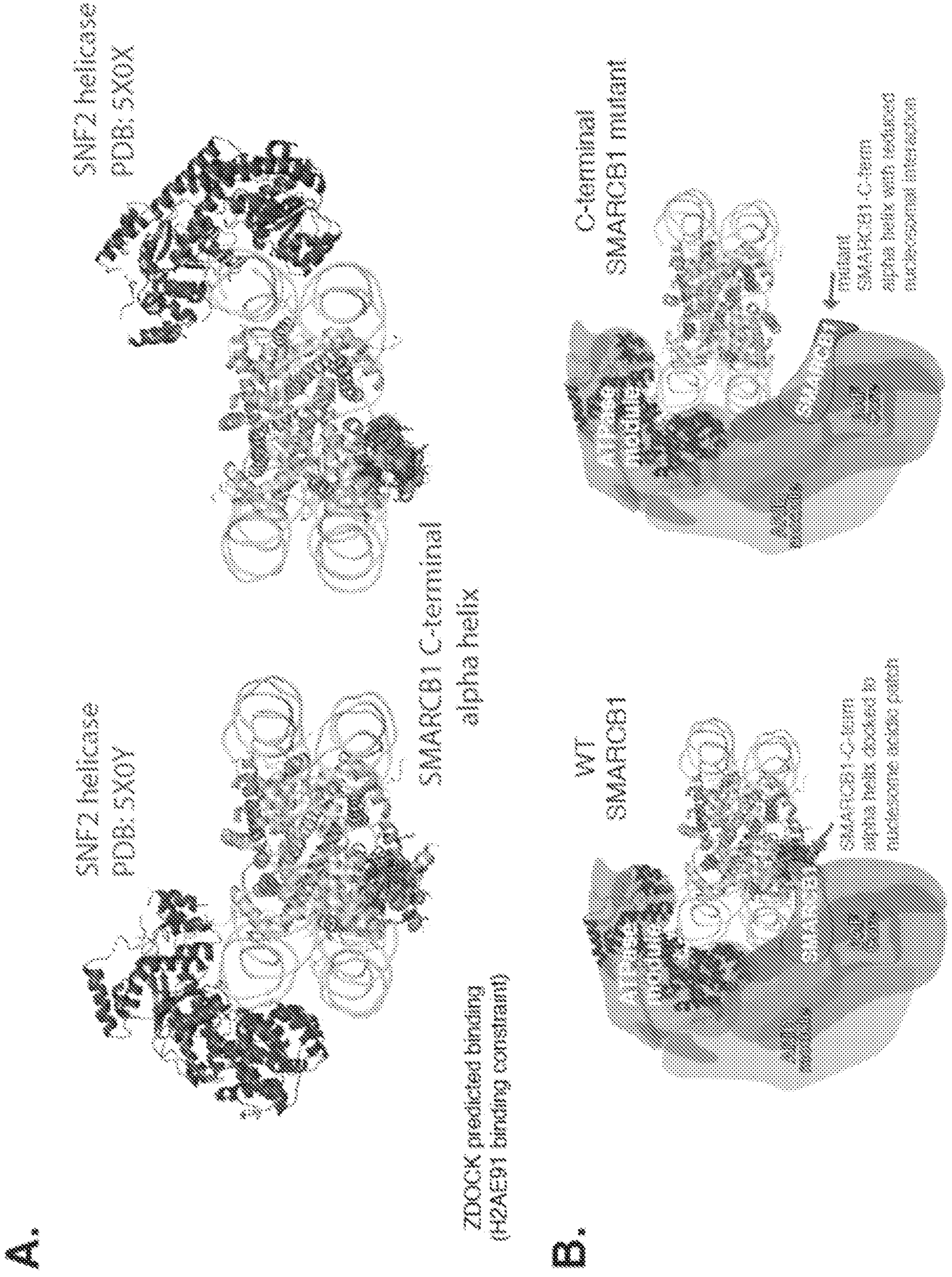
FIG. 11A-FIG. 11C show a model of SMARCB1-mediated nucleosome engagement and remodeling.
Figure 11:
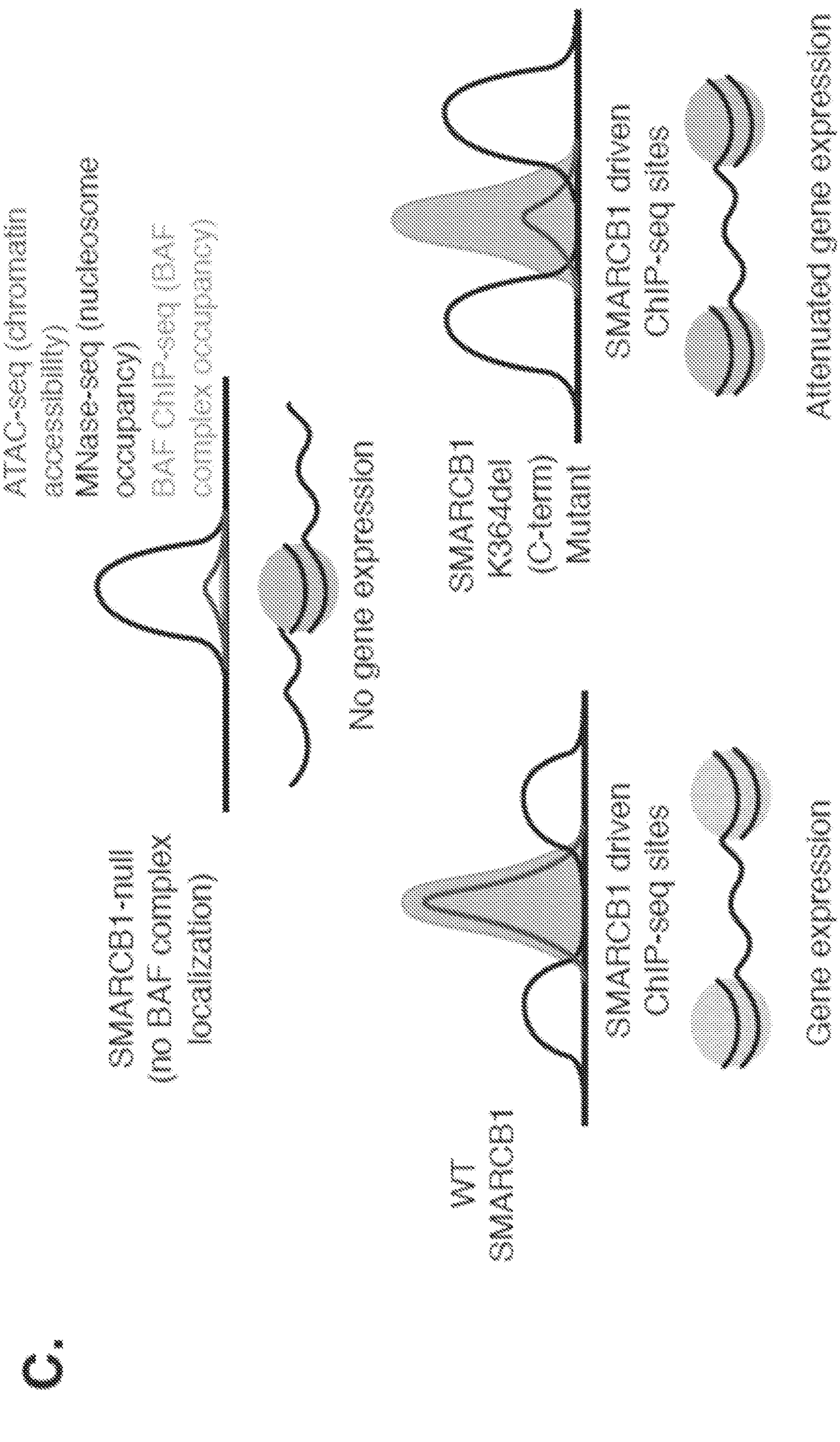

Apart from the recently described yeast Snf2 helicase domain:nucleosome DNA double helix structures (Liu et al. (2017) *Nature* 544:440-445), interactions between mSWI/SNF subunits and the nucleosome and their impacts on overall complex function have not been described. It is described herein by focusing on the SMARCB1 C-terminal domain owing to frequent mutations in ID and cancer, a dense cluster of basic, positively charged amino acids within an alpha helical structure that are required for SMARCB1 nucleosome acidic patch binding was identified, and hence the mSWI/SNF complex core module: nucleosome acidic patch engagement (Mashtalir et al. (2018) *Cell* 175:1272-1288). Marrying these data with those of Cheng and colleagues (Liu et al. (2017) *Nature* 544:440-445) and Mashtalir and colleagues (Mashtalir et al. (2018) *Cell* 175:1272-1288), and using H2AE91 restraint-containing simulations, a model for mSWI/SNF complex:nucleosome engagement is provided herein (FIG. 11A), and it is further highlight herein how CSS-associated point mutations in the CC domain inhibit mSWI/SNF complex:nucleosome binding. It was indicated that inhibition of remodeling of mSWI/SNF complexes on their nucleosomal substrates then results in reduced DNA accessibility, reduced nucleosome displacement (and hence increased nucleosome occupancy) at BAF target sites, and reduced gene expression (FIGS. 11B and 11C).

There is significant interest by the global research community in developing small molecule inhibitors of mSWI/SNF complex activities. While the majority of drug discovery efforts have been directed toward ATPase inhibition (i.e., catalytic inhibition of the SMARCA4 and SMARCA2 components), it is believed that the SMARCB1 CC:nucleosome interface described here is the first allosteric interface identified that, if disrupted via small molecules, would be expected to specifically inhibit the remodeling activity of mSWI/SNF complexes, and even of specific subcomplexes within the mSWI/SNF family (canonical BAF and PBAF, but not ncBAF as ncBAF does not contain the SMARCB1 subunit).

Finally, at the transcriptional and cell physiologic level, the data highlight and reinforce the importance of mSWI/

SNF-mediated chromatin remodeling for the maintenance of stem cell pluripotency factors and their networks (Singhal et al. (2010) *Cell* 141:943-955), as well as for cell type-specific development, such as nervous system differentiation. With human genetics, biochemistry, structural biology woven together, the results highlight the power of examining recurrent disease-associated mutations to advance mechanistic understanding of mSWI/SNF complex function in healthy and disease states.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments encompassed by the present invention described herein. Such equivalents are intended to be encompassed by the following claims.

What is claimed is:

1. An isolated modified protein complex selected from the group consisting of BAF, PBAF, BAF Core, ARID/BAF Core intermediate_1, ARID/BAF Core intermediate_2, ARID/PBAF Core intermediate_1, and ARID/PBAF Core intermediate_2, wherein the isolated modified protein complex comprises a modified SMARCB1 subunit that comprises a deletion or missense mutation at residue K363, K364, R366, Q368, R370, R373, R374, R376, R377 and/or a deletion of at least one residue within residues 357-378 of human SMARCB1, or a corresponding residue in an ortholog thereof.

2. The isolated modified protein complex of claim 1, wherein the isolated modified protein complex comprising the modified SMARCB1 subunit has at least one of the following as compared to the protein complex comprising the wild-type SMARCB1 subunit rather than the modified SMARCB1 subunit:

a) reduced nucleosome binding activity;
b) reduced nucleosome remodeling activity;
c) reduced nucleosome ATPase activity;
d) reduced chromatin accessibility activity; or
e) reduced gene expression at mSWI/SNF target genes.

3. The isolated modified protein complex of claim 1, wherein the modified SMARCB1 subunit has one or more of the following modifications as compared to the wild-type SMARCB1 subunit:

a) replacement of at least one basic amino acid for a neutral or an acidic amino acid;
b) deletion of at least one basic amino acid;
c) reduced isoelectric point, reduced charge potential, and/or reduced net positive charge;
d) reduced or eliminated interaction with the canonical nucleosome acidic patch
e) reduced or eliminated interaction with histone residues H2AE56, H2AE61, H2AE64, H2AD90, H2AE91, H2AE92, H2BE105, H2BE113, and/or H4E52; and/or
f) comprises a sequence selected from the group of sequences set forth in SEQ ID NOs: 14-27 and 33-37, or a sequence that is at least 30% identical to the sequence and has a positively charged face.

4. The isolated modified protein complex of claim 1, wherein at least one subunit comprises a heterologous amino acid sequence, optionally wherein the at least one subunit is SMARCB1.

5. The isolated modified protein complex of claim 4, wherein the heterologous amino acid sequence comprises an affinity tag or a label, optionally wherein i) the affinity tag is selected from the group consisting of Glutathione-S-Transferase (GST), calmodulin binding protein (CBP), protein C tag, Myc tag, HaloTag, HA tag, Flag tag, His tag, biotin tag, and V5 tag; and/or
ii) the label is a fluorescent protein.

6. A pharmaceutical composition comprising the isolated modified protein complex of claim 1 and a carrier.

7. A process for preparing an isolated modified protein complex of claim 1 comprising:

a) expressing the modified SMARCB1 subunit of the modified protein complex, optionally further expressing a subunit comprising a heterologous amino acid sequence, in a host cell or organism; and
b) isolating the modified protein complex comprising the modified subunit, optionally wherein the isolating step comprises density sedimentation analysis.

8. A method for screening for an agent that modulates the formation or stability of an interaction between the modified protein complex of claim 1 and a nucleosome, comprising:

a) contacting the modified protein complex, or a host cell or organism expressing the modified protein complex, with a test agent, and
b) determining the amount of the modified protein complex bound to the nucleosome in the presence of the test agent, wherein a difference in the amount of the modified protein complex bound to the nucleosome as determined in step (b) relative to the amount of the modified protein complex bound to a nucleosome determined in the absence of the test agent indicates that the test agent modulates the formation or stability of the interaction between the modified protein complex and the nucleosome.

9. The method of claim 8, wherein the SMARCB1 subunit of the isolated modified protein complex is a mutant form that is identified in a human disease selected from lymphoma, synovial cell sarcoma, and acoustic neuroma.

10. A method for screening for an agent that modulates the formation or stability of an interaction between a modified SMARCB1 protein of claim 4 and a nucleosome, comprising:

a) contacting the modified SMARCB1 protein, or a host cell or organism expressing the modified SMARCB1 protein, with a test agent, and
b) determining the amount of the modified SMARCB1 protein bound to the nucleosome in the presence of the test agent, wherein a difference in the amount of the modified SMARCB1 protein bound to the nucleosome as determined in step (b) relative to the amount of the modified SMARCB1 protein bound to the nucleosome determined in the absence of the test agent indicates that the test agent modulates the formation or stability of the interaction between the modified SMARCB1 protein and the nucleosome.

11. The method of claim 8, further comprising determining the presence and/or amount of the individual subunits in the isolated modified protein complex.

12. The method of claim 8, wherein the step of contacting occurs ex vivo or in vitro.

13. The method of claim 8, wherein the agent increases the formation or stability of the interaction between the isolated modified protein complex and the nucleosome.

14. The method of claim 10, further comprising determining the presence and/or amount of the contacts between residues of the modified SMARCB1 protein and residues of the nucleosome.

15. The method of claim 10, wherein the step of contacting occurs ex vivo, in vitro, or in silico.

16. The method of claim 10, wherein the agent increases the formation or stability of the interaction between the modified SMARCB1 protein and the nucleosome.

17. The method of claim 10, wherein the modified SMARCB1 protein is a mutant form that is identified in a human disease selected from lymphoma, synovial cell sarcoma, and acoustic neuroma.

* * * * *